United States Patent
Cohen et al.

(10) Patent No.: US 9,399,636 B2
(45) Date of Patent: Jul. 26, 2016

(54) SUBSTITUTED DIPYRIDYLAMINES AND USES THEREOF

(71) Applicant: Genentech, Inc., South San Francisco, CA (US)

(72) Inventors: Frederick Cohen, San Francisco, CA (US); Malcolm Huestis, San Francisco, CA (US); Cuong Ly, Daly City, CA (US); Snahel Patel, Foster City, CA (US); Michael Siu, Burlingame, CA (US); Xianrui Zhao, San Mateo, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 14/550,528

(22) Filed: Nov. 21, 2014

(65) Prior Publication Data

US 2015/0080367 A1    Mar. 19, 2015

Related U.S. Application Data

(63) Continuation of application No. PCT/EP2013/060351, filed on May 21, 2013.

(60) Provisional application No. 61/650,281, filed on May 22, 2012.

(51) Int. Cl.
| | |
|---|---|
| *C07D 401/14* | (2006.01) |
| *C07D 401/12* | (2006.01) |
| *C07D 405/14* | (2006.01) |
| *C07D 487/08* | (2006.01) |
| *C07D 491/107* | (2006.01) |

(52) U.S. Cl.
CPC ............ *C07D 401/14* (2013.01); *C07D 401/12* (2013.01); *C07D 405/14* (2013.01); *C07D 487/08* (2013.01); *C07D 491/107* (2013.01)

(58) Field of Classification Search
CPC .. C07D 487/08; C07D 401/12; C07D 405/14; C07D 401/14; C07D 491/107
USPC ................. 514/210.18, 318, 278, 210.2, 333; 546/194, 193, 256, 15
See application file for complete search history.

(56) References Cited

U.S. PATENT DOCUMENTS

| | | | | |
|---|---|---|---|---|
| 2010/0317643 | A1* | 12/2010 | Goodacre | C07D 401/12 514/210.02 |
| 2011/0065726 | A1* | 3/2011 | Chen | C07D 417/04 514/256 |
| 2013/0090309 | A1* | 4/2013 | Romeo | A61K 31/444 514/64 |
| 2013/0225548 | A1* | 8/2013 | Fujihara et al. | 514/210.2 |
| 2015/0175619 | A1* | 6/2015 | Siu | C07D 401/04 514/210.2 |
| 2016/0002228 | A1* | 1/2016 | Estrada | C07D 401/14 514/210.18 |
| 2016/0046608 | A1* | 2/2016 | Cohen | C07D 401/14 424/93.7 |

FOREIGN PATENT DOCUMENTS

| | | | |
|---|---|---|---|
| EP | 1 854 793 | A1 | 11/2007 |
| WO | 02/072571 | | 9/2002 |
| WO | WO 2010068806 | * | 6/2010 |
| WO | 2011/014515 | A1 | 2/2011 |
| WO | WO 2011014515 | * | 2/2011 |
| WO | 2011/044181 | A1 | 4/2011 |
| WO | 2011/050192 | A1 | 4/2011 |
| WO | WO 2012041476 | * | 4/2012 |
| WO | 2012/057262 | A1 | 5/2012 |
| WO | WO 2012057262 | * | 5/2012 |
| WO | WO 2012154518 | * | 11/2012 |
| WO | WO 2012154520 | * | 11/2012 |
| WO | 2013/034238 | A1 | 3/2013 |

OTHER PUBLICATIONS

Chemical Abstracts STN Registry database record for RN 724721-57-7, entered Aug. 10, 2004.*
International Search Report issued in International Application No. PCT/EP2013/060351, dated Jan. 7, 2013.
Probst et al., "Highly selective c-Jun-terminal kinase (JNK) 2 and 3 inhibitors with in vitro CNS-like pharmacokinetic properties prevent neurodegeneration" Bioorganic & Medicinal Chemistry Letters 21:315-319 (2011).

* cited by examiner

*Primary Examiner* — Andrew D Kosar
*Assistant Examiner* — Daniel Carcanague
(74) *Attorney, Agent, or Firm* — Mark D. Kafka

(57) ABSTRACT

The present invention provides for compounds of Formula I and various embodiments thereof, and compositions comprising compounds of Formula I and various embodiments thereof.

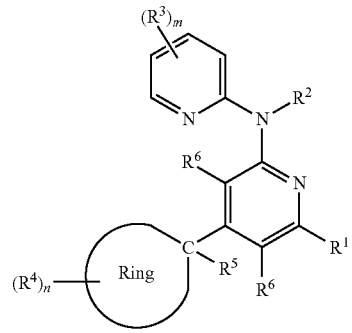

In compounds of Formula I, the groups $R^1$, $R^2$, $R^3$, $R^4$, $R^5$, $R^6$, m, n and the C-linked Ring have the meaning as described herein. The present invention also provides for methods of using compounds of Formula I and compositions comprising compounds of Formula I as DLK inhibitors and for treating neurodegeneration diseases and disorders.

17 Claims, No Drawings

SUBSTITUTED DIPYRIDYLAMINES AND USES THEREOF

CROSS-REFERENCE TO RELATED APPLICATIONS

This application is a continuation of International Patent Application No. PCT/EP2013/060351, filed on May 21, 2013, which claims the benefit of U.S. Provisional Application No. 61/650,281, filed May 22, 2012, each of which is incorporated herein by reference in its entirety.

FIELD OF THE INVENTION

The present invention relates to organic compounds useful for therapy and/or prophylaxis in a mammal, and in particular to inhibitors of DLK useful for treating neurodegeneration diseases and disorders.

BACKGROUND OF THE INVENTION

Neuron or axon degeneration plays a central role in the proper development of the nervous system and is a hall mark of many neurodegenerative diseases including for example, amyotrophic lateral sclerosis (ALS), glaucoma, Alzheimer's disease, and Parkinson's disease, as well a traumatic injury to the brain and spinal cord. Recent patent publication WO2011/050192, incorporated herein by reference, describes the role of the Dual Leucine Zipper Kinase (DLK), also referred to as MAP3K12, to cause neuronal cell death. Neurodegenerative diseases and injuries are devastating to patients and caregivers, and also result in great financial burdens, with annual costs currently exceeding several hundred billion dollars in the United States alone. Most current treatments for these diseases and conditions are inadequate. Adding to the urgency of the problems created by these diseases is the fact that many such diseases are age related, and thus their incidence is increasing rapidly as population demographics change. There is a great need for the development of effective approaches to treating neurodegenerative diseases and nervous system injuries, including for example, through the inhibitors of DLK in neurons.

SUMMARY OF THE INVENTION

In one aspect the present invention provides for novel compounds. In a first embodiment of such compounds (Embodiment 1; abbreviated as "E1") the compounds have Formula I

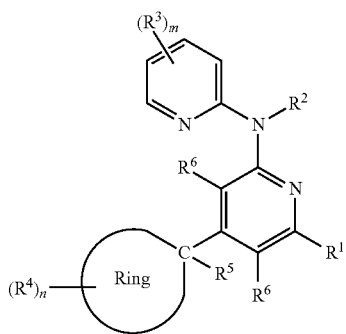

(I)

wherein $R^1$ is selected from the group consisting of hydrogen, fluoro, chloro, bromo, $C_{1-6}$ alkyl, $C_{1-6}$ haloalkyl, $C_{1-6}$ heteroalkyl, $C_{1-6}$ alkoxy, 3-10 membered cycloalkyl, 3-10 membered heterocycloalkyl, 6-10 membered aryl, 5-10 membered heteroaryl, $—OR^{1a}$, $—SR^{1a}$, $—N(H)(R^{1a})$, and $—N(R^{1a})(R^{1b})$ wherein $R^{1a}$ and $R^{1b}$ are each independently selected from the group consisting of $C_{1-6}$ alkyl, $C_{1-6}$ haloalkyl, $C_{1-6}$ heteroalkyl, 3-10 membered cycloalkyl and 3-10 membered heterocycloalkyl, and wherein the aliphatic and aromatic portions of $R^1$ are independently further substituted with 0 to 5 $R^{A1}$ substituents selected from the group consisting of —F, —Cl, —Br, —I, —CN, —NO$_2$, —SF$_5$, —OH, —NH$_2$, —CF$_3$, =O, $C_{1-4}$ alkyl, $C_{1-4}$ haloalkyl, $C_{1-4}$ heteroalkyl, $C_{1-4}$ alkoxy, $C_{1-4}$ alkylthio, $C_{1-4}$ alkylamino, $C_{1-4}$ dialkylamino, $R^{1c}$—C(=O)—, $R^{1c}$—C(=O)N(H)—, $R^{1c}$—C(=O)N($R^{1d}$)—, $R^{1c}$—C(=O)O—, $R^{1c}$—S(O)$_{1-2}$—, $R^{1c}$—S(O)$_{1-2}$N($R^{1d}$)—, $R^{1c}$—S(O)$_{1-2}$N(H)—, 3-6 membered cycloalkyl, phenyl, 5-6 membered heteroaryl and 3-7 membered heterocycloalkyl, wherein $R^{1c}$ is selected from the group consisting of $C_{1-6}$ alkyl, $C_{1-6}$ haloalkyl, $C_{5-6}$ heteroaryl, 3-7 membered heterocycloalkyl, phenyl and 3-6 membered cycloalkyl, $R^{1d}$ is selected from the group consisting of hydrogen, $C_{1-3}$ alkyl and $C_{1-3}$ haloalkyl, and wherein said 5-6 membered heteroaryl, phenyl, 3-6 membered cycloalkyl and 3-7 membered heterocycloalkyl of a $R^{A1}$ substituent are substituted with from 0-4 substituents selected from —F, —Cl, —Br, I, —CN, —NO$_2$, —SF$_5$, —OH, —NH$_2$, —CF$_3$, $C_{1-4}$ alkyl, $C_{1-4}$ haloalkyl, $C_{1-4}$ alkoxy, $C_{1-4}$ alkylthio, $C_{1-4}$ alkylamino and $C_{1-4}$ dialkylamino; $R^2$ is selected from the group consisting of hydrogen, $C_{1-6}$ alkyl and $C_{1-6}$ haloalkyl; $R^3$ is selected from the group consisting of —F, —Cl, —Br, —I, $—(X^3)_{0-1}$—CN, $—(X^3)_{0-1}$—NO$_2$, $—(X^3)_{0-1}$—SF$_5$, $—(X^3)_{0-1}$—OH, $—(X^3)_{0-1}$—NH$_2$, $—(X^3)_{0-1}$—N(H)($R^{3a}$), $—(X^3)_{0-1}$—N($R^{3b}$)($R^{3a}$), $—(X^3)_{0-1}$—CF$_3$, —S-(Phenyl), $C_{1-6}$ alkyl, $C_{1-6}$ haloalkyl, $C_{1-6}$ heteroalkyl, $C_{1-6}$ alkoxy, $C_{1-6}$ alkylthio, $—(X^3)_{0-1}$-3-7 membered cycloalkyl, $—(X^3)_{0-1}$-3-7 membered heterocycloalkyl, $—(X^3)_{0-1}$-5-6 membered heteroaryl, $—(X^3)_{0-1}$—$C_6$ aryl, $—(X^3)_{0-1}$—C(=$Y^3$)N(H)($R^{3a}$), $—(X^3)_{0-1}$—C(=$Y^3$)NH$_2$, $—(X^3)_{0-1}$—C(=$Y^3$)N($R^{3a}$)($R^{3b}$), $—(X^3)_{0-1}$—C(=$Y^3$)OR$^{3a}$, $—(X^3)_{0-1}$—C(=$Y^3$)OH, $—(X^3)_{0-1}$—N(H)C(=$Y^3$)($R^{3a}$), $—(X^3)_{0-1}$—N($R^{3b}$)C(=$Y^3$)($R^{3a}$), $—(X^3)_{0-1}$—N(H)C(=$Y^3$)OR$^{3a}$, $—(X^3)_{0-1}$—N($R^{3b}$)C(=$Y^3$)OR$^{3a}$, $—(X^3)_{0-1}$—S(=$Y^3$)$_{1-2}$R$^{3a}$, $—(X^3)_{0-1}$—N(H)S(=$Y^3$)$_{1-2}$R$^{3a}$, $—(X^3)_{0-1}$—N($R^{3b}$)S(=$Y^3$)$_{1-2}$R$^{3a}$, $—(X^3)_{0-1}$—S(=$Y^3$)$_{1-2}$N(H)($R^{3a}$), $—(X^3)_{0-1}$—S(=$Y^3$)$_{1-2}$N($R^{3b}$)($R^{3a}$), $—(X^3)_{0-1}$—S(=$Y^3$)$_{1-2}$NH$_2$, $—(X^3)_{0-1}$—C(=$Y^3$)R$^{3a}$, $—(X^3)_{0-1}$—C(=$Y^3$)H, $—(X^3)_{0-1}$—C(=NOH)R$^{3a}$, $—(X^3)_{0-1}$—C(=NOR$^{3b}$)R$^{3a}$, $—(X^3)_{0-1}$—NHC(=$Y^3$)N(H)($R^{3a}$), $—(X^3)_{0-1}$—NHC(=$Y^3$)NH$_2$, $—(X^3)_{0-1}$—NHC(=$Y^3$)N($R^{3b}$)($R^{3a}$), $—(X^3)_{0-1}$—N($R^{3a}$)C(=$Y^3$)N(H)($R^{3a}$), $—(X^3)_{0-1}$—N($R^{3a}$)C(=$Y^3$)NH$_2$, $—(X^3)_{0-1}$—OC(=$Y^3$)R$^{3a}$, $—(X^3)_{0-1}$—OC(=$Y^3$)H, $—(X^3)_{0-1}$—OC(=$Y^3$)OR$^{3a}$, $—(X^3)_{0-1}$—OP(=$Y^3$)(OR$^{3a}$)(OR$^{3b}$), $—(X^3)$—SC(=$Y^3$)OR$^{3a}$ and $—(X^3)$—SC(=$Y^3$)N($R^{3a}$)($R^{3b}$) wherein $X^3$ is selected from the group consisting of $C_{1-4}$ alkylene, $C_{1-4}$ haloalkylene, $C_{1-4}$ heteroalkylene, $C_{2-4}$ alkenylene, and $C_{2-4}$ alkynylene, $R^{3a}$ and $R^{3b}$ are each independently selected from the group consisting of $C_{1-6}$ alkyl, $C_{1-6}$ haloalkyl, $C_{1-6}$ heteroalkyl, 3-7 membered cycloalkyl, 3-7 membered cycloalkyl-$C_{1-4}$ alkyl, 3-7 membered heterocycloalkyl, 3-7 membered heterocycloalkyl-$C_{1-4}$ alkyl, 5-6 membered heteroaryl, 5-6 membered heteroaryl-$C_{1-4}$ alkyl, $C_6$ aryl, $C_6$ aryl-$C_{1-4}$ alkyl and benzyl; $Y^3$ is O, NR$^{3d}$ or S wherein $R^{3d}$ is hydrogen or $C_{1-6}$ alkyl; wherein aliphatic or aromatic portion of $R^3$ is independently further substituted with from 0 to 4 $R^{A3}$ substituents selected from the group consisting of —F, —Cl, —Br, —I, —CN, —NO$_2$, —SF$_5$, —OH, —NH$_2$, —CF$_3$, =O, $C_{1-6}$ alkyl, $C_{1-6}$ haloalkyl, $C_{1-6}$ heteroalkyl, $C_{1-6}$ alkoxy, $C_{1-6}$ alkylthio, 3-6 membered cycloalkyl, 3-6 membered heterocycloalkyl, —C(=O)N(H)($C_{1-6}$ alkyl), —C(=O)N($C_{1-6}$ alkyl)$_2$, —C(=O)NH$_2$, —C(=O)O$C_{1-6}$ alkyl, —C(=O)OH, —N(H)C(=O)($C_{1-6}$ alkyl), —N($C_{1-6}$ alkyl)C(=O)($C_{1-6}$ alkyl), —N(H)C(=O)O$C_{1-6}$ alkyl, —N($C_{1-6}$ alkyl)C(=O)O$C_{1-6}$ alkyl, —S(O)$_{1-2}C_{1-6}$ alkyl, —N(H)S(O)$_{1-2}C_{1-6}$ alkyl, —N($C_{1-6}$ alkyl)S(O)$_{1-2}C_{1-6}$ alkyl, —S(O)$_{0-1}$N(H)($C_{1-6}$ alkyl), —S(O)$_{0-1}$N($C_{1-6}$ alkyl)$_2$, —S(O)$_{0-1}$NH$_2$, —C(=O)$C_{1-6}$ alkyl, —C(=NOH)$C_{1-6}$ alkyl, —C(=NO$C_{1-6}$ alkyl)$C_{1-6}$ alkyl, —NHC(=O)N(H)($C_{1-6}$ alkyl), —NHC(=O)N($C_{1-6}$ alkyl)$_2$, —NHC(=O)NH$_2$, —N($C_{1-6}$ alkyl)C(=O)N(H)($C_{1-6}$ alkyl), —N($C_{1-6}$ alkyl)C(=O)NH$_2$, —OC(=O)$C_{1-6}$ alkyl, —OC(=O)O$C_{1-6}$ alkyl, —OP(=O)(O$C_{1-6}$ alkyl)$_2$, —SC(=O)O$C_{1-6}$ alkyl and —SC(=O)N($C_{1-6}$ alkyl)$_2$; alternatively any two $R^3$ substituents located on adjacent atoms are optionally combined to form a 5-6 membered heteroaryl ring comprising 1-2 heteroatoms selected from N, O and S and further comprising 0 to 4 $R^{3a}$ substituents; m is an integer from 0 to 4; the ring represented by the structure

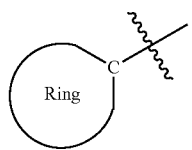 [SMILES: *C(C)C]

is a 4 to 10 membered C-linked heterocyclic ring comprising 1 to 2 heteroatoms selected from N, O and S, or is a 3 to 10 membered cycloalkyl ring, wherein the ring represented by said structure is optionally substituted with 1 to 3 $R^4$ groups; $R^4$ is selected from the group consisting of —F, —Cl, —Br, —I, —($X^4$)$_{0-1}$—CN, —($X^4$)$_{0-1}$—NO$_2$, —($X^4$)$_{0-1}$—SF$_5$, —($X^4$)$_{0-1}$—OH, —($X^4$)$_{0-1}$—NH$_2$, —($X^4$)$_{0-1}$—N(H)($R^{4a}$), —($X^4$)$_{0-1}$—N($R^{4b}$)($R^{4a}$), —($X^4$)$_{0-1}$—CF$_3$, $C_{1-6}$ alkyl, $C_{1-6}$ haloalkyl, $C_{1-6}$ heteroalkyl, $C_{1-6}$ alkoxy, $C_{1-6}$ alkylthio, —($X^4$)$_{0-1}$-(3-10 membered heterocycloalkyl), —($X^4$)$_{0-1}$-(5-10 membered heteroaryl), —($X^4$)$_{0-1}$-(3-7 membered cycloalkyl), —($X^4$)$_{0-1}$-(6-10 membered aryl), —($X^4$)$_{0-1}$—C(=$Y^4$)N(H)($R^{4a}$), —($X^4$)$_{0-1}$—C(=$Y^4$)NH$_2$, —($X^4$)$_{0-1}$—C(=$Y^4$)N($R^{4a}$)($R^{4b}$), —($X^4$)$_{0-1}$—C(=$Y^4$)O$R^{4a}$, —($X^4$)$_{0-1}$—C(=$Y^4$)OH, —($X^4$)$_{0-1}$—N(H)C(=$Y^4$)($R^{4a}$), —($X^4$)$_{0-1}$—N($R^{4b}$)C(=$Y^4$)($R^{4a}$), —($X^4$)$_{0-1}$—N(H)C(=$Y^4$)O$R^{4a}$, —($X^4$)$_{0-1}$—N($R^{4b}$)C(=$Y^4$)O$R^{4a}$, —($X^4$)$_{0-1}$—S(=$Y^4$)$_{1-2}R^{4a}$, —($X^4$)$_{0-1}$—N(H)S(=$Y^4$)$_{1-2}R^{4a}$, —($X^4$)$_{0-1}$—N($R^{4b}$)S(=$Y^4$)$_{1-2}R^{4a}$, —($X^4$)$_{0-1}$—S(=$Y^4$)$_{1-2}$N(H)($R^{4a}$), —($X^4$)$_{0-1}$—S(=$Y^4$)$_{1-2}$N($R^{4b}$)($R^{4a}$), —($X^4$)$_{0-1}$—S(=$Y^4$)$_{1-2}$NH$_2$, —($X^4$)$_{0-1}$—C(=$Y^4$)$R^{4a}$, —($X^4$)$_{0-1}$—C(=$Y^4$)H, —($X^4$)$_{0-1}$—C(=NOH)$R^{4a}$, —($X^4$)$_{0-1}$—C(=NO$R^{4b}$)$R^{4a}$, —($X^4$)$_{0-1}$—NHC(=$Y^4$)N(H)($R^{4a}$), —($X^4$)$_{0-1}$—NHC(=$Y^4$)NH$_2$, —($X^4$)$_{0-1}$—NHC(=$Y^4$)N($R^{4b}$)($R^{4a}$), —($X^4$)$_{0-1}$—N$R^{4a}$C(=$Y^4$)N(H)($R^{4a}$), —($X^4$)$_{0-1}$—N($R^{4a}$)C(=$Y^4$)NH$_2$, —($X^4$)$_{0-1}$—OC(=$Y^4$)$R^{4a}$, —($X^4$)$_{0-1}$—OC(=$Y^4$)H, —($X^4$)$_{0-1}$—OC(=$Y^4$)O$R^{4a}$, —($X^4$)$_{0-1}$—OP(=$Y^4$)(O$R^{4a}$)(O$R^{4b}$), —SC(=$Y^4$)O$R^{4a}$ and —SC(=$Y^4$)N($R^{4a}$)($R^{4b}$) wherein $R^{4a}$ and $R^{4b}$ at each occurrence are each independently selected from the group consisting of $C_{1-6}$ alkyl, $C_{1-6}$ haloalkyl, $C_{1-6}$ heteroalkyl, 6-10 membered aryl, 3-7 membered cycloalkyl, 5-10 membered heteroaryl, 3-7 membered heterocycloalkyl, 6-10 membered aryl-$C_{1-4}$ alkyl, 3-7 membered cycloalkyl-$C_{1-4}$ alkyl, 5-10 membered heteroaryl-$C_{1-4}$ alkyl and 3-7 membered heterocycloalkyl-$C_{1-4}$ alkyl, and $X^4$ is selected from the group consisting of $C_{1-4}$ alkylene, $C_{1-4}$ haloalkylene, $C_{1-4}$ heteroalkylene, $C_{2-4}$ alkenylene and $C_{2-4}$ alkynylene; $Y^4$ is O, N$R^{4c}$ or S wherein $R^{4c}$ is hydrogen or $C_{1-6}$ alkyl; wherein the aromatic and aliphatic portions of $R^4$ is independently further substituted with 0 to 4 $R^{44}$ substituents selected from the group consisting of —F, —Cl, —Br, I, —CN, —NO$_2$, —SF$_5$, —OH, —NH$_2$, —CF$_3$, =O, $C_{1-6}$ alkyl, $C_{1-6}$ haloalkyl, $C_{1-6}$ heteroalkyl, $C_{1-6}$ alkoxy, $C_{1-6}$ alkylthio, 3-6 membered cycloalkyl, 3-6 membered heterocycloalkyl, —C(=O)N(H)($C_{1-6}$ alkyl), —C(=O)N($C_{1-6}$ alkyl)$_2$, —C(=O)NH$_2$, —C(=O)O$C_{1-6}$ alkyl, —C(=O)OH, —N(H)C(=O)($C_{1-6}$ alkyl), —N($C_{1-6}$ alkyl)C(=O)($C_{1-6}$ alkyl), —N(H)C(=O)O$C_{1-6}$ alkyl, —N($C_{1-6}$ alkyl)C(=O)O$C_{1-6}$ alkyl, —S(O)$_{1-2}C_{1-6}$ alkyl, —N(H)S(O)$_{1-2}C_{1-6}$ alkyl, —N($C_{1-6}$ alkyl)S(O)$_{1-2}C_{1-6}$ alkyl, —S(O)$_{0-1}$N(H)($C_{1-6}$ alkyl), —S(O)$_{0-1}$N($C_{1-6}$ alkyl), —S(O)$_{0-1}$NH$_2$, —C(=O)$C_{1-6}$ alkyl, —C(=NOH)$C_{1-6}$ alkyl, —C(=NO$C_{1-6}$ alkyl)$C_{1-6}$ alkyl, —NHC(=O)N(H)($C_{1-6}$ alkyl), —NHC(=O)N($C_{1-6}$ alkyl)$_2$, —NHC(=O)NH$_2$, —N($C_{1-6}$ alkyl)C(=O)N(H)($C_{1-6}$ alkyl), —N($C_{1-6}$ alkyl)C(=O)NH$_2$, —OC(=O)$C_{1-6}$ alkyl, —OC(=O)O$C_{1-6}$ alkyl, —OP(=O)(O$C_{1-6}$ alkyl)$_2$, —SC(=O)O$C_{1-6}$ alkyl and —SC(=O)N($C_{1-6}$ alkyl)$_2$; n is an integer from 0 to 5; $R^5$ is absent or is selected from the group consisting of hydrogen, $C_{1-6}$ alkyl, $C_{1-6}$ haloalkyl, —OH, O$R^{5a}$, —CN and halogen, wherein $R^{5a}$ is selected from the group consisting of $C_{1-6}$ alkyl, $C_{1-6}$ haloalkyl and $C_{1-6}$ heteroalkyl; or optionally $R^4$ and $R^5$ are optionally combined to form a 5-7 membered cycloalkyl or heterocycloalkyl and is independently further substituted with 0-4 $R^{44}$ substituents; $R^6$ is independently selected from the group consisting of hydrogen, —F, Cl, Br, I, $C_{1-3}$ alkyl, $C_{1-3}$ haloalkyl; and with the proviso that compounds having the Chemical Abstract Service (CAS) registry numbers selected from the group consisting of 1286775-49-2, 1268247-50-2, 909291-41-4; and compounds wherein the C-linked ring is 1,3-dioxolane are not included.

Further embodiments (E) of the first embodiment of compounds of the invention, are described below.

E2 A compound of E1, wherein said compound of formula I has the subformula selected from the group consisting of:

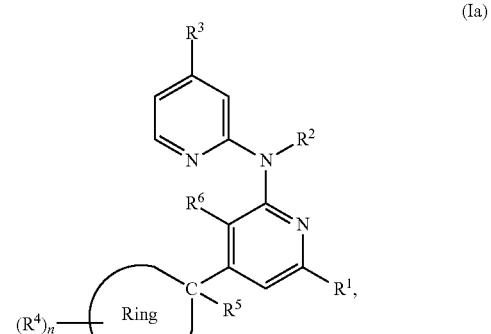

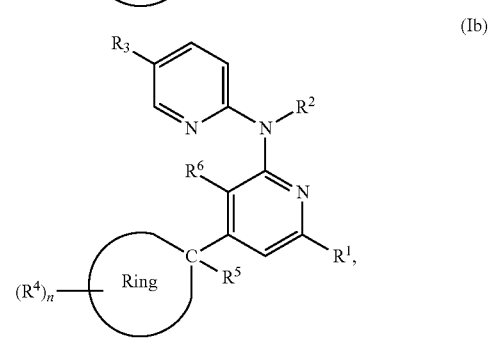

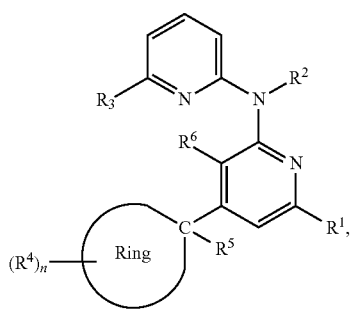

(Ic)

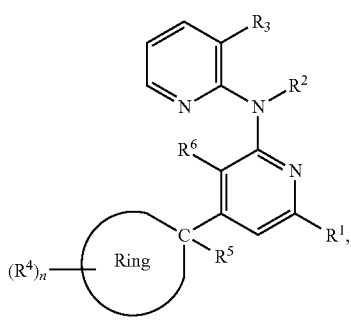

(Id)

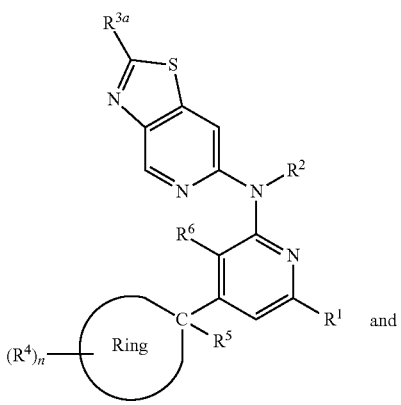

(Ie)

and

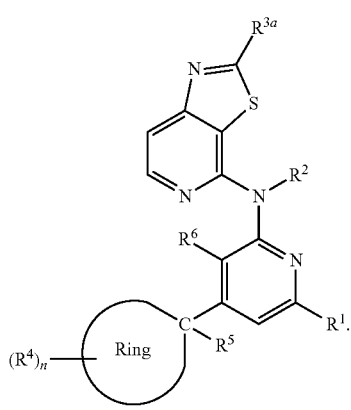

(If)

E3 A compound of E2, wherein said compound of formula I has the subformula (Ia).

E4 A compound of E1, E2 or E3, wherein the ring represented by

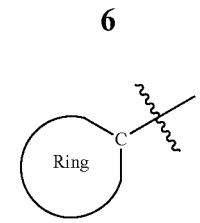

is an optionally substituted C-linked 4 to 10 membered heterocyclic ring selected from the group consisting of morpholine, morpholinone, piperazine, piperazinone, thiomorpholine, thiomorpholinone, homopiperidine, homopiperidinone, piperidine, valerolactam, pyrrolidine, butyrolactam, azetidine, azetidinone, thiazepane-1,1-dioxide, thiazinane-1,1-dioxide, isothiazolidine-1,1-dioxide, pyridinone, tetrahydropyran, oxetane and tetrahydrofuran attached to the remainder of the compound represented by formula I.

E5 A compound of E1, E2, E3 or E4, wherein the ring represented by the structure

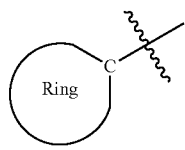 [SMILES: *C(C)C]

is selected from the group consisting of:

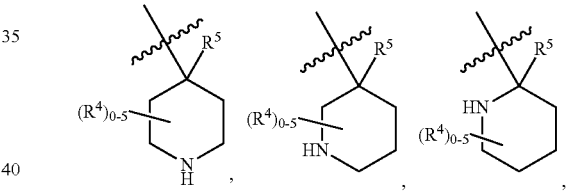

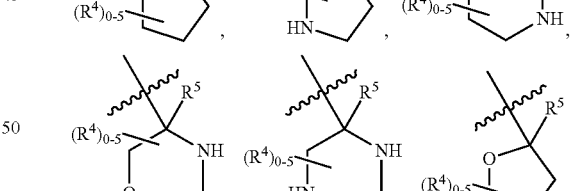

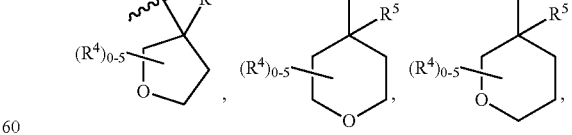

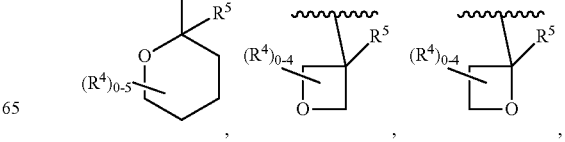

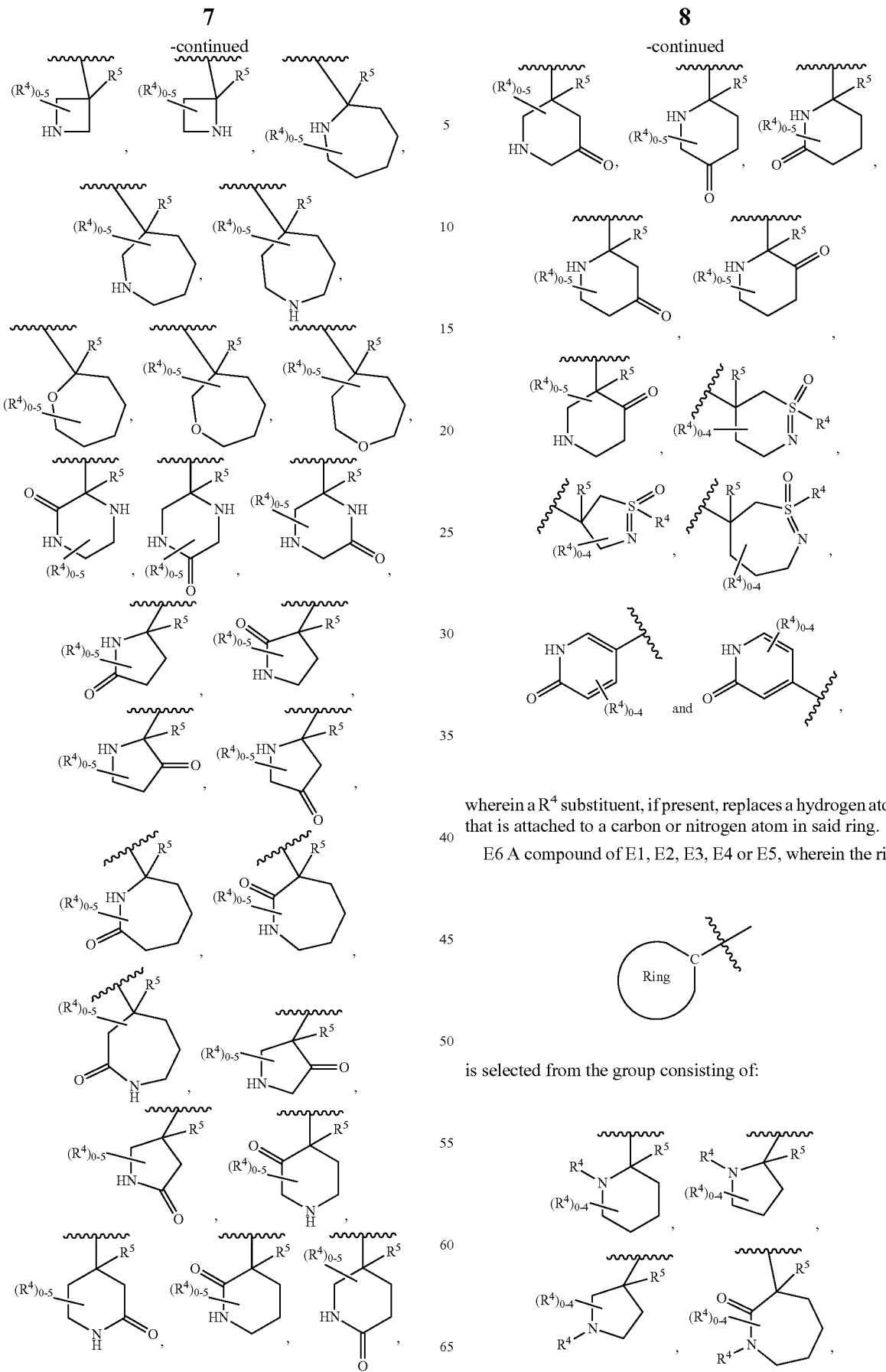
wherein a $R^4$ substituent, if present, replaces a hydrogen atom that is attached to a carbon or nitrogen atom in said ring.
E6 A compound of E1, E2, E3, E4 or E5, wherein the ring
is selected from the group consisting of:

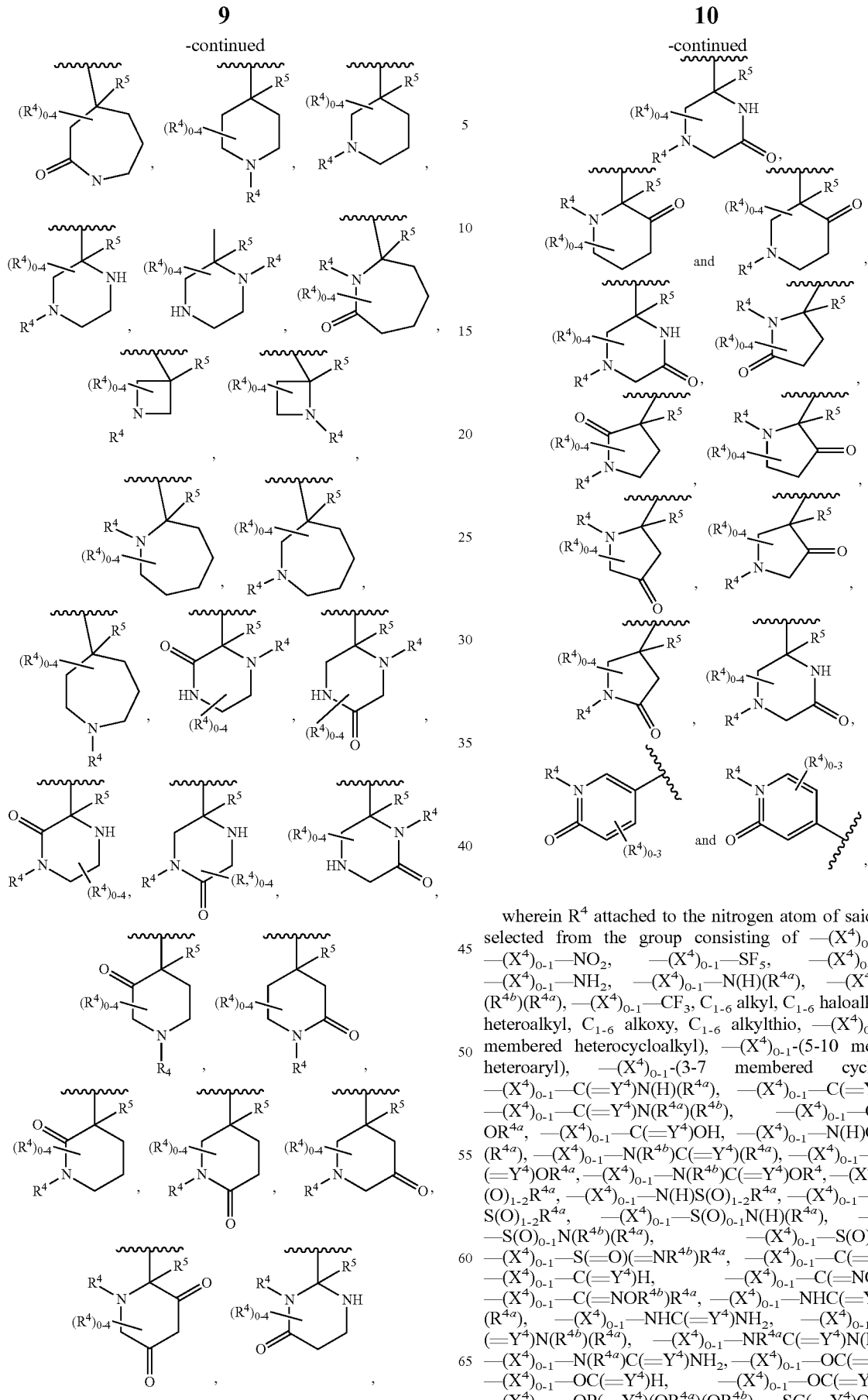

wherein $R^4$ attached to the nitrogen atom of said ring is selected from the group consisting of $-(X^4)_{0-1}-CN$, $-(X^4)_{0-1}-NO_2$, $-(X^4)_{0-1}-SF_5$, $-(X^4)_{0-1}-OH$, $-(X^4)_{0-1}-NH_2$, $-(X^4)_{0-1}-N(H)(R^{4a})$, $-(X^4)_{0-1}-N(R^{4b})(R^{4a})$, $-(X^4)_{0-1}-CF_3$, $C_{1-6}$ alkyl, $C_{1-6}$ haloalkyl, $C_{1-6}$ heteroalkyl, $C_{1-6}$ alkoxy, $C_{1-6}$ alkylthio, $-(X^4)_{0-1}$-(3-10 membered heterocycloalkyl), $-(X^4)_{0-1}$-(5-10 membered heteroaryl), $-(X^4)_{0-1}$-(3-7 membered cycloalkyl), $-(X^4)_{0-1}-C(=Y^4)N(H)(R^{4a})$, $-(X^4)_{0-1}-C(=Y^4)NH_2$, $-(X^4)_{0-1}-C(=Y^4)N(R^{4a})(R^{4b})$, $-(X^4)_{0-1}-C(=Y^4)OR^{4a}$, $-(X^4)_{0-1}-C(=Y^4)OH$, $-(X^4)_{0-1}-N(H)C(=Y^4)(R^{4a})$, $-(X^4)_{0-1}-N(R^{4b})C(=Y^4)(R^{4a})$, $-(X^4)_{0-1}-N(H)C(=Y^4)OR^{4a}$, $-(X^4)_{0-1}-N(R^{4b})C(=Y^4)OR^4$, $-(X^4)_{0-1}-S(O)_{1-2}R^{4a}$, $-(X^4)_{0-1}-N(H)S(O)_{1-2}R^{4a}$, $-(X^4)_{0-1}-N(R^{4b})S(O)_{1-2}R^{4a}$, $-(X^4)_{0-1}-S(O)_{0-1}N(H)(R^{4a})$, $-(X^4)_{0-1}-S(O)_{0-1}N(R^{4b})(R^{4a})$, $-(X^4)_{0-1}-S(O)_{0-1}NH_2$, $-(X^4)_{0-1}-S(=O)(=NR^{4b})R^{4a}$, $-(X^4)_{0-1}-C(=Y^4)R^{4a}$, $-(X^4)_{0-1}-C(=Y^4)H$, $-(X^4)_{0-1}-C(=NOH)R^{4a}$, $-(X^4)_{0-1}-C(=NOR^{4b})R^{4a}$, $-(X^4)_{0-1}-NHC(=Y^4)N(H)(R^{4a})$, $-(X^4)_{0-1}-NHC(=Y^4)NH_2$, $-(X^4)_{0-1}-NHC(=Y^4)N(R^{4b})(R^{4a})$, $-(X^4)_{0-1}-NR^{4a}C(=Y^4)N(H)(R^{4a})$, $-(X^4)_{0-1}-N(R^{4a})C(=Y^4)NH_2$, $-(X^4)_{0-1}-OC(=Y^4)R^{4a}$, $-(X^4)_{0-1}-OC(=Y^4)H$, $-(X^4)_{0-1}-OC(=Y^4)OR^{4a}$, $-(X^4)_{0-1}-OP(=Y^4)(OR^{4a})(OR^{4b})$, $-SC(=Y^4)OR^{4a}$ and —SC(=Y⁴)N(R⁴ᵃ)(R⁴ᵇ) wherein R⁴ᵃ and R⁴ᵇ at each occurrence are each independently selected from the group consisting of $C_{1-6}$ alkyl, $C_{1-6}$ haloalkyl, $C_{1-6}$ heteroalkyl, 6-10 membered aryl, 3-7 membered cycloalkyl, 5-10 membered heteroaryl, 3-7 membered heterocycloalkyl, 6-10 membered aryl-$C_{1-4}$ alkyl, 3-7 membered cycloalkyl-$C_{1-4}$ alkyl, 5-10 membered heteroaryl-$C_{1-4}$ alkyl and 3-7 membered heterocycloalkyl-$C_{1-4}$ alkyl, and $X^4$ is selected from the group consisting of $C_{1-4}$ alkylene, $C_{1-4}$ haloalkylene, $C_{1-4}$ heteroalkylene, $C_{2-4}$ alkenylene and $C_{2-4}$ alkynylene; $Y^4$ is O, $NR^{4c}$ or S wherein $R^{4c}$ is hydrogen or $C_{1-6}$ alkyl; wherein the aromatic and aliphatic portions of $R^4$ is independently further substituted with 0 to 4 $R^{44}$ substituents selected from the group consisting of —F, —Cl, —Br, I, —CN, —NO₂, —SF₅, —OH, —NH₂, —CF₃, =O, $C_{1-6}$ alkyl, $C_{1-6}$ haloalkyl, $C_{1-6}$ heteroalkyl, $C_{1-6}$ alkoxy, $C_{1-6}$ alkylthio, 3-6 membered cycloalkyl, 3-6 membered heterocycloalkyl, —C(=O)N(H)($C_{1-6}$ alkyl), —C(=O)N($C_{1-6}$ alkyl)₂, —C(=O)NH₂, —C(=O)O$C_{1-6}$ alkyl, —C(=O)OH, —N(H)C(=O)($C_{1-6}$ alkyl), —N($C_{1-6}$ alkyl)C(=O)($C_{1-6}$ alkyl), —N(H)C(=O)O$C_{1-6}$ alkyl, —N($C_{1-6}$ alkyl)C(=O)O$C_{1-6}$ alkyl, —S(O)$_{1-2}$$C_{1-6}$ alkyl, —N(H)S(O)$_{1-2}$$C_{1-6}$ alkyl, —N($C_{1-6}$ alkyl)S(O)$_{1-2}$$C_{1-6}$ alkyl, —S(O)$_{0-1}$N(H)($C_{1-6}$ alkyl), —S(O)$_{0-1}$N($C_{1-6}$ alkyl), —S(O)$_{0-1}$NH₂, —C(=O)$C_{1-6}$ alkyl, —C(=NOH)$C_{1-6}$ alkyl, —C(=NO$C_{1-6}$ alkyl)$C_{1-6}$ alkyl, —NHC(=O)N(H)($C_{1-6}$ alkyl), —NHC(=O)N($C_{1-6}$ alkyl), —NHC(=O)NH₂, —N($C_{1-6}$ alkyl)C(=O)N(H)($C_{1-6}$ alkyl), —N($C_{1-6}$ alkyl)C(=O)NH₂, —OC(=O)$C_{1-6}$ alkyl, —OC(=O)O$C_{1-6}$ alkyl, —OP(=O)(O$C_{1-6}$ alkyl)₂, —SC(=O)O$C_{1-6}$ alkyl and —SC(=O)N($C_{1-6}$ alkyl)₂; and the remainder $R^4$, if present on said ring, is each independently selected from the group consisting of —F, —Cl, —Br, I, —$(X^4)_{0-1}$—CN, —$(X^4)_{0-1}$—NO₂, —$(X^4)_{0-1}$—SF₅, —$(X^4)_{0-1}$—OH, —$(X^4)_{0-1}$—NH₂, —$(X^4)_{01}$—N(H)($R^{4a}$), —$(X^4)_{01}$—N($R^{4b}$)($R^{4a}$), —$(X^4)_{0-1}$—CF₃, —$(X^4)_{0-1}$—C(=Y⁴)$R^{4a}$, —$(X^4)_{0-1}$—C(=Y⁴)H, $C_{1-6}$ alkyl, $C_{1-6}$ haloalkyl, $C_{1-6}$ heteroalkyl, $C_{1-6}$ alkoxy and $C_{1-6}$ alkylthio wherein $X^4$ is selected from the group consisting of $C_{1-4}$ alkylene, $C_{1-4}$ haloalkylene, $C_{1-4}$ heteroalkylene, $C_{2-4}$ alkenylene and $C_{2-4}$ alkynylene and $R^{4a}$ and $R^{4b}$ is each independently selected from the group consisting of: $C_{1-6}$ alkyl, $C_{1-6}$ haloalkyl and $C_{1-6}$ heteroalkyl.

E7 A compound of E1, E2, E3, E4, E5 or E6, wherein the ring

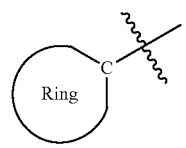 [SMILES: *C(C)C]

is selected from the group consisting of:

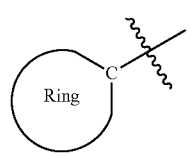 [SMILES: *C(C)C]

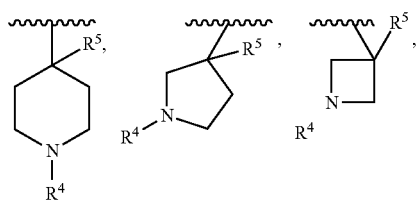

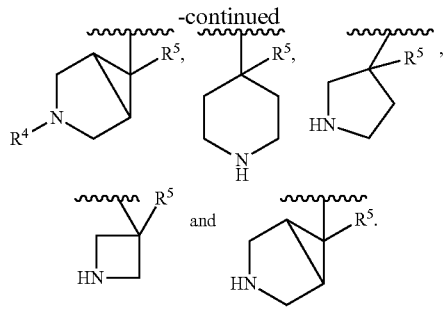

E8 A compound of E4, E5 or E6 wherein $R^4$ attached to the nitrogen atom of said ring is selected from the group consisting of $C_{1-6}$ alkyl, $C_{1-6}$ haloalkyl, $C_{1-6}$ heteroalkyl, $C_{1-6}$ alkoxy, $C_{1-6}$ alkylthio, —$(X^4)_{0-1}$-(3-10 membered heterocycloalkyl), —$(X^4)_{0-1}$-(5-10 membered heteroaryl), —$(X^4)_{0-1}$-(3-7 membered cycloalkyl), —$(X^4)_{0-1}$—S(O)$_{1-2}$$R^{4a}$ and —$(X^4)_{0-1}$—C(=Y⁴)$R^{4a}$, wherein $Y^4$ is O.

E9 A compound of E8, wherein $R^4$ is selected from the group consisting of methyl, trifluoromethyl, difluoromethyl, monofluoromethyl, ethyl, trifluoroethyl, difluoroethyl, monofluoroethyl and acetyl.

E10 A compound of E1, E2, E3, E4 or E5, wherein said

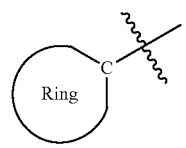 [SMILES: *C(C)C]

is selected from the group consisting of:

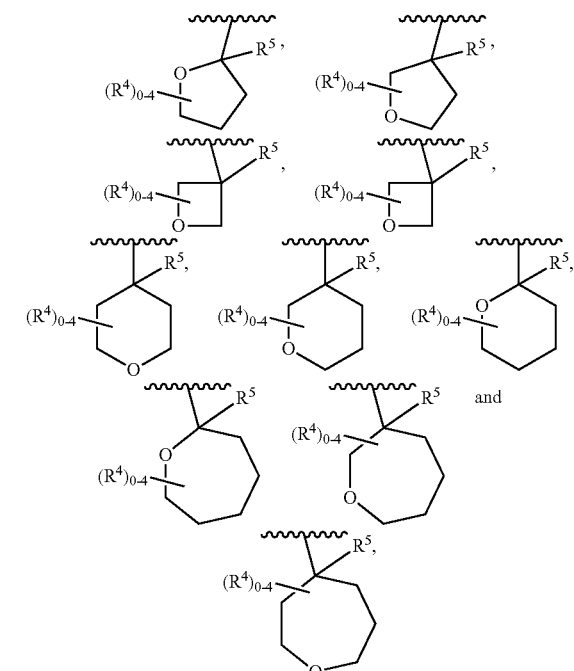

wherein $R^4$ is selected from the group consisting of: —F, —Cl, —Br, —I, —$(X^4)_{0-1}$—CN, —$(X^4)_{0-1}$—NO₂, —$(X^4)_{0-1}$—SF₅, —$(X^4)_{0-1}$—OH, —$(X^4)_{0-1}$—NH₂, —$(X^4)_{0-1}$—$N(H)(R^{4a})$, —$(X^4)_{0-1}$—$N(R^{4b})(R^{4a})$, —$(X^4)_{0-1}$—$CF_3$, $C_{1-6}$ alkyl, $C_{1-6}$ haloalkyl, $C_{1-6}$ heteroalkyl, $C_{1-6}$ alkoxy and $C_{1-6}$ alkylthio wherein $X^4$ is selected from the group consisting of $C_{1-4}$ alkylene, $C_{1-4}$ haloalkylene, $C_{1-4}$ heteroalkylene, $C_{2-4}$ alkenylene and $C_{2-4}$ alkynylene and $R^{4a}$ and $R^{4b}$ is each independently selected from the group consisting of: $C_{1-6}$ alkyl, $C_{1-6}$ haloalkyl and $C_{1-6}$ heteroalkyl.

E11 A compound of E10, wherein the group

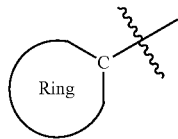

is selected from the group consisting of:

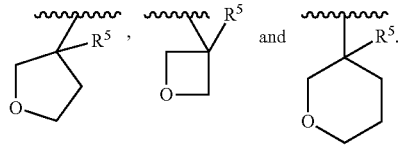

E12 A compound of E1, E2 or E3, wherein the group

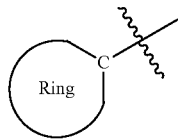 [SMILES: *C(C)C]

is an optionally substituted 3 to 10 membered carbocyclic ring selected from the group consisting of cyclopropane, cyclobutane, cyclopentane, cyclohexane, cycloheptane, bicyclo[1.1.1]pentane, bicyclo[2.1.0]pentane, bicyclo[3.1.0]hexane, bicyclo[2.1.1]hexane, bicyclo[2.2.1]heptane, bicyclo[3.2.0]heptane, bicyclo[3.1.1]heptane, bicyclo[2.2.2]octane, bicyclo[4.1.0]heptane, bicyclo[3.2.1]octane, bicyclo[4.2.0]octane, octahydropentalene, octahydro-1H-indene and decahydronaphthalene.

E13 A compound of E12, wherein said 3 to 10 membered carbocyclic ring is an optionally substituted ring selected from the group consisting of cyclopropane, cyclobutane, and cyclohexane.

E14 A compound of E12, wherein said 3 to 10 membered carbocyclic ring is selected from the group consisting of:

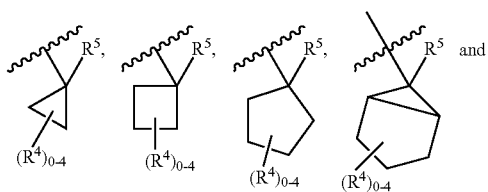

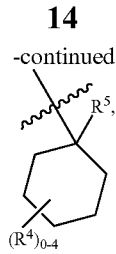

wherein $R^4$ is of $C_{1-6}$ alkyl, $C_{1-6}$ haloalkyl, $C_{1-6}$ heteroalkyl, $C_{1-6}$ alkoxy, $C_{1-6}$ alkylthio, —$(X^4)_{0-1}$-(3-10 membered heterocycloalkyl), —$(X^4)_{0-1}$-(5-10 membered heteroaryl), —$(X^4)_{0-1}$-(3-7 membered cycloalkyl), —$(X^4)_{0-1}$—$S(O)_{1-2}R^{4a}$ and —$(X^4)_{0-1}$—$C(=Y^4)R^{4a}$, wherein $Y^4$ is O.

E15 A compound of E1, E2, E3, E4, E5, E6, E7, E8, E9, E10, E11, E12, E13 or E14, wherein $R^5$ is selected from the group consisting of hydrogen, $C_{1-4}$ alkyl, $C_{1-4}$ haloalkyl, hydroxy, $OR^{5a}$, —CN, —F, —Cl, —Br and —I.

E16 A compound of E15, wherein $R^5$ is selected from the group consisting of hydrogen, methyl, ethyl, trifluoromethyl, methoxy, ethoxy, F, Cl and Br.

E17 A compound of E1, E2, E3, E4, E5, E6, E7, E8, E9, E10, E11, E12, E13, E14, E15 or E16, wherein $R^1$ is selected from the group consisting of $C_{1-6}$ alkyl, $C_{1-6}$ haloalkyl, $C_{1-6}$ heteroalkyl, —$OR^{1a}$, —$SR^{1a}$, —$N(H)(R^{1a})$, and —$N(R^{1a})(R^{1b})$, methyl, ethyl, propyl, isopropyl, butyl, sec-butyl, tert-butyl, cyclopropane, cyclobutane, cyclopentane, cyclohexane, cycloheptane, morpholine, homomorpholine, piperidine, homopiperidine, piperazine, homopiperazine, azetidine, pyrrolidine, benzene, pyrrole, pyrazole, imidazole, triazole, tetrazole, pyridine, pyrimidine, pyrazine, pyridazine, oxetane, tetrahydrofuran, tetrahydropyran, -oxa-5-azabicyclo[2.2.1]heptane, 2-oxa-6-azaspiro[3.3]heptane, 8-oxa-3-azabicyclo[3.2.1]octane, 3-oxa-8-azabicyclo[3.2.1]octane, 7-oxabicyclo[2.2.1]heptane, 7-azabicyclo[2.2.1]heptane, norbornane, bicyclo[2.2.2]octane, 2-azabicyclo[2.2.2]octane, 2-oxabicyclo[2.2.2]octane, 2-oxa-5-azabicyclo[2.2.2]octane and 2,5-diazabicyclo[2.2.2]octane, 5,6,7,8-tetrahydroimidazo[1,2-a]pyrazine, 4,5,6,7-tetrahydro-3H-imidazo[4,5-c]pyridine, wherein $R^{1a}$ and $R^{1b}$ are each independently selected from the group consisting of $C_{1-6}$ alkyl, $C_{1-6}$ haloalkyl, $C_{1-6}$ heteroalkyl, 3-10 membered cycloalkyl and 3-10 membered heterocycloalkyl, and wherein the aliphatic and aromatic portions of $R^1$ are independently further substituted with 0 to 5 $R^{41}$ substituents selected from the group consisting of —F, —Cl, —Br, I, —CN, —$NO_2$, —$SF_5$, —OH, —$NH_2$, —$CF_3$, =O, $C_{1-4}$ alkyl, $C_{1-4}$ haloalkyl, $C_{1-4}$ heteroalkyl, $C_{1-4}$ alkoxy, $C_{1-4}$ alkylthio, $C_{1-4}$ alkylamino, $C_{1-4}$ dialkylamino, $R^{1c}$—C(=O)—, —$R^{1c}$—C(=O)N(H)—, $R^{1c}$—C(=O)N($R^{1d}$)—, $R^{1c}$—C(=O)O—, $R^{1c}$—$S(O)_{1-2}$—, $R^{1c}$—$S(O)_{1-2}N(R^{1d})$—, $R^{1c}$—$S(O)_{1-2}N(H)$—, 3-6 membered cycloalkyl, phenyl, 5-6 membered heteroaryl and 3-7 membered heterocycloalkyl, wherein $R^{1c}$ is selected from the group consisting of $C_{1-6}$ alkyl, $C_{1-6}$ haloalkyl, $C_{5-6}$ heteroaryl, 3-7 membered heterocycloalkyl, phenyl and 3-6 membered cycloalkyl, $R^{1d}$ is selected from the group consisting of hydrogen, $C_{1-3}$ alkyl and $C_{1-3}$ haloalkyl, and wherein said 5-6 membered heteroaryl, phenyl, 3-6 membered heteroaryl, 3-6 membered cycloalkyl and 3-7 membered heterocycloalkyl of the $R^{41}$ substituent are substituted with from 0-4 substituents selected from —F, —Cl, —Br, I, —CN, —$NO_2$, —$SF_5$, —OH, —$NH_2$, —$CF_3$, $C_{1-4}$ alkyl, $C_{1-4}$ haloalkyl, $C_{1-4}$ alkoxy, $C_{1-4}$ alkylthio, $C_{1-4}$ alkylamino and $C_{1-4}$ dialkylamino.

E18 A compound of E17, wherein $R^1$ is selected from the group consisting of pyrrolidin-1-yl, phenyl, piperidin-1-yl, pyrrol-1-yl, azetidin-1-yl, morpholin-4-yl, homomorpholin-4-yl, 2-oxa-5-azabicyclo[2.2.1]hept-5-yl, 3-oxa-8-azabicyclo[3.2.1]oct-8-yl, 2-oxa-6-azaspiro[3.3]hept-6-yl, -8-oxa-3-azabicyclo[3.2.1]octane, methyl, isopropyl, isobutyl, cyclopropyl, pyrazol-1-yl, 4,5,6,7-tetrahydro-1H-imidazo[4,5-c]pyridin-5-yl, 3,5,6,7,8,8a-hexahydroimidazo[1,2-a]pyrazin-7-yl, 3-azabicyclo[3.2.0]heptan-3-yl, 3-azabicyclo[3.1.0]hexan-3-yl, 2-azabicyclo[2.1.1]hexan-2-yl, 2-azabicyclo[3.1.0]hexan-2-yl, 2-oxa-7-azaspiro[4.4]nonan-7-yl, 2-oxa-6-azaspiro[3.4]octan-6-yl, —N(H)R$^{1a}$), and —N(R$^{1a}$)(R$^{1b}$).

E19 A compound of E18, wherein R$^1$ is selected from the group consisting of pyrrolidin-1-yl, phenyl, piperidin-1-yl, pyrrol-1-yl, azetidin-1-yl, morpholin-4-yl, homomorpholin-4-yl, 2-oxa-5-azabicyclo[2.2.1]hept-5-yl, 3-oxa-8-azabicyclo[3.2.1]oct-8-yl, 2-oxa-6-azaspiro[3.3]hept-6-yl, -8-oxa-3-azabicyclo[3.2.1]octane, methyl, isopropyl, isobutyl, cyclopropyl, pyrazol-1-yl, 4,5,6,7-tetrahydro-1H-imidazo[4,5-c]pyridin-5-yl, 3,5,6,7,8,8a-hexahydroimidazo[1,2-a]pyrazin-7-yl, 3-azabicyclo[3.2.0]heptan-3-yl, 3-azabicyclo[3.1.0]hexan-3-yl, 2-azabicyclo[2.1.1]hexan-2-yl, 2-azabicyclo[3.1.0]hexan-2-yl, 2-oxa-7-azaspiro[4.4]nonan-7-yl, 2-oxa-6-azaspiro[3.4]octan-6-yl, —N(H)R$^{1a}$), and —N(R$^{1a}$)(R$^{1b}$) wherein R$^{1a}$ and R$^{1b}$ are each independently selected from the group consisting of methyl, ethyl, propyl, butyl, methoxyethyl, ethoxyethyl, hydroxymethyl, methoxypropyl, ethyoxypropyl and hydroxypropyl, wherein the aliphatic and/or aromatic portions or R$^1$ is substituted with 0 to 4 substituents selected from the group consisting of methyl, ethyl, propyl, isopropyl, butyl, isobutyl, fluoro, chloro, bromo, iodo, cyano, methoxy, ethoxy, isopropoxy, methoxymethyl, methoxyethyl, methoxypropyl, trifluoromethyl, monofluoromethyl, difluoromethyl, 2-methylpyrimidin-4-yl, 4-methyltriazol-3-yl, 1,2,4-triazol-3-yl, morphlinocarbonyl, morpholino, 2-methyl-pyrimidin-6-yl, 6-methyl-pyrimidin-2-yl, 4-methyl-1,2,4-triazol-3-yl, methylaminomethylcarbonyl and hydroxy.

E20 A compound of E1, E2, E3, E4, E5, E6, E7, E8, E9, E10, E11, E12, E13, E14, E15, E16, E17, E18 or E19, wherein R$^3$ is selected from the group consisting of —F, —Cl, —Br, I, C$_{1-6}$ alkyl, C$_{1-6}$ haloalkyl, C$_{1-6}$ heteroalkyl, C$_{1-6}$ alkoxy, —(X$^3$)$_{0-1}$—CN, —(X$^3$)$_{0-1}$—N(H)C(=O)(R$^{3a}$), —(X$^3$)$_{0-1}$—N(R$^{3b}$)C(=O)(R$^{3a}$), —(X$^3$)$_{0-1}$—C(=O)N(H)(R$^{3a}$), —(X$^3$)$_{0-1}$—C(=O)NH$_2$, —(X$^3$)$_{0-1}$—C(=O)N(R$^{3a}$)(R$^{3b}$), thiophene, wherein if R$^3$ is thiophene or R$^{3a}$ and R$^{3b}$ is independently 3-7 membered cycloalkyl, 3-7 membered cycloalkyl-C$_{1-4}$ alkyl, 3-7 membered heterocycloalkyl, 3-7 membered heterocycloalkyl-C$_{1-4}$ alkyl, 5-6 membered heteroaryl, 5-6 membered heteroaryl-C$_{1-4}$ alkyl, C$_6$ aryl, C$_6$ aryl-C$_{1-4}$ alkyl or benzyl then said thiophene, 3-7 membered cycloalkyl, 3-7 membered cycloalkyl-C$_{1-4}$ alkyl, 3-7 membered heterocycloalkyl, 3-7 membered heterocycloalkyl-C$_{1-4}$ alkyl, 5-6 membered heteroaryl, 5-6 membered heteroaryl-C$_{1-4}$ alkyl, C$_6$ aryl, C$_6$ aryl-C$_{1-4}$ alkyl or benzyl is substituted from 0 to 4 R$^{A3}$ substituents, or alternatively, any two R$^3$ substituents located on adjacent atoms are optionally combined to form a thiazole ring further comprising 0 to 4 R$^{3a}$ substituents, and m is an integer from 1 to 4.

E21 A compound of E20, wherein R$^3$ is selected from the group consisting of trifluoromethyl, difluoromethyl, monofluoromethyl, methyl, ethyl, propyl, butyl, isopropyl, sec-butyl, tert-butyl, methoxy, ethoxy, cyclopropyl, cyclobutyl, —CN, thienyl and —C(=O)NH$_2$.

E22 A compound of E1, E2, E3, E4, E5, E6, E7, E8, E9, E10, E11, E12, E13, E14, E15, E16, wherein a compound of formula I has the subformula selected from the group consisting of:

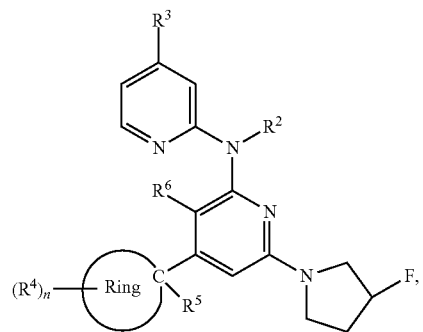

(IIIa)

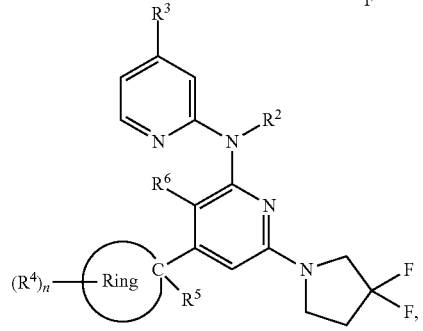

(IIIb)

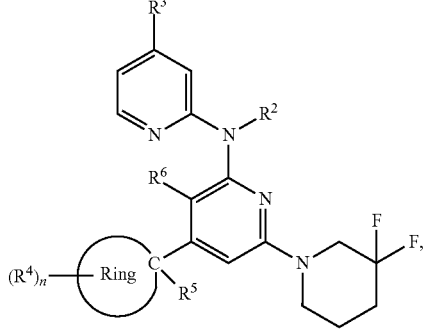

(IIIc)

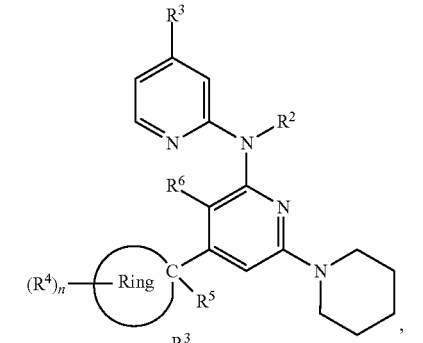

(IIId)

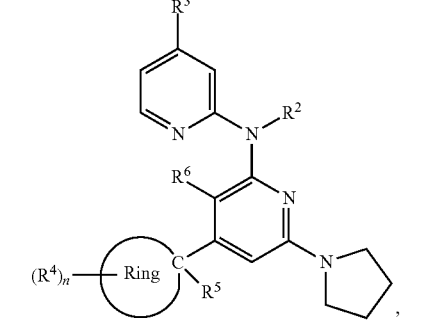

(IIIe)

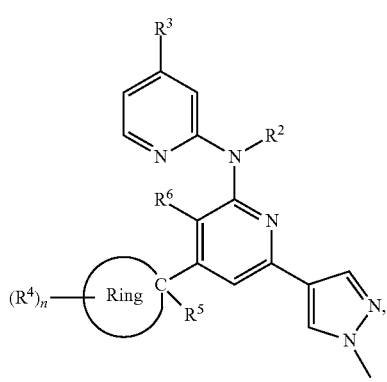
(IIIf)
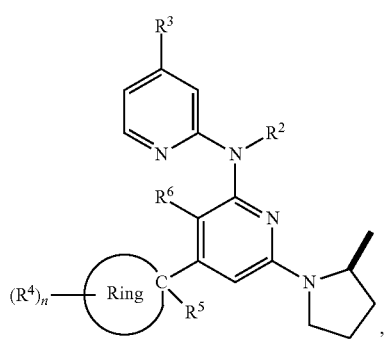
(IIIg)
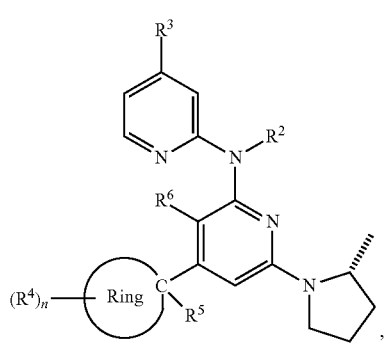
(IIIh)
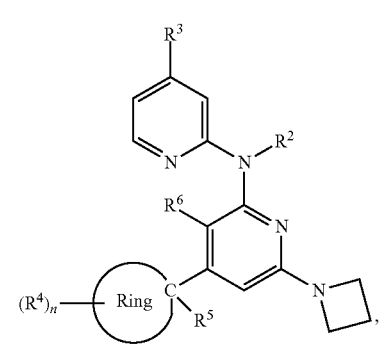
(IIIi)
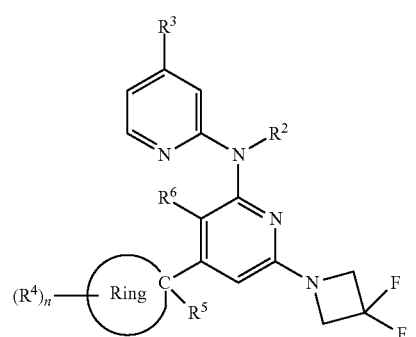
(IIIj)
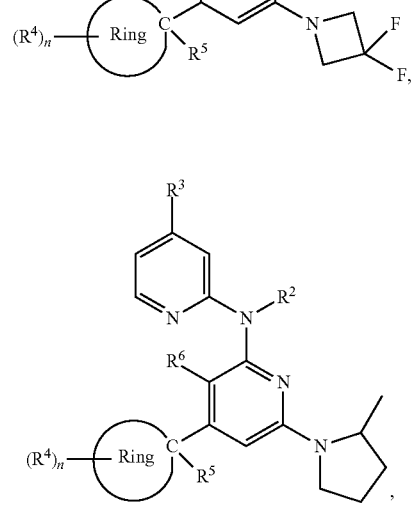
(IIIk)
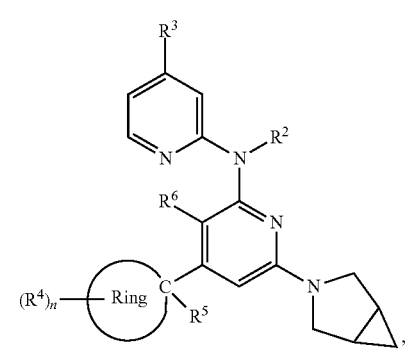
(IIIl)
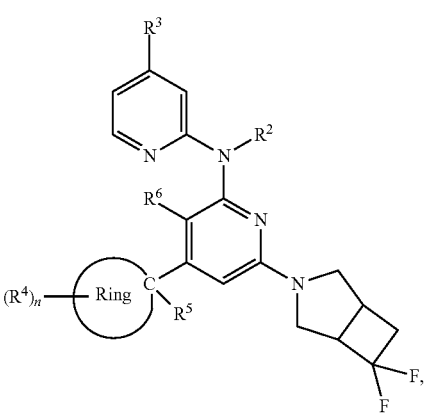
(IIIm)

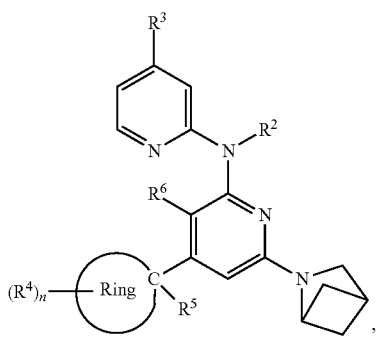
(IIIn)

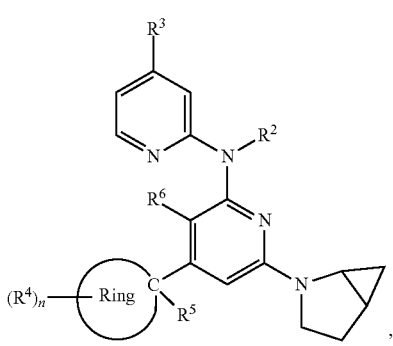
(IIIo)

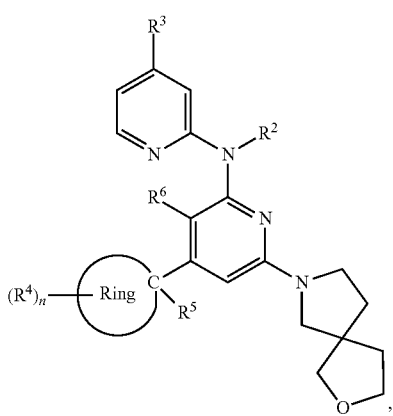
(IIIp)

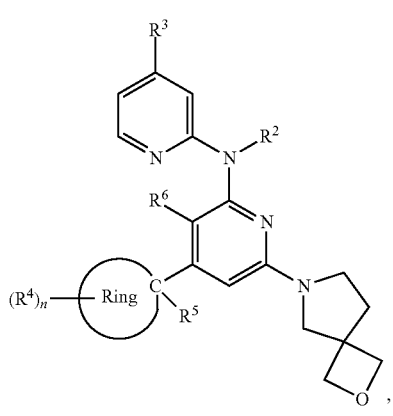
(IIIq)

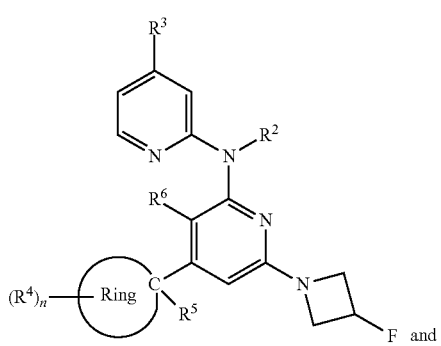
(IIIr)

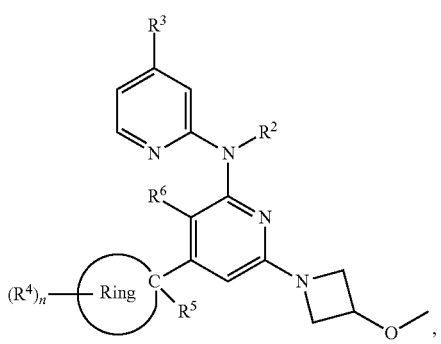
(IIIs)

wherein $R^3$ is selected from the group consisting of methyl, monofluoromethyl, difluoromethyl, trifluoromethyl, —CN, isopropyl, cyclopropyl, cyclobutyl and methoxy.

In another aspect, the invention provides for a compound of formula I, wherein $R^1$ is selected from the group consisting of hydrogen, chloro, $C_{1-6}$ alkyl, $C_{1-6}$ alkoxy, 3-10 membered cycloalkyl, 3-10 membered heterocycloalkyl, 5-10 membered heteroaryl, and —N($R^{1a}$)($R^{1b}$) wherein $R^{1a}$ and $R^{1b}$ are each independently selected from the group consisting of $C_{1-6}$ alkyl, and wherein the aliphatic and aromatic portions of $R^1$ are independently further substituted with 0 to 5 $R^{41}$ substituents selected from the group consisting of —F, —OH, =O, $C_{1-4}$ alkyl, $C_{1-4}$ haloalkyl and $C_{1-4}$ alkoxy;

$R^2$ is hydrogen;

m is 0 or 1;

$R^3$ is selected from the group consisting of —$(X^3)_{0-1}$—CN, —$(X^3)_{0-1}$—NH$_2$, $C_{1-6}$ alkyl, $C_{1-6}$ haloalkyl, and —$(X^3)_{0-1}$-3-7 membered cycloalkyl, and $(X^3)$ is CH$_2$;

n is 0 or 1;

$R^4$ is selected from the group consisting of $C_{1-6}$ alkyl, $C_{1-6}$ haloalkyl, —$(X^4)_{0-1}$-(3-10 membered heterocycloalkyl), —$(X^4)_{0-1}$—C(=$Y^4$)O$R^{4a}$, —$(X^4)_{0-1}$—S(=$Y^4$)$_{1-2}R^{4a}$, and —$(X^4)_{0-1}$—C(=$Y^4$)$R^{4a}$, wherein $R^{4a}$ is selected from the group consisting of $C_{1-6}$ alkyl, $C_{1-6}$ haloalkyl, 3-7 membered cycloalkyl, 5-10 membered heteroaryl, and 3-7 membered heterocycloalkyl, and $X^4$ is CH$_2$, and $Y^4$ is O; wherein the aromatic and aliphatic portions of $R^4$ is independently further substituted with 0 to 4 $R^{44}$ substituents selected from the group consisting of —OH, and $C_{1-6}$ alkyl;

$R^5$ is absent or is selected from the group consisting of hydrogen and —CN;

$R^6$ is hydrogen; and the ring represented by the structure

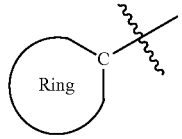 [SMILES: *C(C)C]

is selected from the group consisting of azetidinyl, cyclobutyl, dihydro-2H-pyranyl, piperidinyl, pyrrolidinyl, tetrahydro-pyranyl.

In another aspect, the invention provides for a compound of formula I, wherein $R^1$ is selected from the group consisting of (R)-2-methyl-pyrrolidin-1-yl, (R)-2-trifluoromethyl-pyrrolidin-1-yl, 1-methyl-1H-pyrazol-4-yl, 2-aza-bicyclo[2.1.1]hex-2-yl, 2-aza-bicyclo[3.1.0]hex-2-yl, 2-methyl-pyrrolidin-1-yl, 2-oxa-6-aza-spiro[3.3]hept-6-yl, 2-oxa-7-aza-spiro[4.4]non-7-yl, 3,3-difluoro-azetidin-1-yl, 3,3-difluoro-pyrrolidin-1-yl, 3-aza-bicyclo[3.1.0]hex-3-yl, 3-ethoxy-azetidin-1-yl, 3-fluoro-azetidin-1-yl, 3-methoxy-azetidin-1-yl, 3-methoxy-pyrrolidin-1-yl, 4-trifluoromethyl-pyridin-2-yl, 5,5-difluoro-2-aza-spiro[3.3]hept-2-yl, 6,6-difluoro-3-aza-bicyclo[3.2.0]hept-3-yl, azetidin-1-yl, butoxy, $C(H_2,OH)$—$CH_2N(CH_3)$—, Cl, cyclopropyl, ethyl, hydrogen, isopropoxy, methyl, methoxy, oxa-2-aza-spiro[3.4]oct-2-yl, oxa-6-aza-spiro[3.3]hept-6-yl and pyrrolidin-2-one;

$R^2$ is hydrogen;

m is 0 or 1;

$R^3$ is selected from the group consisting of $CF_3$, $CH_2NH_2$, $CHF_2$, CN, cyclopropyl, hydrogen, methyl and $OCHF_2$;

n is 0 or 1;

$R^4$ is selected from the group consisting of (S)-piperidin-2-yl-(C=O)—, 1-methyl-1H-imidazol-4-yl-(C=O)—, $C(CH_3)_3$—O—(C=O)—, $C(H_2,OH)$—$CH_2$—, $CH_2FCH_2$—, cyclohexyl-(C=O)—, $CHF_2CH_2$—, $F_3C$—(C=O)—, $F_3C$—$CH_2$—, $H_3C$—(C=O)—, methyl, $H_3CO_2S$—, oxetanyl, and tetrahydro-pyran-4-ylmethyl;

$R^5$ is absent or is selected from the group consisting of hydrogen and —CN;

$R^6$ is hydrogen; and the ring represented by the structure

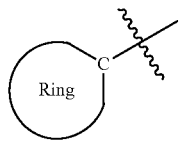

is selected from the group consisting of azetidinyl, cyclobutyl, dihydro-2H-pyranyl, piperidinyl, pyrrolidinyl, tetrahydro-pyranyl.

In another aspect, the invention provides for a compound of formula I; $R^1$ is chloro, $R^2$ is hydrogen, m is 1, $R^3$ is CN, n is 0, $R^5$ is CN, $R^6$ is hydrogen and the ring represented by the structure

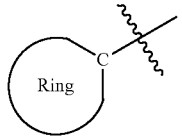 [SMILES: *C(C)C]

is tetrahydro-pyranyl.

In another aspect, the invention provides for a compound of formula I, wherein $R^1$ is selected from the group consisting of hydrogen, chloro, $C_{1-6}$ alkyl, $C_{1-6}$ alkoxy, 3-10 membered cycloalkyl, 3-10 membered heterocycloalkyl, 5-10 membered heteroaryl, and —$N(R^{1a})(R^{1b})$ wherein $R^{1a}$ and $R^{1b}$ are each independently selected from the group consisting of $C_{1-6}$ alkyl, and wherein the aliphatic and aromatic portions of $R^1$ are independently further substituted with 0 to 5 $R^{41}$ substituents selected from the group consisting of —F, —OH, =O, $C_{1-4}$ alkyl, $C_{1-4}$ haloalkyl and $C_{1-4}$ alkoxy.

In another aspect, the invention provides for a compound of formula I, wherein $R^1$ is selected from the group consisting of (R)-2-methyl-pyrrolidin-1-yl, (R)-2-trifluoromethyl-pyrrolidin-1-yl, 1-methyl-1H-pyrazol-4-yl, 2-aza-bicyclo[2.1.1]hex-2-yl, 2-aza-bicyclo[3.1.0]hex-2-yl, 2-methyl-pyrrolidin-1-yl, 2-oxa-6-aza-spiro[3.3]hept-6-yl, 2-oxa-7-aza-spiro[4.4]non-7-yl, 3,3-difluoro-azetidin-1-yl, 3,3-difluoro-pyrrolidin-1-yl, 3-aza-bicyclo[3.1.0]hex-3-yl, 3-ethoxy-azetidin-1-yl, 3-fluoro-azetidin-1-yl, -methoxy-azetidin-1-yl, 3-methoxy-pyrrolidin-1-yl, 4-trifluoromethyl-pyridin-2-yl, 5,5-difluoro-2-aza-spiro[3.3]hept-2-yl, 6,6-difluoro-3-aza-bicyclo[3.2.0]hept-3-yl, azetidin-1-yl, butoxy, $(H_2,OH)$—$CH_2N(CH_3)$—, Cl, cyclopropyl, ethyl, hydrogen, isopropoxy, methyl, methoxy, oxa-2-aza-spiro[3.4]oct-2-yl, oxa-6-aza-spiro[3.3]hept-6-yl and pyrrolidin-2-one.

In another aspect, the invention provides for a compound of formula I, wherein $R^2$ is hydrogen.

In another aspect, the invention provides for a compound of formula I, wherein m is 0.

In another aspect, the invention provides for a compound of formula I, wherein m is 1.

In another aspect, the invention provides for a compound of formula I, wherein $R^3$ is selected from the group consisting of —$(X^3)_{0-1}$—CN, —$(X^3)_{0-1}$—$NH_2$, $C_{1-6}$ alkyl, $C_{1-6}$ haloalkyl, and —$(X^3)_{0-1}$-3-7 membered cycloalkyl, and $(X^3)$ is $CH_2$.

In another aspect, the invention provides for a compound of formula I, wherein $R^3$ is selected from the group consisting of $CF_3$, $CH_2NH_2$, $CHF_2$, CN, cyclopropyl, hydrogen, methyl and $OCHF_2$.

In another aspect, the invention provides for a compound of formula I, wherein n is 0.

In another aspect, the invention provides for a compound of formula I, wherein n is 1.

In another aspect, the invention provides for a compound of formula I, wherein $R^4$ is selected from the group consisting of $C_{1-6}$ alkyl, $C_{1-6}$ haloalkyl, —$(X^4)_{0-1}$-(3-10 membered heterocycloalkyl), —$(X^4)_{0-1}$—$C(=Y^4)OR^{4a}$, —$(X^4)_{0-1}$—$S(=Y^4)_{1-2}R^{4a}$, and —$(X^4)_{0-1}$—$C(=Y^4)R^{4a}$, wherein $R^{4a}$ is selected from the group consisting of $C_{1-6}$ alkyl, $C_{1-6}$ haloalkyl, 3-7 membered cycloalkyl, 5-10 membered heteroaryl, and 3-7 membered heterocycloalkyl, and $X^4$ is $CH_2$, and $Y^4$ is O; wherein the aromatic and aliphatic portions of $R^4$ is independently further substituted with 0 to 4 $R^{44}$ substituents selected from the group consisting of —OH, and $C_{1-6}$ alkyl.

In another aspect, the invention provides for a compound of formula I, wherein $R^4$ is selected from the group consisting of (S)-piperidin-2-yl-(C=O)—, 1-methyl-1H-imidazol-4-yl-(C=O)—, $C(CH_3)_3$—O—(C=O)—, $C(H_2,OH)$—$CH_2$—, CH₂FCH₂—, cyclohexyl-(C=O)—, CHF₂CH₂—, F₃C—(C=O)—, F₃C—CH₂—, H₃C—(C=O)—, methyl, H₃CO₂S—, oxetanyl, and tetrahydro-pyran-4-ylmethyl.

In another aspect, the invention provides for a compound of formula I, wherein $R^5$ is absent.

In another aspect, the invention provides for a compound of formula I, wherein $R^5$ is hydrogen.

In another aspect, the invention provides for a compound of formula I, wherein $R^5$ is —CN.

In another aspect, the invention provides for a compound of formula I, wherein $R^5$ is absent or is selected from the group consisting of hydrogen and —CN In another aspect, the invention provides for a compound of formula I, wherein $R^6$ is hydrogen.

In another aspect, the invention provides for a compound of formula I, wherein the ring represented by the structure

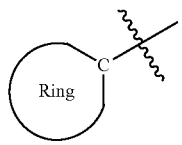

is selected from the group consisting of azetidinyl, cyclobutyl, dihydro-2H-pyranyl, piperidinyl, pyrrolidinyl, tetrahydro-pyranyl.

In another aspect, the invention provides for a compound of formula I, wherein the ring represented by the structure

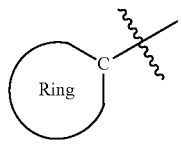

is selected from the group consisting of azetidinyl.

In another aspect, the invention provides for a compound of formula I, wherein the ring represented by the structure

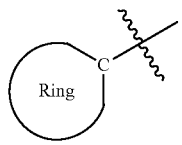

is selected from the group consisting of cyclobutyl.

In another aspect, the invention provides for a compound of formula I, wherein the ring represented by the structure

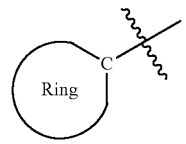 [SMILES: *C(C)C]

is selected from the group consisting of dihydro-2H-pyranyl.

In another aspect, the invention provides for a compound of formula I, wherein the ring represented by the structure

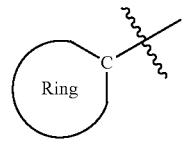 [SMILES: *C(C)C]

is selected from the group consisting of piperidinyl.

In another aspect, the invention provides for a compound of formula I, wherein the ring represented by the structure

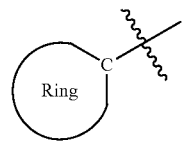 [SMILES: *C(C)C]

is selected from the group consisting of pyrrolidinyl.

In another aspect, the invention provides for a compound of formula I, wherein the ring represented by the structure

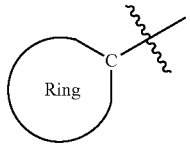 [SMILES: *C(C)C]

is selected from the group consisting of tetrahydro-pyranyl.

In another aspect, the invention provides for a compound of formula I selected from the group of compounds in Table 1.

TABLE 1

| NO | Structure | Name |
|---|---|---|
| 1 | 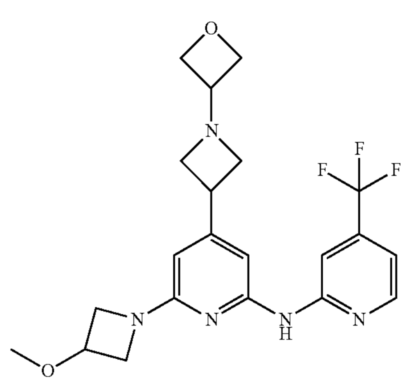 [SMILES: COC1CN(c2cc(C3CN(C4COC4)C3)cc(Nc3cc(C(F)(F)F)ccn3)n2)C1] | [6-(3-Methoxy-azetidin-1-yl)-4-(1-oxetan-3-yl-azetidin-3-yl)-pyridin-2-yl]-(4-trifluoro-methyl-pyridin-2-yl)-amine |

TABLE 1-continued

| NO | Structure | Name |
|---|---|---|
| 2 | 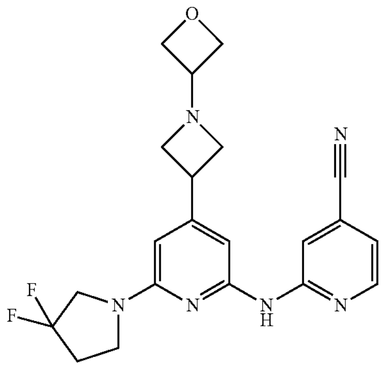 [SMILES: N#Cc1ccnc(Nc2cc(C3CN(C4COC4)C3)cc(N3CCC(F)(F)C3)n2)c1] | 2-[6-(3,3-Difluoro-pyrrolidin-1-yl)-4-(1-oxetan-3-yl-azetidin-3-yl)-pyridin-2-ylamino]-isonicotinonitrile |
| 3 | 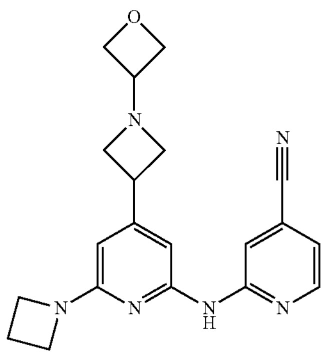 [SMILES: N#Cc1ccnc(Nc2cc(C3CN(C4COC4)C3)cc(N3CCC3)n2)c1] | 2-[6-Azetidin-1-yl-4-(1-oxetan-3-yl-azetidin-3-yl)-pyridin-2-ylamino]-isonicotinonitrile |
| 4 | 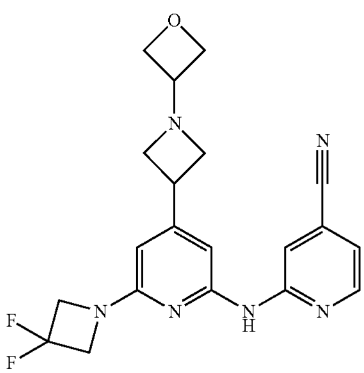 [SMILES: N#Cc1ccnc(Nc2cc(C3CN(C4COC4)C3)cc(N3CC(F)(F)C3)n2)c1] | 2-[6-(3,3-Difluoro-azetidin-1-yl)-4-(1-oxetan-3-yl-azetidin-3-yl)-pyridin-2-ylamino]-isonicotinonitrile |
| 5 | 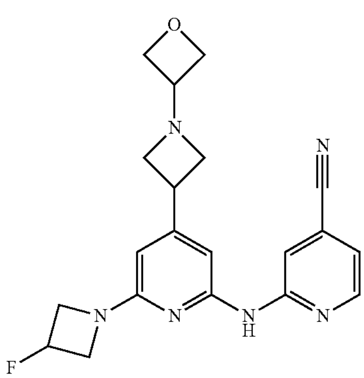 [SMILES: N#Cc1ccnc(Nc2cc(C3CN(C4COC4)C3)cc(N3CC(F)C3)n2)c1] | 2-[6-(3-Fluoro-azetidin-1-yl)-4-(1-oxetan-3-yl-azetidin-3-yl)-pyridin-2-ylamino]-isonicotinonitrile |

TABLE 1-continued

| NO | Structure | Name |
|---|---|---|
| 6 | 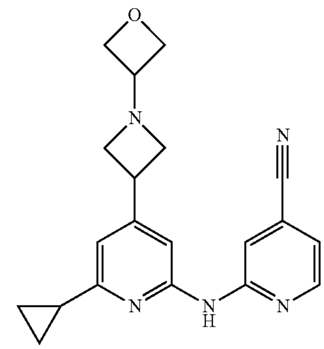 [SMILES: N#Cc1ccnc(Nc2cc(C3CN(C4COC4)C3)cc(C3CC3)n2)c1] | 2-[6-Cyclopropyl-4-(1-oxetan-3-yl-azetidin-3-yl)-pyridin-2-ylamino]-isonicotinonitrile |
| 7 | 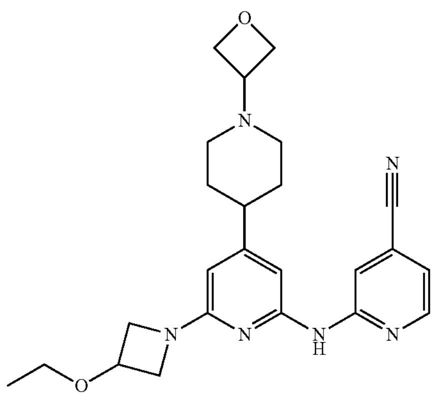 [SMILES: CCOC1CN(c2cc(C3CCN(C4COC4)CC3)cc(Nc3cc(C#N)ccn3)n2)C1] | 2-[6-(3-Ethoxy-azetidin-1-yl)-1'-oxetan-3-yl-1',2',3',4',5',6'-hexahydro-[4,4']bipyridinyl-2-ylamino]-isonicotinonitrile |
| 8 | 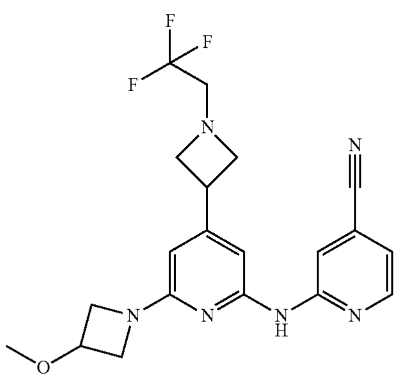 [SMILES: COC1CN(c2cc(C3CN(CC(F)(F)F)C3)cc(Nc3cc(C#N)ccn3)n2)C1] | 2-{6-(3-Methoxy-azetidin-1-yl)-4-[1-(2,2,2-trifluoro-ethyl)-azetidin-3-yl]-pyridin-2-ylamino}-isonicotinonitrile |
| 9 | 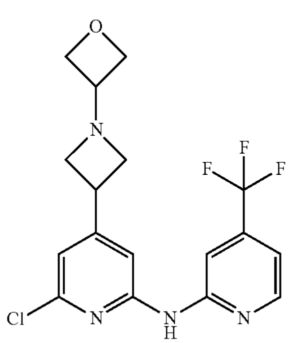 [SMILES: FC(F)(F)c1ccnc(Nc2cc(C3CN(C4COC4)C3)cc(Cl)n2)c1] | [6-Chloro-4-(1-oxetan-3-yl-azetidin-3-yl)-pyridin-2-yl]-(4-trifluoromethyl-pyridin-2-yl)-amine |

TABLE 1-continued

| NO | Structure | Name |
|---|---|---|
| 10 | 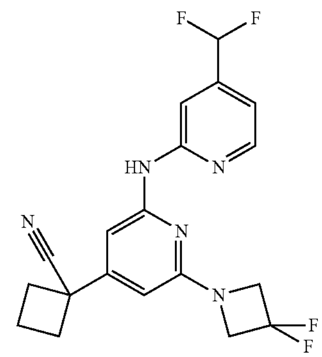 [SMILES: N#CC1(c2cc(Nc3cc(C(F)F)ccn3)nc(N3CC(F)(F)C3)c2)CCC1] | 1-[2-(3,3-Difluoro-azetidin-1-yl)-6-(4-difluoromethyl-pyridin-2-ylamino)-pyridin-4-yl]-cyclobutanecarbonitrile |
| 11 | 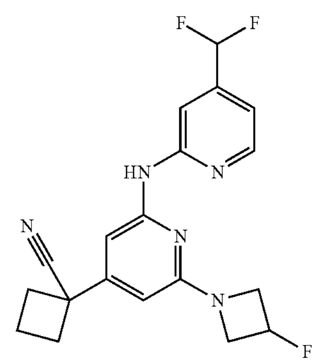 [SMILES: N#CC1(c2cc(Nc3cc(C(F)F)ccn3)nc(N3CC(F)C3)c2)CCC1] | 1-[2-(4-Difluoromethyl-pyridin-2-ylamino)-6-(3-fluoro-azetidin-1-yl)-pyridin-4-yl]-cyclobutanecarbonitrile |
| 12 | 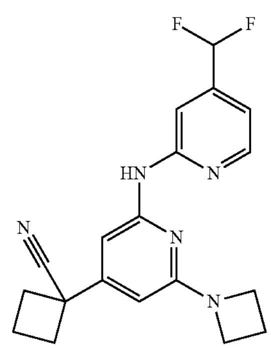 [SMILES: N#CC1(c2cc(Nc3cc(C(F)F)ccn3)nc(N3CCC3)c2)CCC1] | 1-[2-Azetidin-1-yl-6-(4-difluoromethyl-pyridin-2-ylamino)-pyridin-4-yl]-cyclobutanecarbonitrile |
| 13 | 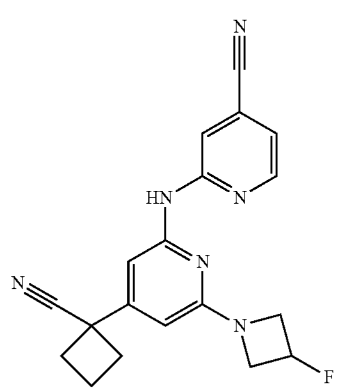 [SMILES: N#Cc1ccnc(Nc2cc(C3(C#N)CCC3)cc(N3CC(F)C3)n2)c1] | 2-[4-(1-Cyano-cyclobutyl)-6-(3-fluoro-azetidin-1-yl)-pyridin-2-ylamino]-isonicotinonitrile |

TABLE 1-continued

| NO | Structure | Name |
|----|-----------|------|
| 14 | 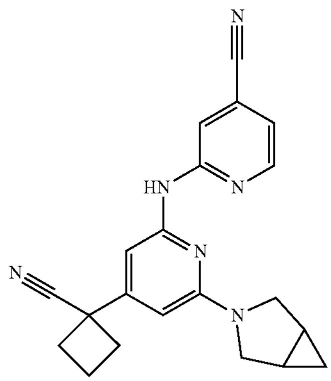 [SMILES: N#Cc1ccnc(Nc2cc(C3(C#N)CCC3)cc(N3CC4CC4C3)n2)c1] | 2-[6-(3-Aza-bicyclo[3.1.0]hex-3-yl)-4-(1-cyano-cyclobutyl)-pyridin-2-ylamino]-isonicotinonitrile |
| 15 | 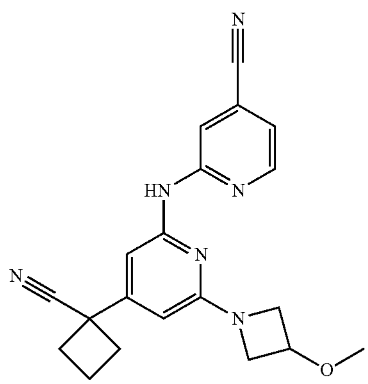 [SMILES: COC1CN(c2cc(C3(C#N)CCC3)cc(Nc3cc(C#N)ccn3)n2)C1] | 2-[4-(1-Cyano-cyclobutyl)-6-(3-methoxy-azetidin-1-yl)-pyridin-2-ylamino]-isonicotinonitrile |
| 16 | 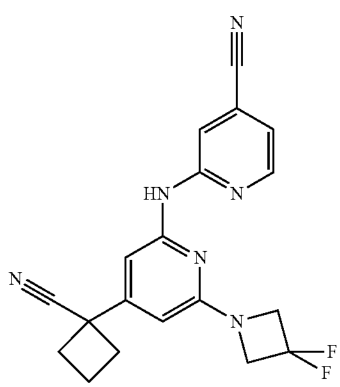 [SMILES: N#Cc1ccnc(Nc2cc(C3(C#N)CCC3)cc(N3CC(F)(F)C3)n2)c1] | 2-[4-(1-Cyano-cyclobutyl)-6-(3,3-difluoro-azetidin-1-yl)-pyridin-2-ylamino]-isonicotinonitrile |
| 17 | 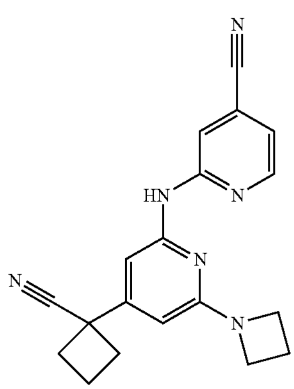 [SMILES: N#Cc1ccnc(Nc2cc(C3(C#N)CCC3)cc(N3CCC3)n2)c1] | 2-[6-Azetidin-1-yl-4-(1-cyano-cyclobutyl)-pyridin-2-ylamino]-isonicotinonitrile |

TABLE 1-continued

| NO | Structure | Name |
|---|---|---|
| 18 | 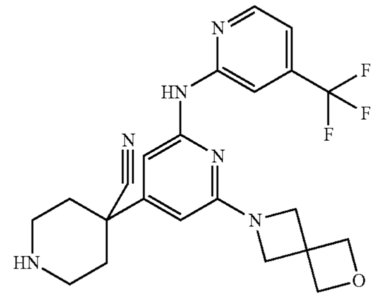 [SMILES: N#CC1(c2cc(Nc3cc(C(F)(F)F)ccn3)nc(N3CC4(COC4)C3)c2)CCNCC1] | 6'-(2-Oxa-6-aza-spiro[3.3]hept-6-yl)-2'-(4-trifluoromethyl-pyridin-2-ylamino)-2,3,5,6-tetrahydro-1H-[4,4']bipyridinyl-4-carbonitrile |
| 19 | 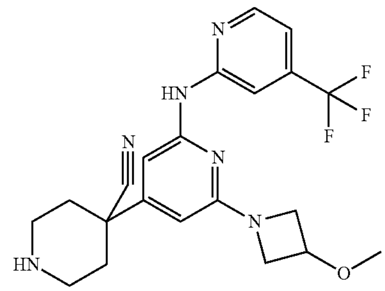 [SMILES: COC1CN(c2cc(C3(C#N)CCNCC3)cc(Nc3cc(C(F)(F)F)ccn3)n2)C1] | 6'-(3-Methoxy-azetidin-1-yl)-2'-(4-trifluoromethyl-pyridin-2-ylamino)-2,3,5,6-tetrahydro-1H-[4,4']bipyridinyl-4-carbonitrile |
| 20 | 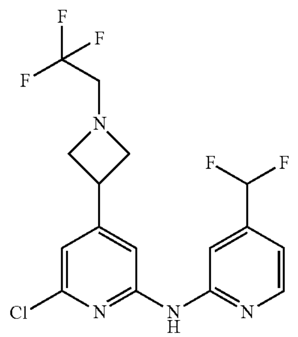 [SMILES: FC(F)c1ccnc(Nc2cc(C3CN(CC(F)(F)F)C3)cc(Cl)n2)c1] | {6-Chloro-4-[1-(2,2,2-trifluoro-ethyl)-azetidin-3-yl]-pyridin-2-yl}-(4-difluoromethyl-pyridin-2-yl)-amine |
| 21 | 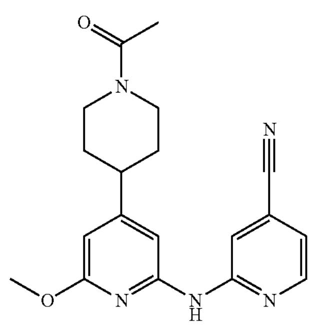 [SMILES: COc1cc(C2CCN(C(C)=O)CC2)cc(Nc2cc(C#N)ccn2)n1] | 2-(1'-Acetyl-6-methoxy-1',2',3',4',5',6'-hexahydro-[4,4']bipyridinyl-2-ylamino)-isonicotinonitrile |
| 22 | 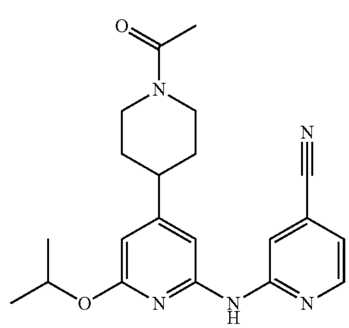 [SMILES: CC(=O)N1CCC(c2cc(Nc3cc(C#N)ccn3)nc(OC(C)C)c2)CC1] | 2-(1'-Acetyl-6-isopropoxy-1',2',3',4',5',6'-hexahydro-[4,4']bipyridinyl-2-ylamino)-isonicotinonitrile |

TABLE 1-continued

| NO | Structure | Name |
|---|---|---|
| 23 | 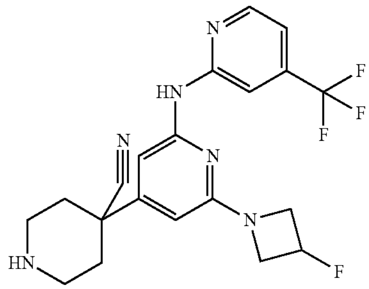 [SMILES: N#CC1(c2cc(Nc3cc(C(F)(F)F)ccn3)nc(N3CC(F)C3)c2)CCNCC1] | 6'-(3-Fluoro-azetidin-1-yl)-2'-(4-trifluoromethyl-pyridin-2-ylamino)-2,3,5,6-tetrahydro-1H-[4,4']bipyridinyl-4-carbonitrile |
| 24 | 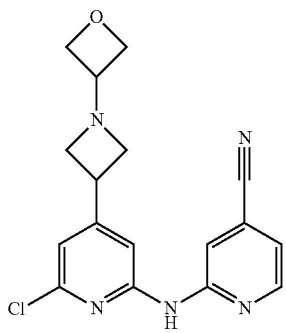 [SMILES: N#Cc1ccnc(Nc2cc(C3CN(C4COC4)C3)cc(Cl)n2)c1] | 2-[6-Chloro-4-(1-oxetan-3-yl-azetidin-3-yl)-pyridin-2-ylamino]-isonicotinonitrile |
| 25 | 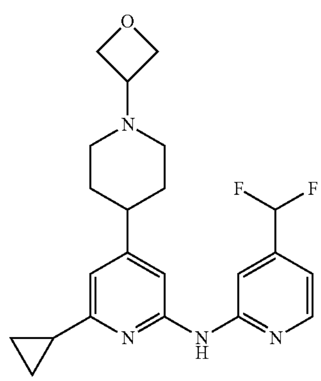 [SMILES: FC(F)c1ccnc(Nc2cc(C3CCN(C4COC4)CC3)cc(C3CC3)n2)c1] | (6-Cyclopropyl-1'-oxetan-3-yl-1',2',3',4',5',6'-hexahydro-[4,4']bipyridinyl-2-yl)-(4-difluoromethyl-pyridin-2-yl)-amine |
| 26 | 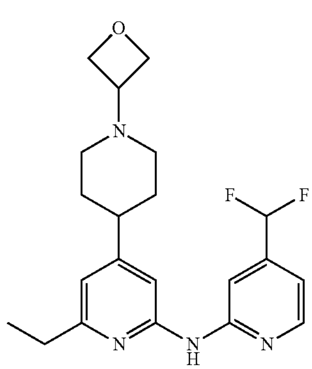 [SMILES: CCc1cc(C2CCN(C3COC3)CC2)cc(Nc2cc(C(F)F)ccn2)n1] | (4-Difluoromethyl-pyridin-2-yl)-(6-ethyl-1'-oxetan-3-yl-1',2',3',4',5',6'-hexahydro-[4,4']bipyridinyl-2-yl)-amine |

TABLE 1-continued

| NO | Structure | Name |
|---|---|---|
| 27 | 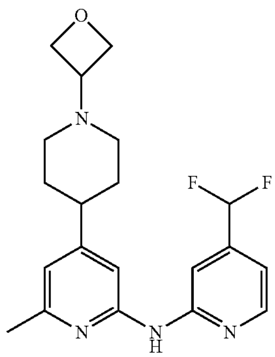 [SMILES: Cc1cc(C2CCN(C3COC3)CC2)cc(Nc2cc(C(F)F)ccn2)n1] | (4-Difluoromethyl-pyridin-2-yl)-(6-methyl-1'-oxetan-3-yl-1',2',3',4',5',6'-hexahydro-[4,4']bipyridinyl-2-yl)-amine |
| 28 | 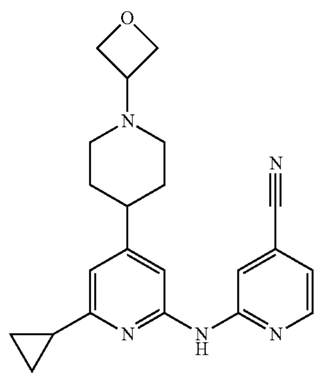 [SMILES: N#Cc1ccnc(Nc2cc(C3CCN(C4COC4)CC3)cc(C3CC3)n2)c1] | 2-(6-Cyclopropyl-1'-oxetan-3-yl-1',2',3',4',5',6'-hexahydro-[4,4']bipyridinyl-2-ylamino)-isonicotinonitrile |
| 29 | 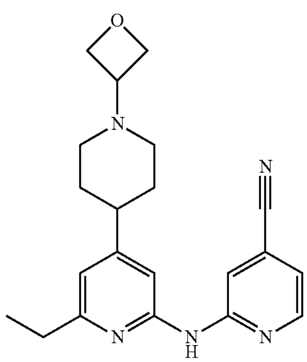 [SMILES: CCc1cc(C2CCN(C3COC3)CC2)cc(Nc2cc(C#N)ccn2)n1] | 2-(6-Ethyl-1'-oxetan-3-yl-1',2',3',4',5',6'-hexahydro-[4,4']bipyridinyl-2-ylamino)-isonicotinonitrile |
| 30 | 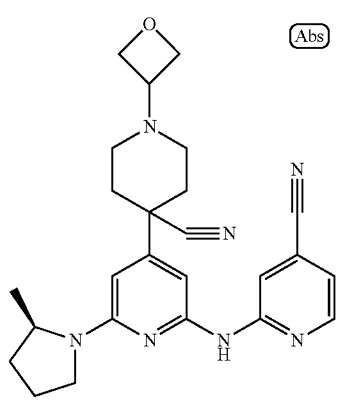 [SMILES: C[C@@H]1CCCN1c1cc(C2(C#N)CCN(C3COC3)CC2)cc(Nc2cc(C#N)ccn2)n1] | 2'-(4-Cyano-pyridin-2-ylamino)-6'-((R)-2-methyl-pyrrolidin-1-yl)-1-oxetan-3-yl-2,3,5,6-tetrahydro-1H-[4,4']bipyridinyl-4-carbonitrile |

TABLE 1-continued

| NO | Structure | Name |
|---|---|---|
| 31 | 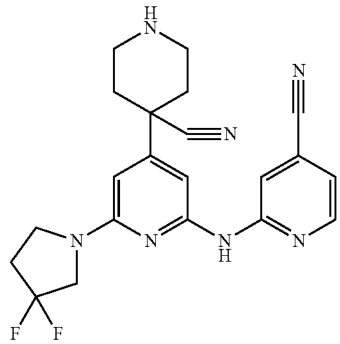 [SMILES: N#Cc1ccnc(Nc2cc(C3(C#N)CCNCC3)cc(N3CCC(F)(F)C3)n2)c1] | 2'-(4-Cyano-pyridin-2-ylamino)-6'-(3,3-difluoro-pyrrolidin-1-yl)-2,3,5,6-tetrahydro-1H-[4,4']bipyridinyl-4-carbonitrile |
| 32 | 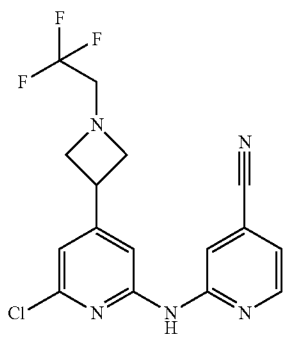 [SMILES: N#Cc1ccnc(Nc2cc(C3CN(CC(F)(F)F)C3)cc(Cl)n2)c1] | 2-{6-Chloro-4-[1-(2,2,2-trifluoro-ethyl)-azetidin-3-yl]-pyridin-2-ylamino}-isonicotinonitrile |
| 33 | (Abs) | 2'-(4-Cyano-pyridin-2-ylamino)-1-methyl-6'-((R)-2-methyl-pyrrolidin-1-yl)-2,3,5,6-tetrahydro-1H-[4,4']bipyridinyl-4-carbonitrile |
| 34 | 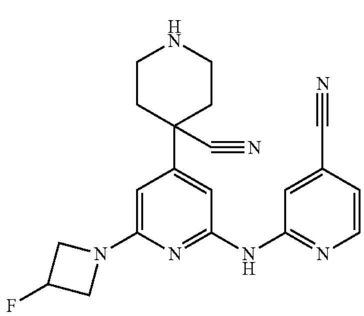 [SMILES: N#Cc1ccnc(Nc2cc(C3(C#N)CCNCC3)cc(N3CC(F)C3)n2)c1] | 2'-(4-Cyano-pyridin-2-ylamino)-6'-(3-fluoro-azetidin-1-yl)-2,3,5,6-tetrahydro-1H-[4,4']bipyridinyl-4-carbonitrile |

TABLE 1-continued

| NO | Structure | Name |
|---|---|---|
| 35 | 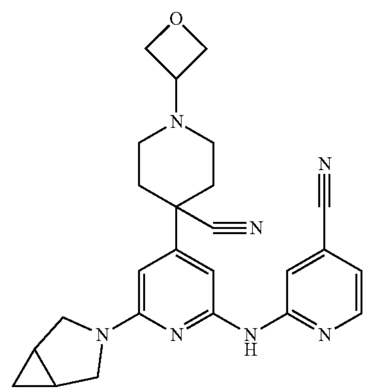 [SMILES: N#Cc1ccnc(Nc2cc(C3(C#N)CCN(C4COC4)CC3)cc(N3CC4CC4C3)n2)c1] | 6'-(3-Aza-bicyclo[3.1.0]hex-3-yl)-2'-(4-cyano-pyridin-2-ylamino)-1-oxetan-3-yl-2,3,5,6-tetrahydro-1H-[4,4']bipyridinyl-4-carbonitrile |
| 36 | 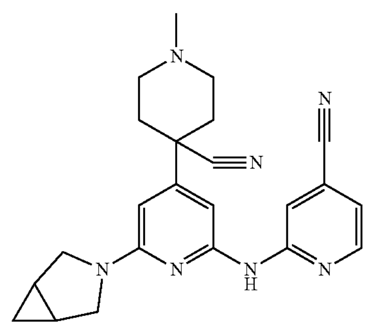 [SMILES: CN1CCC(C#N)(c2cc(Nc3cc(C#N)ccn3)nc(N3CC4CC4C3)c2)CC1] | 6'-(3-Aza-bicyclo[3.1.0]hex-3-yl)-2'-(4-cyano-pyridin-2-ylamino)-1-methyl-2,3,5,6-tetrahydro-1H-[4,4']bipyridinyl-4-carbonitrile |
| 37 | 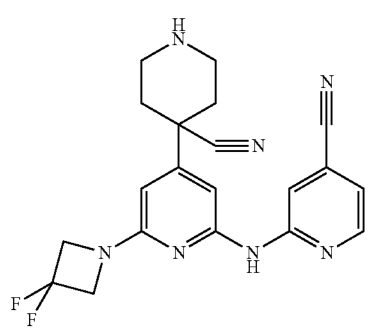 [SMILES: N#Cc1ccnc(Nc2cc(C3(C#N)CCNCC3)cc(N3CC(F)(F)C3)n2)c1] | 2'-(4-Cyano-pyridin-2-ylamino)-6'-(3,3-difluoro-azetidin-1-yl)-2,3,5,6-tetrahydro-1H-[4,4']bipyridinyl-4-carbonitrile |
| 38 | 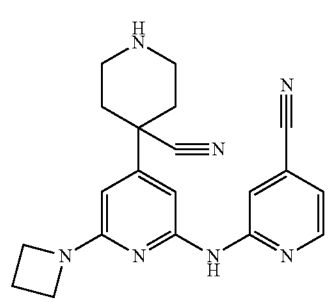 [SMILES: N#Cc1ccnc(Nc2cc(C3(C#N)CCNCC3)cc(N3CCC3)n2)c1] | 6'-Azetidin-1-yl-2'-(4-cyano-pyridin-2-ylamino)-2,3,5,6-tetrahydro-1H-[4,4']bipyridinyl-4-carbonitrile |

TABLE 1-continued

| NO | Structure | Name |
|---|---|---|
| 39 | 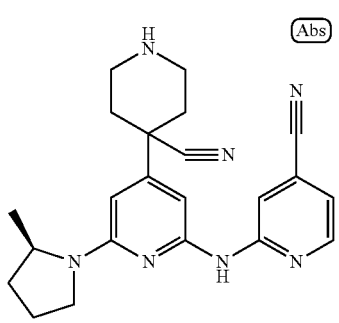 [SMILES: C[C@@H]1CCCN1c1cc(C2(C#N)CCNCC2)cc(Nc2cc(C#N)ccn2)n1] | 2'-(4-Cyano-pyridin-2-ylamino)-6'-((R)-2-methyl-pyrrolidin-1-yl)-2,3,5,6-tetrahydro-1H-[4,4']bipyridinyl-4-carbonitrile |
| 40 | 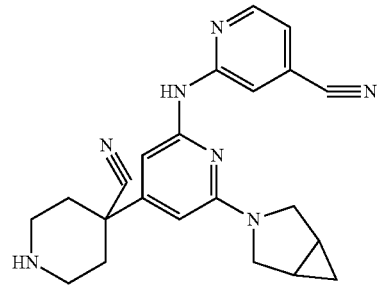 [SMILES: N#Cc1ccnc(Nc2cc(C3(C#N)CCNCC3)cc(N3CC4CC4C3)n2)c1] | 6'-(3-Aza-bicyclo[3.1.0]hex-3-yl)-2'-(4-cyano-pyridin-2-ylamino)-2,3,5,6-tetrahydro-1H-[4,4']bipyridinyl-4-carbonitrile |
| 41 | 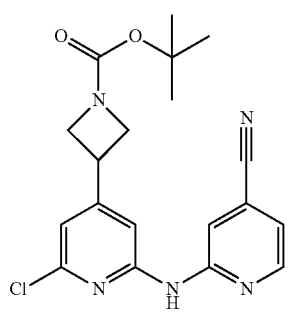 [SMILES: CC(C)(C)OC(=O)N1CC(c2cc(Cl)nc(Nc3cc(C#N)ccn3)c2)C1] | 3-[2-Chloro-6-(4-cyano-pyridin-2-ylamino)-pyridin-4-yl]-azetidine-1-carboxylic acid tert-butyl ester |
| 42 | 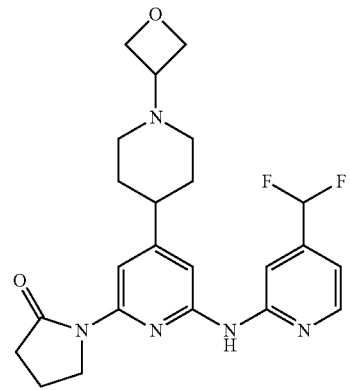 | 1-[6-(4-Difluoromethyl-pyridin-2-ylamino)-1'-oxetan-3-yl-1',2',3',4',5',6'-hexahydro-[4,4']bipyridinyl-2-yl]-pyrrolidin-2-one |

TABLE 1-continued

| NO | Structure | Name |
|----|-----------|------|
| 43 | 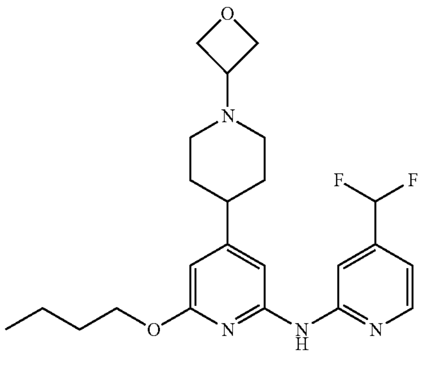 [SMILES: CCCCOc1cc(C2CCN(C3COC3)CC2)cc(Nc2cc(C(F)F)ccn2)n1] | (6-Butoxy-1'-oxetan-3-yl-1',2',3',4',5',6'-hexahydro-[4,4']bipyridinyl-2-yl)-(4-difluoro-methyl-pyridin-2-yl)-amine |
| 44 | 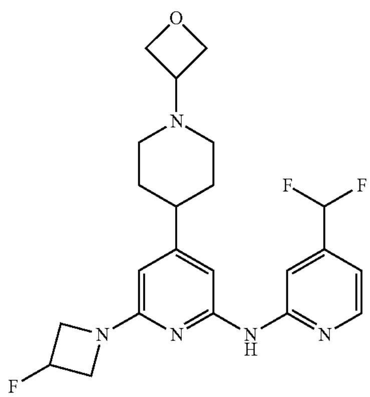 [SMILES: FC1CN(c2cc(C3CCN(C4COC4)CC3)cc(Nc3cc(C(F)F)ccn3)n2)C1] | (4-Difluoromethyl-pyridin-2-yl)-[6-(3-fluoro-azetidin-1-yl)-1'-oxetan-3-yl-1',2',3',4',5',6'-hexahydro-[4,4']bipyridinyl-2-yl]-amine |
| 45 | 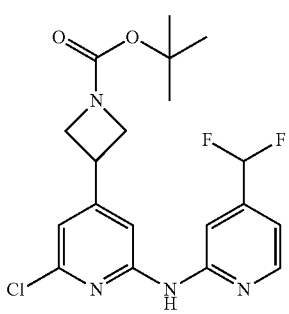 [SMILES: CC(C)(C)OC(=O)N1CC(c2cc(Cl)nc(Nc3cc(C(F)F)ccn3)c2)C1] | 3-[2-Chloro-6-(4-difluoromethyl-pyridin-2-ylamino)-pyridin-4-yl]-azetidine-1-carboxylic acid tert-butyl ester |
| 46 | 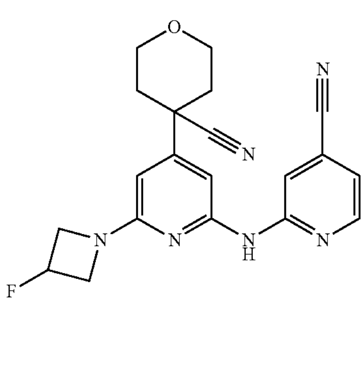 [SMILES: N#Cc1ccnc(Nc2cc(C3(C#N)CCOCC3)cc(N3CC(F)C3)n2)c1] | 2-[4-(4-Cyano-tetrahydro-pyran-4-yl)-6-(3-fluoro-azetidin-1-yl)-pyridin-2-ylamino]-isonicotinonitrile |

TABLE 1-continued

| NO | Structure | Name |
|---|---|---|
| 47 | 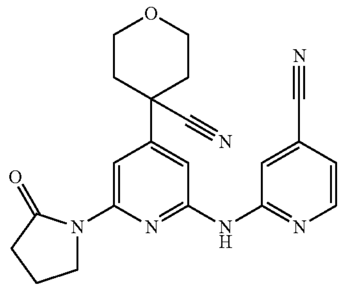 [SMILES: N#Cc1ccnc(Nc2cc(C3(C#N)CCOCC3)cc(N3CCCC3=O)n2)c1] | 2-[4-(4-Cyano-tetrahydro-pyran-4-yl)-6-(2-oxo-pyrrolidin-1-yl)-pyridin-2-ylamino]-isonicotinonitrile |
| 48 | 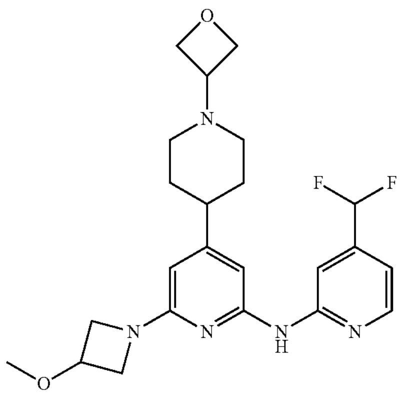 [SMILES: COC1CN(c2cc(C3CCN(C4COC4)CC3)cc(Nc3cc(C(F)F)ccn3)n2)C1] | (4-Difluoromethyl-pyridin-2-yl)-[6-(3-methoxy-azetidin-1-yl)-1'-oxetan-3-yl-1',2',3',4',5',6'-hexahydro-[4,4']bipyridinyl-2-yl]-amine |
| 49 | 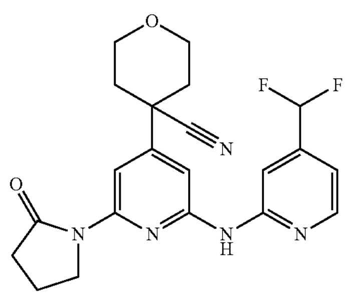 [SMILES: N#CC1(c2cc(Nc3cc(C(F)F)ccn3)nc(N3CCCC3=O)c2)CCOCC1] | 4-[2-(4-Difluoromethyl-pyridin-2-ylamino)-6-(2-oxo-pyrrolidin-1-yl)-pyridin-4-yl]-tetrahydro-pyran-4-carbonitrile |
| 50 | 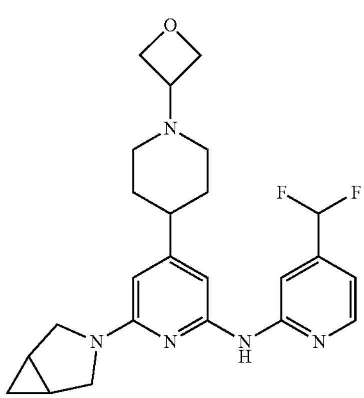 [SMILES: FC(F)c1ccnc(Nc2cc(C3CCN(C4COC4)CC3)cc(N3CC4CC4C3)n2)c1] | [6-(3-Aza-bicyclo[3.1.0]hex-3-yl)-1'-oxetan-3-yl-1',2',3',4',5',6'-hexahydro-[4,4']bipyridinyl-2-yl]-(4-difluoromethyl-pyridin-2-yl)-amine |

TABLE 1-continued

| NO | Structure | Name |
|---|---|---|
| 51 | 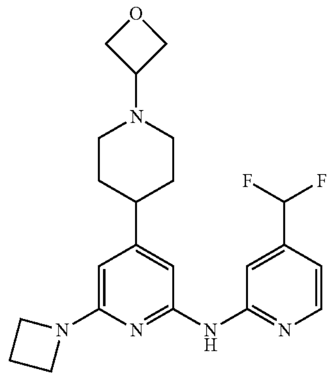 [SMILES: FC(F)c1ccnc(Nc2cc(C3CCN(C4COC4)CC3)cc(N3CCC3)n2)c1] | (6-Azetidin-1-yl-1'-oxetan-3-yl-1',2',3',4',5',6'-hexahydro-[4,4']bipyridinyl-2-yl)-(4-difluoromethyl-pyridin-2-yl)-amine |
| 52 | 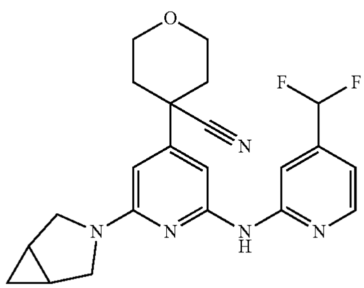 [SMILES: N#CC1(c2cc(Nc3cc(C(F)F)ccn3)nc(N3CC4CC4C3)c2)CCOCC1] | 4-[2-(3-Aza-bicyclo[3.1.0]hex-3-yl)-6-(4-difluoromethyl-pyridin-2-ylamino)-pyridin-4-yl]-tetrahydro-pyran-4-carbonitrile |
| 53 | 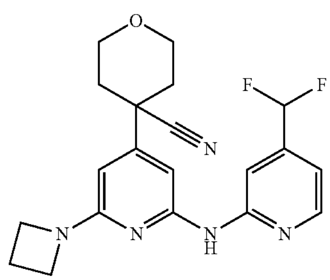 [SMILES: N#CC1(c2cc(Nc3cc(C(F)F)ccn3)nc(N3CCC3)c2)CCOCC1] | 4-[2-Azetidin-1-yl-6-(4-difluoromethyl-pyridin-2-ylamino)-pyridin-4-yl]-tetrahydro-pyran-4-carbonitrile |
| 54 | 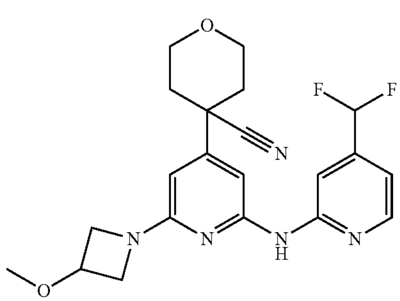 [SMILES: COC1CN(c2cc(C3(C#N)CCOCC3)cc(Nc3cc(C(F)F)ccn3)n2)C1] | 4-[2-(4-Difluoromethyl-pyridin-2-ylamino)-6-(3-methoxy-azetidin-1-yl)-pyridin-4-yl]-tetrahydro-pyran-4-carbonitrile |
| 55 | 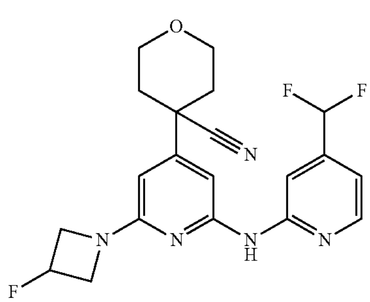 [SMILES: N#CC1(c2cc(Nc3cc(C(F)F)ccn3)nc(N3CC(F)C3)c2)CCOCC1] | 4-[2-(4-Difluoromethyl-pyridin-2-ylamino)-6-(3-fluoro-azetidin-1-yl)-pyridin-4-yl]-tetrahydro-pyran-4-carbonitrile |

TABLE 1-continued

| NO | Structure | Name |
|---|---|---|
| 56 | 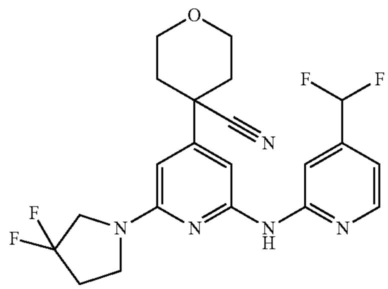 [SMILES: N#CC1(c2cc(Nc3cc(C(F)F)ccn3)nc(N3CCC(F)(F)C3)c2)CCOCC1] | 4-[2-(4-Difluoromethyl-pyridin-2-ylamino)-6-(3,3-difluoro-pyrrolidin-1-yl)-pyridin-4-yl]-tetrahydro-pyran-4-carbonitrile |
| 57 | 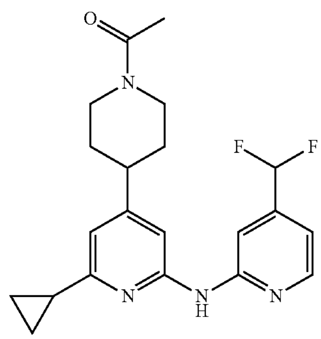 [SMILES: CC(=O)N1CCC(c2cc(Nc3cc(C(F)F)ccn3)nc(C3CC3)c2)CC1] | 1-[6'-Cyclopropyl-2'-(4-difluoromethyl-pyridin-2-ylamino)-3,4,5,6-tetrahydro-2H-[4,4']bipyridinyl-1-yl]-ethanone |
| 58 | 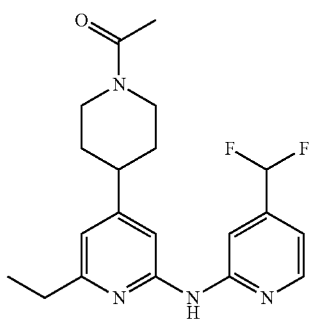 [SMILES: CCc1cc(C2CCN(C(C)=O)CC2)cc(Nc2cc(C(F)F)ccn2)n1] | 1-[2'-(4-Difluoromethyl-pyridin-2-ylamino)-6'-ethyl-3,4,5,6-tetrahydro-2H-[4,4']bipyridinyl-1-yl]-ethanone |
| 59 | 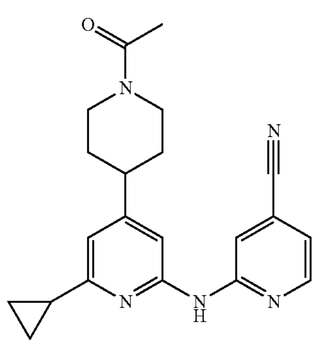 [SMILES: CC(=O)N1CCC(c2cc(Nc3cc(C#N)ccn3)nc(C3CC3)c2)CC1] | 2-(1'-Acetyl-6-cyclopropyl-1',2',3',4',5',6'-hexahydro-[4,4']bipyridinyl-2-ylamino)-isonicotinonitrile |
| 60 | 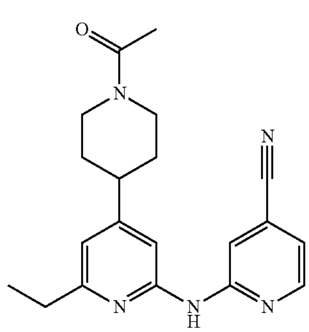 | 2-(1'-Acetyl-6-ethyl-1',2',3',4',5',6'-hexahydro-[4,4']bipyridinyl-2-ylamino)-isonicotinonitrile |

TABLE 1-continued

| NO | Structure | Name |
|---|---|---|
| 61 | 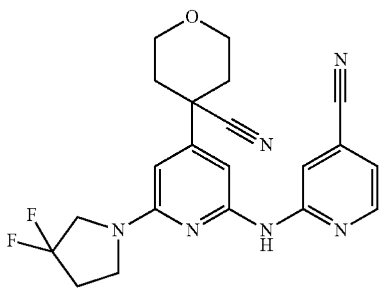 [SMILES: N#Cc1ccnc(Nc2cc(C3(C#N)CCOCC3)cc(N3CCC(F)(F)C3)n2)c1] | 2-[4-(4-Cyano-tetrahydro-pyran-4-yl)-6-(3,3-difluoro-pyrrolidin-1-yl)-pyridin-2-ylamino]-isonicotinonitrile |
| 62 | 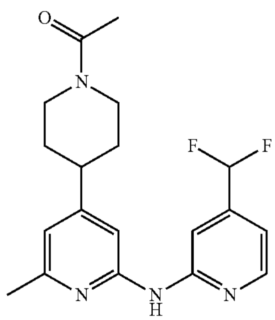 [SMILES: CC(=O)N1CCC(c2cc(C)nc(Nc3cc(C(F)F)ccn3)c2)CC1] | 1-[2'-(4-Difluoromethyl-pyridin-2-ylamino)-6'-methyl-3,4,5,6-tetrahydro-2H-[4,4']bipyridinyl-1-yl]-ethanone |
| 63 | 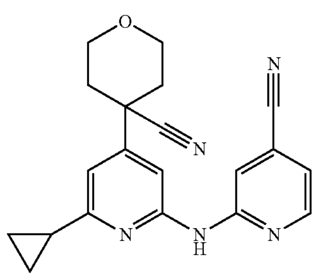 [SMILES: N#Cc1ccnc(Nc2cc(C3(C#N)CCOCC3)cc(C3CC3)n2)c1] | 2-[4-(4-Cyano-tetrahydro-pyran-4-yl)-6-cyclopropyl-pyridin-2-ylamino]-isonicotinonitrile |
| 64 | 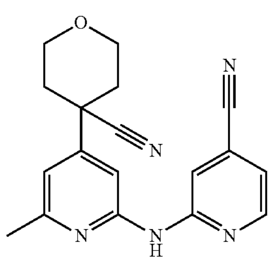 [SMILES: Cc1cc(C2(C#N)CCOCC2)cc(Nc2cc(C#N)ccn2)n1] | 2-[4-(4-Cyano-tetrahydro-pyran-4-yl)-6-methyl-pyridin-2-ylamino]-isonicotinonitrile |
| 65 | 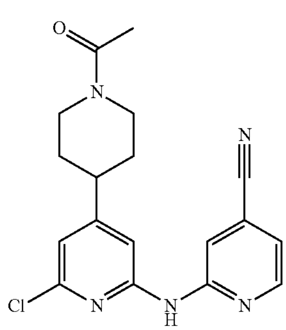 [SMILES: CC(=O)N1CCC(c2cc(Cl)nc(Nc3cc(C#N)ccn3)c2)CC1] | 2-(1'-Acetyl-6-chloro-1',2',3',4',5',6'-hexahydro-[4,4']bipyridinyl-2-ylamino)-isonicotinonitrile |

TABLE 1-continued

| NO | Structure | Name |
| --- | --- | --- |
| 66 | 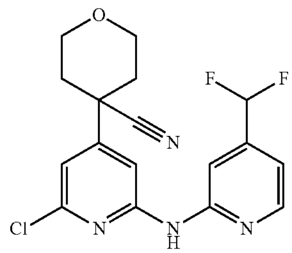 [SMILES: N#CC1(c2cc(Cl)nc(Nc3cc(C(F)F)ccn3)c2)CCOCC1] | 4-[2-Chloro-6-(4-difluoromethyl-pyridin-2-ylamino)-pyridin-4-yl]-tetrahydro-pyran-4-carbonitrile |
| 67 | 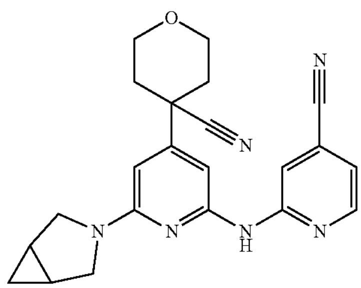 [SMILES: N#Cc1ccnc(Nc2cc(C3(C#N)CCOCC3)cc(N3CC4CC4C3)n2)c1] | 2-[6-(3-Aza-bicyclo[3.1.0]hex-3-yl)-4-(4-cyano-tetrahydro-pyran-4-yl)-pyridin-2-ylamino]-isonicotinonitrile |
| 68 | 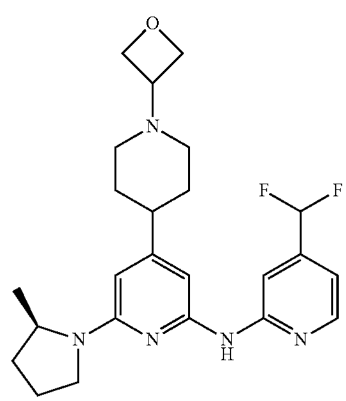 | (4-Difluoromethyl-pyridin-2-yl)-[6-((R)-2-methyl-pyrrolidin-1-yl)-1'-oxetan-3-yl-1',2',3',4',5',6'-hexahydro-[4,4']bipyridinyl-2-yl]-amine |
| 69 | 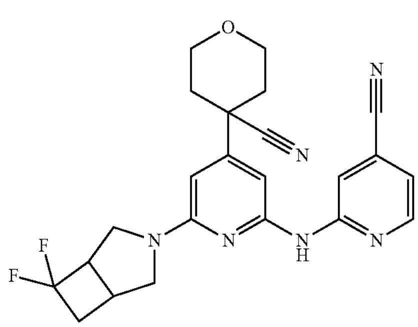 [SMILES: N#Cc1ccnc(Nc2cc(C3(C#N)CCOCC3)cc(N3CC4CC(F)(F)C4C3)n2)c1] | 2-[4-(4-Cyano-tetrahydro-pyran-4-yl)-6-(6,6-difluoro-3-aza-bicyclo[3.2.0]hept-3-yl)-pyridin-2-ylamino]-isonicotinonitrile |

TABLE 1-continued

| NO | Structure | Name |
|---|---|---|
| 70 | 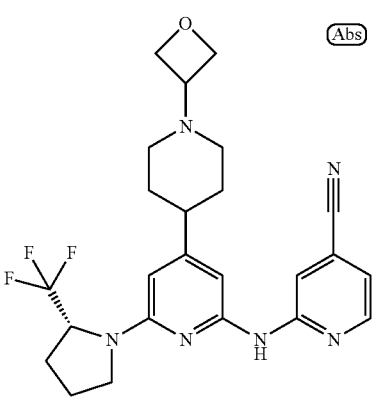 [SMILES: N#Cc1ccnc(Nc2cc(C3CCN(C4COC4)CC3)cc(N3CCC[C@@H]3C(F)(F)F)n2)c1] | 2-[1'-Oxetan-3-yl-6-((R)-2-trifluoromethyl-pyrrolidin-1-yl)-1',2',3',4',5',6'-hexahydro-[4,4']bipyridinyl-2-ylamino]-isonicotinonitrile |
| 71 | 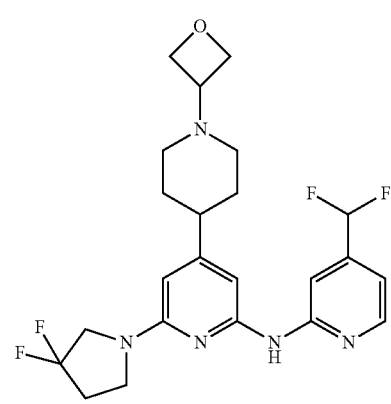 [SMILES: FC(F)c1ccnc(Nc2cc(C3CCN(C4COC4)CC3)cc(N3CCC(F)(F)C3)n2)c1] | (4-Difluoromethyl-pyridin-2-yl)-[6-(3,3-difluoro-pyrrolidin-1-yl)-1'-oxetan-3-yl-1',2',3',4',5',6'-hexahydro-[4,4']bipyridinyl-2-yl]-amine |
| 72 | 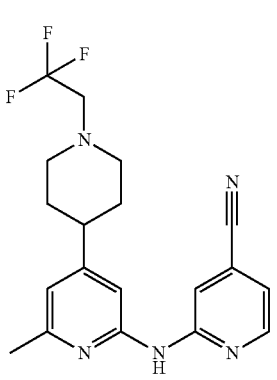 [SMILES: Cc1cc(C2CCN(CC(F)(F)F)CC2)cc(Nc2cc(C#N)ccn2)n1] | 2-[6-Methyl-1'-(2,2,2-trifluoro-ethyl)-1',2',3',4',5',6'-hexahydro-[4,4']bipyridinyl-2-ylamino]-isonicotinonitrile |
| 73 | 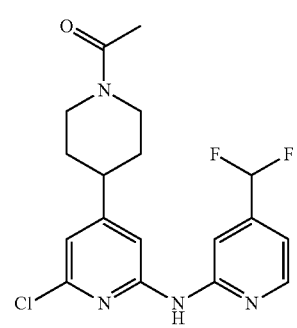 [SMILES: CC(=O)N1CCC(c2cc(Cl)nc(Nc3cc(C(F)F)ccn3)c2)CC1] | 1-[6'-Chloro-2'-(4-difluoromethyl-pyridin-2-ylamino)-3,4,5,6-tetrahydro-2H-[4,4']bipyridinyl-1-yl]-ethanone |

TABLE 1-continued

| NO | Structure | Name |
|---|---|---|
| 74 | 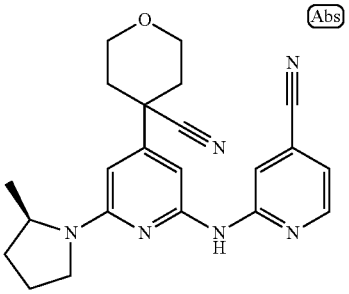 [SMILES: C[C@@H]1CCCN1c1cc(C2(C#N)CCOCC2)cc(Nc2cc(C#N)ccn2)n1] | 2-[4-(4-Cyano-tetrahydro-pyran-4-yl)-6-((R)-2-methyl-pyrrolidin-1-yl)-pyridin-2-ylamino]-isonicotinonitrile |
| 75 | 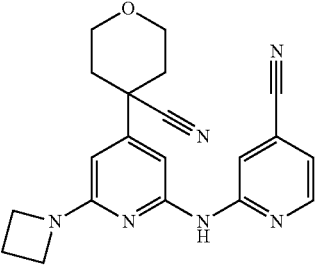 [SMILES: N#Cc1ccnc(Nc2cc(C3(C#N)CCOCC3)cc(N3CCC3)n2)c1] | 2-[6-Azetidin-1-yl-4-(4-cyano-tetrahydro-pyran-4-yl)-pyridin-2-ylamino]-isonicotinonitrile |
| 76 | 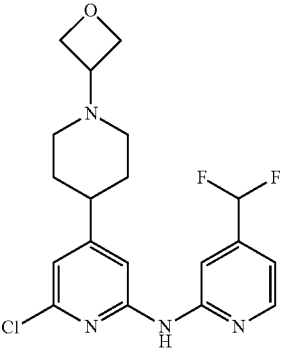 [SMILES: FC(F)c1ccnc(Nc2cc(C3CCN(C4COC4)CC3)cc(Cl)n2)c1] | (6-Chloro-1'-oxetan-3-yl-1',2',3',4',5',6'-hexahydro-[4,4']bipyridinyl-2-yl)-(4-difluoromethyl-pyridin-2-yl)-amine |
| 77 | 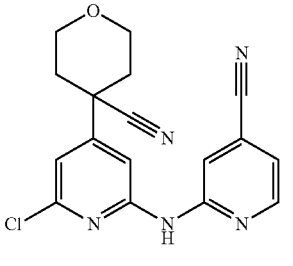 [SMILES: N#Cc1ccnc(Nc2cc(C3(C#N)CCOCC3)cc(Cl)n2)c1] | 2-[6-Chloro-4-(4-cyano-tetrahydro-pyran-4-yl)-pyridin-2-ylamino]-isonicotinonitrile |
| 78 | 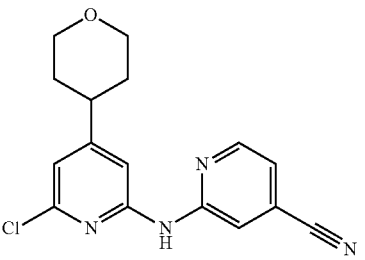 [SMILES: N#Cc1ccnc(Nc2cc(C3CCOCC3)cc(Cl)n2)c1] | 2-[6-Chloro-4-(tetrahydro-pyran-4-yl)-pyridin-2-ylamino]-isonicotinonitrile |

TABLE 1-continued

| NO | Structure | Name |
|---|---|---|
| 79 | 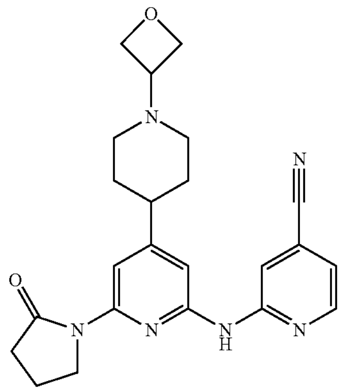 [SMILES: N#Cc1ccnc(Nc2cc(C3CCN(C4COC4)CC3)cc(N3CCCC3=O)n2)c1] | 2-[1'-Oxetan-3-yl-6-(2-oxo-pyrrolidin-1-yl)-1',2',3',4',5',6'-hexahydro-[4,4']bipyridinyl-2-ylamino]-isonicotinonitrile |
| 80 | 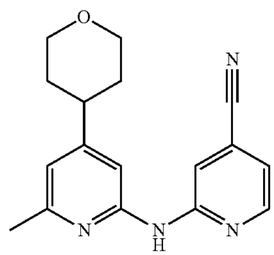 [SMILES: Cc1cc(C2CCOCC2)cc(Nc2cc(C#N)ccn2)n1] | 2-[6-Methyl-4-(tetrahydro-pyran-4-yl)-pyridin-2-ylamino]-isonicotinonitrile |
| 81 | 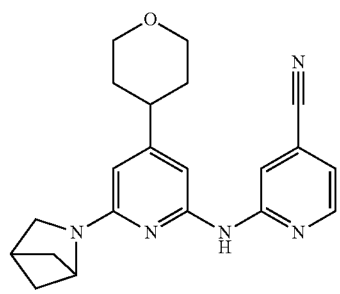 [SMILES: N#Cc1ccnc(Nc2cc(C3CCOCC3)cc(N3CC4CC3C4)n2)c1] | 2-[6-(2-Aza-bicyclo[2.1.1]hex-2-yl)-4-(tetrahydro-pyran-4-yl)-pyridin-2-ylamino]-isonicotinonitrile |
| 82 | 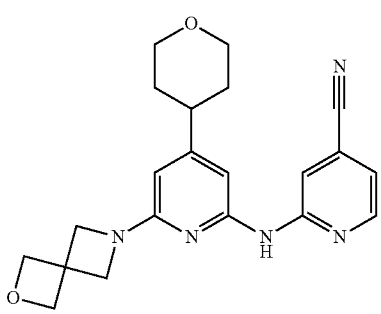 [SMILES: N#Cc1ccnc(Nc2cc(C3CCOCC3)cc(N3CC4(COC4)C3)n2)c1] | 2-[6-(2-Oxa-6-aza-spiro[3.3]hept-6-yl)-4-(tetrahydro-pyran-4-yl)-pyridin-2-ylamino]-isonicotinonitrile |
| 83 | 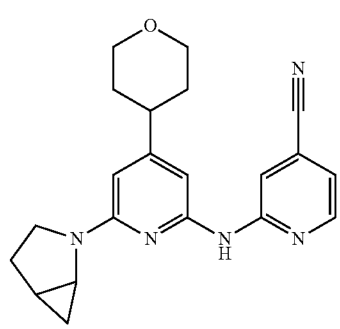 [SMILES: N#Cc1ccnc(Nc2cc(C3CCOCC3)cc(N3CCC4CC43)n2)c1] | 2-[6-(2-Aza-bicyclo[3.1.0]hex-2-yl)-4-(tetrahydro-pyran-4-yl)-pyridin-2-ylamino]-isonicotinonitrile |

TABLE 1-continued

| NO | Structure | Name |
|---|---|---|
| 84 | 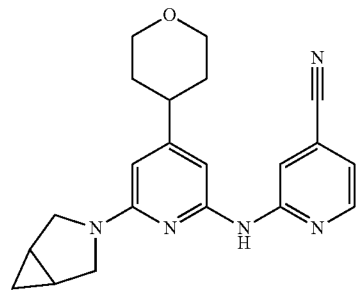 [SMILES: N#Cc1ccnc(Nc2cc(C3CCOCC3)cc(N3CC4CC4C3)n2)c1] | 2-[6-(3-Aza-bicyclo[3.1.0]hex-3-yl)-4-(tetrahydro-pyran-4-yl)-pyridin-2-ylamino]-isonicotinonitrile |
| 85 | 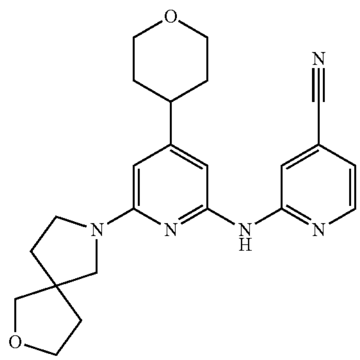 [SMILES: N#Cc1ccnc(Nc2cc(C3CCOCC3)cc(N3CCC4(CCOC4)C3)n2)c1] | 2-[6-(2-Oxa-7-aza-spiro[4.4]non-7-yl)-4-(tetrahydro-pyran-4-yl)-pyridin-2-ylamino]-isonicotinonitrile |
| 86 | 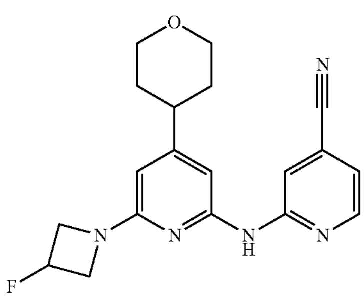 [SMILES: N#Cc1ccnc(Nc2cc(C3CCOCC3)cc(N3CC(F)C3)n2)c1] | 2-[6-(3-Fluoro-azetidin-1-yl)-4-(tetrahydro-pyran-4-yl)-pyridin-2-ylamino]-isonicotinonitrile |
| 87 | 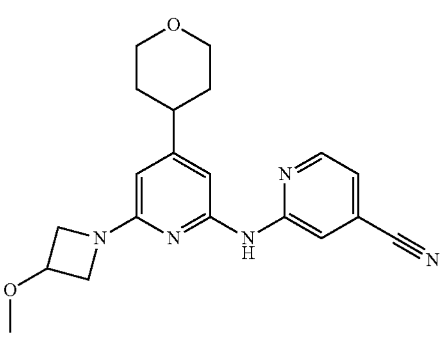 [SMILES: COC1CN(c2cc(C3CCOCC3)cc(Nc3cc(C#N)ccn3)n2)C1] | 2-[6-(3-Methoxy-azetidin-1-yl)-4-(tetrahydro-pyran-4-yl)-pyridin-2-ylamino]-isonicotinonitrile |

TABLE 1-continued

| NO | Structure | Name |
|---|---|---|
| 88 | 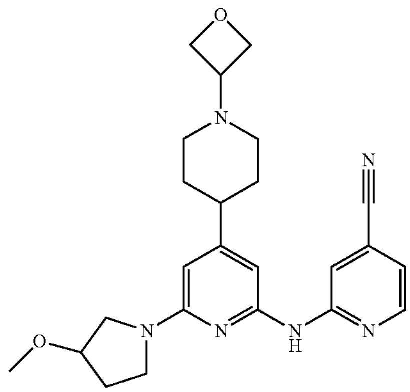 [SMILES: COC1CCN(c2cc(C3CCN(C4COC4)CC3)cc(Nc3cc(C#N)ccn3)n2)C1] | 2-[6-(3-Methoxy-pyrrolidin-1-yl)-1'-oxetan-3-yl-1',2',3',4',5',6'-hexahydro-[4,4']bipyridinyl-2-ylamino]-isonicotinonitrile |
| 89 | 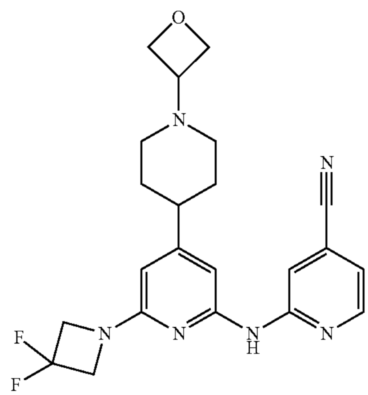 [SMILES: N#Cc1ccnc(Nc2cc(C3CCN(C4COC4)CC3)cc(N3CC(F)(F)C3)n2)c1] | 2-[6-(3,3-Difluoro-azetidin-1-yl)-1'-oxetan-3-yl-1',2',3',4',5',6'-hexahydro-[4,4']bipyridinyl-2-ylamino]-isonicotinonitrile |
| 90 | 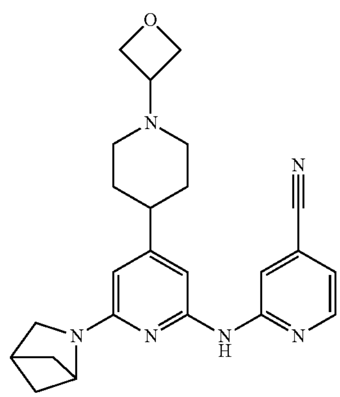 [SMILES: N#Cc1ccnc(Nc2cc(C3CCN(C4COC4)CC3)cc(N3CC4CC3C4)n2)c1] | 2-[6-(2-Aza-bicyclo[2.1.1]hex-2-yl)-1'-oxetan-3-yl-1',2',3',4',5',6'-hexahydro-[4,4']bipyridinyl-2-ylamino]-isonicotinonitrile |
| 91 | 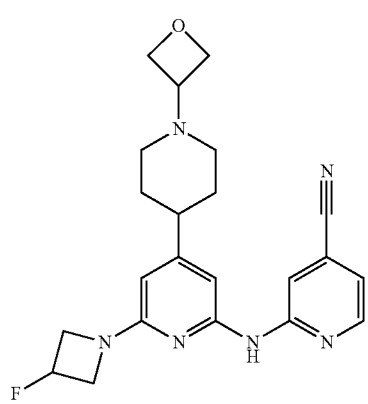 [SMILES: N#Cc1ccnc(Nc2cc(C3CCN(C4COC4)CC3)cc(N3CC(F)C3)n2)c1] | 2-[6-(3-Fluoro-azetidin-1-yl)-1'-oxetan-3-yl-1',2',3',4',5',6'-hexahydro-[4,4']bipyridinyl-2-ylamino]-isonicotinonitrile |

TABLE 1-continued

| NO | Structure | Name |
|---|---|---|
| 92 | 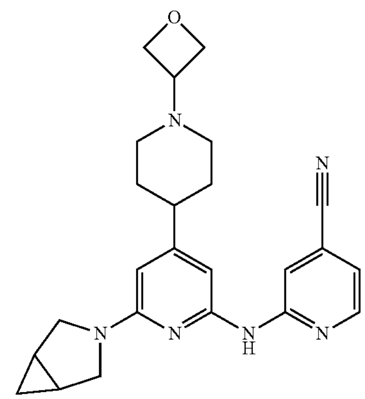 [SMILES: N#Cc1ccnc(Nc2cc(C3CCN(C4COC4)CC3)cc(N3CC4CC4C3)n2)c1] | 2-[6-(3-Aza-bicyclo[3.1.0]hex-3-yl)-1'-oxetan-3-yl-1',2',3',4',5',6'-hexahydro-[4,4']bipyridinyl-2-ylamino]-isonicotinonitrile |
| 93 | 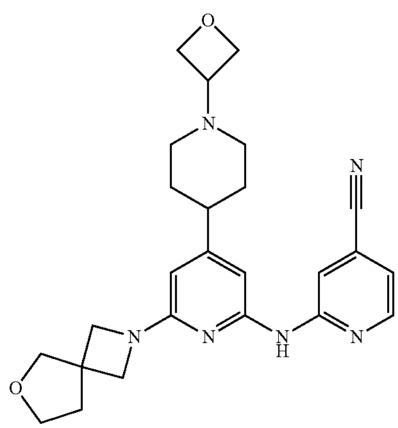 [SMILES: N#Cc1ccnc(Nc2cc(C3CCN(C4COC4)CC3)cc(N3CC4(CCOC4)C3)n2)c1] | 2-[6-(6-Oxa-2-aza-spiro[3.4]oct-2-yl)-1'-oxetan-3-yl-1',2',3',4',5',6'-hexahydro-[4,4']bipyridinyl-2-ylamino]-isonicotinonitrile |
| 94 | 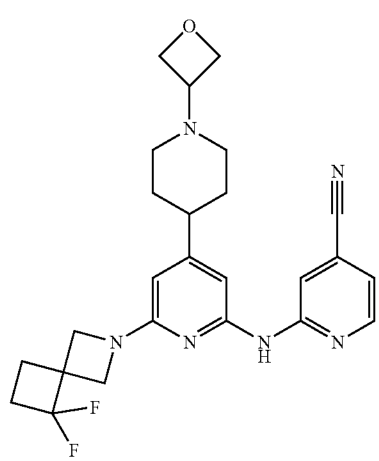 [SMILES: N#Cc1ccnc(Nc2cc(C3CCN(C4COC4)CC3)cc(N3CC4(CCC4(F)F)C3)n2)c1] | 2-[6-(5,5-Difluoro-2-aza-spiro[3.3]hept-2-yl)-1'-oxetan-3-yl-1',2',3',4',5',6'-hexahydro-[4,4']bipyridinyl-2-ylamino]-isonicotinonitrile |

TABLE 1-continued

| NO | Structure | Name |
|---|---|---|
| 95 | 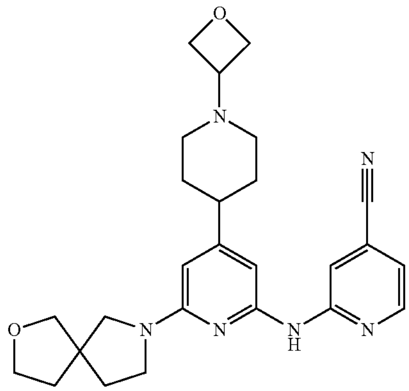 [SMILES: N#Cc1ccnc(Nc2cc(C3CCN(C4COC4)CC3)cc(N3CCC4(CCOC4)C3)n2)c1] | 2-[6-(2-Oxa-7-aza-spiro[4.4]non-7-yl)-1'-oxetan-3-yl-1',2',3',4',5',6'-hexahydro-[4,4']bipyridinyl-2-ylamino]-isonicotinonitrile |
| 96 | 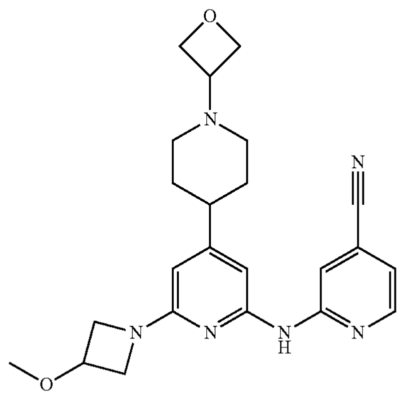 [SMILES: COC1CN(c2cc(C3CCN(C4COC4)CC3)cc(Nc3cc(C#N)ccn3)n2)C1] | 2-[6-(3-Methoxy-azetidin-1-yl)-1'-oxetan-3-yl-1',2',3',4',5',6'-hexahydro-[4,4']bipyridinyl-2-ylamino]-isonicotinonitrile |
| 97 | 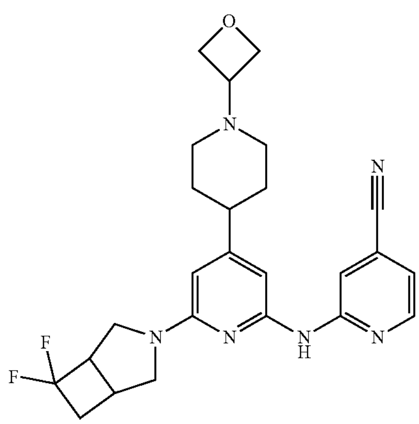 [SMILES: N#Cc1ccnc(Nc2cc(C3CCN(C4COC4)CC3)cc(N3CC4CC(F)(F)C4C3)n2)c1] | 2-[6-(6,6-Difluoro-3-aza-bicyclo[3.2.0]hept-3-yl)-1'-oxetan-3-yl-1',2',3',4',5',6'-hexahydro-[4,4']bipyridinyl-2-ylamino]-isonicotinonitrile |
| 98 | 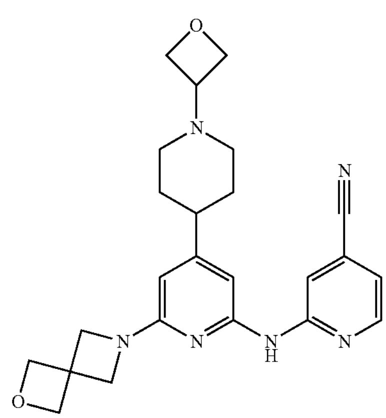 [SMILES: N#Cc1ccnc(Nc2cc(C3CCN(C4COC4)CC3)cc(N3CC4(COC4)C3)n2)c1] | 2-[6-(2-Oxa-6-aza-spiro[3.3]hept-6-yl)-1'-oxetan-3-yl-1',2',3',4',5',6'-hexahydro-[4,4']bipyridinyl-2-ylamino]-isonicotinonitrile |

TABLE 1-continued

| NO | Structure | Name |
|---|---|---|
| 99 | 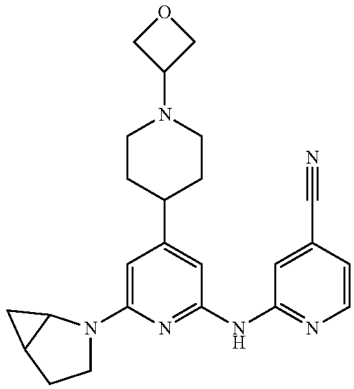 [SMILES: N#Cc1ccnc(Nc2cc(C3CCN(C4COC4)CC3)cc(N3CCC4CC43)n2)c1] | 2-[6-(2-Aza-bicyclo[3.1.0]hex-2-yl)-1'-oxetan-3-yl-1',2',3',4',5',6'-hexahydro-[4,4']bipyridinyl-2-ylamino]-isonicotinonitrile |
| 100 | 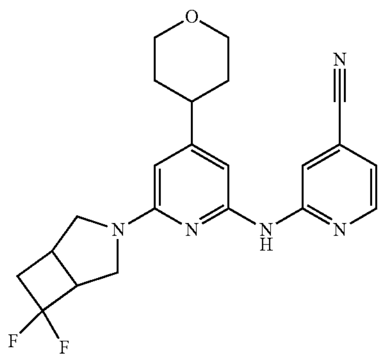 [SMILES: N#Cc1ccnc(Nc2cc(C3CCOCC3)cc(N3CC4CC(F)(F)C4C3)n2)c1] | 2-[6-(6,6-Difluoro-3-aza-bicyclo[3.2.0]hept-3-yl)-4-(tetrahydro-pyran-4-yl)-pyridin-2-ylamino]-isonicotinonitrile |
| 101 | 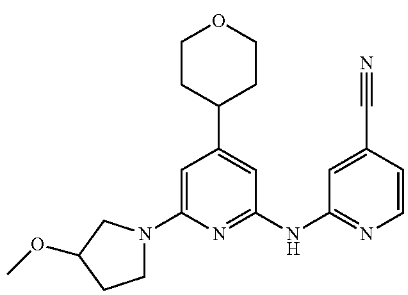 [SMILES: COC1CCN(c2cc(C3CCOCC3)cc(Nc3cc(C#N)ccn3)n2)C1] | 2-[6-(3-Methoxy-pyrrolidin-1-yl)-4-(tetrahydro-pyran-4-yl)-pyridin-2-ylamino]-isonicotinonitrile |
| 102 | 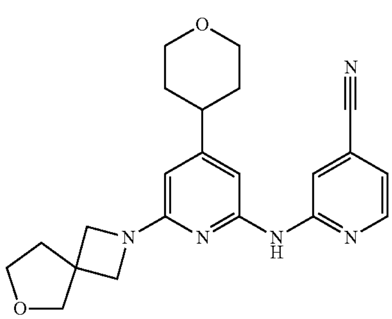 [SMILES: N#Cc1ccnc(Nc2cc(C3CCOCC3)cc(N3CC4(CCOC4)C3)n2)c1] | 2-[6-(6-Oxa-2-aza-spiro[3.4]oct-2-yl)-4-(tetrahydro-pyran-4-yl)-pyridin-2-ylamino]-isonicotinonitrile |

TABLE 1-continued

| NO | Structure | Name |
|---|---|---|
| 103 | 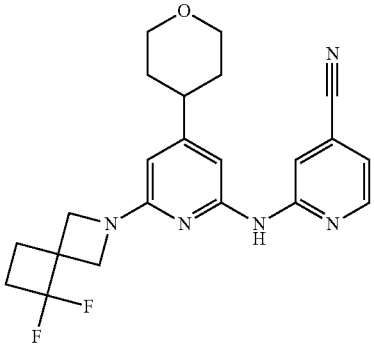 [SMILES: N#Cc1ccnc(Nc2cc(C3CCOCC3)cc(N3CC4(CCC4(F)F)C3)n2)c1] | 2-[6-(5,5-Difluoro-2-aza-spiro[3.3]hept-2-yl)-4-(tetrahydro-pyran-4-yl)-pyridin-2-ylamino]-isonicotinonitrile |
| 104 | 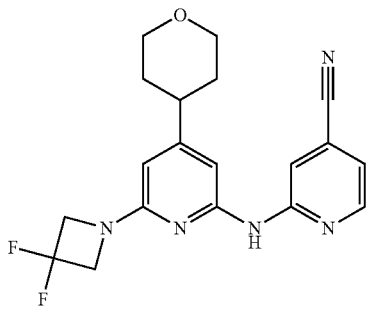 [SMILES: N#Cc1ccnc(Nc2cc(C3CCOCC3)cc(N3CC(F)(F)C3)n2)c1] | 2-[6-(3,3-Difluoro-azetidin-1-yl)-4-(tetrahydro-pyran-4-yl)-pyridin-2-ylamino]-isonicotinonitrile |
| 105 | 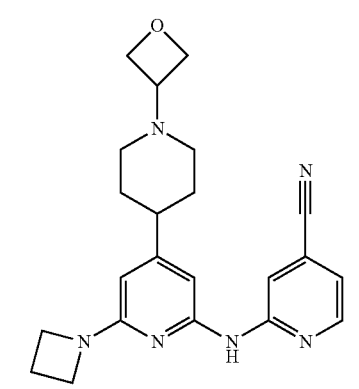 [SMILES: N#Cc1ccnc(Nc2cc(C3CCN(C4COC4)CC3)cc(N3CCC3)n2)c1] | 2-(6-Azetidin-1-yl-1'-oxetan-3-yl-1',2',3',4',5',6'-hexahydro-[4,4']bipyridinyl-2-ylamino)-isonicotinonitrile |
| 106 | 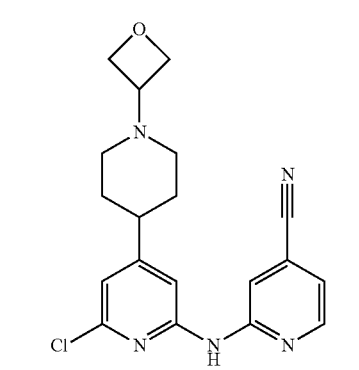 [SMILES: N#Cc1ccnc(Nc2cc(C3CCN(C4COC4)CC3)cc(Cl)n2)c1] | 2-(6-Chloro-1'-oxetan-3-yl-1',2',3',4',5',6'-hexahydro-[4,4']bipyridinyl-2-ylamino)-isonicotinonitrile |

TABLE 1-continued

| NO | Structure | Name |
|---|---|---|
| 107 | 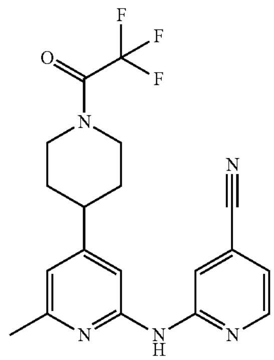 [SMILES: Cc1cc(C2CCN(C(=O)C(F)(F)F)CC2)cc(Nc2cc(C#N)ccn2)n1] | 2-[6-Methyl-1'-(2,2,2-trifluoro-acetyl)-1',2',3',4',5',6'-hexahydro-[4,4']bipyridinyl-2-ylamino]-isonicotinonitrile |
| 108 | 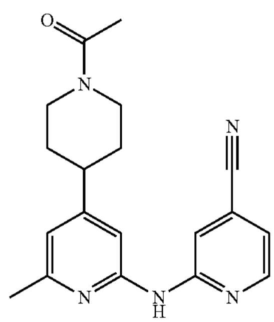 [SMILES: CC(=O)N1CCC(c2cc(C)nc(Nc3cc(C#N)ccn3)c2)CC1] | 2-(1'-Acetyl-6-methyl-1',2',3',4',5',6'-hexahydro[4,4']bipyridinyl-2-ylamino)-isonicotinonitrile |
| 109 | 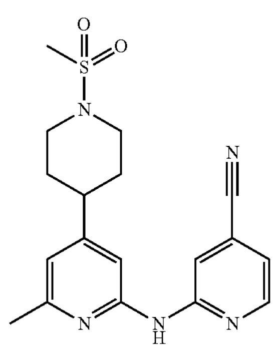 [SMILES: Cc1cc(C2CCN(S(C)(=O)=O)CC2)cc(Nc2cc(C#N)ccn2)n1] | 2-(1'-Methanesulfonyl-6-methyl-1',2',3',4',5',6'-hexahydro-[4,4']bipyridinyl-2-ylamino)-isonicotinonitrile |
| 110 | 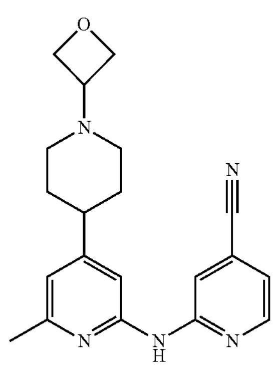 [SMILES: Cc1cc(C2CCN(C3COC3)CC2)cc(Nc2cc(C#N)ccn2)n1] | 2-(6-Methyl-1'-oxetan-3-yl-1',2',3',4',5',6'-hexahydro-[4,4']bipyridinyl-2-ylamino)-isonicotinonitrile |

TABLE 1-continued

| NO | Structure | Name |
|---|---|---|
| 111 | 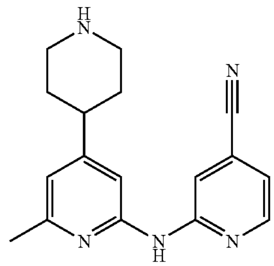 [SMILES: Cc1cc(C2CCNCC2)cc(Nc2cc(C#N)ccn2)n1] | 2-(6-Methyl-1',2',3',4',5',6'-hexahydro-[4,4']bipyridinyl-2-ylamino)-isonicotinonitrile |
| 112 | 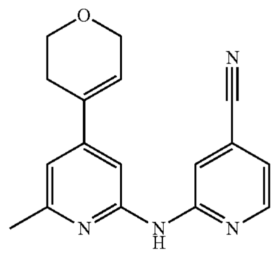 [SMILES: Cc1cc(C2=CCOCC2)cc(Nc2cc(C#N)ccn2)n1] | 2-[4-(3,6-Dihydro-2H-pyran-4-yl)-6-methyl-pyridin-2-ylamino]-isonicotinonitrile |
| 113 | 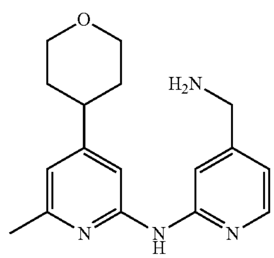 [SMILES: Cc1cc(C2CCOCC2)cc(Nc2cc(CN)ccn2)n1] | (4-Aminomethyl-pyridin-2-yl)-[6-methyl-4-(tetrahydro-pyran-4-yl)-pyridin-2-yl]-amine |
| 114 | 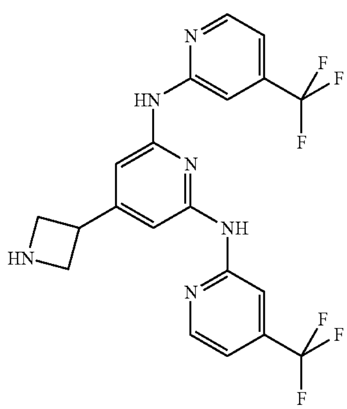 [SMILES: FC(F)(F)c1ccnc(Nc2cc(C3CNC3)cc(Nc3cc(C(F)(F)F)ccn3)n2)c1] | 4-Azetidin-3-yl-N,N'-bis-(4-trifluoromethyl-pyridin-2-yl)-pyridine-2,6-diamine |
| 115 | 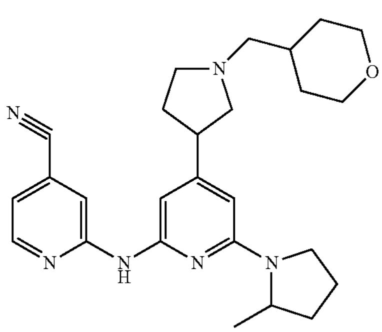 [SMILES: CC1CCCN1c1cc(C2CCN(CC3CCOCC3)C2)cc(Nc2cc(C#N)ccn2)n1] | 2-{6-(2-Methyl-pyrrolidin-1-yl)-4-[1-(tetrahydro-pyran-4-ylmethyl)-pyrrolidin-3-yl]-pyridin-2-ylamino}-isonicotinonitrile |

TABLE 1-continued

| NO | Structure | Name |
|---|---|---|
| 116 | 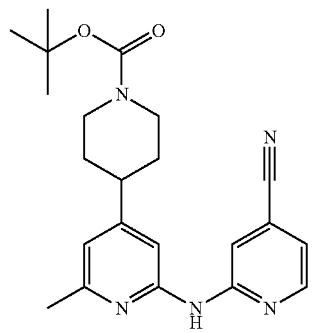 [SMILES: Cc1cc(C2CCN(C(=O)OC(C)(C)C)CC2)cc(Nc2cc(C#N)ccn2)n1] | 2'-(4-Cyano-pyridin-2-ylamino)-6'-methyl-3,4,5,6-tetrahydro-2H-[4,4']bipyridinyl-1-carboxylic acid tert-butyl ester |
| 117 | 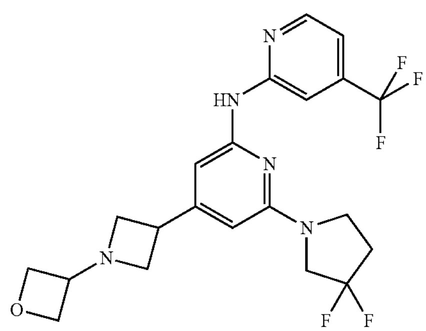 [SMILES: FC1(F)CCN(c2cc(C3CN(C4COC4)C3)cc(Nc3cc(C(F)(F)F)ccn3)n2)C1] | [6-(3,3-Difluoro-pyrrolidin-1-yl)-4-(1-oxetan-3-yl-azetidin-3-yl)-pyridin-2-yl]-(4-trifluoromethyl-pyridin-2-yl)-amine |
| 118 | 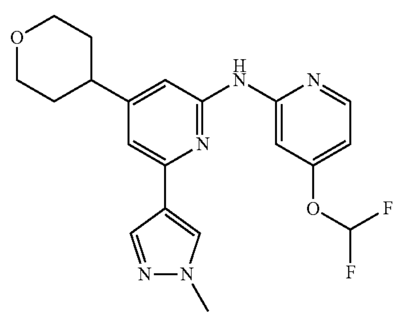 [SMILES: Cn1cc(-c2cc(C3CCOCC3)cc(Nc3cc(OC(F)F)ccn3)n2)cn1] | (4-Difluoromethoxy-pyridin-2-yl)-[6-(1-methyl-1H-pyrazol-4-yl)-4-(tetrahydro-pyran-4-yl)-pyridin-2-yl]-amine |
| 119 | 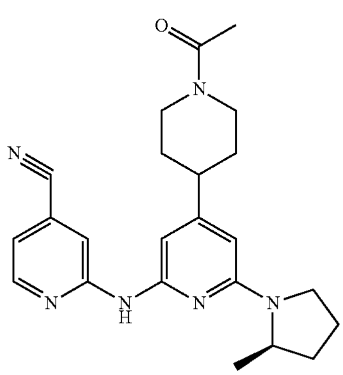 [SMILES: CC(=O)N1CCC(c2cc(Nc3cc(C#N)ccn3)nc(N3CCC[C@H]3C)c2)CC1] | 2-[1'-Acetyl-6-((R)-2-methyl-pyrrolidin-1-yl)-1',2',3',4',5',6'-hexahydro-[4,4']bipyridinyl-2-ylamino]-isonicotinonitrile |

TABLE 1-continued

| NO | Structure | Name |
|---|---|---|
| 120 | 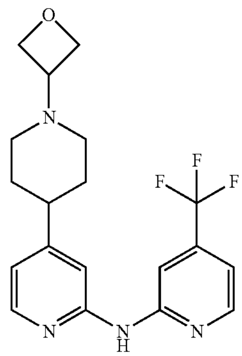 [SMILES: FC(F)(F)c1ccnc(Nc2cc(C3CCN(C4COC4)CC3)ccn2)c1] | (1'-Oxetan-3-yl-1',2',3',4',5',6'-hexahydro-[4,4']bipyridinyl-2-yl)-(4-trifluoromethyl-pyridin-2-yl)-amine |
| 121 | 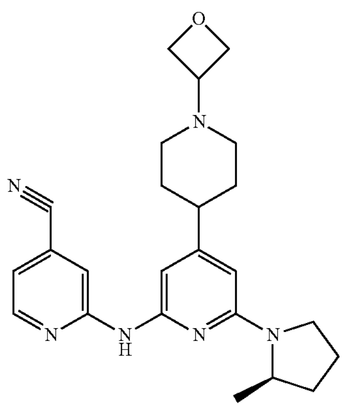 [SMILES: C[C@@H]1CCCN1c1cc(C2CCN(C3COC3)CC2)cc(Nc2cc(C#N)ccn2)n1] | 2-[6-((R)-2-Methyl-pyrrolidin-1-yl)-1'-oxetan-3-yl-1',2',3',4',5',6'-hexahydro-[4,4']bipyridinyl-2-ylamino]-isonicotinonitrile |
| 122 | 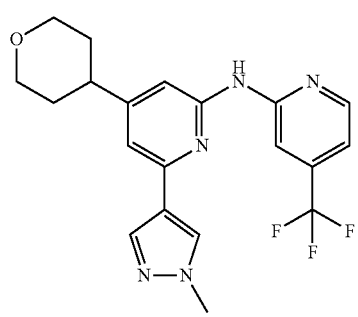 [SMILES: Cn1cc(-c2cc(C3CCOCC3)cc(Nc3cc(C(F)(F)F)ccn3)n2)cn1] | [6-(1-Methyl-1H-pyrazol-4-yl)-4-(tetrahydro-pyran-4-yl)-pyridin-2-yl]-(4-trifluoromethyl-pyridin-2-yl)-amine |
| 123 | 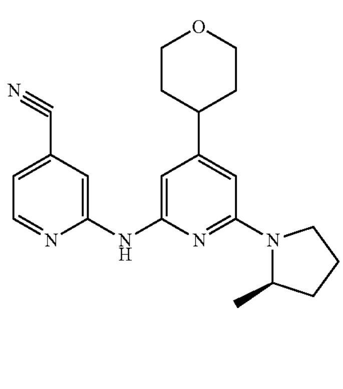 [SMILES: C[C@@H]1CCCN1c1cc(C2CCOCC2)cc(Nc2cc(C#N)ccn2)n1] | 2-[6-((R)-2-Methyl-pyrrolidin-1-yl)-4-(tetrahydro-pyran-4-yl)-pyridin-2-ylamino]-isonicotinonitrile |

TABLE 1-continued

| NO | Structure | Name |
|---|---|---|
| 124 | 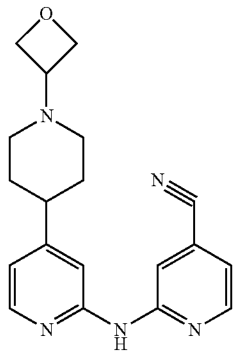 [SMILES: N#Cc1ccnc(Nc2cc(C3CCN(C4COC4)CC3)ccn2)c1] | 2-(1'-Oxetan-3-yl-1',2',3',4',5',6'-hexahydro-[4,4']bipyridinyl-2-ylamino)-isonicotinonitrile |
| 125 | 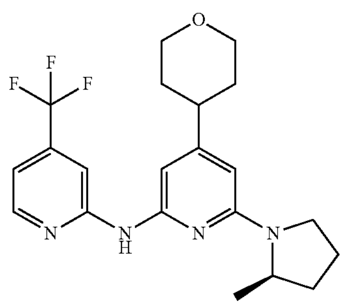 [SMILES: C[C@@H]1CCCN1c1cc(C2CCOCC2)cc(Nc2cc(C(F)(F)F)ccn2)n1] | [6-((R)-2-Methyl-pyrrolidin-1-yl)-4-(tetrahydro-pyran-4-yl)-pyridin-2-yl]-(4-trifluoromethyl-pyridin-2-yl)-amine |
| 126 | 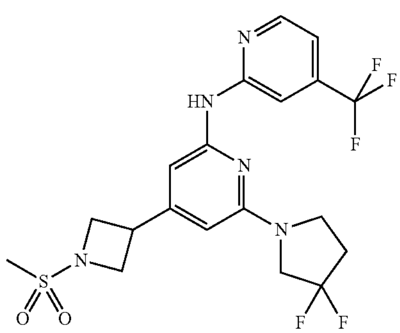 [SMILES: CS(=O)(=O)N1CC(c2cc(Nc3cc(C(F)(F)F)ccn3)nc(N3CCC(F)(F)C3)c2)C1] | [6-(3,3-Difluoro-pyrrolidin-1-yl)-4-(1-methanesulfonyl-azetidin-3-yl)-pyridin-2-yl]-(4-trifluoromethyl-pyridin-2-yl)-amine |
| 127 | 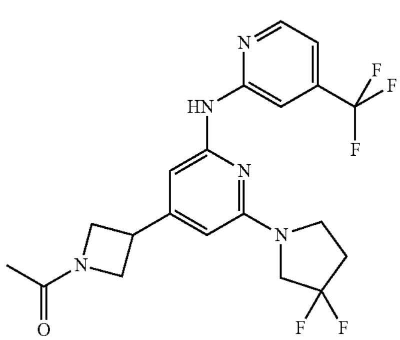 [SMILES: CC(=O)N1CC(c2cc(Nc3cc(C(F)(F)F)ccn3)nc(N3CCC(F)(F)C3)c2)C1] | 1-{3-[2-(3,3-Difluoro-pyrrolidin-1-yl)-6-(4-trifluoromethyl-pyridin-2-ylamino)-pyridin-4-yl]-azetidin-1-yl}-ethanone |

TABLE 1-continued

| NO | Structure | Name |
|---|---|---|
| 128 | 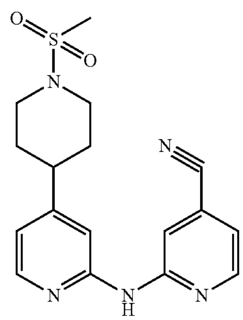 [SMILES: CS(=O)(=O)N1CCC(c2ccnc(Nc3cc(C#N)ccn3)c2)CC1] | 2-(1'-Methanesulfonyl-1',2',3',4',5',6'-hexahydro-[4,4']bipyridinyl-2-ylamino)-isonicotinonitrile |
| 129 | 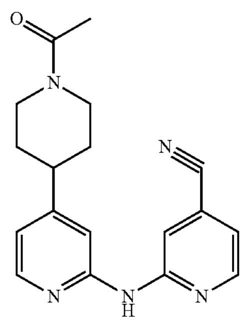 [SMILES: CC(=O)N1CCC(c2ccnc(Nc3cc(C#N)ccn3)c2)CC1] | 2-(1'-Acetyl-1',2',3',4',5',6'-hexahydro-[4,4']bipyridinyl-2-ylamino)-isonicotinonitrile |
| 130 | 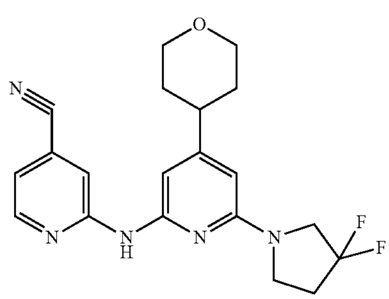 [SMILES: N#Cc1ccnc(Nc2cc(C3CCOCC3)cc(N3CCC(F)(F)C3)n2)c1] | 2-[6-(3,3-Difluoro-pyrrolidin-1-yl)-4-(tetrahydro-pyran-4-yl)-pyridin-2-ylamino]-isonicotinonitrile |
| 131 | 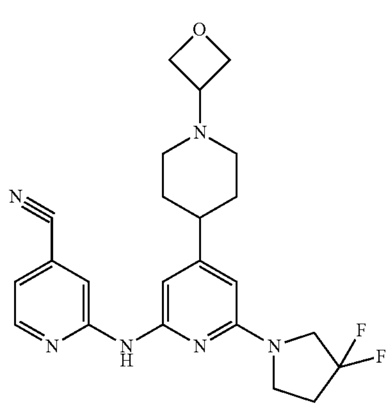 [SMILES: N#Cc1ccnc(Nc2cc(C3CCN(C4COC4)CC3)cc(N3CCC(F)(F)C3)n2)c1] | 2-[6-(3,3-Difluoro-pyrrolidin-1-yl)-1'-oxetan-3-yl-1',2',3',4',5',6'-hexahydro-[4,4']bipyridinyl-2-ylamino]-isonicotinonitrile |

TABLE 1-continued

| NO | Structure | Name |
|---|---|---|
| 132 | 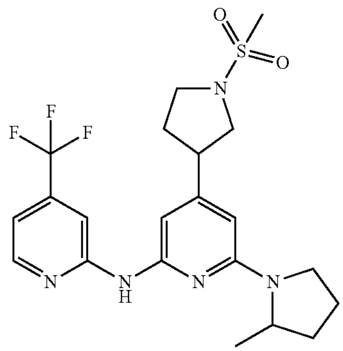 [SMILES: CC1CCCN1c1cc(C2CCN(S(C)(=O)=O)C2)cc(Nc2cc(C(F)(F)F)ccn2)n1] | [4-(1-Methanesulfonyl-pyrrolidin-3-yl)-6-(2-methyl-pyrrolidin-1-yl)-pyridin-2-yl]-(4-trifluoromethyl-pyridin-2-yl)-amine |
| 133 | 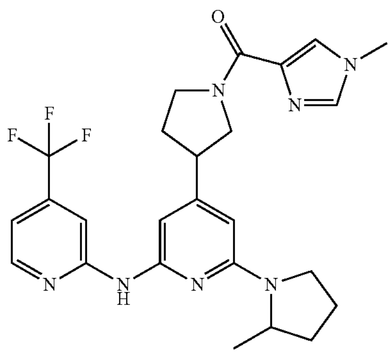 [SMILES: CC1CCCN1c1cc(C2CCN(C(=O)c3cn(C)cn3)C2)cc(Nc2cc(C(F)(F)F)ccn2)n1] | (1-Methyl-1H-imidazol-4-yl)-{3-[2-(2-methyl-pyrrolidin-1-yl)-6-(4-trifluoromethyl-pyridin-2-ylamino)-pyridin-4-yl]-pyrrolidin-1-yl}-methanone |
| 134 | 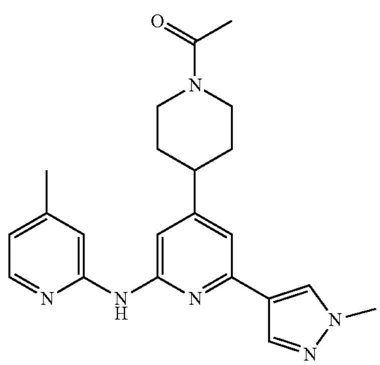 [SMILES: CC(=O)N1CCC(c2cc(Nc3cc(C)ccn3)nc(-c3cnn(C)c3)c2)CC1] | 1-[2'-(1-Methyl-1H-pyrazol-4-yl)-6'-(4-methyl-pyridin-2-ylamino)-3,4,5,6-tetrahydro-2H-[4,4']bipyridinyl-1-yl]-ethanone |
| 135 | 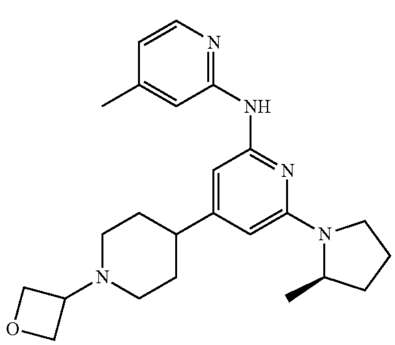 [SMILES: Cc1ccnc(Nc2cc(C3CCN(C4COC4)CC3)cc(N3CCC[C@H]3C)n2)c1] | (4-Methyl-pyridin-2-yl)-[6-((R)-2-methyl-pyrrolidin-1-yl)-1'-oxetan-3-yl-1',2',3',4',5',6'-hexahydro-[4,4']bipyridinyl-2-yl]-amine |

TABLE 1-continued

| NO | Structure | Name |
|---|---|---|
| 136 | 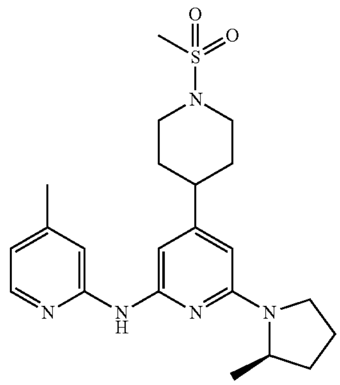 [SMILES: Cc1ccnc(Nc2cc(C3CCN(S(C)(=O)=O)CC3)cc(N3CCC[C@H]3C)n2)c1] | [1'-Methanesulfonyl-6-((R)-2-methyl-pyrrolidin-1-yl)-1',2',3',4',5',6'-hexahydro-[4,4']bipyridinyl-2-yl]-(4-methyl-pyridin-2-yl)-amine |
| 137 | 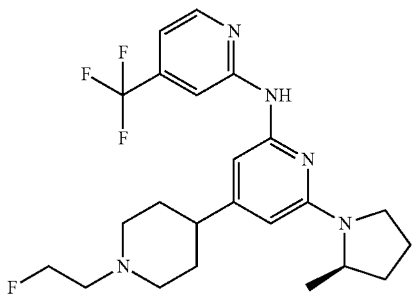 [SMILES: C[C@@H]1CCCN1c1cc(C2CCN(CCF)CC2)cc(Nc2cc(C(F)(F)F)ccn2)n1] | [1'-(2-Fluoro-ethyl)-6-((R)-2-methyl-pyrrolidin-1-yl)-1',2',3',4',5',6'-hexahydro-[4,4']bipyridinyl-2-yl]-(4-trifluoromethyl-pyridin-2-yl)-amine |
| 138 | 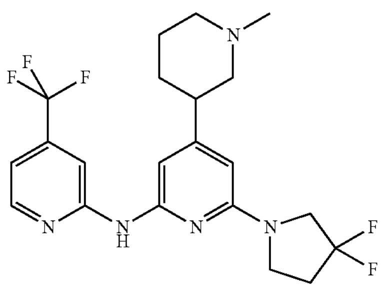 [SMILES: CN1CCCC(c2cc(Nc3cc(C(F)(F)F)ccn3)nc(N3CCC(F)(F)C3)c2)C1] | [6'-(3,3-Difluoro-pyrrolidin-1-yl)-1-methyl-1,2,3,4,5,6-hexahydro-[3,4']bipyridinyl-2'-yl]-(4-trifluoromethyl-pyridin-2-yl)-amine |
| 139 | 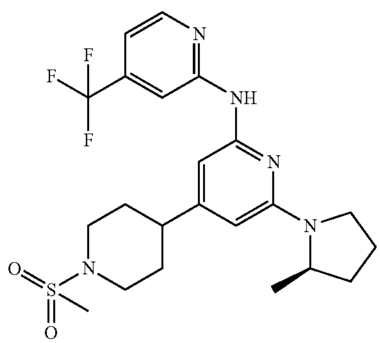 [SMILES: C[C@@H]1CCCN1c1cc(C2CCN(S(C)(=O)=O)CC2)cc(Nc2cc(C(F)(F)F)ccn2)n1] | [1'-Methanesulfonyl-6-((R)-2-methyl-pyrrolidin-1-yl)-1',2',3',4',5',6'-hexahydro-[4,4']bipyridinyl-2-yl]-(4-trifluoromethyl-pyridin-2-yl)-amine |
| 140 | 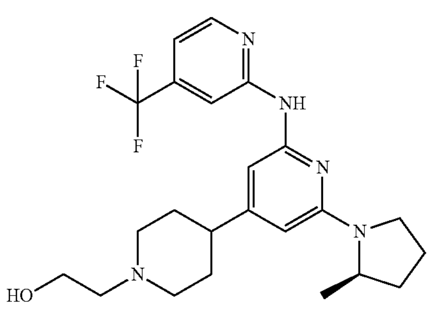 [SMILES: C[C@@H]1CCCN1c1cc(C2CCN(CCO)CC2)cc(Nc2cc(C(F)(F)F)ccn2)n1] | 2-[6'-((R)-2-Methyl-pyrrolidin-1-yl)-2'-(4-trifluoromethyl-pyridin-2-ylamino)-3,4,5,6-tetrahydro-2H-[4,4']bipyridinyl-1-yl]-ethanol |

TABLE 1-continued

| NO | Structure | Name |
|---|---|---|
| 141 | 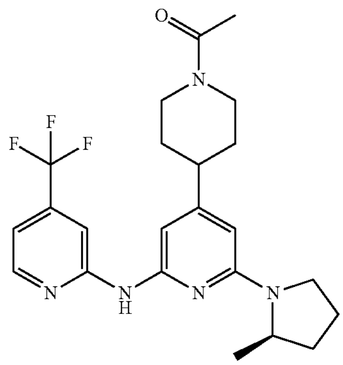 [SMILES: CC(=O)N1CCC(c2cc(Nc3cc(C(F)(F)F)ccn3)nc(N3CCC[C@H]3C)c2)CC1] | 1-[2'-((R)-2-Methyl-pyrrolidin-1-yl)-6'-(4-trifluoromethyl-pyridin-2-ylamino)-3,4,5,6-tetrahydro-2H-[4,4']bipyridinyl-1-yl]-ethanone |
| 142 | 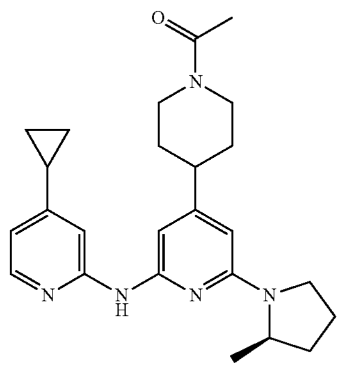 [SMILES: CC(=O)N1CCC(c2cc(Nc3cc(C4CC4)ccn3)nc(N3CCC[C@H]3C)c2)CC1] | 1-[6'-(4-Cyclopropyl-pyridin-2-ylamino)-2'-((R)-2-methyl-pyrrolidin-1-yl)-3,4,5,6-tetrahydro-2H-[4,4']bipyridinyl-1-yl]-ethanone |
| 143 | 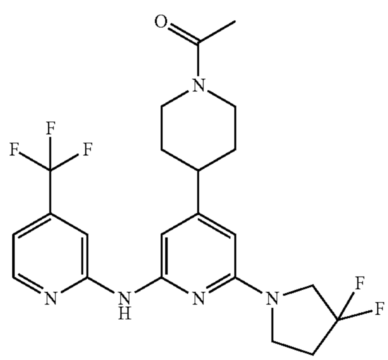 [SMILES: CC(=O)N1CCC(c2cc(Nc3cc(C(F)(F)F)ccn3)nc(N3CCC(F)(F)C3)c2)CC1] | 1-[2'-(3,3-Difluoro-pyrrolidin-1-yl)-6'-(4-trifluoromethyl-pyridin-2-ylamino)-3,4,5,6-tetrahydro-2H-[4,4']bipyridinyl-1-yl]-ethanone |
| 144 | 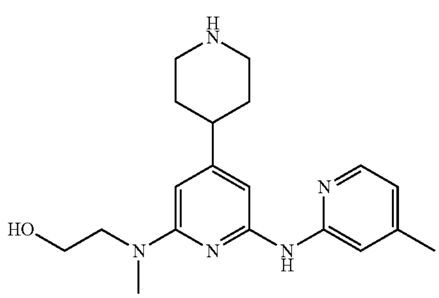 [SMILES: Cc1ccnc(Nc2cc(C3CCNCC3)cc(N(C)CCO)n2)c1] | 2-{Methyl-[6-(4-methyl-pyridin-2-ylamino)-1',2',3',4',5',6'-hexahydro-[4,4']bipyridinyl-2-yl]-amino}-ethanol |
| 145 | 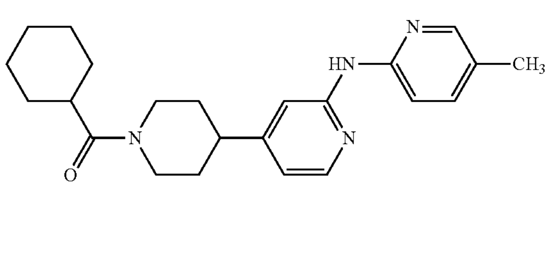 [SMILES: Cc1ccc(Nc2cc(C3CCN(C(=O)C4CCCCC4)CC3)ccn2)nc1] | cyclohexyl(4-(2-((5-methylpyridin-2-yl)amino)pyridin-4-yl)piperidin-1-yl)methanone |

TABLE 1-continued

| NO | Structure | Name |
|----|-----------|------|
| 146 | 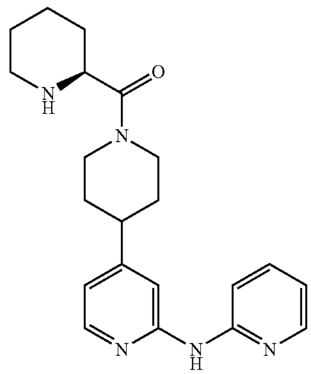 [SMILES: O=C([C@@H]1CCCCN1)N1CCC(c2ccnc(Nc3ccccn3)c2)CC1] | (S)-piperidin-2-yl(4-(2-(pyridin-2-ylamino)pyridin-4-yl)piperidin-1-yl)methanone |
| 147 | 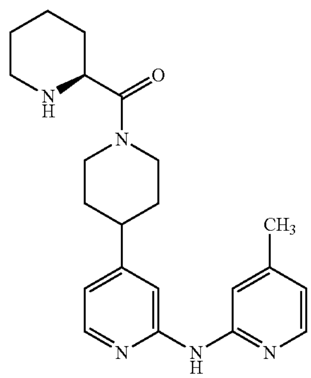 [SMILES: Cc1ccnc(Nc2cc(C3CCN(C(=O)[C@@H]4CCCCN4)CC3)ccn2)c1] | (S)-(4-(2-((4-methylpyridin-2-yl)amino)pyridin-4-yl)piperidin-1-yl)(piperidin-2-yl)methanone |

In another aspect, the present invention provides for a pharmaceutical composition comprising a compound of formula I or an embodiment thereof and a pharmaceutically acceptable carrier, diluent or excipient.

In another aspect, the present invention provides for a method for inhibiting or preventing degeneration of a central nervous system (CNS) neuron or a portion thereof, the method comprising administering to the CNS neuron a compound of formula I. In certain embodiments of this aspect, the administering to the CNS neuron is performed in vitro. In certain embodiments of this aspect, the method further comprises grafting or implanting the CNS neuron into a human patient after administration of the agent. In certain embodiments of this aspect, the CNS neuron is present in a human patient. In certain embodiment of this aspect the administering to the CNS neuron comprises administration of the compound of formula I in a pharmaceutically acceptable carrier, diluent or excipient. In certain aspects of this embodiment, the administering to the CNS neuron is carried out by an administration route selected from the group consisting of parenteral, subcutaneous, intravenous, intraperitoneal, intracerebral, intralesional, intramuscular, intraocular, intraarterial interstitial infusion and implanted delivery device. In certain aspects of this embodiment the invention comprises administering one or more additional pharmaceutical agents.

In another aspect, the present invention provides for a method for inhibiting or preventing degeneration of a central nervous system (CNS) neuron in a patient having or at risk of developing a neurodegenerative disease or condition comprising administering to said patient a therapeutically effective amount of a compound of formula I, or a pharmaceutically acceptable salt thereof. In another aspect, the present invention provides for a method for decreasing or preventing one or more symptoms of a neurodegenerative disease or condition in a patient suffering therefrom comprising administering to said patient a therapeutically effective amount of a compound of formula I or a pharmaceutically acceptable salt thereof. In another aspect, the present invention provides for a method for decreasing the progression of a neurodegenerative disease or condition in a patient suffering therefrom comprising administering to said patient a therapeutically effective amount of a compound of formula I or a pharmaceutically acceptable salt thereof. Within each of these aspects, the neurodegenerative disease of condition may include: Alzheimer's disease, Huntington's disease, Parkinson's disease, Parkinson's-plus diseases, amyotrophic lateral sclerosis (ALS), ischemia, stroke, intracranial hemorrhage, cerebral hemorrhage, trigeminal neuralgia, glossopharyngeal neuralgia, Bell's Palsy, myasthenia gravis, muscular dystrophy, progressive muscular atrophy, primary lateral sclerosis (PLS), pseudobulbar palsy, progressive bulbar palsy, spinal muscular atrophy, inherited muscular atrophy, invertebrate disk syndromes, cervical spondylosis, plexus disorders, thoracic outlet destruction syndromes, peripheral neuropathies, prophyria, multiple system atrophy, progressive supranuclear palsy, corticobasal degeneration, dementia with Lewy bodies, frontotemporal dementia, demyelinating diseases, Guillain-Barré syndrome, multiple sclerosis, Charcot-Marie_Tooth disease, prion disease, Creutzfeldt-Jakob disease, Gerstmann-Sträussler-Scheinker syndrome (GSS), fatal familial insomnia (FFI), bovine spongiform encephalopathy, Pick's disease, epilepsy, AIDS demential complex, nerve damage caused by exposure to toxic compounds selected from the group consisting of heavy metals, industrial solvents, drugs and chemotherapeutic agents; injury to the nervous system caused by physical, mechanical or chemical trauma, glaucoma, lattice dystrophy, retinitis pigmentosa, age-related macular degeneration (AMD), photoreceptor degeneration associated with wet or dry AMD, other retinal degeneration, optic nerve drusen, optic neuropathy and optic neuritis. In certain embodiments these aspects, the compound of formula I is administered in combination with one or more additional pharmaceutical agents.

In another aspect, the present invention provides for pharmaceutical composition comprising a compound formula I as described herein and a pharmaceutically acceptable carrier, diluent or excipient.

In another aspect, the present invention provides for a compound formula I as described herein for use as therapeutically active substance.

In another aspect, the present invention provides for a compound formula I as described herein for the use as therapeutically active substance for inhibiting or preventing degeneration of a central nervous system (CNS) neuron or a portion thereof, the method comprising administering to the CNS neuron.

In another aspect, the present invention provides for a compound formula I as described herein for the use as therapeutically active substance for inhibiting or preventing degeneration of a central nervous system (CNS) neuron or a portion thereof, the method comprising administering to the CNS neuron, wherein the administering of a compound of formula I results in a decrease of cJun phosphorylation, cJun activity, and/or cJun expression.

In another aspect, the present invention provides for a compound formula I as described herein for the use as therapeutically active substance for inhibiting or preventing degeneration of a central nervous system (CNS) neuron or a portion thereof, the method comprising administering to the CNS neuron, wherein the administering of a compound of formula I results in a decrease in p38 phosphorylation, p38 activity, and/or p38 expression.

In another aspect, the present invention provides for a compound formula I as described herein for the use as therapeutically active substance for decreasing the progression of a neurodegenerative disease or condition in a patient suffering therefrom comprising administering to said patient a therapeutically effective amount of a compound of formula I or a pharmaceutically acceptable salt thereof.

In another aspect, the present invention provides for a compound formula I as described herein for the use as therapeutically active substance for decreasing the progression of a neurodegenerative disease or condition in a patient suffering therefrom comprising administering to said patient a therapeutically effective amount of a compound of formula I or a pharmaceutically acceptable salt thereof, wherein said neurodegenerative disease of condition is selected from the group consisting of: Alzheimer's disease, Huntington's disease, Parkinson's disease, Parkinson's-plus diseases, amyotrophic lateral sclerosis (ALS), ischemia, stroke, intracranial hemorrhage, cerebral hemorrhage, trigeminal neuralgia, glossopharyngeal neuralgia, Bell's Palsy, myasthenia gravis, muscular dystrophy, progressive muscular atrophy, primary lateral sclerosis (PLS), pseudobulbar palsy, progressive bulbar palsy, spinal muscular atrophy, inherited muscular atrophy, invertebrate disk syndromes, cervical spondylosis, plexus disorders, thoracic outlet destruction syndromes, peripheral neuropathies, prophyria, multiple system atrophy, progressive supranuclear palsy, corticobasal degeneration, dementia with Lewy bodies, frontotemporal dementia, demyelinating diseases, Guillain-Barré syndrome, multiple sclerosis, Charcot-Marie_Tooth disease, prion disease, Creutzfeldt-Jakob disease, Gerstmann-Sträussler-Scheinker syndrome (GSS), fatal familial insomnia (FFI), bovine spongiform encephalopathy, Pick's disease, epilepsy, AIDS demential complex, nerve damage caused by exposure to toxic compounds selected from the group consisting of heavy metals, industrial solvents, drugs and chemotherapeutic agents; injury to the nervous system caused by physical, mechanical or chemical trauma, glaucoma, lattice dystrophy, retinitis pigmentosa, age-related macular degeneration (AMD), photoreceptor degeneration associated with wet or dry AMD, other retinal degeneration, optic nerve drusen, optic neuropathy and optic neuritis.

In another aspect, the present invention provides for a compound formula I as described herein for the use as therapeutically active substance for decreasing the progression of a neurodegenerative disease or condition in a patient suffering therefrom comprising administering to said patient a therapeutically effective amount of a compound of formula I or a pharmaceutically acceptable salt thereof, wherein said neurodegenerative disease of condition in a patient is selected from the group consisting of: Alzheimer's disease, Parkinson's disease, and amyotrophic lateral sclerosis (ALS).

In another aspect, the present invention provides for a use of a compound formula I as described herein for the preparation of a medicament for inhibiting or preventing degeneration of a central nervous system (CNS) neuron or a portion thereof, the method comprising administering to the CNS neuron.

In another aspect, the present invention provides for a use of a compound formula I as described herein for the preparation of a medicament for inhibiting or preventing degeneration of a central nervous system (CNS) neuron or a portion thereof, the method comprising administering to the CNS neuron, wherein the administering of a compound of formula I results in a decrease of cJun phosphorylation, cJun activity, and/or cJun expression.

In another aspect, the present invention provides for a use of a compound formula I as described herein for the preparation of a medicament for inhibiting or preventing degeneration of a central nervous system (CNS) neuron or a portion thereof, the method comprising administering to the CNS neuron, wherein the administering of a compound of formula I results in a decrease in p38 phosphorylation, p38 activity, and/or p38 expression.

In another aspect, the present invention provides for a use of a compound formula I as described herein for the preparation of a medicament for decreasing the progression of a neurodegenerative disease or condition in a patient suffering therefrom comprising administering to said patient a therapeutically effective amount of a compound of formula I or a pharmaceutically acceptable salt thereof.

In another aspect, the present invention provides for a use of a compound formula I as described herein for the preparation of a medicament for decreasing the progression of a neurodegenerative disease or condition in a patient suffering therefrom comprising administering to said patient a therapeutically effective amount of a compound of formula I or a pharmaceutically acceptable salt thereof, wherein said neurodegenerative disease of condition is selected from the group consisting of: Alzheimer's disease, Huntington's disease, Parkinson's disease, Parkinson's-plus diseases, amyotrophic lateral sclerosis (ALS), ischemia, stroke, intracranial hemorrhage, cerebral hemorrhage, trigeminal neuralgia, glossopharyngeal neuralgia, Bell's Palsy, myasthenia gravis, muscular dystrophy, progressive muscular atrophy, primary lateral sclerosis (PLS), pseudobulbar palsy, progressive bulbar palsy, spinal muscular atrophy, inherited muscular atrophy, invertebrate disk syndromes, cervical spondylosis, plexus disorders, thoracic outlet destruction syndromes, peripheral neuropathies, prophyria, multiple system atrophy, progressive supranuclear palsy, corticobasal degeneration, dementia with Lewy bodies, frontotemporal dementia, demyelinating diseases, Guillain-Barré syndrome, multiple sclerosis, Charcot-Marie_Tooth disease, prion disease, Creutzfeldt-Jakob disease, Gerstmann-Sträussler-Scheinker syndrome (GSS), fatal familial insomnia (FFI), bovine spongiform encephalopathy, Pick's disease, epilepsy, AIDS demential complex, nerve damage caused by exposure to toxic compounds selected from the group consisting of heavy metals, industrial solvents, drugs and chemotherapeutic agents; injury to the nervous system caused by physical, mechanical or chemical trauma, glaucoma, lattice dystrophy, retinitis pigmentosa, age-related macular degeneration (AMD), photoreceptor degeneration associated with wet or dry AMD, other retinal degeneration, optic nerve drusen, optic neuropathy and optic neuritis.

In another aspect, the present invention provides for a use of a compound formula I as described herein for the preparation of a medicament for decreasing the progression of a neurodegenerative disease or condition in a patient suffering therefrom comprising administering to said patient a therapeutically effective amount of a compound of formula I or a pharmaceutically acceptable salt thereof, wherein said neurodegenerative disease of condition in a patient is selected from the group consisting of: Alzheimer's disease, Parkinson's disease, and amyotrophic lateral sclerosis (ALS).

DETAILED DESCRIPTION OF THE INVENTION

A. Definitions

As used herein, the term "alkyl", by itself or as part of another substituent, means, unless otherwise stated, a straight or branched chain hydrocarbon radical, having the number of carbon atoms designated (i.e., $C_{1-8}$ means one to eight carbons). Examples of alkyl groups include methyl, ethyl, n-propyl, iso-propyl, n-butyl, t-butyl, iso-butyl, sec-butyl, n-pentyl, n-hexyl, n-heptyl, n-octyl, and the like. The term "alkenyl" refers to an unsaturated alkyl radical having one or more double bonds. Similarly, the term "alkynyl" refers to an unsaturated alkyl radical having one or more triple bonds. Examples of such unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butyryl, and the higher homologs and isomers. The term "cycloalkyl," "carbocyclic," or "carbocycle" refers to hydrocarbon ring system having 3 to 10 overall number of ring atoms (i.e., 3-10 membered cycloalkyl) and being fully saturated or having no more than one double bond between ring vertices for a 3-5 membered cycloalkyl and being saturated or having no more than two double bonds between ring vertices for 6 or larger membered cycloalkyl. As used herein, "cycloalkyl," "carbocyclic," or "carbocycle" is also meant to refer to bicyclic, polycyclic and spirocyclic hydrocarbon ring system such as, for example, bicyclo[2.2.1]heptane, pinane, bicyclo[2.2.2]octane, adamantane, norborene, spirocyclic $C_{5-12}$ alkane, etc. As used herein, the terms, "alkenyl," "alkynyl," "cycloalkyl,", "carbocycle," and "carbocyclic," are meant to include mono and polyhalogenated variants thereof.

The term "heteroalkyl," by itself or in combination with another term, means, unless otherwise stated, a stable straight or branched chain hydrocarbon radical, consisting of the stated number of carbon atoms and from one to three heteroatoms selected from the group consisting of O, N, Si and S, and wherein the nitrogen and sulfur atoms can optionally be oxidized and the nitrogen heteroatom can optionally be quaternized. The heteroatom(s) O, N and S can be placed at any interior position of the heteroalkyl group. The heteroatom Si can be placed at any position of the heteroalkyl group, including the position at which the alkyl group is attached to the remainder of the molecule. A "heteroalkyl" can contain up to three units of unsaturation, and also include mono- and poly-halogenated variants, or combinations thereof. Examples include —$CH_2$—$CH_2$—O—$CH_3$, —$CH_2$—$CH_2$—O—$CF_3$, —$CH_2$—$CH_2$—NH—$CH_3$, —$CH_2$—$CH_2$—N($CH_3$)—$CH_3$, —$CH_2$—S—$CH_2$—$CH_3$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—O$CH_3$, and —CH=CH=N($CH_3$)—$CH_3$. Up to two heteroatoms can be consecutive, such as, for example, —$CH_2$—NH—O$CH_3$ and —$CH_2$—O—Si($CH_3$)$_3$.

The term "heterocycloalkyl", "heterocyclic," or "heterocycle" refers to a saturated or partially unsaturated ring system radical having from 3 to 10 overall number of ring atoms and containing from one to five heteroatoms selected from N, O, and S, wherein the nitrogen and sulfur atoms are optionally oxidized, nitrogen atom(s) are optionally quaternized, as ring atoms. Unless otherwise stated, a "heterocycloalkyl," "heterocyclic," or "heterocycle" ring system can be a monocyclic, a bicyclic, spirocyclic or a polycylic ring system. A "heterocycloalkyl," "heterocyclic," or "heterocycle" group can be attached to the remainder of the molecule through one or more ring carbons or heteroatoms. Non limiting examples of "heterocycloalkyl," "heterocyclic," or "heterocycle" rings include pyrrolidine, piperidine, N-methylpiperidine, imidazolidine, pyrazolidine, butyrolactam, valerolactam, imidazolidinone, hydantoin, dioxolane, phthalimide, piperidine, pyrimidine-2,4(1H,3H)-dione, 1,4-dioxane, morpholine, thiomorpholine, thiomorpholine-S-oxide, thiomorpholine-S, S-oxide, piperazine, pyran, pyridone, 3-pyrroline, thiopyran, pyrone, tetrahydrofuran, tetrahydrothiophene, quinuclidine, tropane, 2-azaspiro[3.3]heptane, (1R,5S)-3-azabicyclo [3.2.1]octane, (1s,4s)-2-azabicyclo[2.2.2]octane, (1R,4R)-2-oxa-5-azabicyclo[2.2.2]octane and the like. A "heterocycloalkyl," "heterocyclic," or "heterocycle" can include mono- and poly-halogenated variants thereof.

The term "alkylene" by itself or as part of another substituent means a divalent radical derived from an alkane, as exemplified by —$CH_2CH_2CH_2CH_2$—. Typically, an alkyl (or alkylene) group will have from 1 to 24 carbon atoms, with those groups having 10 or fewer carbon atoms being preferred in the present invention. "Alkenylene" and "alkynylene" refer to the unsaturated forms of "alkylene" having double or triple bonds, respectively. "Alkylene", "alkenylene" and "alkynylene" are also meant to include mono and poly-halogenated variants.

The term "heteroalkylene" by itself or as part of another substituent means a divalent radical, saturated or unsaturated or polyunsaturated, derived from heteroalkyl, as exemplified by —$CH_2$—$CH_2$—S—$CH_2CH_2$— and —$CH_2$—S—$CH_2$—$CH_2$—NH—$CH_2$—, —O—$CH_2$—CH=CH—, —$CH_2$—CH=C(H)$CH_2$—O—$CH_2$— and —S—$CH_2$—C≡C—. For heteroalkylene groups, heteroatoms can also occupy either or both of the chain termini (e.g., alkyleneoxy, alkylenedioxy, alkyleneamino, alkylenediamino, and the like). The term "heteroalkylene" is also meant to include mono and poly-halogenated variants.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively, and further include mono- and poly-halogenated variants thereof. Additionally, for dialkylamino groups, the alkyl portions can be the same or different.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$ haloalkyl" is mean to include trifluoromethyl, 2,2,2-trifluoroethyl, 4-chlorobutyl, 3-bromopropyl, difluoromethyl, and the like.

The term "aryl" means, unless otherwise stated, a polyunsaturated, typically aromatic, hydrocarbon ring, which can be a single ring or multiple rings (up to three rings) which are fused together. The term "heteroaryl" refers to aryl ring(s) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl groups include phenyl, naphthyl and biphenyl, while non-limiting examples of heteroaryl groups include pyridyl, pyridazinyl, pyrazinyl, pyrimindinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. Optional substituents for each of the above noted aryl and heteroaryl ring systems can be selected from the group of acceptable substituents described further below.

The above terms (e.g., "alkyl," "aryl" and "heteroaryl"), in some embodiments, will include both substituted and unsubstituted forms of the indicated radical. Preferred substituents for each type of radical are provided below.

Substituents for the alkyl radicals (including those groups often referred to as alkylene, alkenyl, alkynyl, heteroalkyl and cycloalkyl) can be a variety of groups including, but not limited to, -halogen, —OR', —NR'R", —SR', —SiR'R"R''', —OC(O)R', —C(O)R', —CO$_2$R', —CONR'R", —OC(O)NR'R", —NR"C(O)R', —NR"C(O)NR'R''', —NR"C(O)$_2$R', —NHC(NH$_2$)=NH, —NR'C(NH$_2$)=NH, —NHC(NH$_2$)=NR', —NR'''C(NR'R")=N—CN, —NR'''C(NR'R") =NOR', —NHC(NH$_2$)=NR', —S(O)R', —S(O)$_2$R', —S(O)$_2$NR'R", —NR'S(O)$_2$R", —NR'''S(O)$_2$NR'R", —CN, —NO$_2$, —(CH$_2$)$_{1-4}$—OR', —(CH$_2$)$_{1-4}$—NR'R", —(CH$_2$)$_{1-4}$—SR', —(CH$_2$)$_{1-4}$—SiR'R"R''', —(CH$_2$)$_{1-4}$—OC(O)R', —(CH$_2$)$_{1-4}$—C(O)R', —(CH$_2$)$_{1-4}$—CO$_2$R', —(CH$_2$)$_{1-4}$CONR'R", in a number ranging from zero to (2 m'+1), where m' is the total number of carbon atoms in such radical. R', R" and R''' each independently refer groups including, for example, hydrogen, unsubstituted $C_{1-6}$ alkyl, unsubstituted heteroalkyl, unsubstituted aryl, aryl substituted with 1-3 halogens, unsubstituted $C_{1-6}$ alkyl, $C_{1-6}$ alkoxy or $C_{1-6}$ thioalkoxy groups, or unsubstituted aryl-$C_{1-4}$ alkyl groups, unsubstituted heteroaryl, substituted heteroaryl, among others. When R' and R" are attached to the same nitrogen atom, they can be combined with the nitrogen atom to form a 3-, 4-, 5-, 6-, or 7-membered ring. For example, —NR'R" is meant to include 1-pyrrolidinyl and 4-morpholinyl. Other substituents for alkyl radicals, including heteroalkyl, alkylene, include for example, =O, =NR', =N—OR', =N—CN, =NH, wherein R' include substituents as described above. When a substituent for the alkyl radicals (including those groups often referred to as alkylene, alkenyl, alkynyl, heteroalkyl and cycloalkyl) contains an alkylene, alkenylene, alkynylene linker (e.g., —(CH$_2$)$_{1-4}$—NR'R" for alkylene), the alkylene linker includes halo variants as well. For example, the linker "—(CH$_2$)$_{1-4}$—" when used as part of a substituent is meant to include difluoromethylene, 1,2-difluoroethylene, etc.

Similarly, substituents for the aryl and heteroaryl groups are varied and are generally selected from the group including, but not limited to, -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'C(O)NR"R''', —NHC(NH$_2$)=NH, —NR'C(NH$_2$)=NH, —NHC(NH$_2$)=NR', —S(O)R', —S(O)$_2$R', —S(O)$_2$NR'R", —NR'S(O)$_2$R", —N$_3$, perfluoro-$C_{1-4}$ alkoxy, and perfluoro-$C_{1-4}$ alkyl, —(CH$_2$)$_{1-4}$—OR', —(CH$_2$)$_{1-4}$—NR'R", —(CH$_2$)$_{1-4}$—SR', —(CH$_2$)$_{1-4}$—SiR'R"R''', —(CH$_2$)$_{1-4}$—OC(O)R', —(CH$_2$)$_{1-4}$—C(O)R', —(CH$_2$)$_{1-4}$—CO$_2$R', —(CH$_2$)$_{1-4}$CONR'R", in a number ranging from zero to the total number of open valences on the aromatic ring system; and where R', R" and R''' are independently selected from hydrogen, $C_{1-6}$ alkyl, $C_{3-6}$ cycloalkyl, $C_{2-6}$ alkenyl, $C_{2-6}$ alkynyl, unsubstituted aryl and heteroaryl, (unsubstituted aryl)-$C_{1-4}$ alkyl, and unsubstituted aryloxy-$C_{1-4}$ alkyl. Other suitable substituents include each of the above aryl substituents attached to a ring atom by an alkylene tether of from 1-4 carbon atoms. When a substituent for the aryl or heteroaryl group contains an alkylene, alkenylene, alkynylene linker (e.g., —(CH$_2$)$_{1-4}$—NR'R" for alkylene), the alkylene linker includes halo variants as well. For example, the linker "—(CH$_2$)$_{1-4}$—" when used as part of a substituent is meant to include difluoromethylene, 1,2-difluoroethylene, etc.

As used herein, the term "heteroatom" is meant to include oxygen (O), nitrogen (N), sulfur (S) and silicon (Si).

As used herein, the term "chiral" refers to molecules which have the property of non-superimposability of the mirror image partner, while the term "achiral" refers to molecules which are superimposable on their mirror image partner.

As used herein, the term "stereoisomers" refers to compounds which have identical chemical constitution, but differ with regard to the arrangement of the atoms or groups in space.

As used herein a wavy line "∿∿∿" that intersects a bond in a chemical structure fragment indicates the point of attachment of the bond to which the wavy bond intersects in the chemical structure fragment to the remainder of a molecule or structural formula.

As used herein, the representation of a group (e.g., $X^d$) in parenthesis followed by a subscript integer range (e.g., $(X^d)_{0-2}$) means that the group can have the number of occurrences as designated by the integer range. For example, $(X^d)_{0-1}$ means the group $X^d$ can be absent or can occur one time.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers can separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. The compounds of the invention can contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer can also be referred to as an enantiomer, and a mixture of such isomers is often called an enantiomeric mixture. A 50:50 mixture of enantiomers is referred to as a racemic mixture or a racemate, which can occur where there has been no stereoselection or stereospecificity in a chemical reaction or process. The terms "racemic mixture" and "racemate" refer to an equimolar mixture of two enantiomeric species, devoid of optical activity.

As used herein, the term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

As used herein, the term "solvate" refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

As used herein, the term "protecting group" refers to a substituent that is commonly employed to block or protect a particular functional group on a compound. For example, an "amino-protecting group" is a substituent attached to an amino group that blocks or protects the amino functionality in the compound. Suitable amino-protecting groups include acetyl, trifluoroacetyl, t-butoxycarbonyl (BOC), benzyloxycarbonyl (CBZ) and 9-fluorenylmethylenoxycarbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include phenylsulfonylethyl, cyanoethyl, 2-(trimethylsilyl)ethyl, 2-(trimethylsilyl)ethoxymethyl, 2-(p-toluenesulfonyl)ethyl, 2-(p-nitrophenylsulfenyl)ethyl, 2-(diphenylphosphino)-ethyl, nitroethyl and the like. For a general description of protecting groups and their use, see P. G. M. Wuts and T. W. Greene, Greene's Protective Groups in Organic Synthesis 4$^{th}$ edition, Wiley-Interscience, New York, 2006.

As used herein, the term "mammal" includes, but is not limited to, humans, mice, rats, guinea pigs, monkeys, dogs, cats, horses, cows, pigs, and sheep As used herein, the term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al., "Pharmaceutical Salts", Journal of Pharmaceutical Science, 1977, 66, 1-19). Certain specific compounds of the present invention contain both basic and acidic functionalities that allow the compounds to be converted into either base or acid addition salts.

The neutral forms of the compounds can be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. As used herein the term "prodrug" refers to those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Prodrugs of the invention include compounds wherein an amino acid residue, or a polypeptide chain of two or more (e.g., two, three or four) amino acid residues, is covalently joined through an amide or ester bond to a free amino, hydroxy or carboxylic acid group of a compound of the present invention. The amino acid residues include but are not limited to the 20 naturally occurring amino acids commonly designated by three letter symbols and also includes phosphoserine, phosphothreonine, phosphotyrosine, 4-hydroxyproline, hydroxylysine, demosine, isodemosine, gamma-carboxyglutamate, hippuric acid, octahydroindole-2-carboxylic acid, statine, 1,2,3,4-tetrahydroisoquinoline-3-carboxylic acid, penicillamine, ornithine, 3-methylhistidine, norvaline, beta-alanine, gamma-aminobutyric acid, citrulline, homocysteine, homoserine, methyl-alanine, para-benzoylphenylalanine, phenylglycine, propargylglycine, sarcosine, methionine sulfone and tert-butylglycine.

Additional types of prodrugs are also encompassed. For instance, a free carboxyl group of a compound of the invention can be derivatized as an amide or alkyl ester. As another example, compounds of this invention comprising free hydroxy groups can be derivatized as prodrugs by converting the hydroxy group into a group such as, but not limited to, a phosphate ester, hemisuccinate, dimethylaminoacetate, or phosphoryloxymethyloxycarbonyl group, as outlined in Fleisher, D. et al., (1996) Improved oral drug delivery: solubility limitations overcome by the use of prodrugs Advanced Drug Delivery Reviews, 19:115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers, wherein the acyl group can be an alkyl ester optionally substituted with groups including, but not limited to, ether, amine and carboxylic acid functionalities, or where the acyl group is an amino acid ester as described above, are also encompassed. Prodrugs of this type are described in J. Med. Chem., (1996), 39:10. More specific examples include replacement of the hydrogen atom of the alcohol group with a group such as $(C_{1-6})$alkanoyloxymethyl, 1-$((C_{1-6})$alkanoyloxy)ethyl, 1-methyl-1-$((C_{1-6})$alkanoyloxy)ethyl, $(C_{1-6})$alkoxycarbonyloxymethyl, N—$(C_{1-6})$alkoxycarbonylaminomethyl, succinoyl, $(C_{1-6})$alkanoyl, alpha-amino $(C_{1-4})$alkanoyl, arylacyl and alpha-aminoacyl, or alpha-aminoacyl-alpha-aminoacyl, where each alpha-aminoacyl group is independently selected from the naturally occurring L-amino acids, $P(O)(OH)_2$, —$P(O)(O(C_{1-6})alkyl)_2$ or glycosyl (the radical resulting from the removal of a hydroxyl group of the hemiacetal form of a carbohydrate).

For additional examples of prodrug derivatives, see, for example, a) Design of Prodrugs, edited by H. Bundgaard, (Elsevier, 1985) and Methods in Enzymology, Vol. 42, p. 309-396, edited by K. Widder, et al. (Academic Press, 1985); b) A Textbook of Drug Design and Development, edited by Krogsgaard-Larsen and H. Bundgaard, Chapter 5 "Design and Application of Prodrugs," by H. Bundgaard p. 113-191 (1991); c) H. Bundgaard, Advanced Drug Delivery Reviews, 8:1-38 (1992); d) H. Bundgaard, et al., Journal of Pharmaceutical Sciences, 77:285 (1988); and e) N. Kakeya, et al., Chem. Pharm. Bull., 32:692 (1984), each of which is specifically incorporated herein by reference.

Additionally, the present invention provides for metabolites of compounds of the invention. As used herein, a "metabolite" refers to a product produced through metabolism in the body of a specified compound or salt thereof. Such products can result for example from the oxidation, reduction, hydrolysis, amidation, deamidation, esterification, deesterification, enzymatic cleavage, and the like, of the administered compound.

Metabolite products typically are identified by preparing a radiolabelled (e.g., $^{14}C$ or $^{3}H$) isotope of a compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention can exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention.

The compounds of the present invention can also contain unnatural proportions of atomic isotopes at one or more of the atoms that constitute such compounds. For example, the present invention also embraces isotopically-labeled variants of the present invention which are identical to those recited herein, bur the for the fact that one or more atoms are replace by an atom having the atomic mass or mass number different from the predominant atomic mass or mass number usually found in nature for the atom. All isotopes of any particular atom or element as specified are contemplated within the scope of the compounds of the invention, and their uses. Exemplary isotopes that can be incorporated in to compounds of the invention include isotopes of hydrogen, carbon, nitrogen, oxygen, phosphorous, sulfur, fluorine, chlorine and iodine, such as $^{2}H$ ("D"), $^{3}H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$ and $^{125}I$. Certain isotopically labeled compounds of the present invention (e.g., those labeled with $^{3}H$ or $^{14}C$) are useful in compound and/or substrate tissue distribution assays. Tritiated ($^{3}H$) and carbon-14 ($^{14}C$) isotopes are useful for their ease of preparation and detectability. Further substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Positron emitting isotopes such as $^{15}O$, 13N, $^{11}C$, and $^{18}F$ are useful for positron emission tomography (PET) studies to examine substrate receptor occupancy. Isotopically labeled compounds of the present inventions can generally be prepared by following procedures analogous to those disclosed in the Schemes and/or in the Examples herein below, by substituting an isotopically labeled reagent for a non-isotopically labeled reagent.

The terms "treat" and "treatment" refer to both therapeutic treatment and/or prophylactic treatment or preventative measures, wherein the object is to prevent or slow down (lessen) an undesired physiological change or disorder, such as, for example, the development or spread of cancer. For purposes of this invention, beneficial or desired clinical results include, but are not limited to, alleviation of symptoms, diminishment of extent of disease or disorder, stabilized (i.e., not worsening) state of disease or disorder, delay or slowing of disease progression, amelioration or palliation of the disease state or disorder, and remission (whether partial or total), whether detectable or undetectable. "Treatment" can also mean prolonging survival as compared to expected survival if not receiving treatment. Those in need of treatment include those already with the disease or disorder as well as those prone to have the disease or disorder or those in which the disease or disorder is to be prevented.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In some embodiments, a therapeutically effective amount is an amount of a chemical entity described herein sufficient to significantly decrease or delay neuronal cell death.

The term "administering" as used herein refers to contacting a neuron or portion thereof with a compound described herein. This includes administration of the compound to a subject in which the neuron or portion thereof is present, as well as introducing the inhibitor into a medium in which a neuron or portion thereof is cultured.

The term "patient" as used herein refers to any mammal, including humans, higher non-human primates, rodents domestic and farm animals such as cow, horses, dogs and cats. In one embodiment, the patient is a human patient.

The term "bioavailability" refers to the systemic availability (i.e., blood/plasma levels) of a given amount of drug administered to a patient. Bioavailability is an absolute term that indicates measurement of both the time (rate) and total amount (extent) of drug that reaches the general circulation from an administered dosage form.

The phrases "preventing axon degeneration," "preventing neuron degeneration," "preventing CNS neuron degeneration," "inhibiting axon degeneration," "inhibiting neuron degeneration" "inhibiting CNS neuron degeneration" as used herein include (i) the ability to inhibit or preserve axon or neuron degeneration in patients diagnosed as having a neurogenerative disease or risk of developing a neurodegenerative disease and (ii) the ability to inhibit or prevent further axon or neuron degeneration in patients who are already suffering from, or have symptoms of a neurodegenerative disease. Preventing axon or neuron degeneration includes decreasing or inhibiting axon or neuron degeneration, which may be characterized by complete or partial inhibition or neuron or axon degeneration. This can be assessed, for example, by analysis of neurological function. The above-listed terms also include in vitro and ex vivo methods. Further, the phrases "preventing neuron degeneration" and "inhibiting neuron degeneration" in clued such inhibition with respect to the entire neuron or a portion thereof, such as the neuron ell body, axons and dendrites. The administration of one or more agent as described herein may result in at least a 10% decrease (e.g., at least 15%, 20%, 25%, 30%, 35%, 40%, 45%, 50%, 55%, 60%, 65%, 70%, 75%, 80%, 85%, 90% or even 100% decrease in one or more symptoms of a disorder of the nervous system, a condition of the nervous system that is secondary to a disease, condition, or therapy having a primary effect outside of the nervous system; an injury to the nervous system caused by physical, mechanical or chemical trauma, pain; and ocular related neurodegeneration; memory loss; or a psychiatric disorder (e.g., tremors, slowness of movement, ataxia, loss of balance, depression, decreased cognitive function, short term memory loss, long term memory loss, confusion, changes in personality, language difficulties, loss of sensory perception, sensitivity to touch, numbness in extremities, muscle weakness, muscle paralysis, muscle cramps, muscle spasms, significant changes in eating habits, excessive fear or worry, insomnia, delusions, hallucinations, fatigue, back pain, chest pain, digestive problems, headache, rapid heart rate, dizziness, blurred vision, shadows or missing areas of vision, metamorphopsia, impairment in color vision, decreased recovery of visual function after exposure to bright light, and loss in visual contrast sensitivity) in a subject or population compared to a control subject or population that does not receive the one or more agent described herein. The administration of one or more agent as described herein may result in at least a 10% decrease (e.g., at least 15%, 20%, 25%, 30%, 35%, 40%, 45%, 50%, 55%, 60%, 65%, 70%, 75%, 80%, 85%, 90%, 95%, or even 100% decrease) in the number of neurons (or neuron bodies, axons, or dendrites thereof) that degenerate in a neuron population or in a subject compared to the number of neurons (or neuron bodies, axons, or dendrites thereof) that degenerate in neuron population or in a subject that is not administered the one or more of the agents described herein. The administration of one or more agent as described herein may result in at least a 10% decrease (e.g., at least 15%, 20%, 25%, 30%, 35%, 40%, 45%, 50%, 55%, 60%, 65%, 70%, 75%, 80%, 85%, 90%, 95%, or even 100% decrease) in the likelihood of developing a disorder of the nervous system; a condition of the nervous system that is secondary to a disease, condition, or therapy having a primary effect outside of the nervous system; an injury to the nervous system caused by physical, mechanical, or chemical trauma, pain; an ocular-related neurodegeneration; memory loss; or a psychiatric disorder in a subject or a subject population compared to a control subject or population not treated with the one or more compounds described herein.

The term "neuron" as used herein denotes nervous system cells that include a central cell body or soma, and two types of extensions or projections: dendrites, by which, in general, the majority of neuronal signals are conveyed to the cell body, and axons, by which, in general, the majority of neuronal signals are conveyed from the cell body to effector cells, such as target neurons or muscle. Neurons can convey information from tissues and organs into the central nervous system (afferent or sensory neurons) and transmit signals from the central nervous systems to effector cells (efferent or motor neurons). Other neurons, designated interneurons, connect neurons within the central nervous system (the brain and spinal column). Certain specific examples of neuron types that may be subject to treatment according to the invention include cerebellar granule neurons, dorsal root ganglion neurons, and cortical neurons.

Table 3 list registry numbers and corresponding structures.

TABLE 3

| Registry No. | Structure |
| --- | --- |
| 1286775-49-2 | (structure depicted) |

TABLE 3-continued

| Registry No. | Structure |
|---|---|
| 1268247-50-2 | 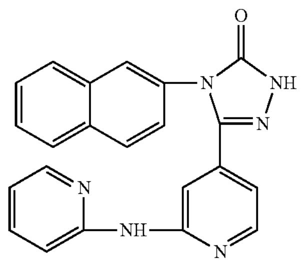 [SMILES: O=c1[nH]nc(-c2ccnc(Nc3ccccn3)c2)n1-c1ccc2ccccc2c1] |
| 909291-41-4 | 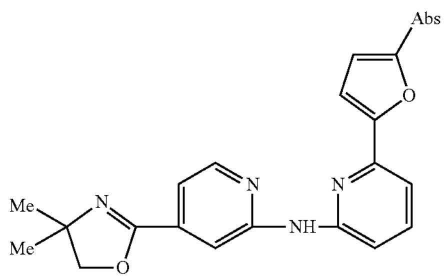 |

B. Compounds

In one aspect the invention are provided compounds of Formula (I)

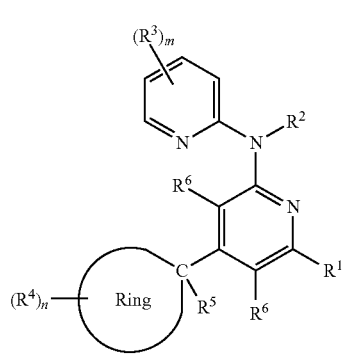

(I)

wherein $R^1$ is selected from the group consisting of hydrogen, fluoro, chloro, bromo, $C_{1-6}$ alkyl, $C_{1-6}$ haloalkyl, $C_{1-6}$ heteroalkyl, $C_{1-6}$ alkoxy, 3-10 membered cycloalkyl, 3-10 membered heterocycloalkyl, 6-10 membered aryl, 5-10 membered heteroaryl, $-OR^{1a}$, $-SR^{1a}$, $-N(H)(R^{1a})$, and $-N(R^{1a})(R^{1b})$ wherein $R^{1a}$ and $R^{1b}$ are each independently selected from the group consisting of $C_{1-6}$ alkyl, $C_{1-6}$ haloalkyl, $C_{1-6}$ heteroalkyl, 3-10 membered cycloalkyl and 3-10 membered heterocycloalkyl, and wherein the aliphatic and aromatic portions of $R^1$ are independently further substituted with 0 to 5 $R^{41}$ substituents selected from the group consisting of —F, —Cl, —Br, —I, —CN, —NO₂, —SF₅, —OH, —NH₂, —CF₃, =O, $C_{1-4}$ alkyl, $C_{1-4}$ haloalkyl, $C_{1-4}$ heteroalkyl, $C_{1-4}$ alkoxy, $C_{1-4}$ alkylthio, $C_{1-4}$ alkylamino, $C_{1-4}$ dialkylamino, $R^{1c}$—C(=O)—, $R^{1c}$—C(=O)N(H)—, $R^{1c}$—C(=O)N($R^{1d}$)—, $R^{1c}$—C(O)O—, $R^{1c}$—S(O)$_{1-2}$—, $R^{1c}$—S(O)$_{1-2}$N($R^{1d}$)—, $R^{1c}$—S(O)$_{1-2}$N(H)—, 3-6 membered cycloalkyl, phenyl, 5-6 membered heteroaryl and 3-7 membered heterocycloalkyl, wherein $R^{1c}$ is selected from the group consisting of $C_{1-6}$ alkyl, $C_{1-6}$ haloalkyl, $C_{5-6}$ heteroaryl, 3-7 membered heterocycloalkyl, phenyl and 3-6 membered cycloalkyl, $R^{1d}$ is selected from the group consisting of hydrogen, $C_{1-3}$ alkyl and $C_{1-3}$ haloalkyl, and wherein said 5-6 membered heteroaryl, phenyl, 3-6 membered cycloalkyl and 3-7 membered heterocycloalkyl of a $R^{41}$ substituent are substituted with from 0-4 substituents selected from —F, —Cl, —Br, I, —CN, —NO₂, —SF₅, —OH, —NH₂, —CF₃, $C_{1-4}$ alkyl, $C_{1-4}$ haloalkyl, $C_{1-4}$ alkoxy, $C_{1-4}$ alkylthio, $C_{1-4}$ alkylamino and $C_{1-4}$ dialkylamino;

$R^2$ is selected from the group consisting of hydrogen, $C_{1-6}$ alkyl and $C_{1-6}$ haloalkyl;

$R^3$ is selected from the group consisting of —F, —Cl, —Br, —I, —$(X^3)_{0-1}$—CN, —$(X^3)_{0-1}$—NO₂, —$(X^3)_{0-1}$—SF₅, —$(X^3)_{0-1}$—OH, —$(X^3)_{0-1}$—NH₂, —$(X^3)_{0-1}$—N(H)($R^{3a}$), —$(X^3)_{0-1}$—N($R^{3b}$)($R^{3a}$), —$(X^3)_{0-1}$—CF₃, —S-(Phenyl), $C_{1-6}$ alkyl, $C_{1-6}$ haloalkyl, $C_{1-6}$ heteroalkyl, $C_{1-6}$ alkoxy, $C_{1-6}$ alkylthio, —$(X^3)_{0-1}$-3-7 membered cycloalkyl, —$(X^3)_{0-1}$-3-7 membered heterocycloalkyl, —$(X^3)_{0-1}$-5-6 membered heteroaryl, —$(X^3)_{0-1}$—$C_6$ aryl, —$(X^3)_{0-1}$—C(=$Y^3$)N(H)($R^{3a}$), —$(X^3)_{0-1}$—C(=$Y^3$)NH₂, —$(X^3)_{0-1}$—C(=$Y^3$)N($R^{3a}$)($R^{3b}$), —$(X^3)_{0-1}$—C(=$Y^3$)O$R^{3a}$, —$(X^3)_{0-1}$—C(=$Y^3$)OH, —$(X^3)_{0-1}$—N(H)C(=$Y^3$)($R^{3a}$), —$(X^3)_{0-1}$—N($R^{3b}$)C(=$Y^3$)($R^{3a}$), —$(X^3)_{0-1}$—N(H)C(=$Y^3$)O$R^{3a}$, —$(X^3)_{0-1}$—N($R^{3b}$)C(=$Y^3$)O$R^{3a}$, —$(X^3)_{0-1}$—S(=$Y^3$)$_{1-2}R^{3a}$, —$(X^3)_{0-1}$—N(H)S(=$Y^3$)$_{1-2}R^{3a}$, —$(X^3)_{0-1}$—N($R^{3b}$)S(=$Y^3$)$_{1-2}R^{3a}$, —$(X^3)_{0-1}$—S(=$Y^3$)$_{1-2}$N(H)($R^{3a}$), —$(X^3)_{0-1}$—S(=$Y^3$)$_{1-2}$N($R^{3b}$)($R^{3a}$), —$(X^3)_{0-1}$—S(=$Y^3$)$_{1-2}$NH₂, —$(X^3)_{0-1}$—C(=$Y^3$)$R^{3a}$, —$(X^3)_{0-1}$—C(=$Y^3$)H, —$(X^3)_{0-1}$—C(=NOH)$R^{3a}$, —$(X^3)_{0-1}$—C(=NO$R^{3b}$)$R^{3a}$, —$(X^3)_{0-1}$—NHC(=$Y^3$)N(H)($R^{3a}$), —$(X^3)_{0-1}$—NHC(=$Y^3$)NH₂, —$(X^3)_{0-1}$—NHC(=$Y^3$)N($R^{3b}$)($R^{3a}$), —$(X^3)_{0-1}$—N($R^{3a}$)C(=$Y^3$)N(H)($R^{3a}$), —$(X^3)_{0-1}$—N($R^{3a}$)C(=$Y^3$)NH₂, —$(X^3)_{0-1}$—OC(=$Y^3$)$R^{3a}$, —$(X^3)_{0-1}$—OC(=$Y^3$)H, —$(X^3)_{0-1}$—OC(=$Y^3$)O$R^{3a}$, —$(X^3)_{0-1}$—OP(=$Y^3$)(O$R^{3a}$)(O$R^{3b}$), —$(X^3)$—SC(=$Y^3$)O$R^{3a}$ and —$(X^3)$—SC(=$Y^3$)N($R^{3a}$)($R^{3b}$) wherein $X^3$ is selected from the group consisting of $C_{1-4}$ alkylene, $C_{1-4}$ haloalkylene, $C_{1-4}$ heteroalkylene, $C_{2-4}$ alkenylene, and $C_{2-4}$ alkynylene, $R^{3a}$ and $R^{3b}$ are each independently selected from the group consisting of $C_{1-6}$ alkyl, $C_{1-6}$ haloalkyl, $C_{1-6}$ heteroalkyl, 3-7 membered cycloalkyl, 3-7 membered cycloalkyl-$C_{1-4}$ alkyl, 3-7 membered heterocycloalkyl, 3-7 membered heterocycloalkyl-$C_{1-4}$ alkyl, 5-6 membered heteroaryl, 5-6 membered heteroaryl-$C_{1-4}$ alkyl, $C_6$ aryl, $C_6$ aryl-$C_{1-4}$ alkyl and benzyl; $Y^3$ is O, $NR^{3d}$ or S wherein $R^{3d}$ is hydrogen or $C_{1-6}$ alkyl; wherein aliphatic or aromatic portion of $R^3$ is independently further substituted with from 0 to 4 $R^{43}$ substituents selected from the group consisting of —F, —Cl, —Br, —I, —CN, —NO₂, —SF₅, —OH, —NH₂, —CF₃, =O, $C_{1-6}$ alkyl, $C_{1-6}$ haloalkyl, $C_{1-6}$ heteroalkyl, $C_{1-6}$ alkoxy, $C_{1-6}$ alkylthio, 3-6 membered cycloalkyl, 3-6 membered heterocycloalkyl, —C(=O)N(H)($C_{1-6}$ alkyl), —C(=O)N($C_{1-6}$ alkyl)₂, —C(=O)NH₂, —C(=O)O$C_{1-6}$ alkyl, —C(=O)OH, —N(H)C(=O)($C_{1-6}$ alkyl), —N($C_{1-6}$ alkyl)C(=O)($C_{1-6}$ alkyl), —N(H)C(=O)O$C_{1-6}$ alkyl, —N($C_{1-6}$ alkyl)C(=O)O$C_{1-6}$ alkyl, —S(O)$_{1-2}C_{1-6}$ alkyl, —N(H)S(O)$_{1-2}C_{1-6}$ alkyl, —N($C_{1-6}$ alkyl)S(O)$_{1-2}C_{1-6}$ alkyl, —S(O)$_{0-1}$N(H)($C_{1-6}$ alkyl), —S(O)$_{0-1}$N($C_{1-6}$ alkyl)₂, —S(O)$_{0-1}$NH₂, —C(=O)$C_{1-6}$ alkyl, —C(=NOH)$C_{1-6}$ alkyl, —C(=NO$C_{1-6}$ alkyl)$C_{1-6}$ alkyl, —NHC(=O)N(H)($C_{1-6}$ alkyl), —NHC(=O)N($C_{1-6}$ alkyl)₂, —NHC(=O)NH₂, —N($C_{1-6}$ alkyl)C(=O)N(H)($C_{1-6}$ alkyl), —N($C_{1-6}$ alkyl)C(=O)NH₂, —OC(=O)$C_{1-6}$ alkyl, —OC(=O)O$C_{1-6}$ alkyl, —OP(=O)(O$C_{1-6}$ alkyl)₂, —SC(=O)O$C_{1-6}$ alkyl and —SC(=O)N($C_{1-6}$ alkyl)₂; alternatively any two $R^3$ substituents located on adjacent atoms are optionally combined to form a 5-6 membered heteroaryl ring comprising 1-2 heteroatoms selected from N, O and S and further comprising 0 to 4 $R^{3a}$ substituents;

m is an integer from 0 to 4;

the ring represented by the structure

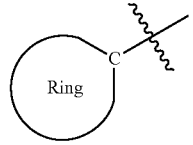 [SMILES: *C(C)C]

is a 4 to 10 membered C-linked heterocyclic ring comprising 1 to 2 heteroatoms selected from N, O and S, or is a 3 to 10 membered cycloalkyl ring, wherein the ring represented by said structure is optionally substituted with 1 to 3 $R^4$ groups;

$R^4$ is selected from the group consisting of —F, —Cl, —Br, —I, —$(X^4)_{0-1}$—CN, —$(X^4)_{0-1}$—$NO_2$, —$(X^4)_{0-1}$—$SF_5$, —$(X^4)_{0-1}$—OH, —$(X^4)_{0-1}$—$NH_2$, —$(X^4)_{0-1}$—N(H)($R^{4a}$), —$(X^4)_{0-1}$—N($R^{4b}$)($R^{4a}$), —$(X^4)_{0-1}$—$CF_3$, $C_{1-6}$ alkyl, $C_{1-6}$ haloalkyl, $C_{1-6}$ heteroalkyl, $C_{1-6}$ alkoxy, $C_{1-6}$ alkylthio, —$(X^4)_{0-1}$-(3-10 membered heterocycloalkyl), —$(X^4)_{0-1}$-(5-10 membered heteroaryl), —$(X^4)_{0-1}$-(3-7 membered cycloalkyl), —$(X^4)_{0-1}$-(6-10 membered aryl), —$(X^4)_{0-1}$—C(=$Y^4$)N(H)($R^{4a}$), —$(X^4)_{0-1}$—C(=$Y^4$)$NH_2$, —$(X^4)_{0-1}$—C(=$Y^4$)N($R^{4a}$)($R^{4b}$), —$(X^4)_{0-1}$—C(=$Y^4$)$OR^{4a}$, —$(X^4)_{0-1}$—C(=$Y^4$)OH, —$(X^4)_{0-1}$—N(H)C(=$Y^4$)($R^{4a}$), —$(X^4)_{0-1}$—N($R^{4b}$)C(=$Y^4$)($R^{4a}$), —$(X^4)_{0-1}$—N(H)C(=$Y^4$)$OR^{4a}$, —$(X^4)_{0-1}$—N($R^{4b}$)C(=$Y^4$)$OR^4$, —$(X^4)_{0-1}$—S(=$Y^4$)$_{1-2}R^{4a}$, —$(X^4)_{0-1}$—N(H)S(=$Y^4$)$_{1-2}R^{4a}$, —$(X^4)_{0-1}$—N($R^{4b}$)S(=$Y^4$)$_{1-2}R^{4a}$, —$(X^4)_{0-1}$—S(=$Y^4$)$_{1-2}$N(H)($R^{4a}$), —$(X^4)_{0-1}$—S(=$Y^4$)$_{1-2}$N($R^{4b}$)($R^{4a}$), —$(X^4)_{0-1}$—S(=$Y^4$)$_{1-2}NH_2$, —$(X^4)_{0-1}$—C(=$Y^4$)$R^{4a}$, —$(X^4)_{0-1}$—C(=$Y^4$)H, —$(X^4)_{0-1}$—C(=NOH)$R^{4a}$, —$(X^4)_{0-1}$—C(=$NOR^{4b}$)$R^{4a}$, —$(X^4)_{0-1}$—NHC(=$Y^4$)N(H)($R^{4a}$), —$(X^4)_{0-1}$—NHC(=$Y^4$)$NH_2$, —$(X^4)_{0-1}$—NHC(=$Y^4$)N($R^{4b}$)($R^{4a}$), —$(X^4)_{0-1}$—$NR^{4a}$C(=$Y^4$)N(H)($R^{4a}$), —$(X^4)_{0-1}$—N($R^{4a}$)C(=$Y^4$)$NH_2$, —$(X^4)_{0-1}$—OC(=$Y^4$)$R^{4a}$, —$(X^4)_{0-1}$—OC(=$Y^4$)H, —$(X^4)_{0-1}$—OC(=$Y^4$)$OR^{4a}$, —$(X^4)_{0-1}$—OP(=$Y^4$)($OR^{4a}$)($OR^{4b}$), —SC(=$Y^4$)$OR^{4a}$ and —SC(=$Y^4$)N($R^{4a}$)($R^{4b}$) wherein $R^{4a}$ and $R^{4b}$ at each occurrence are each independently selected from the group consisting of $C_{1-6}$ alkyl, $C_{1-6}$ haloalkyl, $C_{1-6}$ heteroalkyl, 6-10 membered aryl, 3-7 membered cycloalkyl, 5-10 membered heteroaryl, 3-7 membered heterocycloalkyl, 6-10 membered aryl-$C_{1-4}$ alkyl, 3-7 membered cycloalkyl-$C_{1-4}$ alkyl, 5-10 membered heteroaryl-$C_{1-4}$ alkyl and 3-7 membered heterocycloalkyl-$C_{1-4}$ alkyl, and $X^4$ is selected from the group consisting of $C_{1-4}$ alkylene, $C_{1-4}$ haloalkylene, $C_{1-4}$ heteroalkylene, $C_{2-4}$ alkenylene and $C_{2-4}$ alkynylene; $Y^4$ is O, $NR^{4c}$ or S wherein $R^{4c}$ is hydrogen or $C_{1-6}$ alkyl; wherein the aromatic and aliphatic portions of $R^4$ is independently further substituted with 0 to 4 $R^{44}$ substituents selected from the group consisting of —F, —Cl, —Br, I, —CN, —$NO_2$, —$SF_5$, —OH, —$NH_2$, —$CF_3$, =O, $C_{1-6}$ alkyl, $C_{1-6}$ haloalkyl, $C_{1-6}$ heteroalkyl, $C_{1-6}$ alkoxy, $C_{1-6}$ alkylthio, 3-6 membered cycloalkyl, 3-6 membered heterocycloalkyl, —C(=O)N(H)($C_{1-6}$ alkyl), —C(=O)N($C_{1-6}$ alkyl)$_2$, —C(=O)$NH_2$, —C(=O)O$C_{1-6}$ alkyl, —C(=O)OH, —N(H)C(=O)($C_{1-6}$ alkyl), —N($C_{1-6}$ alkyl)C(=O)($C_{1-6}$ alkyl), —N(H)C(=O)O$C_{1-6}$ alkyl, —N($C_{1-6}$ alkyl)C(=O)O$C_{1-6}$ alkyl, —S(O)$_{1-2}C_{1-6}$ alkyl, —N(H)S(O)$_{1-2}C_{1-6}$ alkyl, —N($C_{1-6}$ alkyl)S(O)$_{1-2}C_{1-6}$ alkyl, —S(O)$_{0-1}$N(H)($C_{1-6}$ alkyl), —S(O)$_{0-1}$N($C_{1-6}$ alkyl)$_2$, —S(O)$_{0-1}NH_2$, —C(=O)$C_{1-6}$ alkyl, —C(=NOH)$C_{1-6}$ alkyl, —C(=NO$C_{1-6}$ alkyl)$C_{1-6}$ alkyl, —NHC(=O)N(H)($C_{1-6}$ alkyl), —NHC(=O)N($C_{1-6}$ alkyl)$_2$, —NHC(=O)$NH_2$, —N($C_{1-6}$ alkyl)C(=O)N(H)($C_{1-6}$ alkyl), —N($C_{1-6}$ alkyl)C(=O)$NH_2$, —OC(=O)$C_{1-6}$ alkyl, —OC(=O)O$C_{1-6}$ alkyl, —OP(=O)(O$C_{1-6}$ alkyl)$_2$, —SC(=O)O$C_{1-6}$ alkyl and —SC(=O)N($C_{1-6}$ alkyl)$_2$;

n is an integer from 0 to 5;

$R^5$ is absent or is selected from the group consisting of hydrogen, $C_{1-6}$ alkyl, $C_{1-6}$ haloalkyl, —OH, $OR^{5a}$, —CN and halogen, wherein $R^{5a}$ is selected from the group consisting of $C_{1-6}$ alkyl, $C_{1-6}$ haloalkyl and $C_{1-6}$ heteroalkyl; or optionally $R^4$ and $R^5$ are optionally combined to form a 5-7 membered cycloalkyl or heterocycloalkyl and is independently further substituted with 0-4 $R^{44}$ substituents;

$R^6$ is independently selected from the group consisting of hydrogen, —F, Cl, Br, I, $C_{1-3}$ alkyl, $C_{1-3}$haloalkyl; and with the proviso that compounds having the Chemical Abstract Service (CAS) registry numbers selected from the group consisting of 1286775-49-2, 1268247-50-2, 909291-41-4; and compounds wherein the C-linked ring is 1,3-dioxolane are not included.

In one embodiment, a compound of formula I has the subformula selected from the group consisting of:

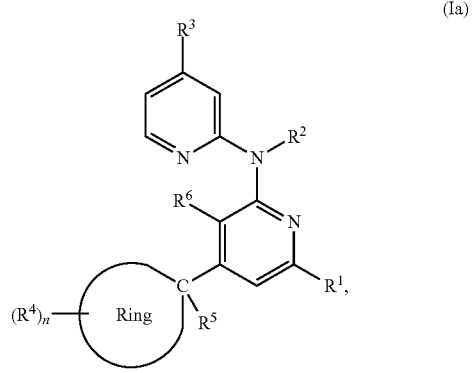

(Ia)

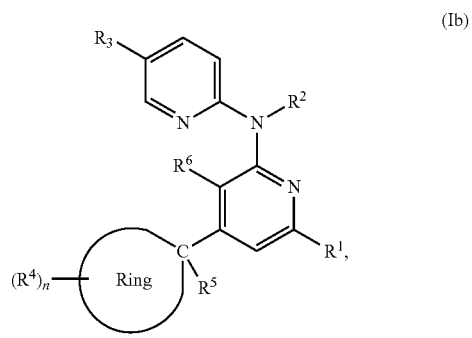

(Ib)

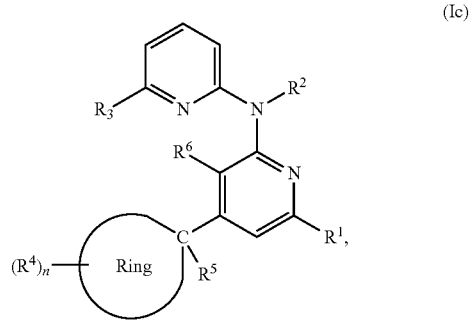

(Ic)

-continued

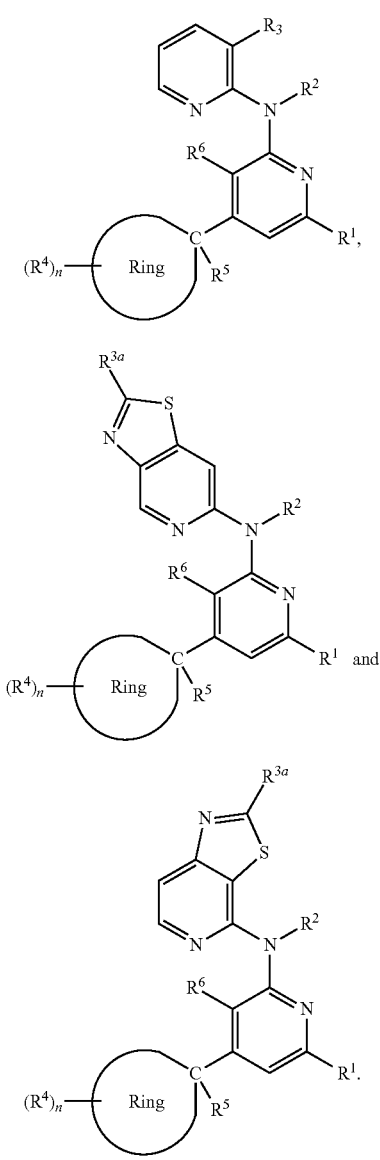

In another embodiment, a compound of formula I has the subformula (Ia).

In another embodiment, in compounds of formula I, the ring represented by

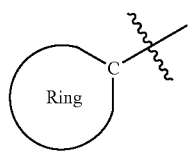 [SMILES: *C(C)C]

is an optionally substituted C-linked 4 to 10 membered heterocyclic ring selected from the group consisting of morpholine, morpholinone, piperazine, piperazinone, thiomorpholine, thiomorpholinone, homopiperidine, homopiperidinone, piperidine, valerolactam, pyrrolidine, butyrolactam, azetidine, azetidinone, thiazepane-1,1-dioxide, thiazinane-1,1-dioxide, isothiazolidine-1,1-dioxide, pyridinone, tetrahydropyran, oxetane and tetrahydrofuran attached to the remainder of the compound represented by formula I.

In another embodiment, in compounds of formula I, the ring represented by the structure

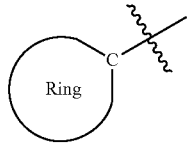 [SMILES: *C(C)C]

is selected from the group consisting of:

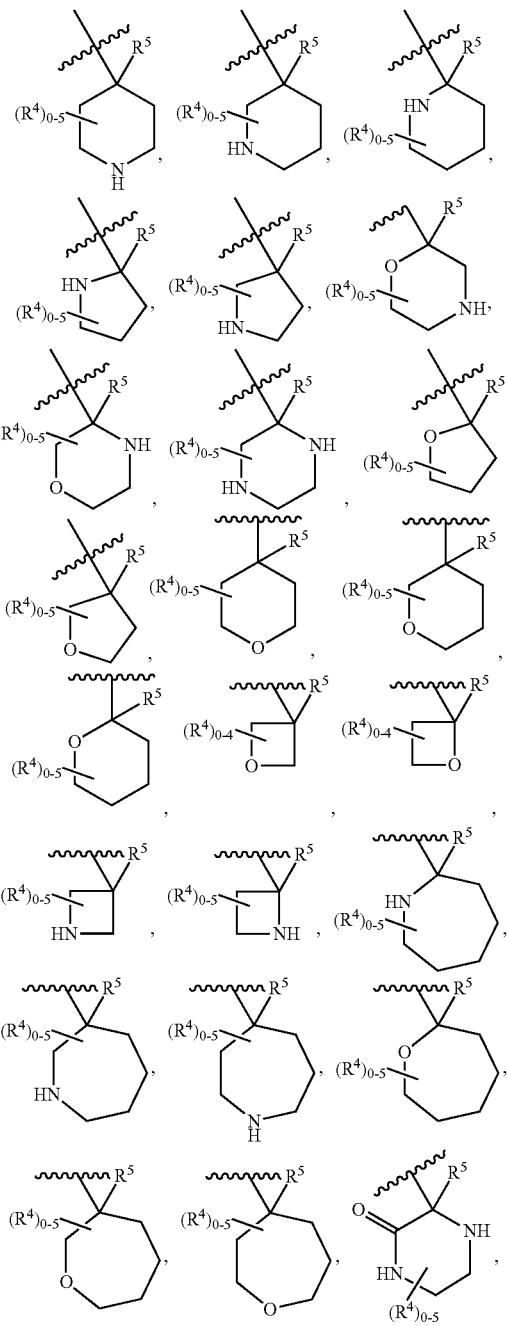

-continued
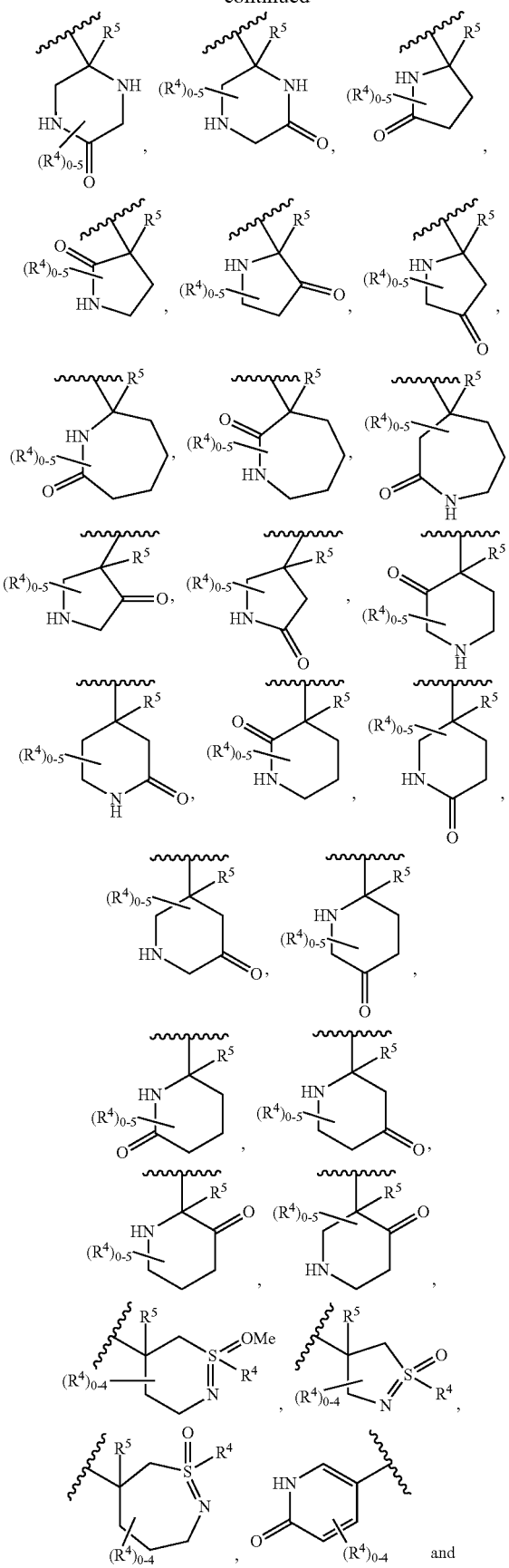
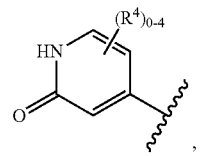
wherein a $R^4$ substituent, if present, replaces a hydrogen atom that is attached to a carbon or nitrogen atom in said ring.
In another embodiment, in compounds of formula I, the ring
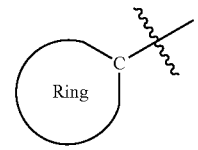
is selected from the group consisting of:
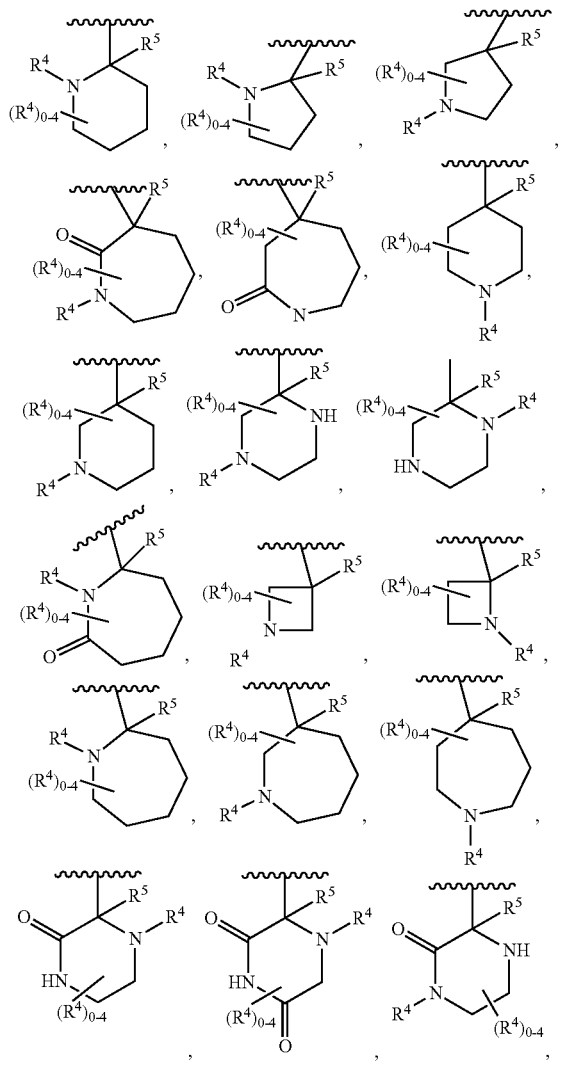

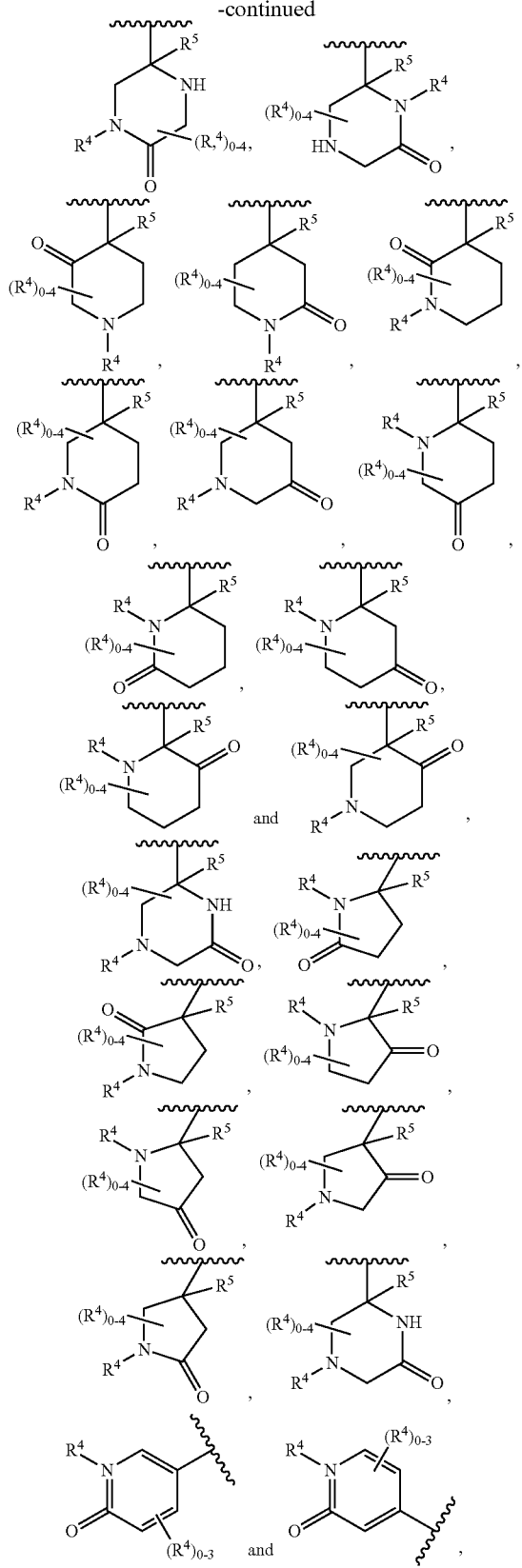

wherein R⁴ attached to the nitrogen atom of said ring is selected from the group consisting of —(X⁴)₀₋₁—CN, —(X⁴)₀₋₁—NO₂, —(X⁴)₀₋₁—SF₅, —(X⁴)₀₋₁—OH, —(X⁴)₀₋₁—NH₂, —(X⁴)₀₋₁—N(H)(R⁴ᵃ), —(X⁴)₀₋₁—N(R⁴ᵇ)(R⁴ᵃ), —(X⁴)₀₋₁—CF₃, C₁₋₆ alkyl, C₁₋₆ haloalkyl, C₁₋₆ heteroalkyl, C₁₋₆ alkoxy, C₁₋₆ alkylthio, —(X⁴)₀₋₁-(3-10 membered heterocycloalkyl), —(X⁴)₀₋₁-(5-10 membered heteroaryl), —(X⁴)₀₋₁-(3-7 membered cycloalkyl), —(X⁴)₀₋₁—C(=Y⁴)N(H)(R⁴ᵃ), —(X⁴)₀₋₁—C(=Y⁴)NH₂, —(X⁴)₀₋₁—C(=Y⁴)N(R⁴ᵃ)(R⁴ᵇ), —(X⁴)₀₋₁—C(=Y⁴)OR⁴ᵃ, —(X⁴)₀₋₁—C(=Y⁴)OH, —(X⁴)₀₋₁—N(H)C(=Y⁴)(R⁴ᵃ), —(X⁴)₀₋₁—N(R⁴ᵇ)C(=Y⁴)(R⁴ᵃ), —(X⁴)₀₋₁—N(H)C(=Y⁴)OR⁴ᵃ, —(X⁴)₀₋₁—N(R⁴ᵇ)C(=Y⁴)OR⁴ᵃ, —(X⁴)₀₋₁—S(O)₁₋₂R⁴ᵃ, —(X⁴)₀₋₁—N(H)S(O)₁₋₂R⁴ᵃ, —(X⁴)₀₋₁—N(R⁴ᵇ)S(O)₁₋₂R⁴ᵃ, —(X⁴)₀₋₁—S(O)₀₋₁N(H)(R⁴ᵃ), —(X⁴)₀₋₁—S(O)₀₋₁N(R⁴ᵇ)(R⁴ᵃ), —(X⁴)₀₋₁—S(O)₀₋₁NH₂, —(X⁴)₀₋₁—S(=O)(=NR⁴ᵇ)R⁴ᵃ, —(X⁴)₀₋₁—C(=Y⁴)R⁴ᵃ, —(X⁴)₀₋₁—C(=Y⁴)H, —(X⁴)₀₋₁—C(=NOH)R⁴ᵃ, —(X⁴)₀₋₁—C(=NOR⁴ᵇ)R⁴ᵃ, —(X⁴)₀₋₁—NHC(=Y⁴)N(H)(R⁴ᵃ), —(X⁴)₀₋₁—NHC(=Y⁴)NH₂, —(X⁴)₀₋₁—NHC(=Y⁴)N(R⁴ᵇ)(R⁴ᵃ), —(X⁴)₀₋₁—NR⁴ᵃC(=Y⁴)N(H)(R⁴ᵃ), —(X⁴)₀₋₁—N(R⁴ᵃ)C(=Y⁴)NH₂, —(X⁴)₀₋₁—OC(=Y⁴)R⁴ᵃ, —(X⁴)₀₋₁—OC(=Y⁴)H, —(X⁴)₀₋₁-0° C. (=Y⁴)OR⁴ᵃ, —(X⁴)₀₋₁—OP(=Y⁴)(OR⁴ᵃ)(OR⁴ᵇ), —SC(=Y⁴)OR⁴ᵃ and —SC(=Y⁴)N(R⁴ᵃ)(R⁴ᵇ) wherein R⁴ᵃ and R⁴ᵇ at each occurrence are each independently selected from the group consisting of C₁₋₆ alkyl, C₁₋₆ haloalkyl, C₁₋₆ heteroalkyl, 6-10 membered aryl, 3-7 membered cycloalkyl, 5-10 membered heteroaryl, 3-7 membered heterocycloalkyl, 6-10 membered aryl-C₁₋₄ alkyl, 3-7 membered cycloalkyl-C₁₋₄ alkyl, 5-10 membered heteroaryl-C₁₋₄ alkyl and 3-7 membered heterocycloalkyl-C₁₋₄ alkyl, and X⁴ is selected from the group consisting of C₁₋₄ alkylene, C₁₋₄ haloalkylene, C₁₋₄ heteroalkylene, C₂₋₄ alkenylene and C₂₋₄ alkynylene; Y⁴ is O, NR⁴ᶜ or S wherein R⁴ᶜ is hydrogen or C₁₋₆ alkyl; wherein the aromatic and aliphatic portions of R⁴ is independently further substituted with 0 to 4 R⁴⁴ substituents selected from the group consisting of —F, —Cl, —Br, I, —CN, —NO₂, —SF₅, —OH, —NH₂, —CF₃, =O, C₁₋₆ alkyl, C₁₋₆ haloalkyl, C₁₋₆ heteroalkyl, C₁₋₆ alkoxy, C₁₋₆ alkylthio, 3-6 membered cycloalkyl, 3-6 membered heterocycloalkyl, —C(=O)N(H)(C₁₋₆ alkyl), —C(=O)N(C₁₋₆ alkyl)₂, —C(=O)NH₂, —C(=O)OC₁₋₆ alkyl, —C(=O)OH, —N(H)C(=O)(C₁₋₆ alkyl), —N(C₁₋₆ alkyl)C(=O)(C₁₋₆ alkyl), —N(H)C(=O)OC₁₋₆ alkyl, —N(C₁₋₆ alkyl)C(=O)OC₁₋₆ alkyl, —S(O)₁₋₂C₁₋₆ alkyl, —N(H)S(O)₁₋₂C₁₋₆ alkyl, —N(C₁₋₆ alkyl)S(O)₁₋₂C₁₋₆ alkyl, —S(O)₀₋₁N(H)(C₁₋₆ alkyl), —S(O)₀₋₁N(C₁₋₆ alkyl)₂, —S(O)₀₋₁NH₂, —C(=O)C₁₋₆ alkyl, —C(=NOH)C₁₋₆ alkyl, —C(=NOC₁₋₆ alkyl)C₁₋₆ alkyl, —NHC(=O)N(H)(C₁₋₆ alkyl), —NHC(=O)N(C₁₋₆ alkyl)₂, —NHC(=O)NH₂, —N(C₁₋₆ alkyl)C(=O)N(H)(C₁₋₆ alkyl), —N(C₁₋₆ alkyl)C(=O)NH₂, —OC(=O)C₁₋₆ alkyl, —OC(=O)OC₁₋₆ alkyl, —OP(=O)(OC₁₋₆ alkyl)₂, —SC(=O)OC₁₋₆ alkyl and —SC(=O)N(C₁₋₆ alkyl)₂; and the remainder R⁴, if present on said ring, is each independently selected from the group consisting of —F, —Cl, —Br, I, —(X⁴)₀₋₁—CN, —(X⁴)₀₋₁—NO₂, —(X⁴)₀₋₁—SF₅, —(X⁴)₀₋₁—OH, —(X⁴)₀₋₁—NH₂, —(X⁴)₀₋₁—N(H)(R⁴ᵃ), —(X⁴)₀₋₁—N(R⁴ᵇ)(R⁴ᵃ), —(X⁴)₀₋₁—CF₃, —(X⁴)₀₋₁—C(=Y⁴)R⁴ᵃ, —(X⁴)₀₋₁—C(=Y⁴)H, C₁₋₆ alkyl, C₁₋₆ haloalkyl, C₁₋₆ heteroalkyl, C₁₋₆ alkoxy and C₁₋₆ alkylthio wherein X⁴ is selected from the group consisting of C₁₋₄ alkylene, C₁₋₄ haloalkylene, C₁₋₄ heteroalkylene, C₂₋₄ alkenylene and C₂₋₄ alkynylene and R⁴ᵃ and R⁴ᵇ is each independently selected from the group consisting of: C₁₋₆ alkyl, C₁₋₆ haloalkyl and C₁₋₆ heteroalkyl.

In another embodiment, in compounds of formula I, the ring

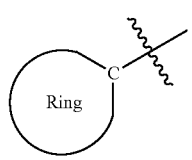

is selected from the group consisting of:

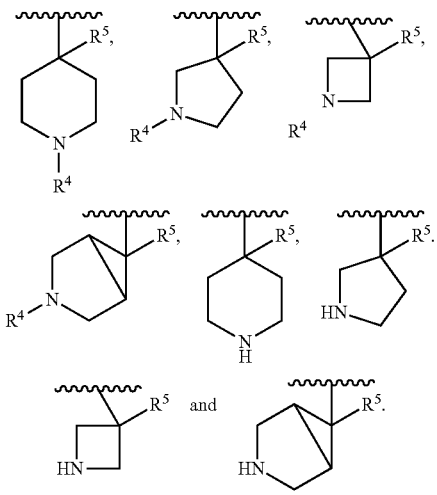

In another embodiment, in compounds of formula I, $R^4$ attached to the nitrogen atom of said ring is selected from the group consisting of $C_{1-6}$ alkyl, $C_{1-6}$ haloalkyl, $C_{1-6}$ heteroalkyl, $C_{1-6}$ alkoxy, $C_{1-6}$ alkylthio, —$(X^4)_{0-1}$-(3-10 membered heterocycloalkyl), —$(X^4)_{0-1}$-(5-10 membered heteroaryl), —$(X^4)_{0-1}$-(3-7 membered cycloalkyl), —$(X^4)_{0-1}$—$S(O)_{1-2}R^{4a}$ and —$(X^4)_{0-1}$—$C(=Y^4)R^{4a}$, wherein $Y^4$ is O.

In another embodiment, in compounds of formula I, $R^4$ is selected from the group consisting of methyl, trifluoromethyl, difluoromethyl, monofluoromethyl, ethyl, trifluororethyl, difluoroethyl, monofluoroethyl and acetyl.

In another embodiment, in compounds of formula I, said

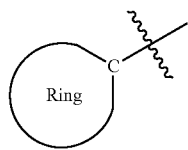 [SMILES: *C(C)C]

is selected from the group consisting of:

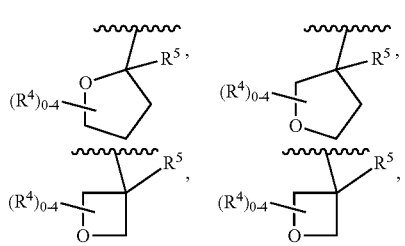

wherein $R^4$ is selected from the group consisting of: —F, —Cl, —Br, —I, —$(X^4)_{0-1}$—CN, —$(X^4)_{0-1}$—NO$_2$, —$(X^4)_{0-1}$—SF$_5$, —$(X^4)_{0-1}$—OH, —$(X^4)_{0-1}$—NH$_2$, —$(X^4)_{0-1}$—N(H)(R$^{4a}$), —$(X^4)_{0-1}$—N(R$^{4b}$)(R$^{4a}$), —$(X^4)_{0-1}$—CF$_3$, $C_{1-6}$ alkyl, $C_{1-6}$ haloalkyl, $C_{1-6}$ heteroalkyl, $C_{1-6}$ alkoxy and $C_{1-6}$ alkylthio wherein $X^4$ is selected from the group consisting of $C_{1-4}$ alkylene, $C_{1-4}$ haloalkylene, $C_{1-4}$ heteroalkylene, $C_{2-4}$ alkenylene and $C_{2-4}$ alkynylene and $R^{4a}$ and $R^{4b}$ is each independently selected from the group consisting of: $C_{1-6}$ alkyl, $C_{1-6}$ haloalkyl and $C_{1-6}$ heteroalkyl.

In another embodiment, in compounds of formula I, the group

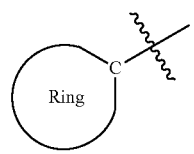 [SMILES: *C(C)C]

is selected from the group consisting of:

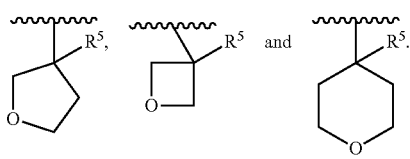

In another embodiment, in compounds of formula I, the group

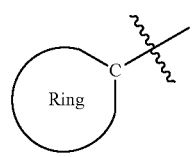 [SMILES: *C(C)C]

is an optionally substituted 3 to 10 membered carbocyclic ring selected from the group consisting of cyclopropane, cyclobutane, cyclopentane, cyclohexane, cycloheptane, bicyclo[1.1.1]pentane, bicyclo[2.1.0]pentane, bicyclo[3.1.0]hexane, bicyclo[2.1.1]hexane, bicyclo[2.2.1]heptane, bicyclo

[3.2.0]heptane, bicyclo[3.1.1]heptane, bicyclo[2.2.2]octane, bicyclo[4.1.0]heptane, bicyclo[3.2.1]octane, bicyclo[4.2.0]octane, octahydropentalene, octahydro-1H-indene and decahydronaphthalene.

In another embodiment, in compounds of formula I, said 3 to 10 membered carbocyclic ring is an optionally substituted ring selected from the group consisting of cyclopropane, cyclobutane, and cyclohexane.

In another embodiment, in compounds of formula I, said 3 to 10 membered carbocyclic ring is selected from the group consisting of:

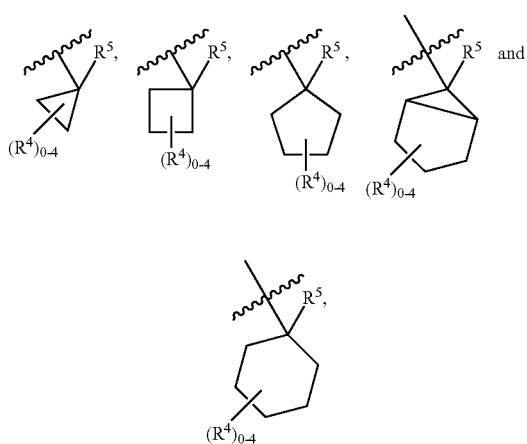

wherein $R^4$ is of $C_{1-6}$ alkyl, $C_{1-6}$ haloalkyl, $C_{1-6}$ heteroalkyl, $C_{1-6}$ alkoxy, $C_{1-6}$ alkylthio, $-(X^4)_{0-1}$-(3-10 membered heterocycloalkyl), $-(X^4)_{0-1}$-(5-10 membered heteroaryl), $-(X^4)_{0-1}$-(3-7 membered cycloalkyl), $-(X^4)_{0-1}-S(O)_{1-2}R^{4a}$ and $-(X^4)_{0-1}-C(=Y^4)R^{4a}$, wherein $Y^4$ is O.

In another embodiment, in compounds of formula I, $R^5$ is selected from the group consisting of hydrogen, $C_{1-4}$ alkyl, $C_{1-4}$ haloalkyl, hydroxy, $OR^{5a}$, —CN, —F, —Cl, —Br and —I.

In another embodiment, in compounds of formula I, $R^5$ is selected from the group consisting of hydrogen, methyl, ethyl, trifluoromethyl, methoxy, ethoxy, F, Cl and Br.

In another embodiment, in compounds of formula I, $R^1$ is selected from the group consisting of $C_{1-6}$ alkyl, $C_{1-6}$ haloalkyl, $C_{1-6}$ heteroalkyl, $-OR^{1a}$, $-SR^{1a}$, $-N(H)(R^{1a})$, and $-N(R^{1a})(R^{1b})$, methyl, ethyl, propyl, isopropyl, butyl, sec-butyl, tert-butyl, cyclopropane, cyclobutane, cyclopentane, cyclohexane, cycloheptane, morpholine, homomorpholine, piperidine, homopiperidine, piperazine, homopiperazine, azetidine, pyrrolidine, benzene, pyrrole, pyrazole, imidazole, triazole, tetrazole, pyridine, pyrimidine, pyrazine, pyridazine, oxetane, tetrahydrofuran, tetrahydropyran, -oxa-5-azabicyclo[2.2.1]heptane, 2-oxa-6-azaspiro[3.3]heptane, 8-oxa-3-azabicyclo[3.2.1]octane, 3-oxa-8-azabicyclo[3.2.1]octane, 7-oxabicyclo[2.2.1]heptane, 7-azabicyclo[2.2.1]heptane, norbornane, bicyclo[2.2.2]octane, 2-azabicyclo[2.2.2]octane, 2-oxabicyclo[2.2.2]octane, 2-oxa-5-azabicyclo[2.2.2]octane and 2,5-diazabicyclo[2.2.2]octane, 5,6,7,8-tetrahydroimidazo[1,2-a]pyrazine, 4,5,6,7-tetrahydro-3H-imidazo[4,5-c]pyridine, wherein $R^{1a}$ and $R^{1b}$ are each independently selected from the group consisting of $C_{1-6}$ alkyl, $C_{1-6}$ haloalkyl, $C_{1-6}$ heteroalkyl, 3-10 membered cycloalkyl and 3-10 membered heterocycloalkyl, and wherein the aliphatic and aromatic portions of $R^1$ are independently further substituted with 0 to 5 $R^{41}$ substituents selected from the group consisting of —F, —Cl, —Br, I, —CN, —NO$_2$, —SF$_5$, —OH, —NH$_2$, —CF$_3$, =O, $C_{1-4}$ alkyl, $C_{1-4}$ haloalkyl, $C_{1-4}$ heteroalkyl, $C_{1-4}$ alkoxy, $C_{1-4}$ alkylthio, $C_{1-4}$ alkylamino, $C_{1-4}$ dialkylamino, $R^{1c}$—C(=O)—, $R^{1c}$—C(=O)N(H)—, $R^{1c}$—C(=O)N($R^{1d}$)—, $R^{1c}$—C(=O)O—, $R^{1c}$—S(O)$_{1-2}$—, $R^{1c}$—S(O)$_{1-2}$N($R^{1d}$)—, $R^{1c}$—S(O)$_{1-2}$N(H)—, 3-6 membered cycloalkyl, phenyl, 5-6 membered heteroaryl and 3-7 membered heterocycloalkyl, wherein $R^{1c}$ is selected from the group consisting of $C_{1-6}$ alkyl, $C_{1-6}$ haloalkyl, $C_{5-6}$ heteroaryl, 3-7 membered heterocycloalkyl, phenyl and 3-6 membered cycloalkyl, $R^{1d}$ is selected from the group consisting of hydrogen, $C_{1-3}$ alkyl and $C_{1-3}$ haloalkyl, and wherein said 5-6 membered heteroaryl, phenyl, 3-6 membered heteroaryl, 3-6 membered cycloalkyl and 3-7 membered heterocycloalkyl of the $R^{41}$ substituent are substituted with from 0-4 substituents selected from —F, —Cl, —Br, I, —CN, —NO$_2$, —SF$_5$, —OH, —NH$_2$, —CF$_3$, $C_{1-4}$ alkyl, $C_{1-4}$ haloalkyl, $C_{1-4}$ alkoxy, $C_{1-4}$ alkylthio, $C_{1-4}$ alkylamino and $C_{1-4}$ dialkylamino.

In another embodiment, in compounds of formula I, $R^1$ is selected from the group consisting of pyrrolidin-1-yl, phenyl, piperidin-1-yl, pyrrol-1-yl, azetidin-1-yl, morpholin-4-yl, homomorpholin-4-yl, 2-oxa-5-azabicyclo[2.2.1]hept-5-yl, 3-oxa-8-azabicyclo[3.2.1]oct-8-yl, 2-oxa-6-azaspiro[3.3]hept-6-yl, -8-oxa-3-azabicyclo[3.2.1]octane, methyl, isopropyl, isobutyl, cyclopropyl, pyrazol-1-yl, 4,5,6,7-tetrahydro-1H-imidazo[4,5-c]pyridin-5-yl, 3,5,6,7,8,8a-hexahydroimidazo[1,2-a]pyrazin-7-yl, 3-azabicyclo[3.2.0]heptan-3-yl, 3-azabicyclo[3.1.0]hexan-3-yl, 2-azabicyclo[2.1.1]hexan-2-yl, 2-azabicyclo[3.1.0]hexan-2-yl, 2-oxa-7-azaspiro[4.4]nonan-7-yl, 2-oxa-6-azaspiro[3.4]octan-6-yl, —N(H)$R^{1a}$, and —N($R^{1a}$)($R^{1b}$).

In another embodiment, in compounds of formula I, $R^1$ is selected from the group consisting of pyrrolidin-1-yl, phenyl, piperidin-1-yl, pyrrol-1-yl, azetidin-1-yl, morpholin-4-yl, homomorpholin-4-yl, 2-oxa-5-azabicyclo[2.2.1]hept-5-yl, 3-oxa-8-azabicyclo[3.2.1]oct-8-yl, 2-oxa-6-azaspiro[3.3]hept-6-yl, -8-oxa-3-azabicyclo[3.2.1]octane, methyl, isopropyl, isobutyl, cyclopropyl, pyrazol-1-yl, 4,5,6,7-tetrahydro-1H-imidazo[4,5-c]pyridin-5-yl, 3,5,6,7,8,8a-hexahydroimidazo[1,2-a]pyrazin-7-yl, 3-azabicyclo[3.2.0]heptan-3-yl, 3-azabicyclo[3.1.0]hexan-3-yl, 2-azabicyclo[2.1.1]hexan-2-yl, 2-azabicyclo[3.1.0]hexan-2-yl, 2-oxa-7-azaspiro[4.4]nonan-7-yl, 2-oxa-6-azaspiro[3.4]octan-6-yl, —N(H)$R^{1a}$, and —N($R^{1a}$)($R^{1b}$), wherein $R^{1a}$ and $R^{1b}$ are each independently selected from the group consisting of methyl, ethyl, propyl, butyl, methoxyethyl, ethoxyethyl, hydroxyethyl, methoxypropyl, ethyoxypropyl and hydroxypropyl, wherein the aliphatic and/or aromatic portions or $R^1$ is substituted with 0 to 4 substituents selected from the group consisting of methyl, ethyl, propyl, isopropyl, butyl, isobutyl, fluoro, chloro, bromo, iodo, cyano, methoxy, ethoxy, isopropoxy, methoxymethyl, methoxyethyl, methoxypropyl, trifluoromethyl, monofluoromethyl, difluoromethyl, 2-methylpyrimidin-4-yl, 4-methyltriazol-3-yl, 1,2,4-triazol-3-yl, morphlinocarbonyl, morpholino, 2-methyl-pyrimidin-6-yl, 6-methyl-pyrimidin-2-yl, 4-methyl-1,2,4-triazol-3-yl, methylaminomethylcarbonyl and hydroxy.

In another embodiment, in compounds of formula I, $R^3$ is selected from the group consisting of —F, —Cl, —Br, I, $C_{1-6}$ alkyl, $C_{1-6}$ haloalkyl, $C_{1-6}$ heteroalkyl, $C_{1-6}$ alkoxy, $-(X^3)_{0-1}$—CN, $-(X^3)_{0-1}$—N(H)C(=O)($R^{3a}$), $-(X^3)_{0-1}$—N($R^{3b}$)C(=O)($R^{3a}$), $-(X^3)_{0-1}$—C(=O)N(H)($R^{3a}$), $-(X^3)_{0-1}$—C(=O)NH$_2$, $-(X^3)_{0-1}$—C(=O)N($R^{3a}$)($R^{3b}$), thiophene, wherein if $R^3$ is thiophene or $R^{3a}$ and $R^{3b}$ is independently 3-7 membered cycloalkyl, 3-7 membered cycloalkyl-$C_{1-4}$ alkyl, 3-7 membered heterocycloalkyl, 3-7 membered heterocycloalkyl-$C_{1-4}$ alkyl, 5-6 membered heteroaryl, 5-6 membered heteroaryl-$C_{1-4}$ alkyl, $C_6$ aryl, $C_6$ aryl-$C_{1-4}$ alkyl or benzyl then said thiophene, 3-7 membered cycloalkyl, 3-7 membered cycloalkyl-$C_{1-4}$ alkyl, 3-7 membered heterocycloalkyl, 3-7 membered heterocycloalkyl-$C_{1-4}$ alkyl, 5-6 membered heteroaryl, 5-6 membered heteroaryl-$C_{1-4}$ alkyl, $C_6$ aryl, $C_6$ aryl-$C_{1-4}$ alkyl or benzyl is substituted from 0 to 4 $R^{43}$ substituents, or alternatively, any two $R^3$ substituents located on adjacent atoms are optionally combined to form a thiazole ring further comprising 0 to 4 $R^{3a}$ substituents, and m is an integer from 1 to 4.

In another embodiment, in compounds of formula I, $R^3$ is selected from the group consisting of trifluoromethyl, difluoromethyl, monofluoromethyl, methyl, ethyl, propyl, butyl, isopropyl, sec-butyl, tert-butyl, methoxy, ethoxy, cyclopropyl, cyclobutyl, —CN, thienyl and —C(=O)NH$_2$.

In another embodiment, in compounds of formula I, formula I has the subformula selected from the group consisting of:

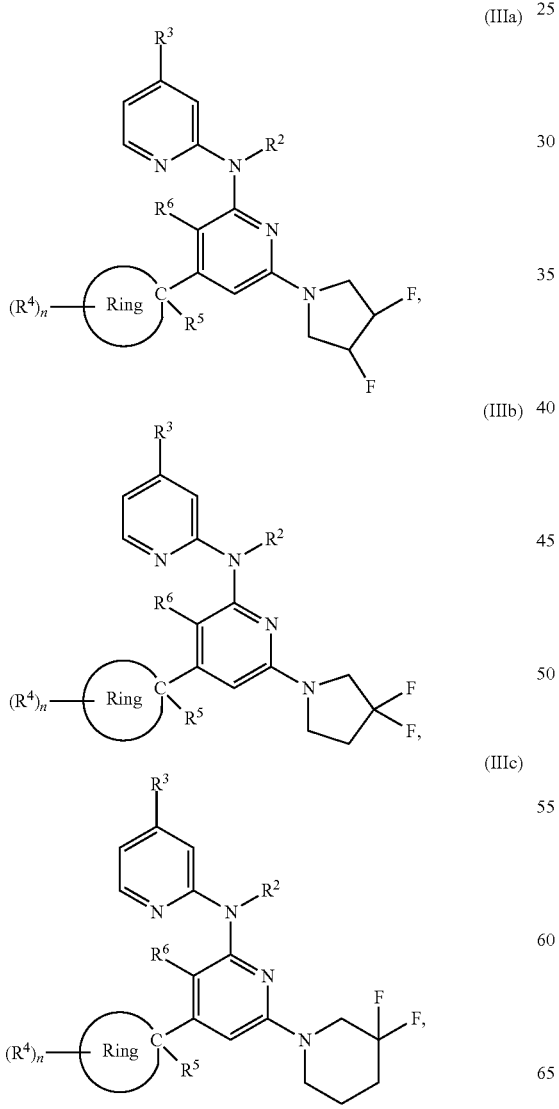

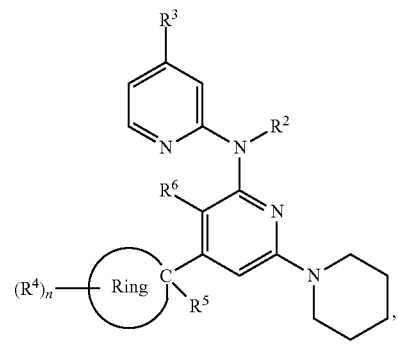

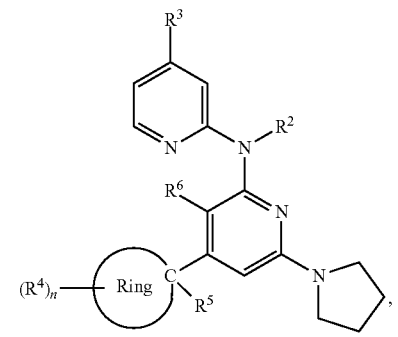

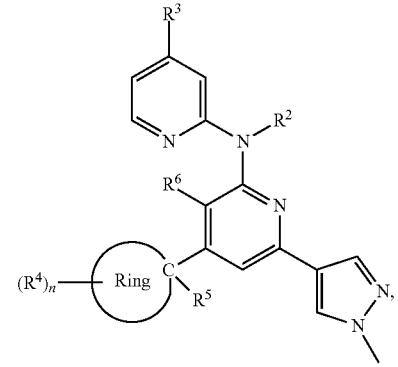

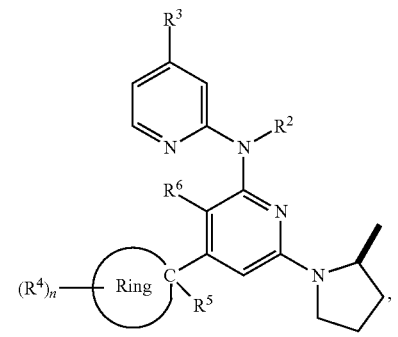

123
-continued
(IIIh)
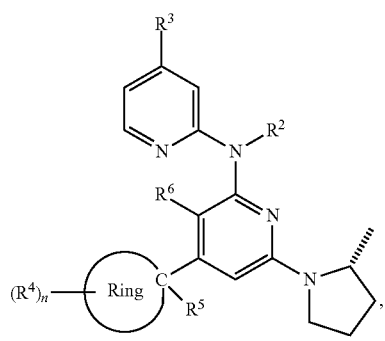
(IIIi)
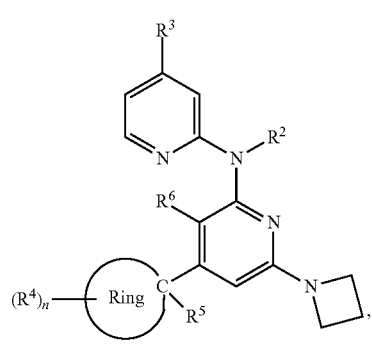
(IIIj)
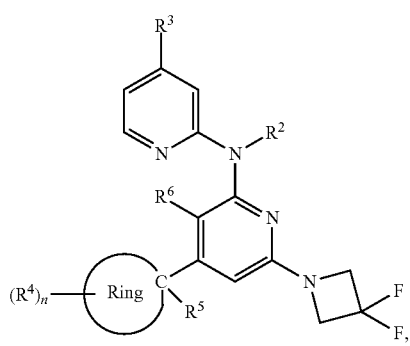
(IIIk)
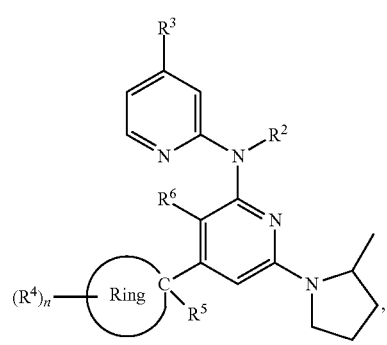
124
-continued
(IIIl)
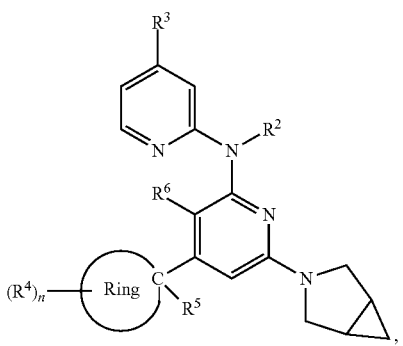
(IIIm)
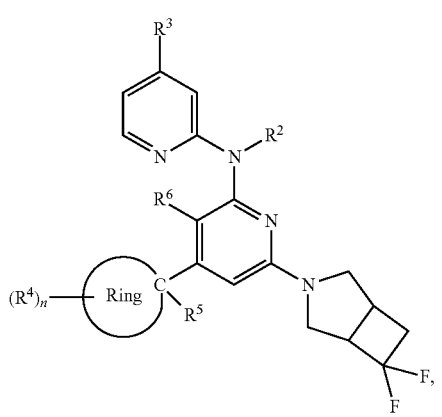
(IIIn)
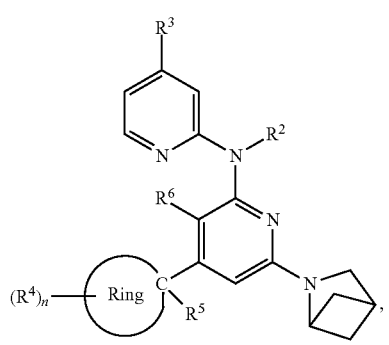
(IIIo)
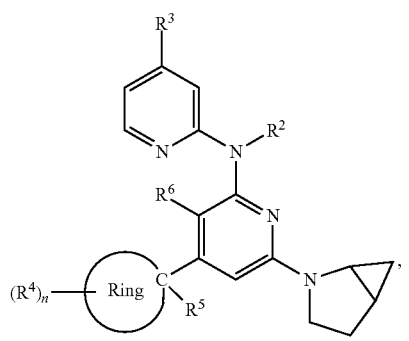

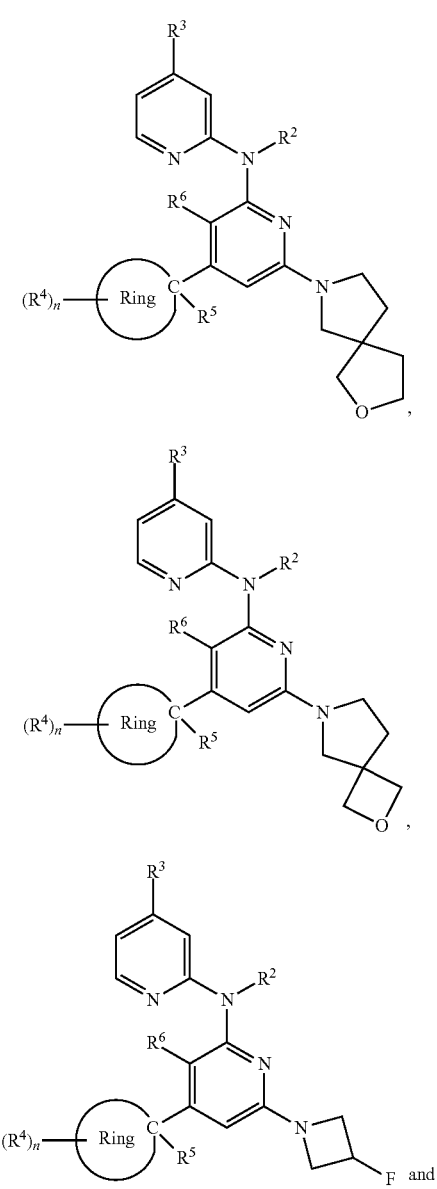

wherein R³ is selected from the group consisting of methyl, monofluoromethyl, difluoromethyl, trifluoromethyl, —CN, isopropyl, cyclopropyl, cyclobutyl and methoxy.

In another embodiment, the compounds of Formula I has the subformula:

In another embodiment, the compounds of Formula I are selected from the group of compounds in Table A.

TABLE A

| NO | Structure | Name |
|---|---|---|
| 1 | 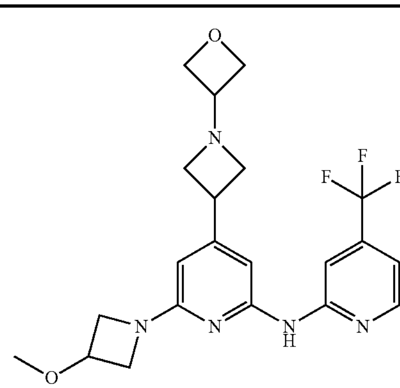 | [6-(3-Methoxy-azetidin-1-yl)-4-(1-oxetan-3-yl-azetidin-3-yl)-pyridin-2-yl]-(4-trifluoromethyl-pyridin-2-yl)-amine |

TABLE A-continued
| NO | Structure | Name |
|---|---|---|
| 2 | 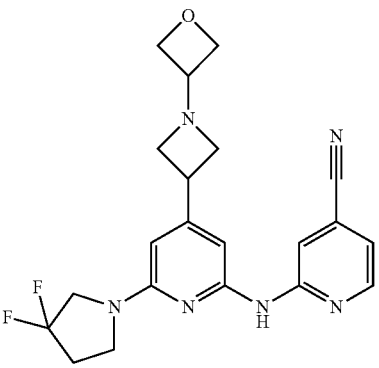 [SMILES: N#Cc1ccnc(Nc2cc(C3CN(C4COC4)C3)cc(N3CCC(F)(F)C3)n2)c1] | 2-[6-(3,3-Difluoro-pyrrolidin-1-yl)-4-(1-oxetan-3-yl-azetidin-3-yl)-pyridin-2-ylamino]-isonicotinonitrile |
| 3 | 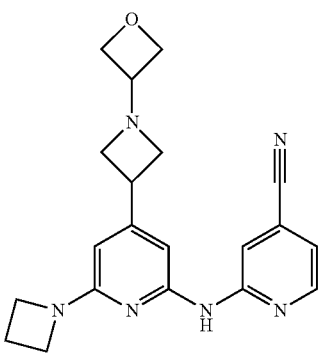 [SMILES: N#Cc1ccnc(Nc2cc(C3CN(C4COC4)C3)cc(N3CCC3)n2)c1] | 2-[6-Azetidin-1-yl-4-(1-oxetan-3-yl-azetidin-3-yl)-pyridin-2-ylamino]-isonicotinonitrile |
| 4 | 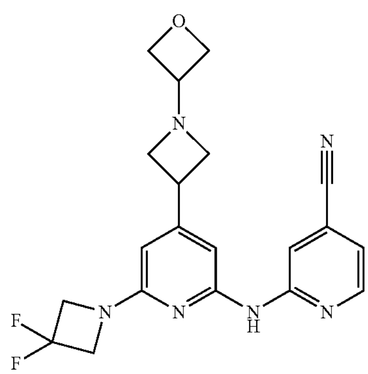 [SMILES: N#Cc1ccnc(Nc2cc(C3CN(C4COC4)C3)cc(N3CC(F)(F)C3)n2)c1] | 2-[6-(3,3-Difluoro-azetidin-1-yl)-4-(1-oxetan-3-yl-azetidin-3-yl)-pyridin-2-ylamino]-isonicotinonitrile |
| 5 | 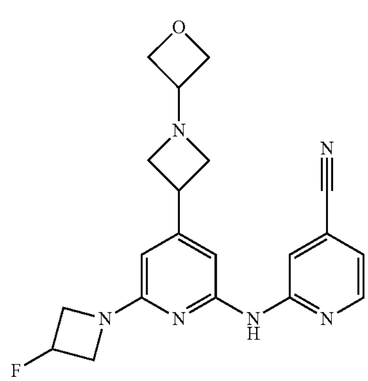 [SMILES: N#Cc1ccnc(Nc2cc(C3CN(C4COC4)C3)cc(N3CC(F)C3)n2)c1] | 2-[6-(3-Fluoro-azetidin-1-yl)-4-(1-oxetan-3-yl-azetidin-3-yl)-pyridin-2-ylamino]-isonicotinonitrile |

TABLE A-continued

| NO | Structure | Name |
|---|---|---|
| 6 | 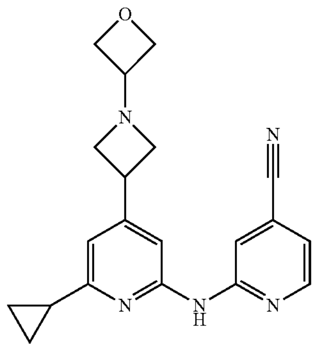 [SMILES: N#Cc1ccnc(Nc2cc(C3CN(C4COC4)C3)cc(C3CC3)n2)c1] | 2-[6-Cyclopropyl-4-(1-oxetan-3-yl-azetidin-3-yl)-pyridin-2-ylamino]-isonicotinonitrile |
| 7 | 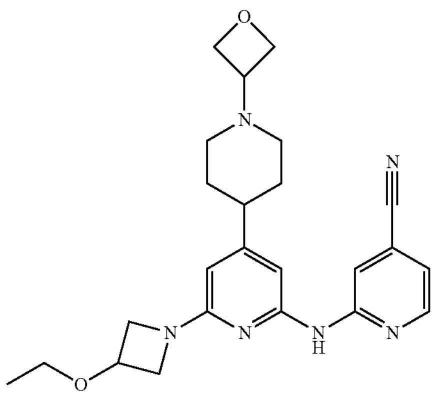 [SMILES: CCOC1CN(c2cc(C3CCN(C4COC4)CC3)cc(Nc3cc(C#N)ccn3)n2)C1] | 2-[6-(3-Ethoxy-azetidin-1-yl)-1'-oxetan-3-yl-1',2',3',4',5',6'-hexahydro-[4,4']bipyridin-2-ylamino]-isonicotinonitrile |
| 8 | 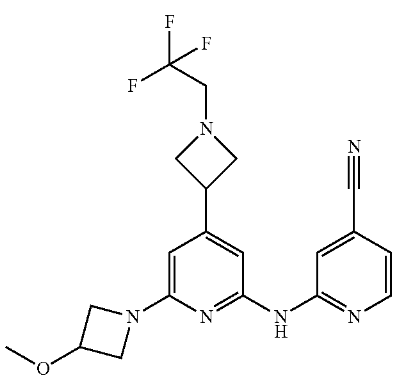 [SMILES: COC1CN(c2cc(C3CN(CC(F)(F)F)C3)cc(Nc3cc(C#N)ccn3)n2)C1] | 2-{6-(3-Methoxy-azetidin-1-yl)-4-[1-(2,2,2-trifluoro-ethyl)-azetidin-3-yl]-pyridin-2-ylamino}-isonicotinonitrile |
| 9 | 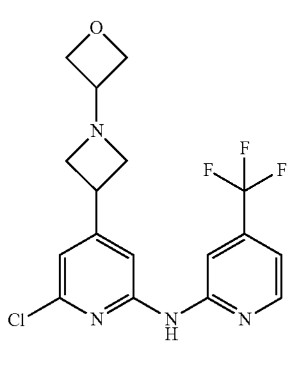 [SMILES: FC(F)(F)c1ccnc(Nc2cc(C3CN(C4COC4)C3)cc(Cl)n2)c1] | [6-Chloro-4-(1-oxetan-3-yl-azetidin-3-yl)-pyridin-2-yl]-(4-trifluoromethyl-pyridin-2-yl)-amine |

TABLE A-continued

| NO | Structure | Name |
| --- | --- | --- |
| 10 | 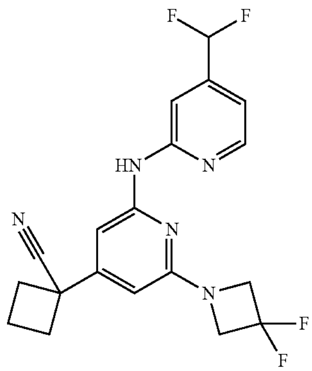 [SMILES: N#CC1(c2cc(Nc3cc(C(F)F)ccn3)nc(N3CC(F)(F)C3)c2)CCC1] | 1-[2-(3,3-Difluoro-azetidin-1-yl)-6-(4-difluoromethyl-pyridin-2-ylamino)-pyridin-4-yl]-cyclobutanecarbonitrile |
| 11 | 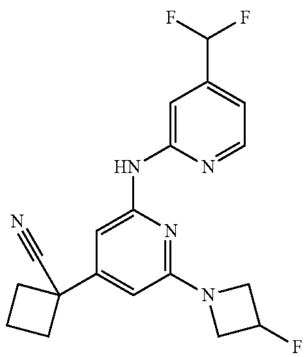 [SMILES: N#CC1(c2cc(Nc3cc(C(F)F)ccn3)nc(N3CC(F)C3)c2)CCC1] | 1-[2-(4-Difluoromethyl-pyridin-2-ylamino)-6-(3-fluoro-azetidin-1-yl)-pyridin-4-yl]-cyclobutanecarbonitrile |
| 12 | 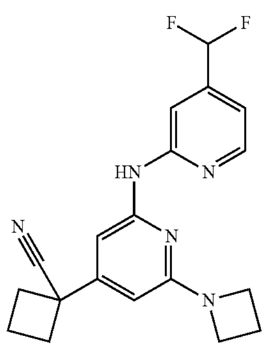 [SMILES: N#CC1(c2cc(Nc3cc(C(F)F)ccn3)nc(N3CCC3)c2)CCC1] | 1-[2-Azetidin-1-yl-6-(4-difluoromethyl-pyridin-2-ylamino)-pyridin-4-yl]-cyclobutanecarbonitrile |
| 13 | 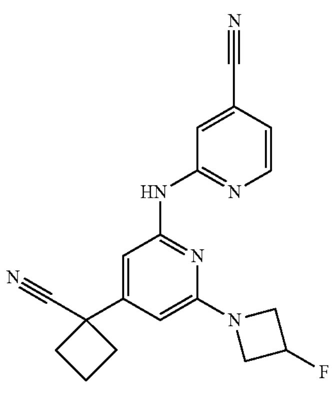 [SMILES: N#Cc1ccnc(Nc2cc(C3(C#N)CCC3)cc(N3CC(F)C3)n2)c1] | 2-[4-(1-Cyano-cyclobutyl)-6-(3-fluoro-azetidin-1-yl)-pyridin-2-ylamino]-isonicotinonitrile |

TABLE A-continued

| NO | Structure | Name |
|---|---|---|
| 14 | 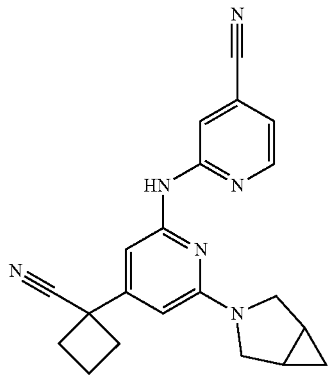 [SMILES: N#Cc1ccnc(Nc2cc(C3(C#N)CCC3)cc(N3CC4CC4C3)n2)c1] | 2-[6-(3-Aza-bicyclo[3.1.0]hex-3-yl)-4-(1-cyano-cyclobuty)-pyridin-2-yl-amino]-isonicotinonitrile |
| 15 | 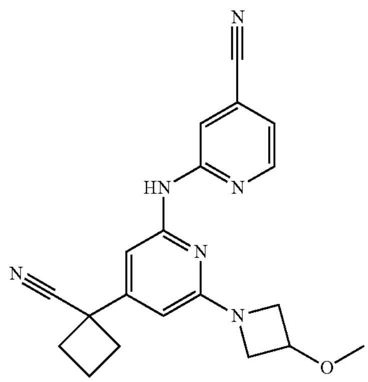 [SMILES: COC1CN(c2cc(C3(C#N)CCC3)cc(Nc3cc(C#N)ccn3)n2)C1] | 2-[4-(1-Cyano-cyclobutyl)-6-(3-methoxy-azetidin-1-yl)-pyridin-2-ylamino]-isonicotinonitrile |
| 16 | 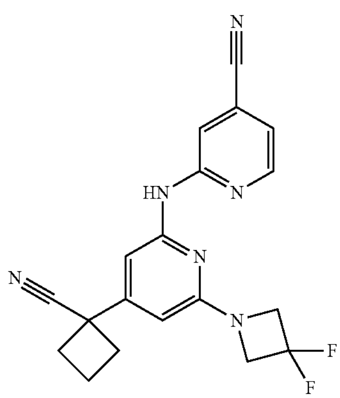 [SMILES: N#Cc1ccnc(Nc2cc(C3(C#N)CCC3)cc(N3CC(F)(F)C3)n2)c1] | 2-[4-(1-Cyano-cyclobutyl)-6-(3,3-difluoro-azetidin-1-yl)-pyridin-2-ylamino]-isonicotinonitrile |
| 17 | 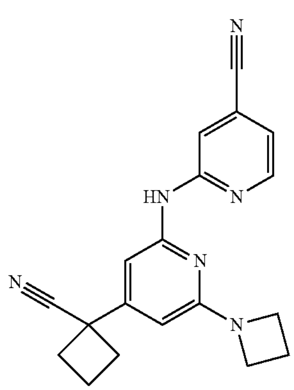 [SMILES: N#Cc1ccnc(Nc2cc(C3(C#N)CCC3)cc(N3CCC3)n2)c1] | 2-[6-Azetidin-1-yl-4-(1-cyano-cyclobutyl)-pyridin-2-ylamino]-isonicotinonitrile |

TABLE A-continued

| NO | Structure | Name |
|---|---|---|
| 18 | 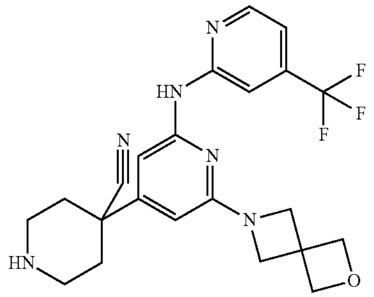 [SMILES: N#CC1(c2cc(Nc3cc(C(F)(F)F)ccn3)nc(N3CC4(COC4)C3)c2)CCNCC1] | 6'-(2-Oxa-6-aza-spiro[3.3]hept-6-yl)-2'-(4-trifluoromethyl-pyridin-2-ylamino)-2,3,5,6-tetrahydro-1H-[4,4']bipyridinyl-4-carbonitrile |
| 19 | 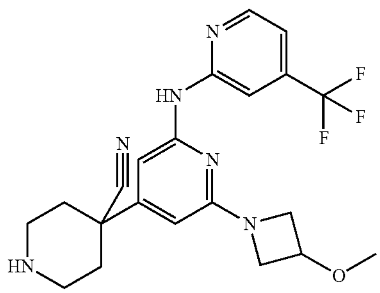 [SMILES: COC1CN(c2cc(C3(C#N)CCNCC3)cc(Nc3cc(C(F)(F)F)ccn3)n2)C1] | 6'-(3-Methoxy-azetidin-1-yl)-2'-(4-trifluoromethyl-pyridin-2-ylamino)-2,3,5,6-tetrahydro-1H-[4,4']bipyridinyl-4-carbonitrile |
| 20 | 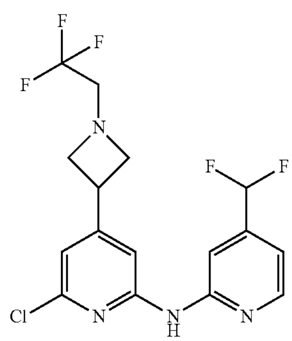 [SMILES: FC(F)c1ccnc(Nc2cc(C3CN(CC(F)(F)F)C3)cc(Cl)n2)c1] | {6-Chloro-4-[1-(2,2,2-trifluoro-ethyl)-azetidin-3-yl]-pyridin-2-yl}-(4-difluoromethyl-pyridin-2-yl)-amine |
| 21 | 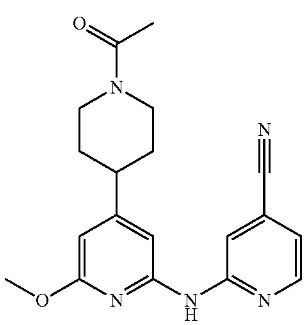 [SMILES: COc1cc(C2CCN(C(C)=O)CC2)cc(Nc2cc(C#N)ccn2)n1] | 2-(1'-Acetyl-6-methoxy-1',2',3',4',5',6'-hexahydro-[4,4']bipyridinyl-2-ylamino)-isonicotinonitrile |
| 22 | 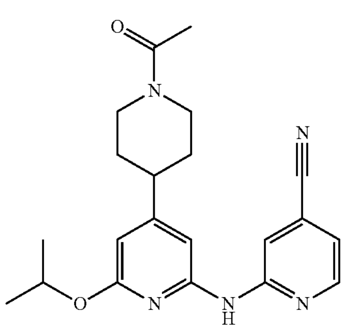 [SMILES: CC(=O)N1CCC(c2cc(Nc3cc(C#N)ccn3)nc(OC(C)C)c2)CC1] | 2-(1'-Acetyl-6-isopropoxy-1',2',3',4',5',6'-hexahydro-[4,4']bipyridinyl-2-yl-amino)-isonicotinonitrile |

TABLE A-continued

| NO | Structure | Name |
|---|---|---|
| 23 | 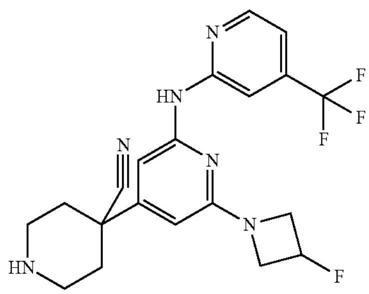 [SMILES: N#CC1(c2cc(Nc3cc(C(F)(F)F)ccn3)nc(N3CC(F)C3)c2)CCNCC1] | 6'-(3-Fluoro-azetidin-1-yl)-2'-(4-trifluoromethyl-pyridin-2-ylamino)-2,3,5,6-tetrahydro-1H-[4,4']bi-pyridinyl-4-carbonitrile |
| 24 | 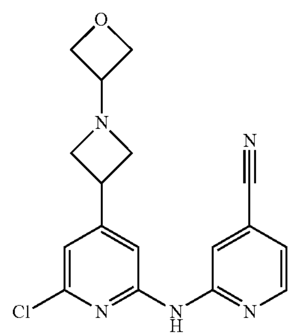 [SMILES: N#Cc1ccnc(Nc2cc(C3CN(C4COC4)C3)cc(Cl)n2)c1] | 2-[6-Chloro-4-(1-oxetan-3-yl-azetidin-3-yl)-pyridin-2-ylamino]-isonicotinonitrile |
| 25 | 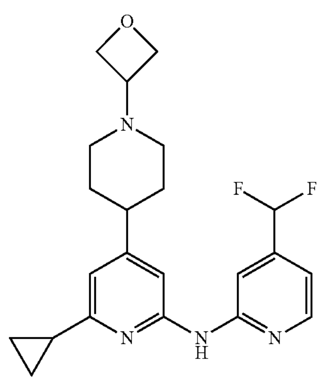 [SMILES: FC(F)c1ccnc(Nc2cc(C3CCN(C4COC4)CC3)cc(C3CC3)n2)c1] | (6-Cyclopropyl-1'-oxetan-3-yl-1',2',3',4',5',6'-hexahydro-[4,4']bipyridinyl-2-yl)-(4-difluoromethyl-pyridin-2-yl)-amine |
| 26 | 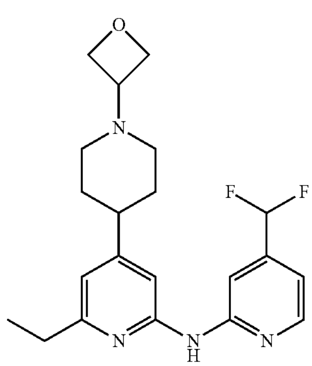 [SMILES: CCc1cc(C2CCN(C3COC3)CC2)cc(Nc2cc(C(F)F)ccn2)n1] | (4-Difluoromethyl-pyridin-2-yl)-(6-ethyl-1'-oxetan-3-yl-1',2',3',4',5',6'-hexahydro-[4,4']bipyridinyl-2-yl)-amine |

TABLE A-continued

| NO | Structure | Name |
| --- | --- | --- |
| 27 | 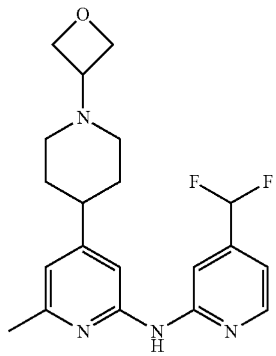 [SMILES: Cc1cc(C2CCN(C3COC3)CC2)cc(Nc2cc(C(F)F)ccn2)n1] | (4-Difluoromethyl-pyridin-2-yl)-(6-methyl-1'-oxetan-3-yl-1',2',3',4',5',6'-hexahydro-[4,4']bipyridinyl-2-yl)-amine |
| 28 | 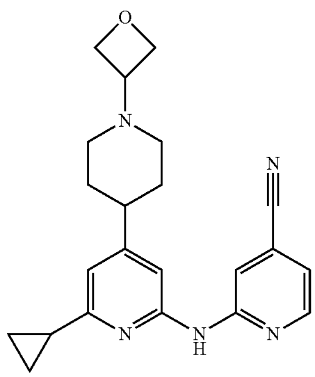 [SMILES: N#Cc1ccnc(Nc2cc(C3CCN(C4COC4)CC3)cc(C3CC3)n2)c1] | 2-(6-Cyclopropyl-1'-oxetan-3-yl-1',2',3',4',5',6'-hexahydro-[4,4']bipyridinyl-2-ylamino)-isonicotinonitrile |
| 29 | 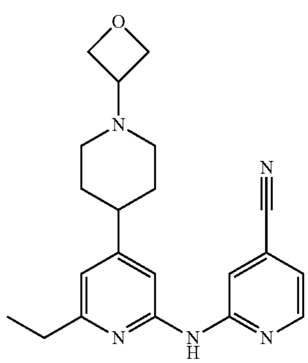 [SMILES: CCc1cc(C2CCN(C3COC3)CC2)cc(Nc2cc(C#N)ccn2)n1] | 2-(6-Ethyl-1'-oxetan-3-yl-1',2',3',4',5',6'-hexahydro-[4,4']bipyridinyl-2-ylamino)-isonicotinonitrile |
| 30 | 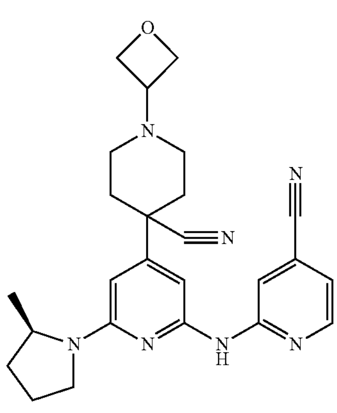 [SMILES: C[C@@H]1CCCN1c1cc(C2(C#N)CCN(C3COC3)CC2)cc(Nc2cc(C#N)ccn2)n1] | 2'-(4-Cyano-pyridin-2-ylamino)-6'-((R)-2-methyl-pyrrolidin-1-yl)-1-oxetan-3-yl-2,3,5,6-tetrahydro-1H-[4,4']bipyridinyl-4-carbonitrile |

TABLE A-continued

| NO | Structure | Name |
|----|-----------|------|
| 31 | 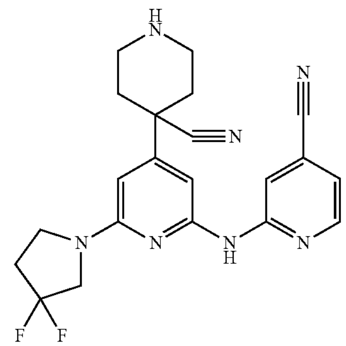 [SMILES: N#Cc1ccnc(Nc2cc(C3(C#N)CCNCC3)cc(N3CCC(F)(F)C3)n2)c1] | 2'-(4-Cyano-pyridin-2-yl-amino)-6'-(3,3-difluoro-pyrrolidin-1-yl)-2,3,5,6-tetrahydro-1H-[4,4']bipyridinyl-4-carbonitrile |
| 32 | 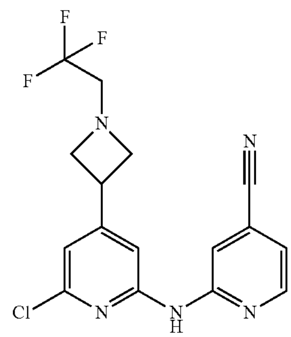 [SMILES: N#Cc1ccnc(Nc2cc(C3CN(CC(F)(F)F)C3)cc(Cl)n2)c1] | 2-{6-Chloro-4-[1-(2,2,2-trifluoro-ethyl)-azetidin-3-yl]-pyridin-2-ylamino}-isonicotinonitrile |
| 33 | 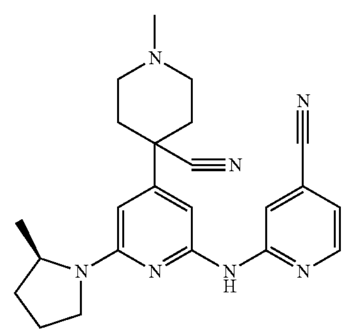 [SMILES: C[C@@H]1CCCN1c1cc(C2(C#N)CCN(C)CC2)cc(Nc2cc(C#N)ccn2)n1] | 2'-(4-Cyano-pyridin-2-yl-amino)-1-methyl-6'-((R)-2-methyl-pyrrolidin-1-yl)-2,3,5,6-tetrahydro-1H-[4,4']bipyridinyl-4-carbonitrile |
| 34 | 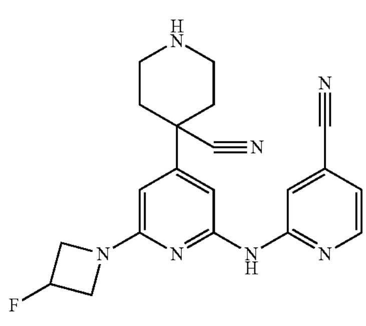 [SMILES: N#Cc1ccnc(Nc2cc(C3(C#N)CCNCC3)cc(N3CC(F)C3)n2)c1] | 2'-(4-Cyano-pyridin-2-yl-amino)-6'-(3-fluoro-azetidin-1-yl)-2,3,5,6-tetrahydro-1H-[4,4']bipyridinyl-4-carbonitrile |

TABLE A-continued

| NO | Structure | Name |
|---|---|---|
| 35 | 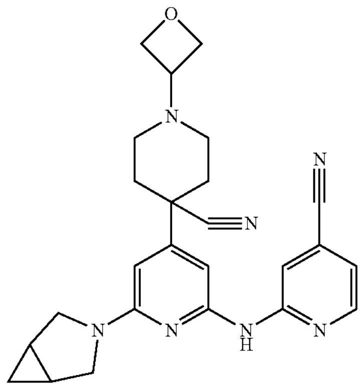 [SMILES: N#Cc1ccnc(Nc2cc(C3(C#N)CCN(C4COC4)CC3)cc(N3CC4CC4C3)n2)c1] | 6'-(3-Aza-bicyclo[3.1.0]hex-3-yl)-2'-(4-cyano-pyridin-2-ylamino)-1-oxetan-3-yl-2,3,5,6-tetrahydro-1H-[4,4']bipyridinyl-4-carbonitrile |
| 36 | 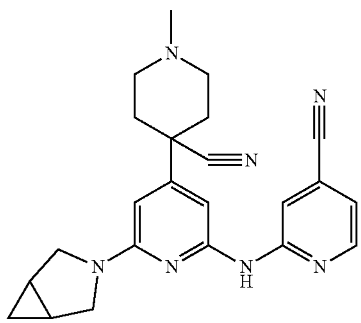 [SMILES: CN1CCC(C#N)(c2cc(Nc3cc(C#N)ccn3)nc(N3CC4CC4C3)c2)CC1] | 6'-(3-Aza-bicyclo[3.1.0]hex-3-yl)-2'-(4-cyano-pyridin-2-ylamino)-1-methyl-2,3,5,6-tetrahydro-1H-[4,4']bipyridinyl-4-carbonitrile |
| 37 | 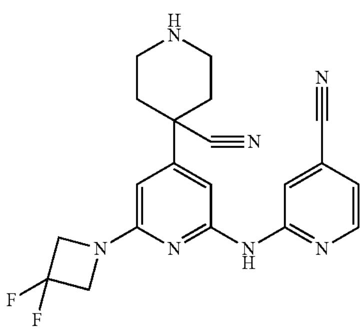 [SMILES: N#Cc1ccnc(Nc2cc(C3(C#N)CCNCC3)cc(N3CC(F)(F)C3)n2)c1] | 2'-(4-Cyano-pyridin-2-yl-amino)-6'-(3,3-difluoro-azetidin-1-yl)-2,3,5,6-tetrahydro-1H-[4,4']bipyridinyl-4-carbonitrile |
| 38 | 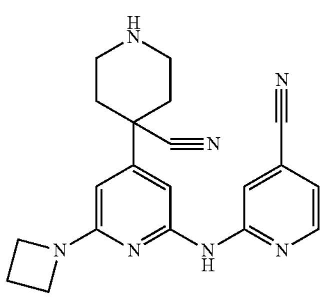 [SMILES: N#Cc1ccnc(Nc2cc(C3(C#N)CCNCC3)cc(N3CCC3)n2)c1] | 6'-Azetidin-1-yl-2'-(4-cyano-pyridin-2-yalmino)-2,3,5,6-tetrahydro-1H-[4,4']bipyridinyl-4-carbonitrile |

TABLE A-continued

| NO | Structure | Name |
|---|---|---|
| 39 | 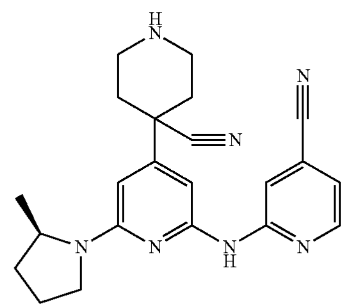 [SMILES: C[C@@H]1CCCN1c1cc(C2(C#N)CCNCC2)cc(Nc2cc(C#N)ccn2)n1] | 2'-(4-Cyano-pyridin-2-yl-amino)-6'-((R)-2-methyl-pyrrolidin-1-yl)-2,3,5,6-tetrahydro-1H-[4,4']bi-pyridinyl-4-carbonitrile |
| 40 | 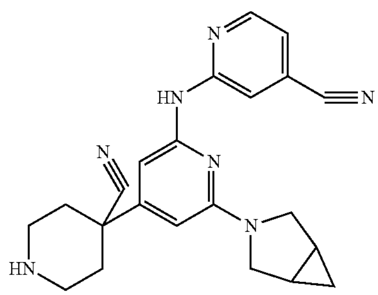 [SMILES: N#Cc1ccnc(Nc2cc(C3(C#N)CCNCC3)cc(N3CC4CC4C3)n2)c1] | 6'-(3-Aza-bicyclo[3.1.0]hex-3-yl)-2'-(4-cyano-pyridin-2-ylamino)-2,3,5,6-tetrahydro-1H-[4,4']bi-pyridinyl-4-carbonitrile |
| 41 | 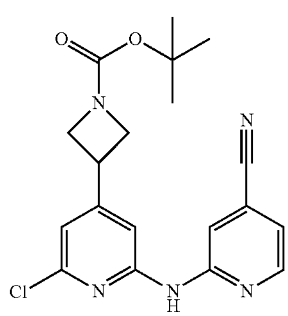 [SMILES: CC(C)(C)OC(=O)N1CC(c2cc(Cl)nc(Nc3cc(C#N)ccn3)c2)C1] | 3-[2-Chloro-6-(4-cyano-pyridin-2-ylamino)-pyridin-4-yl]-azetidine-1-carboxylic acid tert-butyl ester |
| 42 | 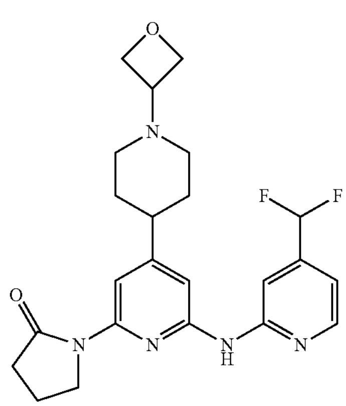 [SMILES: O=C1CCCN1c1cc(C2CCN(C3COC3)CC2)cc(Nc2cc(C(F)F)ccn2)n1] | 1-[6-(4-Difluoromethyl-pyridin-2-ylamino)-1'-oxetan-3-yl-1',2',3',4',5',6'-hexahydro-[4,4']bipyridinyl-2-yl]-pyrrolidin-2-one |

TABLE A-continued

| NO | Structure | Name |
|---|---|---|
| 43 | 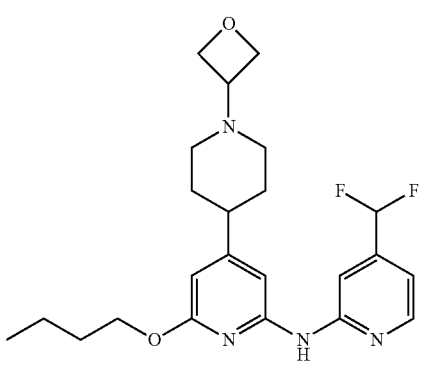 [SMILES: CCCCOc1cc(C2CCN(C3COC3)CC2)cc(Nc2cc(C(F)F)ccn2)n1] | (6-Butoxy-1'-oxetan-3-yl-1',2',3',4',5',6'-hexahydro-[4,4']bipyridinyl-2-yl)-(4-difluoromethyl-pyridin-2-yl)-amine |
| 44 | 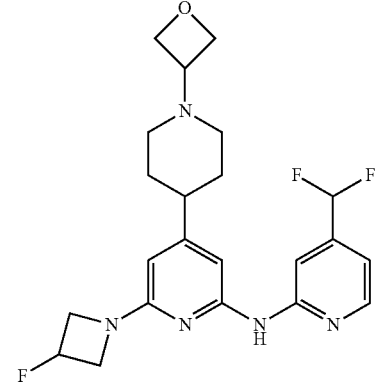 [SMILES: FC1CN(c2cc(C3CCN(C4COC4)CC3)cc(Nc3cc(C(F)F)ccn3)n2)C1] | (4-Difluoromethyl-pyridin-2-yl)-[6-(3-fluoro-azetidin-1-yl)-1'-oxetan-3-yl-1',2',3',4',5',6'-hexahydro-[4,4']bipyridinyl-2-yl]-amine |
| 45 | 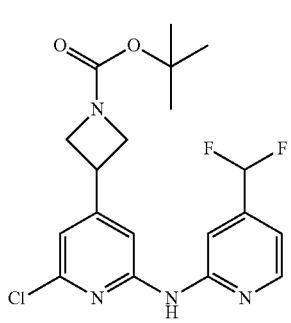 [SMILES: CC(C)(C)OC(=O)N1CC(c2cc(Cl)nc(Nc3cc(C(F)F)ccn3)c2)C1] | 3-[2-Chloro-6-(4-difluoromethyl-pyridin-2-ylamino)-pyridin-4-yl]-azetidine-1-carboxylic acid tert-butyl ester |
| 46 | 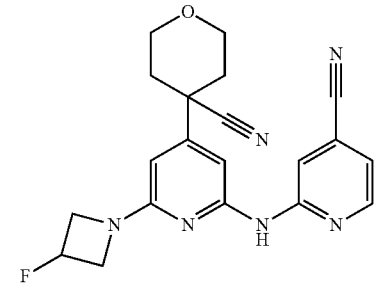 | 2-[4-(4-Cyano-tetrahydro-pyran-4-yl)-6-(3-fluoro-azetidin-1-yl)-pyridin-2-ylamino]-isonicotinonitrile |

TABLE A-continued

| NO | Structure | Name |
|---|---|---|
| 47 | 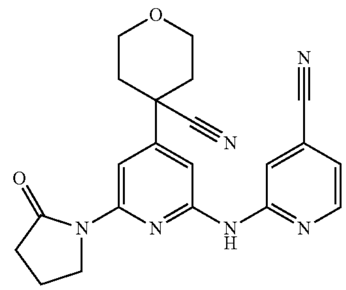 [SMILES: N#Cc1ccnc(Nc2cc(C3(C#N)CCOCC3)cc(N3CCCC3=O)n2)c1] | 2-[4-(4-Cyano-tetrahydro-pyran-4-yl)-6-(2-oxo-pyrrolidin-1-yl)-pyridin-2-ylamino]-isonicotinonitrile |
| 48 | 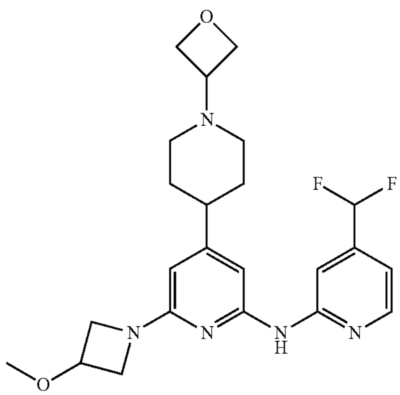 [SMILES: COC1CN(c2cc(C3CCN(C4COC4)CC3)cc(Nc3cc(C(F)F)ccn3)n2)C1] | (4-Difluoromethyl-pyridin-2-yl)-[6-(3-methoxy-azetidin-1-yl)-1'-oxetan-3-yl-1',2',3',4',5',6'-hexahydro-[4,4']bipyridinyl-2-yl]-amine |
| 49 | 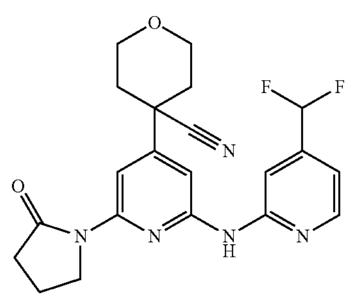 [SMILES: N#CC1(c2cc(Nc3cc(C(F)F)ccn3)nc(N3CCCC3=O)c2)CCOCC1] | 4-[2-(4-Difluoromethyl-pyridin-2-ylamino)-6-(2-oxo-pyrrolidin-1-yl)-pyridin-4-yl]-tetrahydro-pyran-4-carbonitrile |
| 50 | 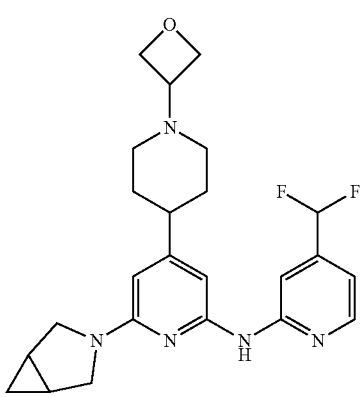 [SMILES: FC(F)c1ccnc(Nc2cc(C3CCN(C4COC4)CC3)cc(N3CC4CC4C3)n2)c1] | [6-(3-Aza-bicyclo[3.1.0]hex-3-yl)-1'-oxetan-3-yl-1',2',3',4',5',6'-hexahydro-[4,4']bipyridinyl-2-yl]-(4-difluoromethyl-pyridin-2-yl)-amine |

TABLE A-continued

| NO | Structure | Name |
|---|---|---|
| 51 | 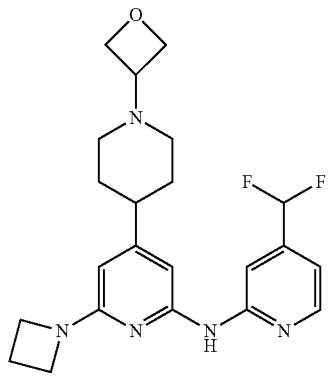 [SMILES: FC(F)c1ccnc(Nc2cc(C3CCN(C4COC4)CC3)cc(N3CCC3)n2)c1] | (6-azetidin-1-yl-1'-oxetan-3-yl-1',2',3',4',5',6'-hexahydro-[4,4']bipyridinyl-2-yl)-(4-difluoromethyl-pyridin-2-yl)-amine |
| 52 | 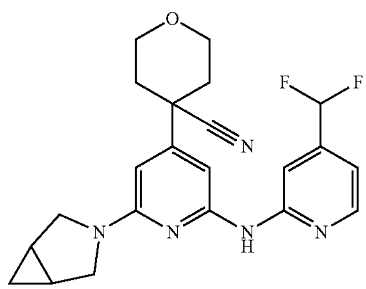 [SMILES: N#CC1(c2cc(Nc3cc(C(F)F)ccn3)nc(N3CC4CC4C3)c2)CCOCC1] | 4-[2-(3-Aza-bicyclo[3.1.0]hex-3-yl)-6-(4-difluoromethyl-pyridin-2-ylamino)-pyridin-4-yl]-tetrahydro-pyran-4-carbonitrile |
| 53 | 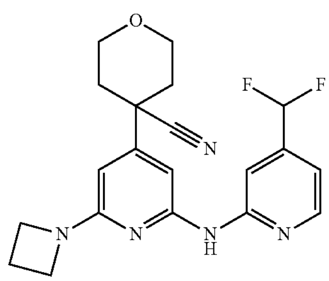 [SMILES: N#CC1(c2cc(Nc3cc(C(F)F)ccn3)nc(N3CCC3)c2)CCOCC1] | 4-[2-Azetidin-1-yl-6-(4-diflfuoromethyl-pyridin-2-ylamino)-pyridin-4-yl]-tetrahydro-pyran-4-carbonitrile |
| 54 | 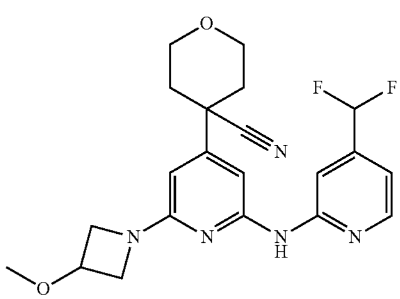 [SMILES: COC1CN(c2cc(C3(C#N)CCOCC3)cc(Nc3cc(C(F)F)ccn3)n2)C1] | 4-[2-(4-Difluoromethyl-pyridin-2-ylamino)-6-(3-methoxy-azetidin-1-yl)-pyridin-4-yl]-tetrahydro-pyran-4-carbonitrile |
| 55 | 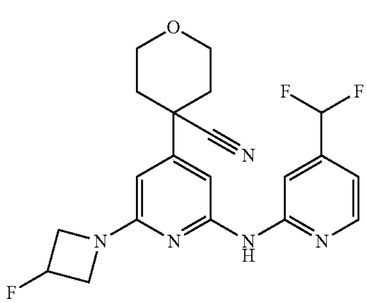 [SMILES: N#CC1(c2cc(Nc3cc(C(F)F)ccn3)nc(N3CC(F)C3)c2)CCOCC1] | 4-[2-(4-Difluoromethyl-pyridin-2-ylamino)-6-(3-fluoro-azetidin-1-yl)-pyridin-4-yl]-tetrahydro-pyran-4-carbonitrile |

TABLE A-continued

| NO | Structure | Name |
|---|---|---|
| 56 | 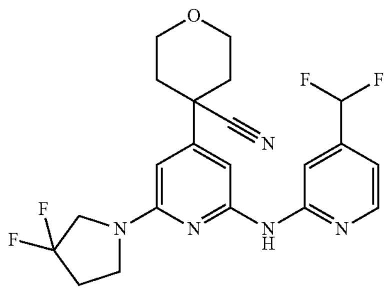 [SMILES: N#CC1(c2cc(Nc3cc(C(F)F)ccn3)nc(N3CCC(F)(F)C3)c2)CCOCC1] | 4-[2-(4-Difluoromethyl-pyridin-2-ylamino)-6-(3,3-difluoro-pyrrolidin-1-yl)-pyridin-4-yl]-tetra-hydro-pyran-4-carbonitrile |
| 57 | 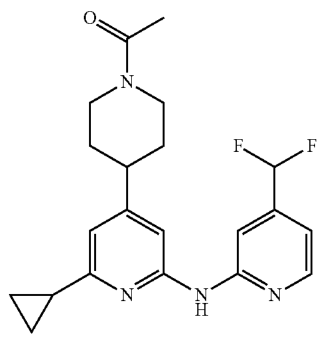 [SMILES: CC(=O)N1CCC(c2cc(Nc3cc(C(F)F)ccn3)nc(C3CC3)c2)CC1] | 1-[6'-Cyclopropyl-2'-(4-difluoromethyl-pyridin-2-ylamino)-3,4,5,6-tetra-hydro-2H-[4,4']bipyridin-yl-1-yl]-ethanone |
| 58 | 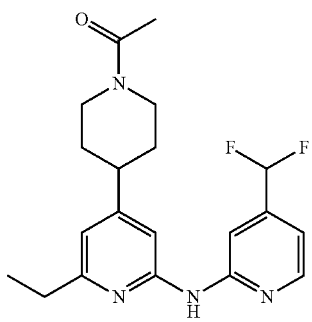 [SMILES: CCc1cc(C2CCN(C(C)=O)CC2)cc(Nc2cc(C(F)F)ccn2)n1] | 1-[2'-(4-Difluoromethyl-pyridin-2-ylamino)-6'-eth-yl-3,4,5,6-tetrahydro-2H-[4,4']bipyridin-1-yl]-ethanone |
| 59 | 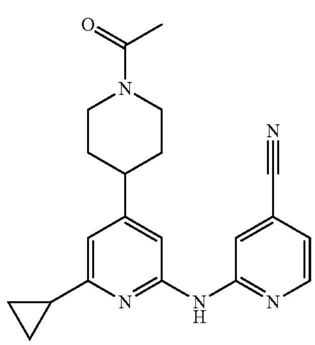 [SMILES: CC(=O)N1CCC(c2cc(Nc3cc(C#N)ccn3)nc(C3CC3)c2)CC1] | 2-(1'-Acetyl-6-cyclopropyl-1',2',3',4',5',6'-hexa-hydro-[4,4']bipyridinyl-2-ylamino)-isonicotinonitrile |
| 60 | 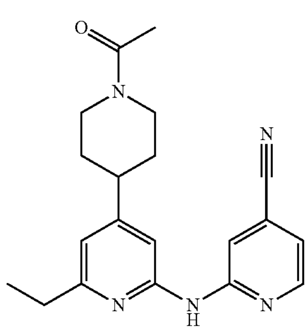 | 2-(1'-Acetyl-6-ethyl-1',2',3',4',5',6'-hexahydro-[4,4']bipyridinyl-2-ylamino)-isonicotinonitrile |

TABLE A-continued

| NO | Structure | Name |
| --- | --- | --- |
| 61 | 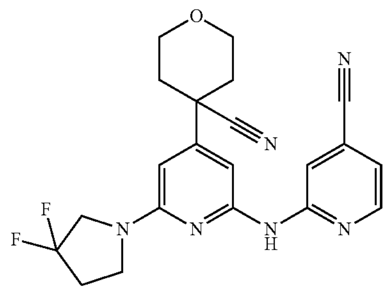 [SMILES: N#Cc1ccnc(Nc2cc(C3(C#N)CCOCC3)cc(N3CCC(F)(F)C3)n2)c1] | 2-[4-(4-Cyano-tetrahydro-pyran-4-yl)-6-(3,3-difluoro-pyrrolidin-1-yl)-pyridin-2-ylamino]-isonicotinonitrile |
| 62 | 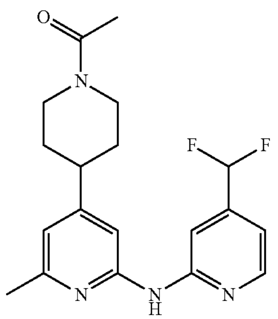 [SMILES: CC(=O)N1CCC(c2cc(C)nc(Nc3cc(C(F)F)ccn3)c2)CC1] | 1-[2'-(4-Difluoromethyl-pyridin-2-ylamino)-6'-methyl-3,4,5,6-tetrahydro-2H-[4,4']bipyridinyl-1-yl]-ethanone |
| 63 | 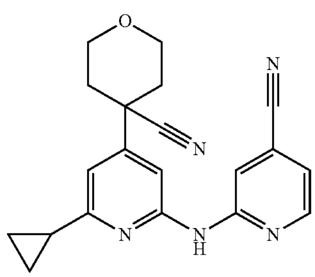 [SMILES: N#Cc1ccnc(Nc2cc(C3(C#N)CCOCC3)cc(C3CC3)n2)c1] | 2-[4-(4-Cyano-tetrahydro-pyran-4-yl)-6-cyclopropyl-pyridin-2-ylamino]-isonicotinonitrile |
| 64 | 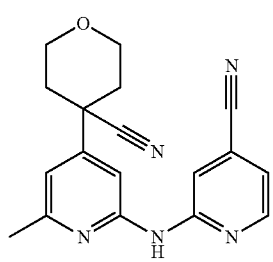 [SMILES: Cc1cc(C2(C#N)CCOCC2)cc(Nc2cc(C#N)ccn2)n1] | 2-[4-(4-Cyano-tetrahydro-pyran-4-yl)-6-methyl-pyridin-2-ylamino]-isonicotinonitrile |
| 65 | 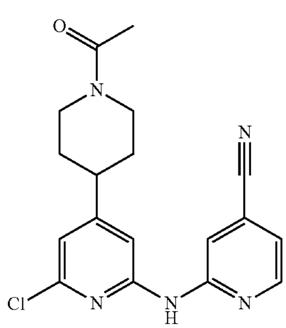 [SMILES: CC(=O)N1CCC(c2cc(Cl)nc(Nc3cc(C#N)ccn3)c2)CC1] | 2-(1'-Acetyl-6-chloro-1',2',3',4',5',6'-hexahydro-[4,4']bipyridinyl-2-ylamino)-isonicotinonitrile |

| NO | Structure | Name |
|---|---|---|
| 66 | 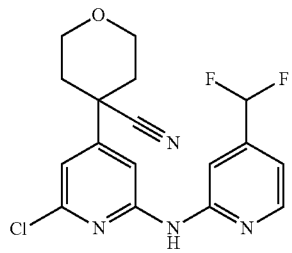 [SMILES: N#CC1(c2cc(Cl)nc(Nc3cc(C(F)F)ccn3)c2)CCOCC1] | 4-[2-Chloro-6-(4-difluoro-methyl-pyridin-2-ylamino)-pyridin-4-yl]-tetra-hydro-pyran-4-carbonitrile |
| 67 | 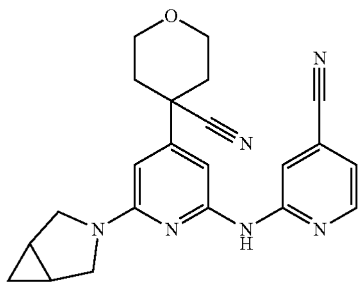 [SMILES: N#Cc1ccnc(Nc2cc(C3(C#N)CCOCC3)cc(N3CC4CC4C3)n2)c1] | 2-[6-(3-Aza-bicyclo[3.1.0]hex-3-yl)-4-(4-cyano-tetrahydro-pyran-4-yl)-pyridin-2-ylamino]-isonicotinonitrile |
| 68 | 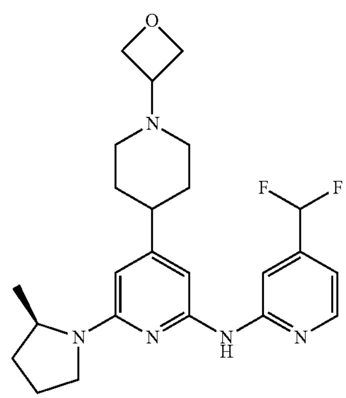 [SMILES: C[C@@H]1CCCN1c1cc(C2CCN(C3COC3)CC2)cc(Nc2cc(C(F)F)ccn2)n1] | (4-Difluoromethyl-pyridin-2-yl)-[6-((R)-2-methyl-pyrrolidin-1-yl)-1'-oxetan-3-yl-1',2',3',4',5',6'-hexahydro-[4,4']bipyridinyl-2-yl]-amine |
| 69 | 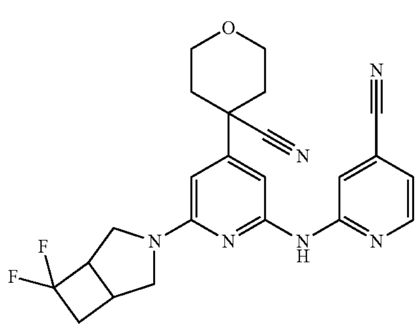 [SMILES: N#Cc1ccnc(Nc2cc(C3(C#N)CCOCC3)cc(N3CC4CC(F)(F)C4C3)n2)c1] | 2-[4-(4-Cyano-tetrahydro-pyran-4-yl)-6-(6,6-difluoro-3-aza-bicyclo[3.2.0]hept-3-yl)-pyridin-2-yl-amino]-isonicotinonitrile |

TABLE A-continued

| NO | Structure | Name |
|---|---|---|
| 70 | 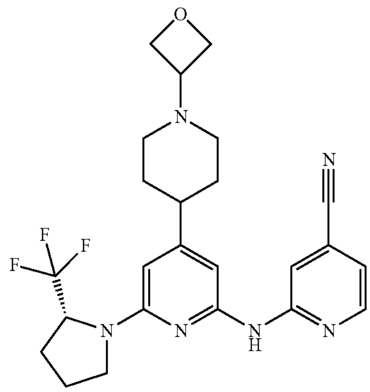 [SMILES: N#Cc1ccnc(Nc2cc(C3CCN(C4COC4)CC3)cc(N3CCC[C@@H]3C(F)(F)F)n2)c1] | 2-[1'-Oxetan-3-yl-6-((R)-2-trifluoromethyl-pyrrolidin-1-yl)-1',2',3',4',5',6'-hexahydro-[4,4']bipyridinyl-2-ylamino]-isonicotinonitrile |
| 71 | 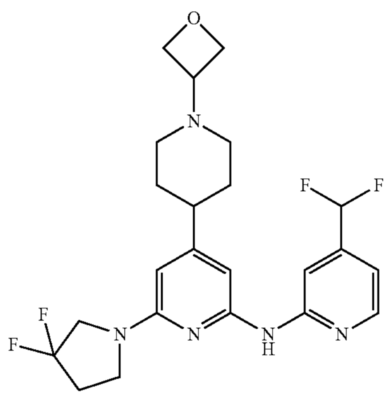 [SMILES: FC(F)c1ccnc(Nc2cc(C3CCN(C4COC4)CC3)cc(N3CCC(F)(F)C3)n2)c1] | (4-Difluoromethyl-pyridin-2-yl)-[6-(3,3-difluoro-pyrrolidin-1-yl)-1'-oxetan-3-yl-1',2',3',4',5',6'-hexahydro-[4,4']bipyridinyl-2-yl]-amine |
| 72 | 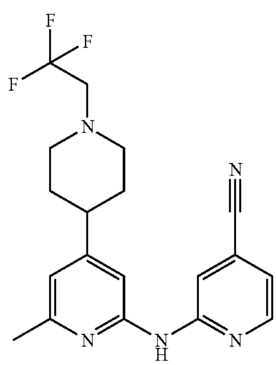 [SMILES: Cc1cc(C2CCN(CC(F)(F)F)CC2)cc(Nc2cc(C#N)ccn2)n1] | 2-[6-Methyl-1'-(2,2,2-trifluoro-ethyl)-1',2',3',4',5',6'-hexahydro-[4,4']bipyridinyl-2-ylamino]-isonicotinonitrile |
| 73 | 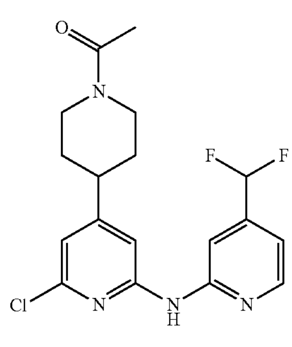 [SMILES: CC(=O)N1CCC(c2cc(Cl)nc(Nc3cc(C(F)F)ccn3)c2)CC1] | 1-[6'-Chloro-2'-(4-difluoromethyl-pyridin-2-ylamino)-3,4,5,6-tetrahydro-2H-[4,4']bipyridinyl-1-yl]-ethanone |

TABLE A-continued

| NO | Structure | Name |
|---|---|---|
| 74 | 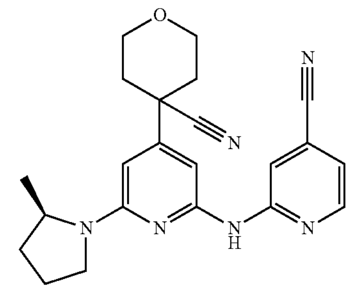 [SMILES: C[C@@H]1CCCN1c1cc(C2(C#N)CCOCC2)cc(Nc2cc(C#N)ccn2)n1] | 2-[4-(4-Cyano-tetrahydro-pyran-4-yl)-6-((R)-2-methyl-pyrrolidin-1-yl)-pyridin-2-ylamino]-iso-nicotinonitrile |
| 75 | 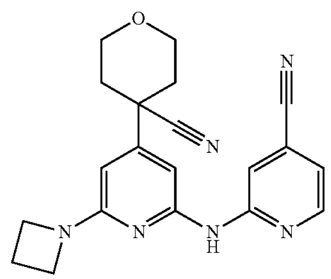 [SMILES: N#Cc1ccnc(Nc2cc(C3(C#N)CCOCC3)cc(N3CCC3)n2)c1] | 2-[6-Azetidin-1-yl-4-(4-cyano-tetrahydro-pyran-4-yl)-pyridin-2-ylamino]-isonicotinonitrile |
| 76 | 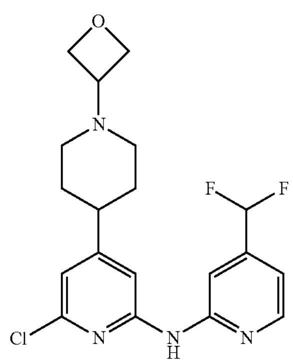 [SMILES: FC(F)c1ccnc(Nc2cc(C3CCN(C4COC4)CC3)cc(Cl)n2)c1] | (6-Chloro-1'-oxetan-3-yl-1',2',3',4',5',6'-hexahydro-[4,4']bipyridinyl-2-yl)-(4-difluoromethyl-pyridin-2-yl)-amine |
| 77 | 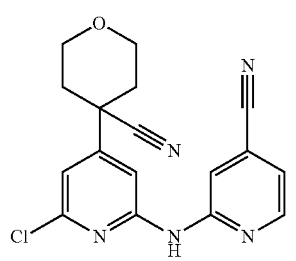 [SMILES: N#Cc1ccnc(Nc2cc(C3(C#N)CCOCC3)cc(Cl)n2)c1] | 2-[6-Chloro-4-(4-cyano-tetrahydro-pyran-4-yl)-pyridin-2-ylamino]-isonico-tinonitrile |
| 78 | 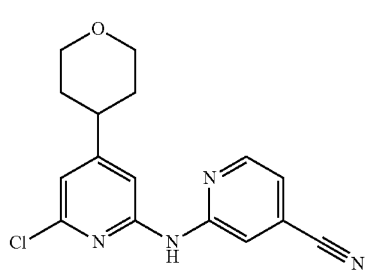 [SMILES: N#Cc1ccnc(Nc2cc(C3CCOCC3)cc(Cl)n2)c1] | 2-[6-Chloro-4-(tetrahydro-pyran-4-yl)-pyridin-2-ylamino]-isonicotinonitrile |

TABLE A-continued

| NO | Structure | Name |
|---|---|---|
| 79 | 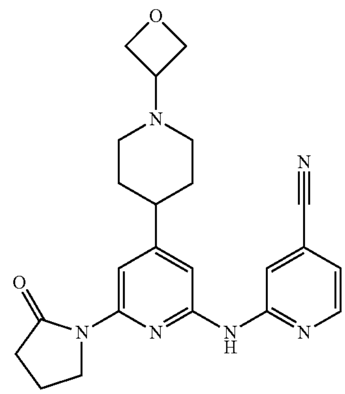 [SMILES: N#Cc1ccnc(Nc2cc(C3CCN(C4COC4)CC3)cc(N3CCCC3=O)n2)c1] | 2-[1'-Oxetan-3-yl-6-(2-oxo-pyrrolidin-1-yl)-1',2',3',4',5',6'-hexahydro-[4,4']bipyridinyl-2-ylamino]-isonicotinonitrile |
| 80 | 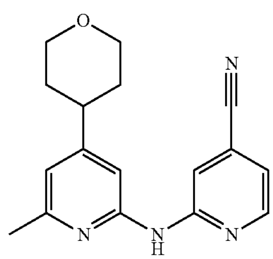 [SMILES: Cc1cc(C2CCOCC2)cc(Nc2cc(C#N)ccn2)n1] | 2-[6-Methyl-4-(tetrahydro-pyran-4-yl)-pyridin-2-ylamino]-isonicotinonitrile |
| 81 | 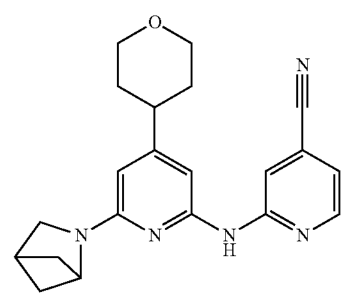 [SMILES: N#Cc1ccnc(Nc2cc(C3CCOCC3)cc(N3CC4CC3C4)n2)c1] | 2-[6-(2-Aza-bicyclo[2.1.1]hex-2-yl)-4-(tetrahydro-pyran-4-yl)-pyridin-2-ylamino]-isonicotinonitrile |
| 82 | 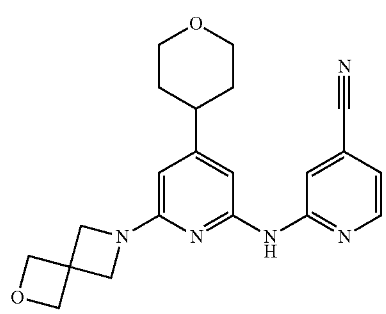 [SMILES: N#Cc1ccnc(Nc2cc(C3CCOCC3)cc(N3CC4(COC4)C3)n2)c1] | 2-[6-(2-Oxa-6-aza-spiro[3.3]hept-6-yl)-4-(tetra-hydro-pyran-4-yl)-pyridin-2-ylamino]-isonicotino-nitrile |
| 83 | 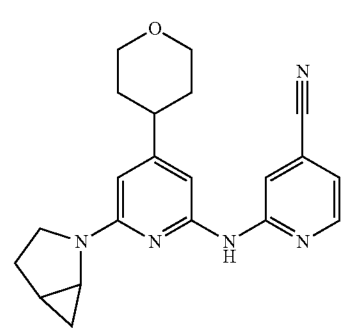 [SMILES: N#Cc1ccnc(Nc2cc(C3CCOCC3)cc(N3CCC4CC43)n2)c1] | 2-[6-(2-Aza-bicyclo[3.1.0]hex-2-yl)-4-(tetrahydro-pyran-4-yl)-pyridin-2-ylamino]-isonicotinonitrile |

TABLE A-continued

| NO | Structure | Name |
|---|---|---|
| 84 | 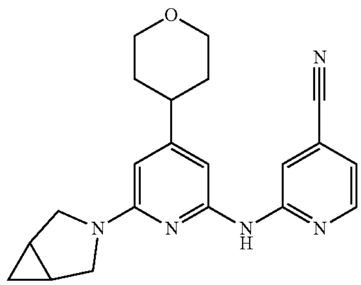 [SMILES: N#Cc1ccnc(Nc2cc(C3CCOCC3)cc(N3CC4CC4C3)n2)c1] | 2-[6-(3-Aza-bicyclo[3.1.0]hex-3-yl)-4-(tetrahydro-pyran-4-yl)-pyridin-2-ylamino]-isonicotinonitrile |
| 85 | 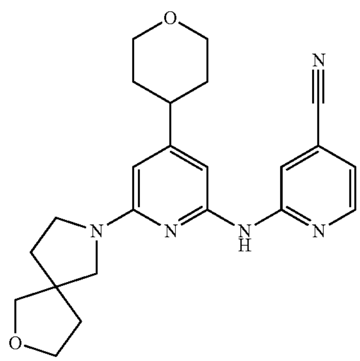 [SMILES: N#Cc1ccnc(Nc2cc(C3CCOCC3)cc(N3CCC4(CCOC4)C3)n2)c1] | 2-[6-(2-Oxa-7-aza-spiro[4.4]non-7-yl)-4-(tetrahydro-pyran-4-yl)-pyridin-2-ylamino]-isonicotinonitrile |
| 86 | 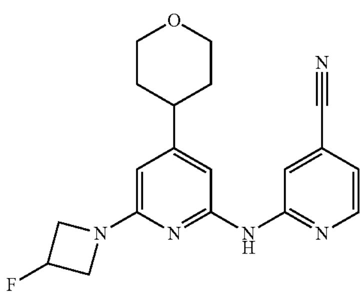 [SMILES: N#Cc1ccnc(Nc2cc(C3CCOCC3)cc(N3CC(F)C3)n2)c1] | 2-[6-(3-Fluoro-azetidin-1-yl)-4-(tetrahydro-pyran-4-yl)-pyridin-2-ylamino]-isonicotinonitrile |
| 87 | 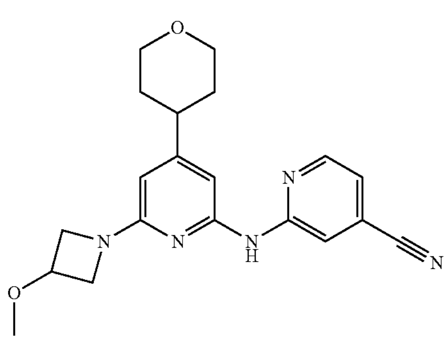 [SMILES: COC1CN(c2cc(C3CCOCC3)cc(Nc3cc(C#N)ccn3)n2)C1] | 2-[6-(3-Methoxy-azetidin-1-yl)-4-(tetrahydro-pyran-4-yl)-pyridin-2-yl-amino]-isonicotinonitrile |

TABLE A-continued

| NO | Structure | Name |
|---|---|---|
| 88 | 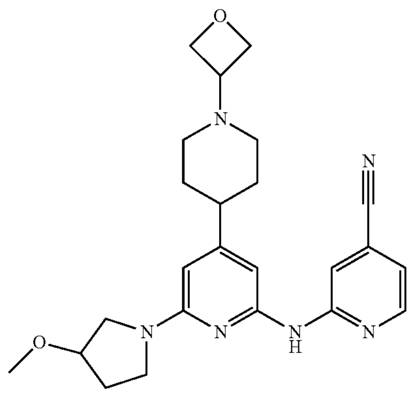 [SMILES: COC1CCN(c2cc(C3CCN(C4COC4)CC3)cc(Nc3cc(C#N)ccn3)n2)C1] | 2-[6-(3-Methoxy-pyrrolidin-1-yl)-1'-oxetan-3-yl-1',2',3',4',5',6'-hexahydro-[4,4']bipyridinyl-2-ylamino]-isonicotinonitrile |
| 89 | 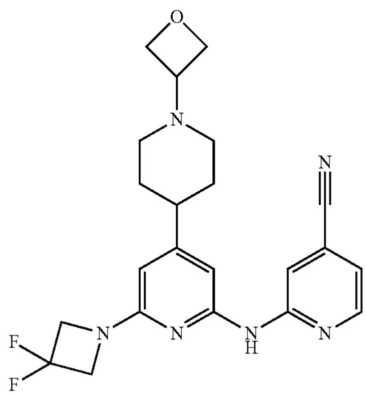 [SMILES: N#Cc1ccnc(Nc2cc(C3CCN(C4COC4)CC3)cc(N3CC(F)(F)C3)n2)c1] | 2-[6-(3,3-Difluoro-azetidin-1-yl)-1'-oxetan-3-yl-1',2',3',4',5',6'-hexahydro-[4,4']bipyridinyl-2-ylamino]-isonicotinonitrile |
| 90 | 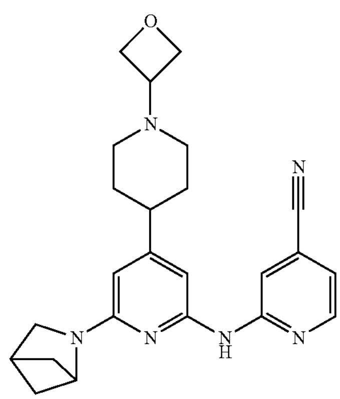 [SMILES: N#Cc1ccnc(Nc2cc(C3CCN(C4COC4)CC3)cc(N3CC4CC3C4)n2)c1] | 2-[6-(2-Aza-bicyclo[2.1.1]hex-2-yl)-1'-oxetan-3-yl-1',2',3',4',5',6'-hexahydro-[4,4']bipyridinyl-2-ylamino]-isonicotinonitrile |
| 91 | 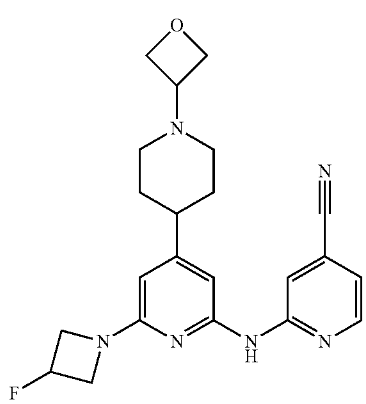 [SMILES: N#Cc1ccnc(Nc2cc(C3CCN(C4COC4)CC3)cc(N3CC(F)C3)n2)c1] | 2-[6-(3-Fluoro-azetidin-1-yl)-1'-oxetan-3-yl-1',2',3',4',5',6'-hexahydro-[4,4']bipyridinyl-2-ylamino]-isonicotinonitrile |

TABLE A-continued
| NO | Structure | Name |
|---|---|---|
| 92 | 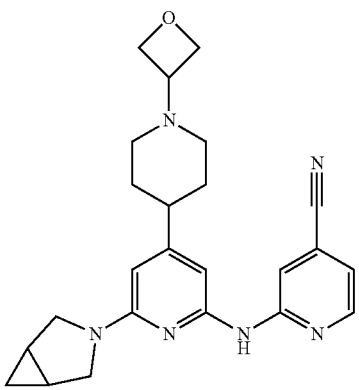 [SMILES: N#Cc1ccnc(Nc2cc(C3CCN(C4COC4)CC3)cc(N3CC4CC4C3)n2)c1] | 2-[6-(3-Aza-bicyclo[3.1.0]hex-3-yl)-1'-oxetan-3-yl-1',2',3',4',5',6'-hexahydro-[4,4']bipyridinyl-2-ylamino]-isonicotinonitrile |
| 93 | 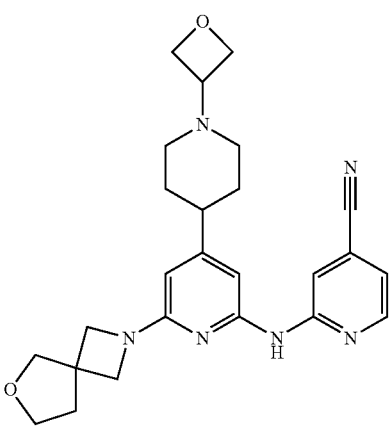 [SMILES: N#Cc1ccnc(Nc2cc(C3CCN(C4COC4)CC3)cc(N3CC4(CCOC4)C3)n2)c1] | 2-[6-(6-Oxa-2-aza-spiro[3.4]oct-2-yl)-1'-oxetan-3-yl-1',2',3',4',5',6'-hexahydro-[4,4']bipyridinyl-2-ylamino]-isonicotinonitrile |
| 94 | 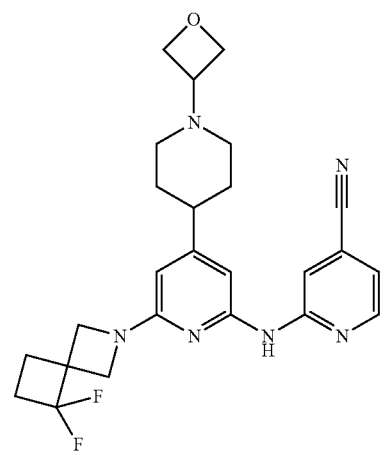 [SMILES: N#Cc1ccnc(Nc2cc(C3CCN(C4COC4)CC3)cc(N3CC4(CCC4(F)F)C3)n2)c1] | 2-[6-(5,5-Difluoro-2-aza-spiro[3.3]hept-2-yl)-1'-oxetan-3-yl-1',2',3',4',5',6'-hexahydro-[4,4']bipyridinyl-2-ylamino]-isonicotinonitrile |

TABLE A-continued

| NO | Structure | Name |
|---|---|---|
| 95 | 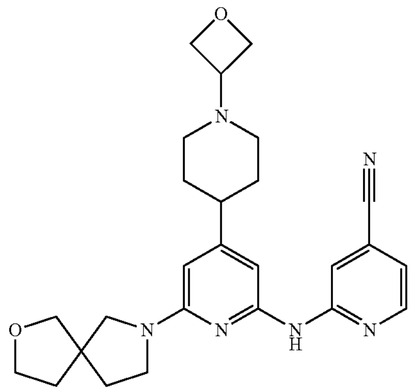 [SMILES: N#Cc1ccnc(Nc2cc(C3CCN(C4COC4)CC3)cc(N3CCC4(CCOC4)C3)n2)c1] | 2-[6-(2-Oxa-7-aza-spiro[4.4]non-7-yl)-1'-oxetan-3-yl-1',2',3',4',5',6'-hexahydro-[4,4']bipyridinyl-2-ylamino]-isonicotinonitrile |
| 96 | 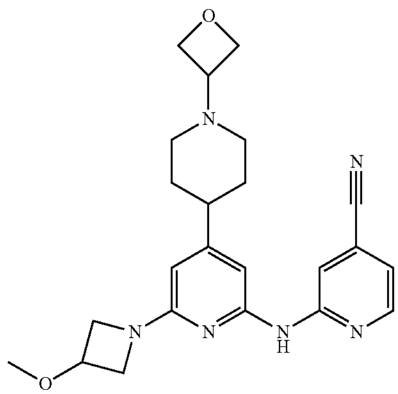 [SMILES: COC1CN(c2cc(C3CCN(C4COC4)CC3)cc(Nc3cc(C#N)ccn3)n2)C1] | 2-[6-(3-Methoxy-azetidin-1-yl)-1'-oxetan-3-yl-1',2',3',4',5',6'-hexahydro-[4,4']bipyridinyl-2-ylamino]-isonicotinonitrile |
| 97 | 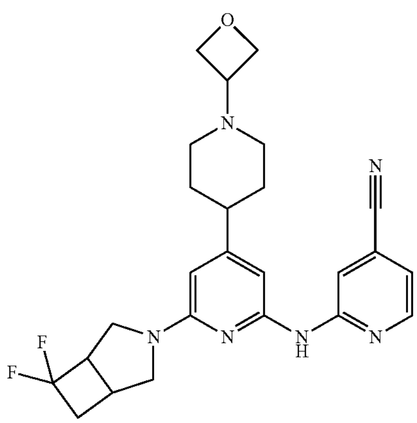 [SMILES: N#Cc1ccnc(Nc2cc(C3CCN(C4COC4)CC3)cc(N3CC4CC(F)(F)C4C3)n2)c1] | 2-[6-(6,6-Difluoro-3-aza-bicyclo[3.2.0]hept-3-yl)-1'-oxetan-3-yl-1',2',3',4',5',6'-hexahydro-[4,4']bipyridinyl-2-ylamino]-isonicotinonitrile |
| 98 | 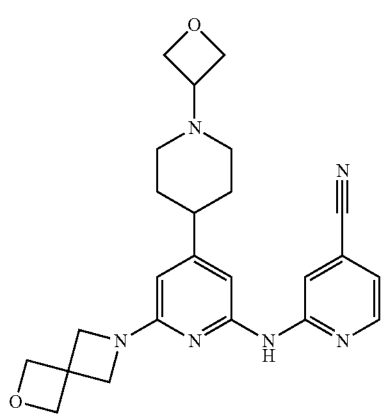 [SMILES: N#Cc1ccnc(Nc2cc(C3CCN(C4COC4)CC3)cc(N3CC4(COC4)C3)n2)c1] | 2-[6-(2-Oxa-6-aza-spiro[3.3]hept-6-yl)-1'-oxetan-3-yl-1',2',3',4',5',6'-hexahydro-[4,4']bipyridinyl-2-ylamino]-isonicotinonitrile |

TABLE A-continued

| NO | Structure | Name |
|---|---|---|
| 99 | 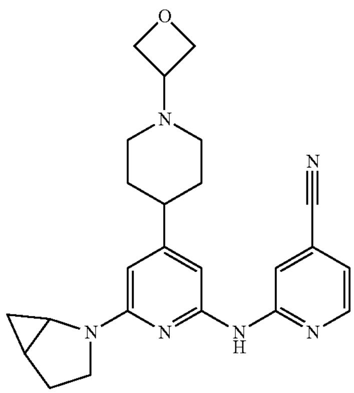 [SMILES: N#Cc1ccnc(Nc2cc(C3CCN(C4COC4)CC3)cc(N3CCC4CC43)n2)c1] | 2-[6-(2-Aza-bicyclo[3.1.0]hex-2-yl)-1'-oxetan-3-yl-1',2',3',4',5',6'-hexahydro-[4,4']bipyridinyl-2-ylamino]-isonicotinonitrile |
| 100 | 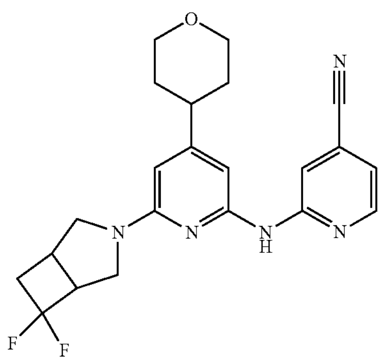 [SMILES: N#Cc1ccnc(Nc2cc(C3CCOCC3)cc(N3CC4CC(F)(F)C4C3)n2)c1] | 2-[6-(6,6-Difluoro-3-aza-bicyclo[3.2.0]hept-3-yl)-4-(tetrahydro-pyran-4-yl)-pyridin-2-ylamino]-isonicotinonitrile |
| 101 | 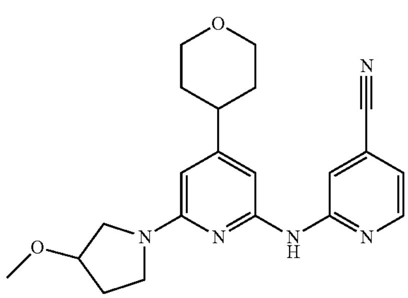 [SMILES: COC1CCN(c2cc(C3CCOCC3)cc(Nc3cc(C#N)ccn3)n2)C1] | 2-[6-(3-Methoxy-pyrrolidin-1-yl)-4-(tetrahydro-pyran-4-yl)-pyridin-2-ylamino]-isonicotinonitrile |
| 102 | 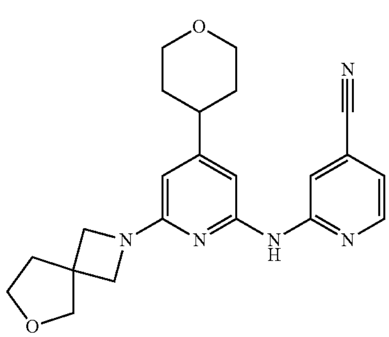 [SMILES: N#Cc1ccnc(Nc2cc(C3CCOCC3)cc(N3CC4(CCOC4)C3)n2)c1] | 2-[6-(6-Oxa-2-aza-spiro[3.4]oct-2-yl)-4-(tetrahydro-pyran-4-yl)-pyridin-2-ylamino]-isonicotinonitrile |

TABLE A-continued

| NO | Structure | Name |
|---|---|---|
| 103 | 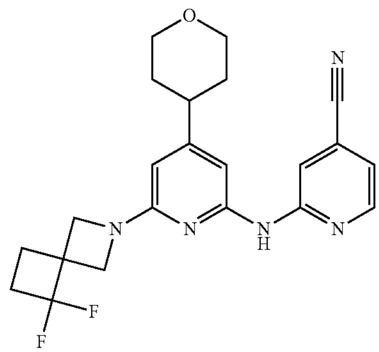 [SMILES: N#Cc1ccnc(Nc2cc(C3CCOCC3)cc(N3CC4(CCC4(F)F)C3)n2)c1] | 2-[6-(5,5-Difluoro-2-aza-spiro[3.3]hept-2-yl)-4-(tetrahydro-pyran-4-yl)-pyridin-2-ylamino]-isonicotinonitrile |
| 104 | 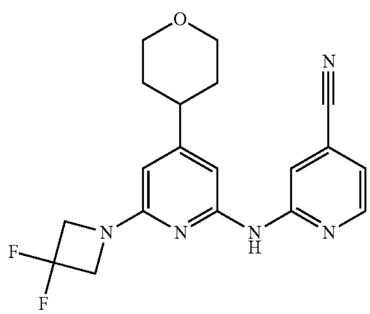 [SMILES: N#Cc1ccnc(Nc2cc(C3CCOCC3)cc(N3CC(F)(F)C3)n2)c1] | 2-[6-(3,3-Difluoro-azeti-din-1-yl)-4-(tetrahydro-pyran-4-yl)-pyridin-2-yl-amino]-isonicotinonitrile |
| 105 | 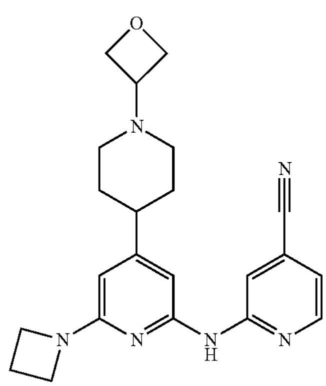 [SMILES: N#Cc1ccnc(Nc2cc(C3CCN(C4COC4)CC3)cc(N3CCC3)n2)c1] | 2-(6-Azeitidin-1-yl-1'-oxetan-3-yl-1',2',3',4',5',6'-hexahydro-[4,4']bipyridinyl-2-ylamino)-isonicotinonitrile |
| 106 | 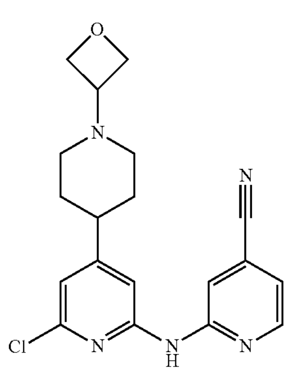 [SMILES: N#Cc1ccnc(Nc2cc(C3CCN(C4COC4)CC3)cc(Cl)n2)c1] | 2-(6-Chloro-1'-oxetan-3-yl-1',2',3',4',5',6'-hexa-hydro-[4,4']bipyridinyl-2-ylamino)-isonicotinonitrile |

TABLE A-continued

| NO | Structure | Name |
|---|---|---|
| 107 | 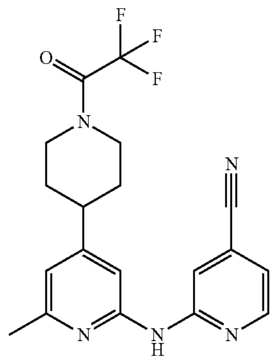 [SMILES: Cc1cc(C2CCN(C(=O)C(F)(F)F)CC2)cc(Nc2cc(C#N)ccn2)n1] | 2-[6-Methyl-1'-(2,2,2-tri-fluoro-acetyl)-1',2',3',4',5',6'-hexahydro-[4,4']bi-pyridinyl-2-ylamino]-isonicotinonitrile |
| 108 | 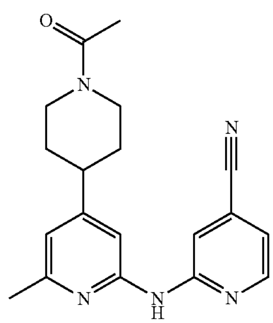 [SMILES: CC(=O)N1CCC(c2cc(C)nc(Nc3cc(C#N)ccn3)c2)CC1] | 2-(1'-Acetyl-6-methyl-1',2',3',4',5',6'-hexahydro-[4,4']bipyridinyl-2-ylamino)-isonicotinonitrile |
| 109 | 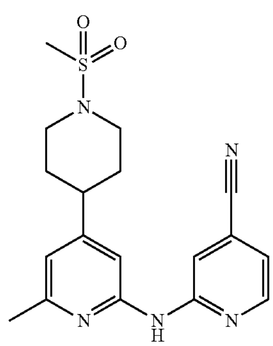 [SMILES: Cc1cc(C2CCN(S(C)(=O)=O)CC2)cc(Nc2cc(C#N)ccn2)n1] | 2-(1'-Methanesulfonyl-6-methyl-1',2',3',4',5',6'-hexahydro-[4,4']bi-pyridinyl-2-ylamino)-isonicotinotrile |
| 110 | 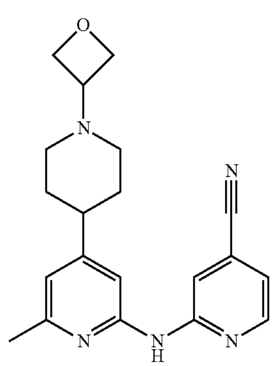 [SMILES: Cc1cc(C2CCN(C3COC3)CC2)cc(Nc2cc(C#N)ccn2)n1] | 2-(6-Methyl-1'-oxetan-3-yl-1',2',3',4',5',6'-hexa-hydro-[4,4']bipyridinyl-2-ylamino)-isonicotinonitrile |

TABLE A-continued

| NO | Structure | Name |
| --- | --- | --- |
| 111 | 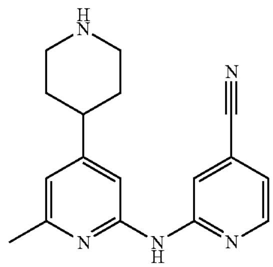 [SMILES: Cc1cc(C2CCNCC2)cc(Nc2cc(C#N)ccn2)n1] | 2-(6-Methyl-1',2',3',4',5',6'-hexahydro-[4,4']bi-pyridinyl-2-ylamino)-isonicotinonitrile |
| 112 | 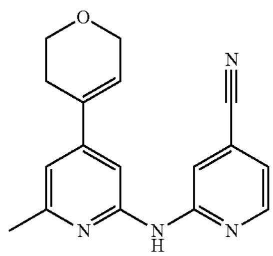 [SMILES: Cc1cc(C2=CCOCC2)cc(Nc2cc(C#N)ccn2)n1] | 2-[4-(3,6-Dihydro-2H-pyran-4-yl)-6-methyl-pyridin-2-ylamino]-isonicotinonitrile |
| 113 | 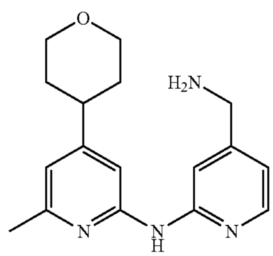 [SMILES: Cc1cc(C2CCOCC2)cc(Nc2cc(CN)ccn2)n1] | (4-Aminomethyl-pyridin-2-yl)-[6-methyl-4-(tetrahydro-pyran-4-yl)-pyridin-2-yl]-amine |
| 114 | 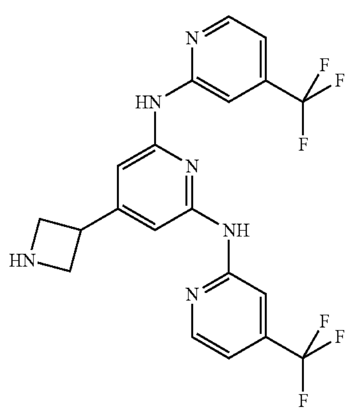 [SMILES: FC(F)(F)c1ccnc(Nc2cc(C3CNC3)cc(Nc3cc(C(F)(F)F)ccn3)n2)c1] | 4-Azetidin-3-yl-N,N'-bis-(4-trifluoromethyl-pyridin-2-yl)-pyridine-2,6-diamine |
| 115 | 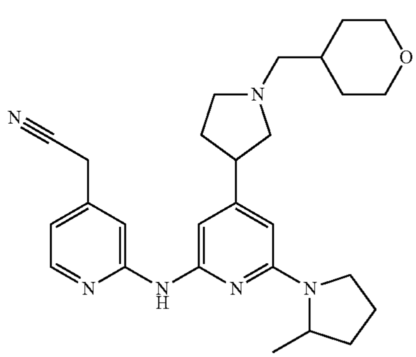 [SMILES: CC1CCCN1c1cc(C2CCN(CC3CCOCC3)C2)cc(Nc2cc(CC#N)ccn2)n1] | 2-{6-(2-Methyl-pyrrolidin-1-yl)-4-[1-(tetrahydro-pyran-4-ylmethyl)-pyrrolidin-2-ylamino}-isonicotinonitrile |

TABLE A-continued

| NO | Structure | Name |
|----|-----------|------|
| 116 | 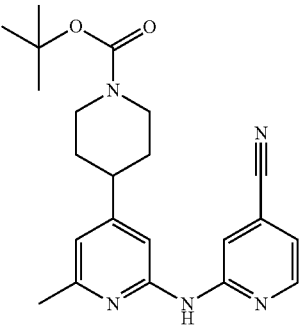 [SMILES: Cc1cc(C2CCN(C(=O)OC(C)(C)C)CC2)cc(Nc2cc(C#N)ccn2)n1] | 2'-(4-Cyano-pyridin-2-yl-amino)-6'-methyl-3,4,5,6-tetrahydro-2H-[4,4']bi-pyridinyl-1-carboxylic acid tert-butyl ester |
| 117 | 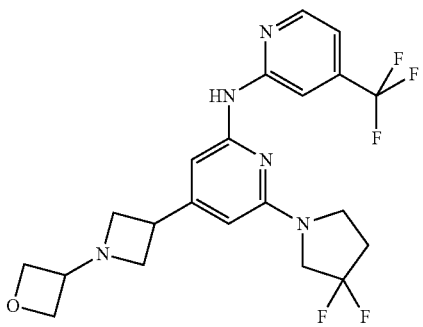 [SMILES: FC1(F)CCN(c2cc(C3CN(C4COC4)C3)cc(Nc3cc(C(F)(F)F)ccn3)n2)C1] | [6-(3,3-Difluoro-pyrrolidin-1-yl)-4-(1-oxetan-3-yl-azetidin-3-yl)-pyridin-2-yl]-(4-trifluoromethyl-pyridin-2-yl)-amine |
| 118 | 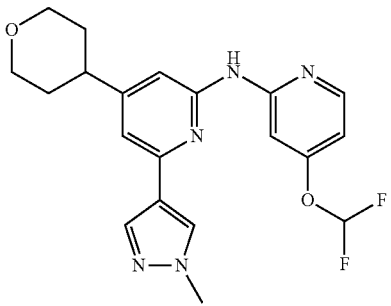 [SMILES: Cn1cc(-c2cc(C3CCOCC3)cc(Nc3cc(OC(F)F)ccn3)n2)cn1] | (4-Difluoromethoxy-pyridin-2-yl)-[6-(1-methyl-1H-pyrazol-4-yl)-4-(tetrahydro-pyran-4-yl)-pyridin-2-yl]-amine |
| 119 | 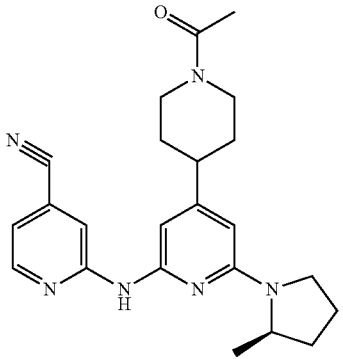 [SMILES: CC(=O)N1CCC(c2cc(Nc3cc(C#N)ccn3)nc(N3CCC[C@H]3C)c2)CC1] | 2-[1'-Acetyl-6-((R)-2-methyl-pyrrolidin-1-yl)-1',2',3',4',5',6'-hexahydro-[4,4']bipyridinyl-2-ylamino]-isonicotinonitrile |

TABLE A-continued

| NO | Structure | Name |
|---|---|---|
| 120 | 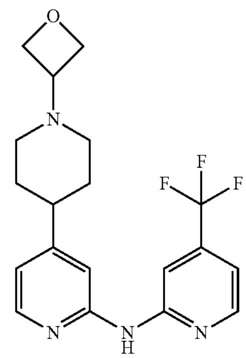 [SMILES: FC(F)(F)c1ccnc(Nc2cc(C3CCN(C4COC4)CC3)ccn2)c1] | (1'-Oxetan-3-yl-1',2',3',4',5',6'-hexahydro-[4,4']bi-pyridinyl-2-yl)-(4-trifluoro-methyl-pyridin-2-yl)-amine |
| 121 | 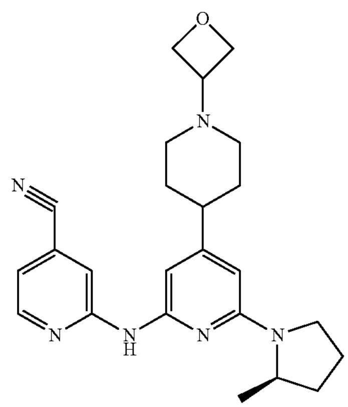 [SMILES: C[C@@H]1CCCN1c1cc(C2CCN(C3COC3)CC2)cc(Nc2cc(C#N)ccn2)n1] | 2-[6-((R)-2-Methyl-pyrro-lidin-1-yl)-1'-oxetan-3-yl-1',2',3',4',5',6'-hexa-hydro-[4,4']bipyridinyl-2-ylamino]-isonicotinonitrile |
| 122 | 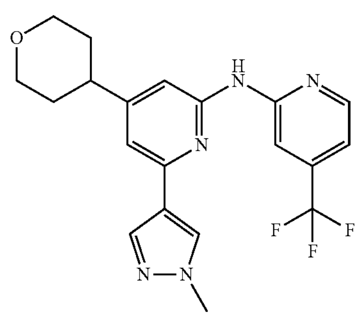 [SMILES: Cn1cc(-c2cc(C3CCOCC3)cc(Nc3cc(C(F)(F)F)ccn3)n2)cn1] | [6-(1-Methyl-1H-pyrazol-4-yl)-4-(tetrahydro-py-ran-4-yl)-pyridin-2-yl]-(4-trifluoromethyl-pyridin-2-yl)-amine |
| 123 | 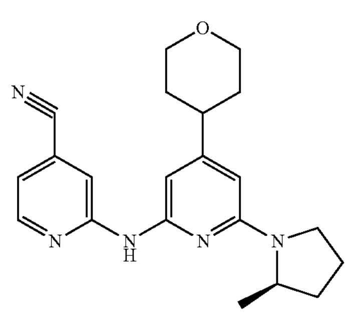 [SMILES: C[C@@H]1CCCN1c1cc(C2CCOCC2)cc(Nc2cc(C#N)ccn2)n1] | 2-[6-((R)-2-Methyl-pyrro-lidin-1-yl)-4-(tetrahydro-pyran-4-yl)-pyridin-2-ylamino]-isonicotinonitrile |

TABLE A-continued

| NO | Structure | Name |
|---|---|---|
| 124 | 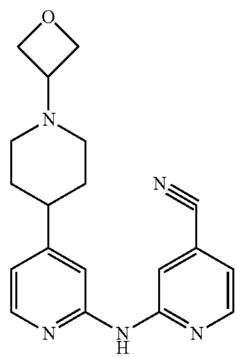 [SMILES: N#Cc1ccnc(Nc2cc(C3CCN(C4COC4)CC3)ccn2)c1] | 2-(1'-Oxetan-3-yl-1',2',3',4',5',6'-hexahydro-[4,4']bipyridinyl-2-ylamino)-isonicotinonitrile |
| 125 | 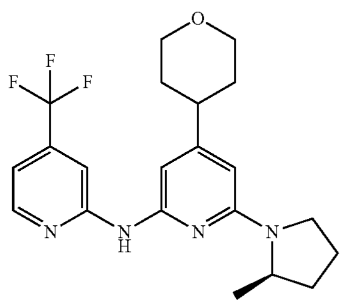 [SMILES: C[C@@H]1CCCN1c1cc(C2CCOCC2)cc(Nc2cc(C(F)(F)F)ccn2)n1] | [6-((R)-2-Methyl-pyrrolidin-1-yl)-4-(tetrahydro-pyran-4-yl)-pyridin-2-yl]-(4-trifluoromethyl-pyridin-2-yl)-amine |
| 126 | 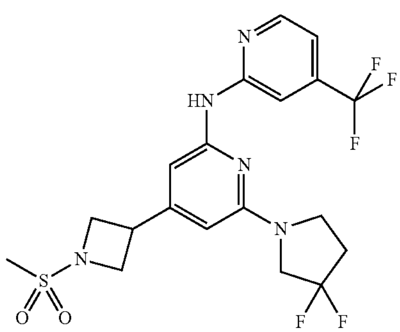 [SMILES: CS(=O)(=O)N1CC(c2cc(Nc3cc(C(F)(F)F)ccn3)nc(N3CCC(F)(F)C3)c2)C1] | [6-(3,3-Difluoro-pyrrolidin-1-yl)-4-(1-methane-sulfonyl-azetidin-3-yl)-pyridin-2-yl]-(4-trifluoromethyl-pyridin-2-yl)-amine |
| 127 | 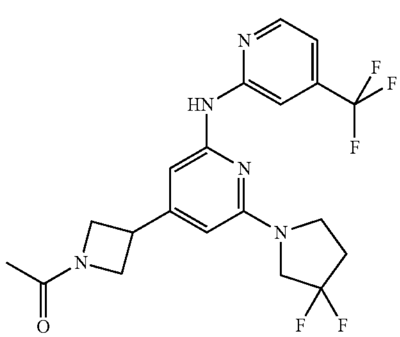 [SMILES: CC(=O)N1CC(c2cc(Nc3cc(C(F)(F)F)ccn3)nc(N3CCC(F)(F)C3)c2)C1] | 1-{3-[2-(3,3-Difluoro-pyrrolidin-1-yl)-6-(4-trifluoromethyl-pyridin-2-ylamino)-pyridin-4-yl]-azetidin-1-yl}-ethanone |

TABLE A-continued

| NO | Structure | Name |
|---|---|---|
| 128 | 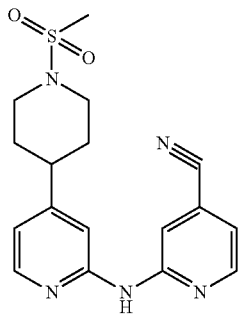 [SMILES: CS(=O)(=O)N1CCC(c2ccnc(Nc3cc(C#N)ccn3)c2)CC1] | 2-(1'-Methanesulfonyl-1',2',3',4',5',6'-hexahydro-[4,4']bipyridinyl-2-yl-amino)-isonicotinonitrile |
| 129 | 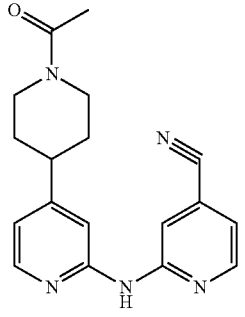 [SMILES: CC(=O)N1CCC(c2ccnc(Nc3cc(C#N)ccn3)c2)CC1] | 2-(1'-Acetyl-1',2',3',4',5',6'-hexahydro-[4,4']bi-pyridinyl-2-ylamino)-isonicotinonitrile |
| 130 | 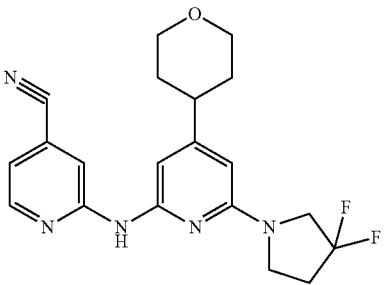 [SMILES: N#Cc1ccnc(Nc2cc(C3CCOCC3)cc(N3CCC(F)(F)C3)n2)c1] | 2-[6-(3,3-Difluoro-pyrro-lidin-1-yl)-4-(tetrahydro-pyran-4-yl)-pyridin-2-yl-amino]-isonicotinonitrile |
| 131 | 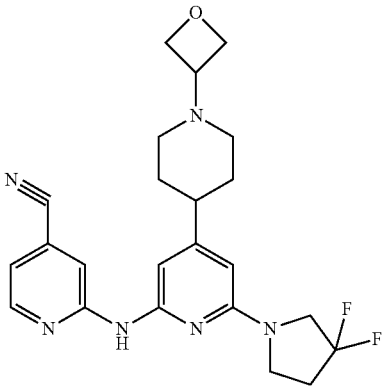 [SMILES: N#Cc1ccnc(Nc2cc(C3CCN(C4COC4)CC3)cc(N3CCC(F)(F)C3)n2)c1] | 2-[6-(3,3-Difluoro-pyrro-lidin-1-yl)-1'-oxetan-3-yl-1',2',3',4',5',6'-hexahydro-[4,4']bipyridinyl-2-yl-amino]-isonicotinonitrile |

TABLE A-continued

| NO | Structure | Name |
|---|---|---|
| 132 | 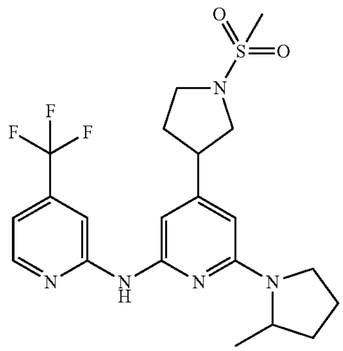 [SMILES: CC1CCCN1c1cc(C2CCN(S(C)(=O)=O)C2)cc(Nc2cc(C(F)(F)F)ccn2)n1] | [4-(1-Methanesulfonyl-pyrrolidin-3-yl)-6-(2-methyl-pyrrolidin-1-yl)-pyridin-2-yl]-(4-trifluoromethyl-pyridin-2-yl)-amine |
| 133 | 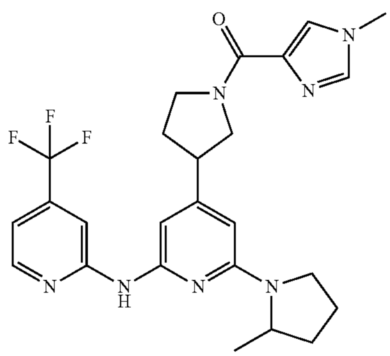 [SMILES: CC1CCCN1c1cc(C2CCN(C(=O)c3cn(C)cn3)C2)cc(Nc2cc(C(F)(F)F)ccn2)n1] | (1-Methyl-1H-imidazol-4-yl)-{3-[2-(2-methyl-pyrrolidin-1-yl)-6-(4-trifluoromethyl-pyridin-2-ylamino)-pyridin-4-yl]-pyrrolidin-1-yl}-methanone |
| 134 | 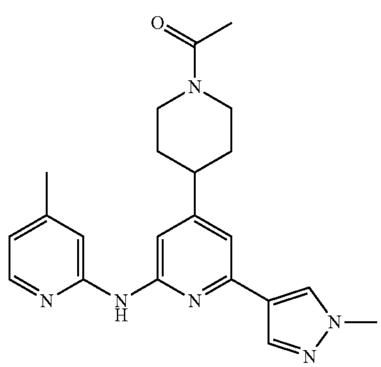 [SMILES: CC(=O)N1CCC(c2cc(Nc3cc(C)ccn3)nc(-c3cnn(C)c3)c2)CC1] | 1-[2'-(1-Methyl-1H-pyrazol-4-yl)-6'-(4-methyl-pyridin-2-ylamino)-3,4,5,6-tetrahydro-2H-[4,4']bipyridinyl-1-yl]-ethanone |
| 135 | 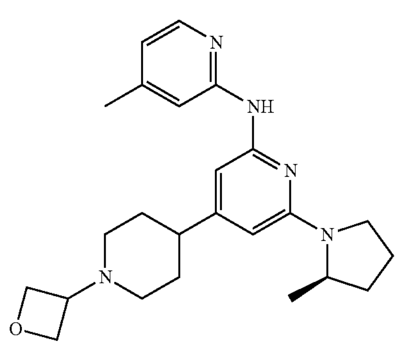 [SMILES: Cc1ccnc(Nc2cc(C3CCN(C4COC4)CC3)cc(N3CCC[C@H]3C)n2)c1] | (4-Methyl-pyridin-2-yl)-[6-((R)-2-methyl-pyrrolidin-1-yl)-1'-oxetan-3-yl-1',2',3',4',5',6'-hexahydro-[4,4']bipyridin-2-yl]-amine |

TABLE A-continued

| NO | Structure | Name |
|---|---|---|
| 136 | 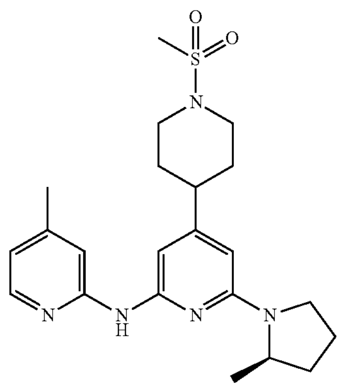 [SMILES: Cc1ccnc(Nc2cc(C3CCN(S(C)(=O)=O)CC3)cc(N3CCC[C@H]3C)n2)c1] | [1'-Methanesulfonyl-6-((R)-2-methyl-pyrrolidin-1-yl)-1',2',3',4',5',6'-hexahydro-[4,4']bipyridinyl-2-yl]-(4-methyl-pyridin-2-yl)-amine |
| 137 | 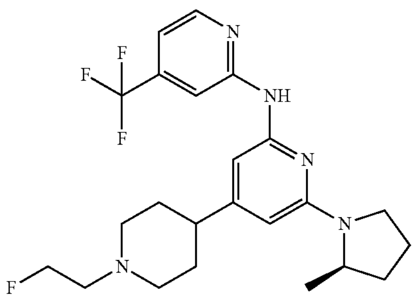 [SMILES: C[C@@H]1CCCN1c1cc(C2CCN(CCF)CC2)cc(Nc2cc(C(F)(F)F)ccn2)n1] | [1'-(2-Fluoro-ethyl)-6-((R)-2-methyl-pyrrolidin-1-yl)-1',2',3',4',5',6'-hexahydro-[4,4']bipyridinyl-2-yl]-(4-trifluoromethyl-pyridin-2-yl)-amine |
| 138 | 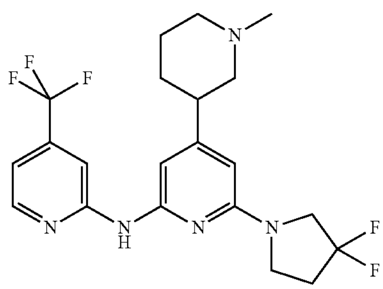 [SMILES: CN1CCCC(c2cc(Nc3cc(C(F)(F)F)ccn3)nc(N3CCC(F)(F)C3)c2)C1] | [6'-(3,3-Difluoro-pyrrolidin-1-yl)-1-methyl-1,2,3,4,5,6-hexahydro-[3,4']bipyridinyl-2'-yl]-(4-trifluoromethyl-pyridin-2-yl)-amine |
| 139 | 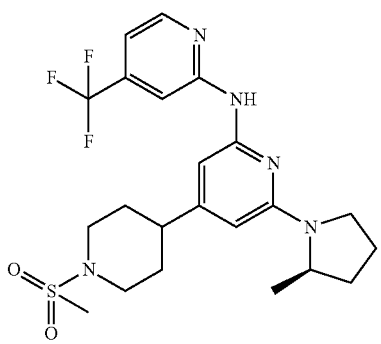 [SMILES: C[C@@H]1CCCN1c1cc(C2CCN(S(C)(=O)=O)CC2)cc(Nc2cc(C(F)(F)F)ccn2)n1] | [1'-Methanesulfonyl-6-((R)-2-methyl-pyrrolidin-1-yl)-1',2',3',4',5',6'-hexahydro-[4,4']bipyridinyl-2-yl]-(4-trifluoromethyl-pyridin-2-yl)-amine |
| 140 | 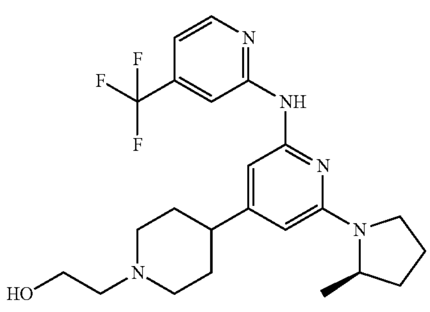 [SMILES: C[C@@H]1CCCN1c1cc(C2CCN(CCO)CC2)cc(Nc2cc(C(F)(F)F)ccn2)n1] | 2-[6'-((R)-2-Methyl-pyrrolidin-1-yl)-2'-(4-trifluoromethyl-pyridin-2-ylamino)-3,4,5,6-tetrahydro-2H-[4,4']bipyridinyl-1-yl]-ethanol |

TABLE A-continued

| NO | Structure | Name |
| --- | --- | --- |
| 141 | 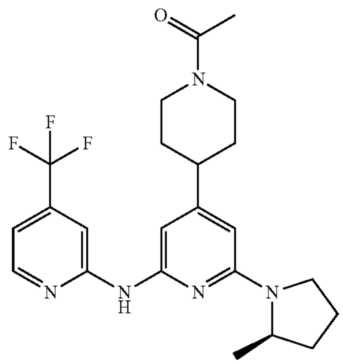 [SMILES: CC(=O)N1CCC(c2cc(Nc3cc(C(F)(F)F)ccn3)nc(N3CCC[C@H]3C)c2)CC1] | 1-[2'-((R)-2-Methyl-pyrrolidin-1-yl)-6'-(4-trifluoromethyl-pyridin-2-ylamino)-3,4,5,6-tetrahydro-2H-[4,4']bipyridinyl-1-yl]-ethanone |
| 142 | 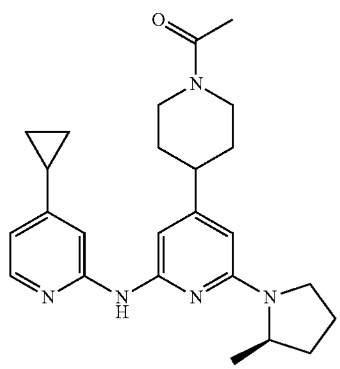 [SMILES: CC(=O)N1CCC(c2cc(Nc3cc(C4CC4)ccn3)nc(N3CCC[C@H]3C)c2)CC1] | 1-[6'-(4-Cyclopropyl-pyridin-2-ylamino)-2'-((R)-2-methyl-pyrrolidin-1-yl)-3,4,5,6-tetrahydro-2H-[4,4']bipyridinyl-1-yl]-ethanone |
| 143 | 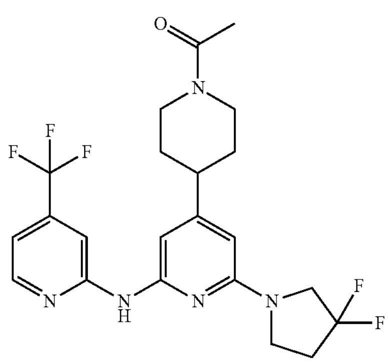 [SMILES: CC(=O)N1CCC(c2cc(Nc3cc(C(F)(F)F)ccn3)nc(N3CCC(F)(F)C3)c2)CC1] | 1-[2'-(3,3-Difluoro-pyrrolidin-1-yl)-6'-(4-trifluoromethyl-pyridin-2-yl-amino)3,4,5,6-tetrahydro-2H-[4,4']bipyridinyl-1-yl]-ethanone |
| 145 | 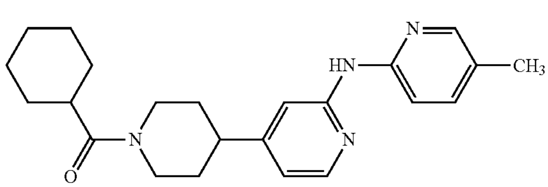 [SMILES: Cc1ccc(Nc2cc(C3CCN(C(=O)C4CCCCC4)CC3)ccn2)nc1] | cyclohexyl(4-(2-((5-methylpyridin-2-yl)amino)pyridin-4-yl)piperidin-1-yl)methanone |

TABLE A-continued

| NO | Structure | Name |
|---|---|---|
| 146 | 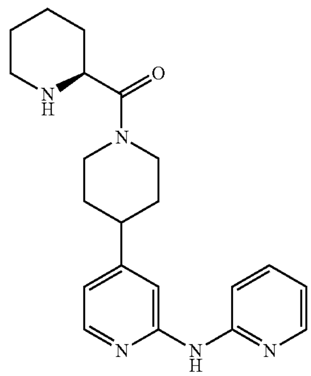 [SMILES: O=C([C@@H]1CCCCN1)N1CCC(c2ccnc(Nc3ccccn3)c2)CC1] | (S)-piperidin-2-yl(4-(2-(pyridin-2-ylamino)pyridin-4-yl)piperidin-1-yl)methanone |
| 147 | 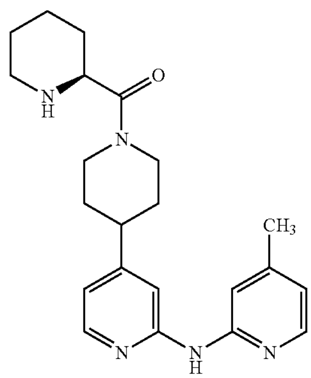 [SMILES: Cc1ccnc(Nc2cc(C3CCN(C(=O)[C@@H]4CCCCN4)CC3)ccn2)c1] | (S)-(4-(2-((4-methylpyridin-2-ylamino)pyridin-4-yl)piperidin-1-yl)(piperidin-2-yl)methanone |
| 144 | 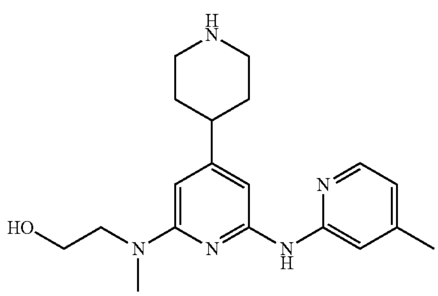 [SMILES: Cc1ccnc(Nc2cc(C3CCNCC3)cc(N(C)CCO)n2)c1] | 2-{Methyl-[6-(4-methyl-pyridin-2-ylamino)-1',2',3',4',5',6'-hexahydro-[4,4']bipyridinyl-2-yl]-amino}-ethanol |

C. Synthesis of Compounds

For illustrative purposes, Schemes 1-4 show general methods for preparing the compounds of the present invention as well as key intermediates. More detailed description of the individual reaction steps, is found in the Examples section below. Those skilled in the art will appreciate that other synthetic routes may be used to synthesize the inventive compounds. Although specific starting materials and reagents are depicted in the Schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

In preparing compounds of Formula I, protection of remote functionality (e.g., primary or secondary amine) of intermediates may be necessary. The need for such protection will vary depending on the nature of the remote functionality and the conditions of the preparation methods. Suitable amino-protecting groups include acetyl, trifluoroacetyl, t-butoxycarbonyl (BOC), benzyloxycarbonyl (CBz) and 9-fluorenylmethylenoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

In Schemes 1-4 the symbol X represents suitable leaving group such as halogen atom or triflate group. $R^1$-$R^6$ and the subscripts m have the meaning as described for compounds of Formula I. Other R substituents represent substituents on the compounds that are non-interfering with the synthetic procedures outlined in the schemes.

In Scheme 1 below illustrates the synthesis of certain compounds of Formula I. In Scheme 1, pyridine compound S-1A is reacted with an amino pyridine S-1B under typical palladium cross-coupling aminations conditions using, for example, a Pd catalyst, phosphine ligand and base (e.g., a carbonate base and heat to provide the dipyridyl compound S-1C. A second palladium cross-coupling amination reaction under typical conditions, for example, of Pd catalyst, phosphine ligand, base and an suitable amine provide compounds of formula I (S-1D) where $R^1$ group in Formula I is an amine (NRR) group.

Scheme 1:

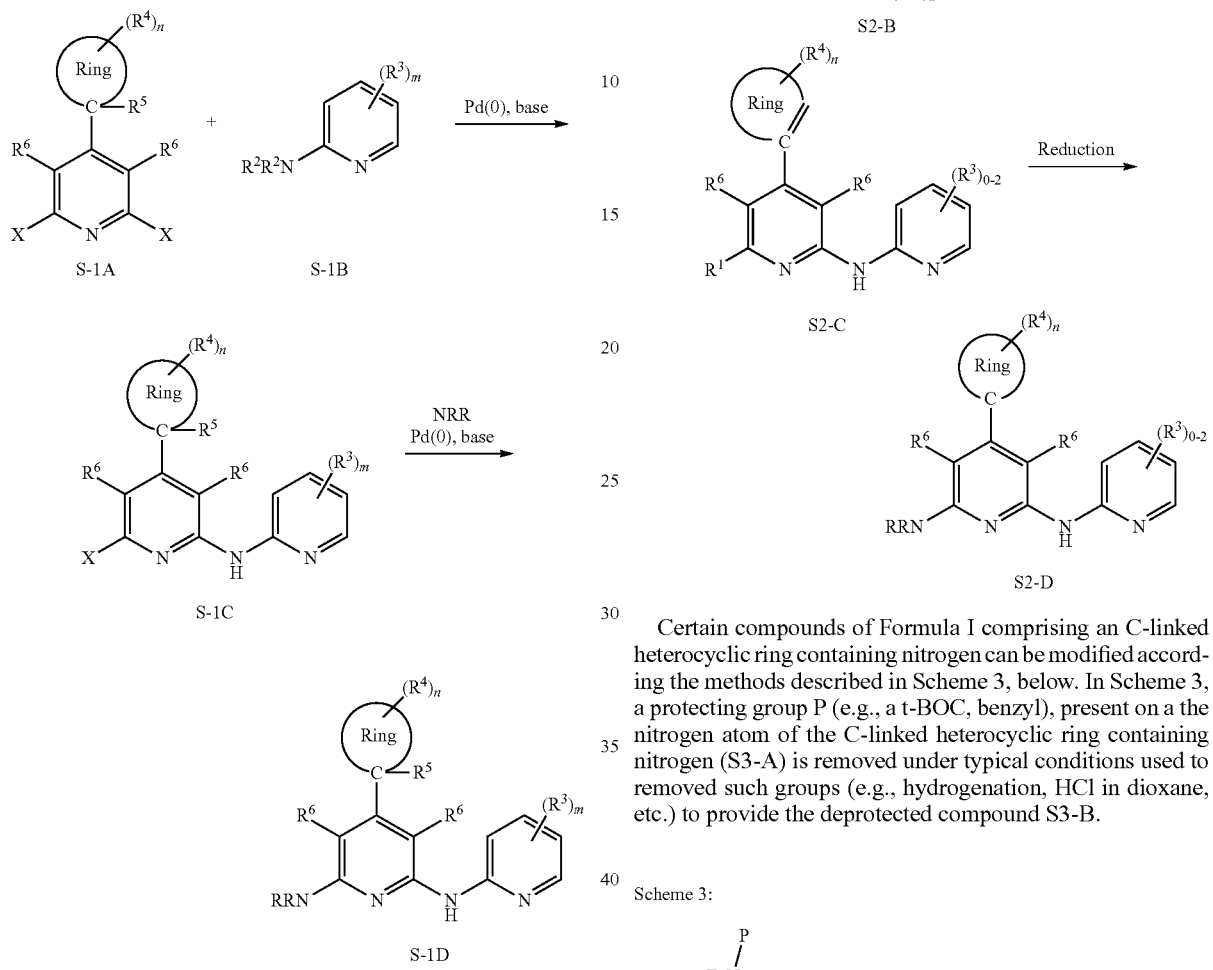

Scheme 2 below illustrates the synthesis of certain compounds of Formula I. In Scheme 2, bis-pyridine compound S2-A (e.g., wherein X in S2-A is halogen or triflate) is coupled with the C-linked ring using typical Suzuki-Miyaura cross-coupling conditions of, for example, a palladium catalyst, phosphine ligand and a boronate ester S2-B, under elevated temperatures. Subsequent reduction of the of the resultant coupling product S2-C under hydrogenation conditions provides compounds for formula I (S2-D).

Scheme 2:

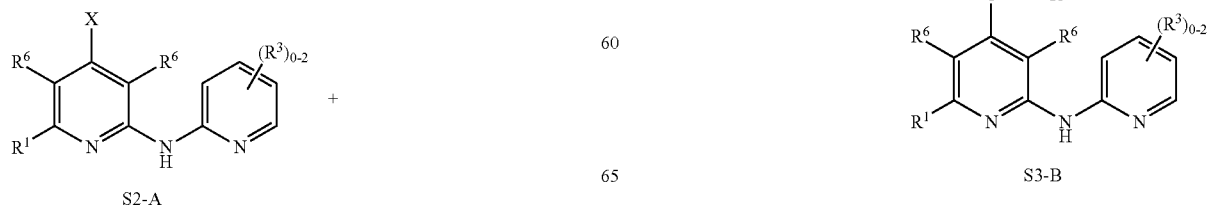

Certain compounds of Formula I comprising an C-linked heterocyclic ring containing nitrogen can be modified according the methods described in Scheme 3, below. In Scheme 3, a protecting group P (e.g., a t-BOC, benzyl), present on a the nitrogen atom of the C-linked heterocyclic ring containing nitrogen (S3-A) is removed under typical conditions used to removed such groups (e.g., hydrogenation, HCl in dioxane, etc.) to provide the deprotected compound S3-B.

Scheme 3:

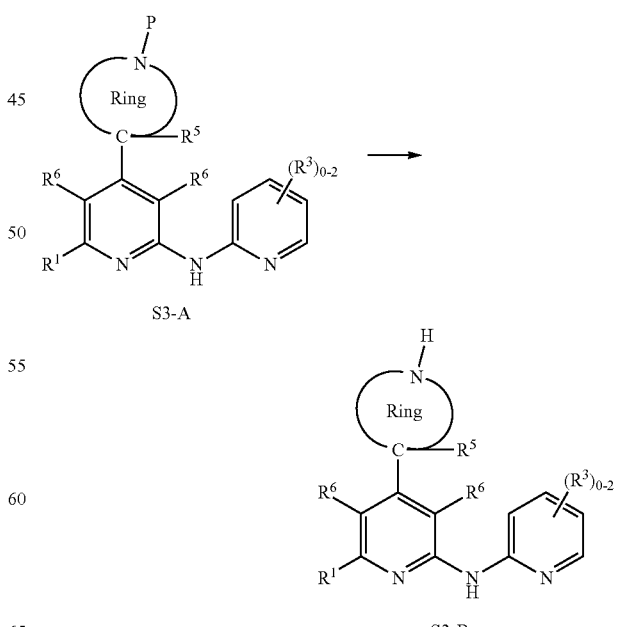

Certain compounds of formula I having a C-linked heterocyclic ring comprising a nitrogen atom can be modified according to the methods described in Scheme 4 below. In Scheme 4, secondary amine compounds S4-A can be N-substituted with an optionally substituted alkyl group, for example, using an alkyl halide in the presence of a base (see, Sch4-A), or under reductive amination conditions with an aldehyde and a hydride reagent (see, Sch4-B). In Scheme 4, secondary amine compounds S4-A can be N-substituted with an optionally substituted sulfonyl group, by reaction S4-A with a optionally substituted sulfonyl halide in the presence of a base (Sch4-C). In Scheme 4, secondary amine compounds S4-A can be N-substituted with an optionally substituted acyl group, by reaction S4-A with a optionally substituted acyl halide in the presence of a base (Sch4-D).

Scheme 4:

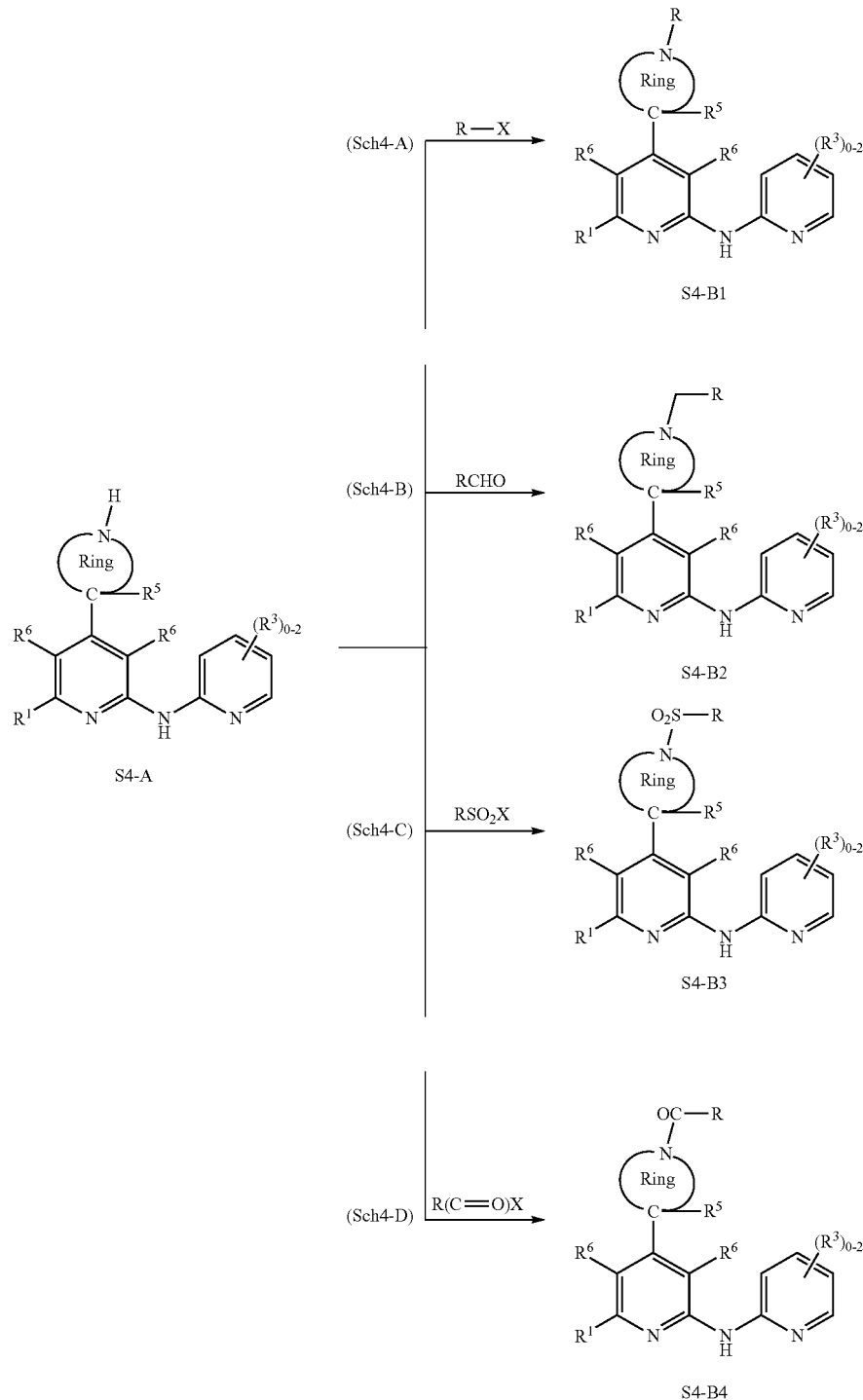

C. Pharmaceutical Compositions and Administrations

In addition to one or more of the compounds provided above (or stereoisomers, geometric isomers, tautomers, solvates, metabolites, isotopes, pharmaceutically acceptable salts, or prodrugs thereof), the invention also provides for compositions and medicaments comprising a compound of Formula I or any subformula thereof and at least one pharmaceutically acceptable carrier, diluent or excipient. The compositions of the invention can be used for inhibiting DLK activity in patients (e.g., humans)

The term "composition," as used herein, is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

In one embodiment, the invention provides for pharmaceutical compositions (or medicaments) comprising a compound of Formula I or I-I (or stereoisomers, geometric isomers, tautomers, solvates, metabolites, isotopes, pharmaceutically acceptable salts, or prodrugs thereof) and a pharmaceutically acceptable carrier, diluent or excipient. In another embodiment, the invention provides for preparing compositions (or medicaments) comprising compounds of the invention. In another embodiment, the invention provides for administering compounds of Formula I or I-I and compositions comprising compounds of Formula I or any embodiment thereof to a patient (e.g., a human patient) in need thereof.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The effective amount of the compound to be administered will be governed by such considerations, and is the minimum amount necessary to inhibit DLK activity as required to prevent or treat the undesired disease or disorder, such as for example, neurodegeneration, amyloidosis, formation of neurofibrillary tangles, or undesired cell growth. For example, such amount may be below the amount that is toxic to normal cells, or the mammal as a whole.

In one example, the therapeutically effective amount of the compound of the invention administered parenterally per dose will be in the range of about 0.01-100 mg/kg, alternatively about e.g., 0.1 to 20 mg/kg of patient body weight per day, with the typical initial range of compound used being 0.3 to 15 mg/kg/day. The daily does is, in certain embodiments, given as a single daily dose or in divided doses two to six times a day, or in sustained release form. In the case of a 70 kg adult human, the total daily dose will generally be from about 7 mg to about 1,400 mg. This dosage regimen may be adjusted to provide the optimal therapeutic response. The compounds may be administered on a regimen of 1 to 4 times per day, preferably once or twice per day.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, intracerebral, intraocular, intralesional or subcutaneous administration.

The compositions comprising compounds of Formula I any embodiment thereof are normally formulated in accordance with standard pharmaceutical practice as a pharmaceutical composition. A typical formulation is prepared by mixing a compound of the present invention and a diluent, carrier or excipient. Suitable diluents, carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which a compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations can also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues)

polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). A active pharmaceutical ingredient of the invention (e.g., compound of Formula I or any embodiment thereof) can also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington: The Science and Practice of Pharmacy: Remington the Science and Practice of Pharmacy (2005) $21^{st}$ Edition, Lippincott Williams & Wilkins, Philadelphia, Pa.

Sustained-release preparations of a compound of the invention (e.g., compound of Formula I or any embodiment thereof) can be prepared. Suitable examples of sustained-release preparations include semipermeable matrices of solid hydrophobic polymers containing a compound of Formula I or an embodiment thereof, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate (Sidman et al., Biopolymers 22:547, 1983), non-degradable ethylene-vinyl acetate (Langer et al., J. Biomed. Mater. Res. 15:167, 1981), degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid (EP 133,988A). Sustained release compositions also include liposomally entrapped compounds, which can be prepared by methods known per se (Epstein et al., Proc. Natl. Acad. Sci. U.S.A. 82:3688, 1985; Hwang et al., Proc. Natl. Acad. Sci. U.S.A. 77:4030, 1980; U.S. Pat. Nos. 4,485,045 and 4,544,545; and EP 102,324A). Ordinarily, the liposomes are of the small (about 200-800 Angstroms) unilamelar type in which the lipid content is greater than about 30 mol % cholesterol, the selected proportion being adjusted for the optimal therapy.

The formulations include those suitable for the administration routes detailed herein. The formulations can conveniently be presented in unit dosage form and can be prepared by any of the methods well known in the art of pharmacy. Techniques and formulations generally are found in Remington: The Science and Practice of Pharmacy: Remington the Science and Practice of Pharmacy (2005) $21^{st}$ Edition, Lippincott Williams & Wilkins, Philadelphia, Pa. Such methods include the step of bringing into association the active ingredient with the carrier which constitutes one or more accessory ingredients.

In general the formulations are prepared by uniformly and intimately bringing into association the active ingredient with liquid carriers, diluents or excipients or finely divided solid carriers, diluents or excipients, or both, and then, if necessary, shaping the product. A typical formulation is prepared by mixing a compound of the present invention and a carrier, diluent or excipient. The formulations can be prepared using conventional dissolution and mixing procedures. For example, the bulk drug substance (i.e., compound of the present invention or stabilized form of the compound (e.g., complex with a cyclodextrin derivative or other known complexation agent) is dissolved in a suitable solvent in the presence of one or more of the excipients described above. A compound of the present invention is typically formulated into pharmaceutical dosage forms to provide an easily controllable dosage of the drug and to enable patient compliance with the prescribed regimen.

In one example, compounds of Formula I or any embodiment thereof may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of Formula I or an embodiment thereof is formulated in an acetate buffer, at pH 5. In another embodiment, the compounds of Formula I or an embodiment thereof are sterile. The compound may be stored, for example, as a solid or amorphous composition, as a lyophilized formulation or as an aqueous solution.

Formulations of a compound of the invention (e.g., compound of Formula I or an embodiment thereof) suitable for oral administration can be prepared as discrete units such as pills, capsules, cachets or tablets each containing a predetermined amount of a compound of the invention.

Compressed tablets can be prepared by compressing in a suitable machine the active ingredient in a free-flowing form such as a powder or granules, optionally mixed with a binder, lubricant, inert diluent, preservative, surface active or dispersing agent. Molded tablets can be made by molding in a suitable machine a mixture of the powdered active ingredient moistened with an inert liquid diluent. The tablets can optionally be coated or scored and optionally are formulated so as to provide slow or controlled release of the active ingredient therefrom.

Tablets, troches, lozenges, aqueous or oil suspensions, dispersible powders or granules, emulsions, hard or soft capsules, e.g., gelatin capsules, syrups or elixirs can be prepared for oral use. Formulations of a compound of the invention (e.g., compound of Formula I or an embodiment thereof) intended for oral use can be prepared according to any method known to the art for the manufacture of pharmaceutical compositions and such compositions can contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients can be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets can be uncoated or can be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax can be employed.

An example of a suitable oral administration form is a tablet containing about 1 mg, 5 mg, 10 mg, 25 mg, 30 mg, 50 mg, 80 mg, 100 mg, 150 mg, 250 mg, 300 mg and 500 mg of the compound of the invention compounded with about 90-30 mg anhydrous lactose, about 5-40 mg sodium croscarmellose, about 5-30 mg polyvinylpyrrolidone (PVP) K30, and about 1-10 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 5-400 mg, of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

For treatment of the eye or other external tissues, e.g., mouth and skin, the formulations are preferably applied as a topical ointment or cream containing the active ingredient(s) in an amount of, for example, 0.075 to 20% w/w. When formulated in an ointment, the active ingredient can be employed with either a paraffinic or a water-miscible ointment base. Alternatively, the active ingredients can be formulated in a cream with an oil-in-water cream base.

If desired, the aqueous phase of the cream base can include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations can desirably include a compound which enhances absorption or penetration of the active ingredient through the skin or other affected areas. Examples of such dermal penetration enhancers include dimethyl sulfoxide and related analogs.

The oily phase of the emulsions of this invention can be constituted from known ingredients in a known manner. While the phase can comprise merely an emulsifier, it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulsifiers and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

Aqueous suspensions of a compound of the invention (e.g., compound of Formula I or an embodiment thereof) contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension can also contain one or more preservatives such as ethyl or n-propyl p-hydroxybenzoate, one or more coloring agents, one or more flavoring agents and one or more sweetening agents, such as sucrose or saccharin.

Formulations of a compound of the invention (e.g., compound of Formula I or I-I) can be in the form of a sterile injectable preparation, such as a sterile injectable aqueous or oleaginous suspension. This suspension can be formulated according to the known art using those suitable dispersing or wetting agents and suspending agents which have been mentioned above. The sterile injectable preparation can also be a sterile injectable solution or suspension in a non-toxic parenterally acceptable diluent or solvent, such as a solution in 1,3-butanediol or prepared as a lyophilized powder. Among the acceptable vehicles and solvents that can be employed are water, Ringer's solution and isotonic sodium chloride solution. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables.

The amount of active ingredient that can be combined with the carrier material to produce a single dosage form will vary depending upon the host treated and the particular mode of administration. For example, a time-release formulation intended for oral administration to humans can contain approximately 1 to 1000 mg of active material compounded with an appropriate and convenient amount of carrier material which can vary from about 5 to about 95% of the total compositions (weight:weight). The pharmaceutical composition can be prepared to provide easily measurable amounts for administration. For example, an aqueous solution intended for intravenous infusion can contain from about 3 to 500 μg of the active ingredient per milliliter of solution in order that infusion of a suitable volume at a rate of about 30 mL/hr can occur.

Formulations suitable for parenteral administration include aqueous and non-aqueous sterile injection solutions which can contain anti-oxidants, buffers, bacteriostats and solutes which render the formulation isotonic with the blood of the intended recipient; and aqueous and non-aqueous sterile suspensions which can include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, for example about 0.5 to 10% w/w, for example about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration can be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration can be prepared according to conventional methods and can be delivered with other therapeutic agents such as compounds heretofore used in the treatment of disorders as described below.

The formulations can be packaged in unit-dose or multi-dose containers, for example sealed ampoules and vials, and can be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

When the binding target is located in the brain, certain embodiments of the invention provide for a compound of formula I (or an embodiment thereof) to traverse the blood-brain barrier. Certain neurodegenerative diseases are associated with an increase in permeability of the blood-brain barrier, such that a compound of formula I (or an embodiment thereof) can be readily introduced to the brain. When the blood-brain barrier remains intact, several art-known approaches exist for transporting molecules across it, including, but not limited to, physical methods, lipid-based methods, and receptor and channel-based methods.

Physical methods of transporting a compound of formula I (or an embodiment thereof) across the blood-brain barrier include, but are not limited to, circumventing the blood-brain barrier entirely, or by creating openings in the blood-brain barrier.

Circumvention methods include, but are not limited to, direct injection into the brain (see, e.g., Papanastassiou et al., Gene Therapy 9:398-406, 2002), interstitial infusion/convection-enhanced delivery (see, e.g., Bobo et al., Proc. Natl. Acad. Sci. U.S.A. 91:2076-2080, 1994), and implanting a delivery device in the brain (see, e.g., Gill et al., Nature Med. 9:589-595, 2003; and Gliadel Wafers™, Guildford. Pharmaceutical). Methods of creating openings in the barrier include, but are not limited to, ultrasound (see, e.g., U.S. Patent Publication No. 2002/0038086), osmotic pressure (e.g., by administration of hypertonic mannitol (Neuwelt, E. A., Implication of the Blood-Brain Barrier and its Manipulation, Volumes 1 and 2, Plenum Press, N.Y., 1989)), and permeabilization by, e.g., bradykinin or permeabilizer A-7 (see, e.g., U.S. Pat. Nos. 5,112,596, 5,268,164, 5,506,206, and 5,686,416).

Lipid-based methods of transporting a compound of formula I (or an embodiment thereof) across the blood-brain barrier include, but are not limited to, encapsulating the a compound of formula I or I-I (or an embodiment thereof) in liposomes that are coupled to antibody binding fragments that bind to receptors on the vascular endothelium of the blood-brain barrier (see, e.g., U.S. Patent Application Publication No. 2002/0025313), and coating a compound of formula I (or an embodiment thereof) in low-density lipoprotein particles (see, e.g., U.S. Patent Application Publication No. 2004/0204354) or apolipoprotein E (see, e.g., U.S. Patent Application Publication No. 2004/0131692).

Receptor and channel-based methods of transporting a compound of formula I (or an embodiment thereof) across the blood-brain barrier include, but are not limited to, using glucocorticoid blockers to increase permeability of the blood-brain barrier (see, e.g., U.S. Patent Application Publication Nos. 2002/0065259, 2003/0162695, and 2005/0124533); activating potassium channels (see, e.g., U.S. Patent Application Publication No. 2005/0089473), inhibiting ABC drug transporters (see, e.g., U.S. Patent Application Publication No. 2003/0073713); coating a compound of formula I or I-I (or an embodiment thereof) with a transferrin and modulating activity of the one or more transferrin receptors (see, e.g., U.S. Patent Application Publication No. 2003/0129186), and cationizing the antibodies (see, e.g., U.S. Pat. No. 5,004,697).

For intracerebral use, in certain embodiments, the compounds can be administered continuously by infusion into the fluid reservoirs of the CNS, although bolus injection may be acceptable. The inhibitors can be administered into the ventricles of the brain or otherwise introduced into the CNS or spinal fluid. Administration can be performed by use of an indwelling catheter and a continuous administration means such as a pump, or it can be administered by implantation, e.g., intracerebral implantation of a sustained-release vehicle. More specifically, the inhibitors can be injected through chronically implanted cannulas or chronically infused with the help of osmotic minipumps. Subcutaneous pumps are available that deliver proteins through a small tubing to the cerebral ventricles. Highly sophisticated pumps can be refilled through the skin and their delivery rate can be set without surgical intervention. Examples of suitable administration protocols and delivery systems involving a subcutaneous pump device or continuous intracerebroventricular infusion through a totally implanted drug delivery system are those used for the administration of dopamine, dopamine agonists, and cholinergic agonists to Alzheimer's disease patients and animal models for Parkinson's disease, as described by Harbaugh, J. Neural Transm. Suppl. 24:271, 1987; and DeYebenes et al., Mov. Disord. 2: 143, 1987.

A compound of formula I (or an embodiment thereof) used in the invention are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. A compound of formula I (or an embodiment thereof) need not be, but is optionally formulated with one or more agent currently used to prevent or treat the disorder in question. The effective amount of such other agents depends on the amount of a compound of the invention present in the formulation, the type of disorder or treatment, and other factors discussed above.

These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of a compound of formula I or I-I (or an embodiment thereof) (when used alone or in combination with other agents) will depend on the type of disease to be treated, the properties of the compound, the severity and course of the disease, whether the compound is administered for preventive or therapeutic purposes, previous therapy, the patient's clinical history and response to the compound, and the discretion of the attending physician. The compound is suitably administered to the patient at one time or over a series of treatments. Depending on the type and severity of the disease, about 1 µg/kg to 15 mg/kg (e.g., 0.1 mg/kg-10 mg/kg) of compound can be an initial candidate dosage for administration to the patient, whether, for example, by one or more separate administrations, or by continuous infusion. One typical daily dosage might range from about 1 µg kg to 100 mg/kg or more, depending on the factors mentioned above. For repeated administrations over several days or longer, depending on the condition, the treatment would generally be sustained until a desired suppression of disease symptoms occurs. One exemplary dosage of a compound of formula I (or an embodiment thereof) would be in the range from about 0.05 mg/kg to about 10 mg/kg. Thus, one or more doses of about 0.5 mg/kg, 2.0 mg/kg, 4.0 mg/kg, or 10 mg/kg (or any combination thereof) may be administered to the patient. Such doses may be administered intermittently, e.g., every week or every three weeks (e.g., such that the patient receives from about two to about twenty, or, e.g., about six doses of the antibody). An initial higher loading dose, followed by one or more lower doses may be administered. An exemplary dosing regimen comprises administering an initial loading dose of about 4 mg/kg, followed by a weekly maintenance dose of about 2 mg kg of the compound. However, other dosage regimens may be useful. The progress of this therapy is easily monitored by conventional techniques and assays.

Other typical daily dosages might range from, for example, about 1 g/kg to up to 100 mg/kg or more (e.g., about 1 µg kg to 1 mg/kg, about 1 µg/kg to about 5 mg/kg, about 1 mg kg to 10 mg/kg, about 5 mg/kg to about 200 mg/kg, about 50 mg/kg to about 150 mg/mg, about 100 mg/kg to about 500 mg/kg, about 100 mg/kg to about 400 mg/kg, and about 200 mg/kg to about 400 mg/kg), depending on the factors mentioned above. Typically, the clinician will administer a compound until a dosage is reached that results in improvement in or, optimally, elimination of, one or more symptoms of the treated disease or condition. The progress of this therapy is easily monitored by conventional assays. One or more agent provided herein may be administered together or at different times (e.g., one agent is administered prior to the administration of a second agent). One or more agent may be administered to a subject using different techniques (e.g., one agent may be administered orally, while a second agent is administered via intramuscular injection or intranasally). One or more agent may be administered such that the one or more agent has a pharmacologic effect in a subject at the same time. Alternatively, one or more agent may be administered, such that the pharmacological activity of the first administered agent is expired prior the administration of one or more secondarily administered agents (e.g., 1, 2, 3, or 4 secondarily administered agents).

D. Indications and Methods of Treatment

In another aspect, the invention provides for methods of inhibiting the Dual Leucine Zipper Kinase (DLK) in an in vitro (e.g., a nerve graft of nerve transplant) or in vivo setting (e.g., in a patient) by contacting DLK present in an in vitro or in vivo setting with compounds of Formula I or an embodiment thereof. In these methods of the invention, the inhibition of DLK signaling or expression with a compound of formula I or an embodiment thereof results in a downstream decrease in JNK phosphorylation (e.g., a decrease in JNK2 and/or JNK3 phosphorylation), JNK activity (e.g., a decrease in JNK2 and/or JNK3 activity), and/or JNK expression (e.g., a decrease in JNK2 and/or JNK3 expression). Accordingly, administering one or more compounds of Formula I or an embodiment thereof according to the methods of the invention can result in decrease in activity of kinase targets downstream of the DLK signalling cascade, e.g., (i) a decrease in JNK phosphorylation, JNK activity, and/or JNK expression, (ii) a decrease in cJun phosphorylation, cJun activity, and/or cJun expression, and/or (iii) a decrease in p38 phosphorylation, p38 activity, and/or p38 expression.

Compounds of the invention can be used in methods for inhibiting neuron or axon degeneration. The inhibitors are, therefore, useful in the therapy of, for example, (i) disorders of the nervous system (e.g., neurodegenerative diseases), (ii) conditions of the nervous system that are secondary to a disease, condition, or therapy having a primary effect outside of the nervous system, (iii) injuries to the nervous system caused by physical, mechanical, or chemical trauma, (iv) pain, (v) ocular-related neurodegeneration, (vi) memory loss, and (vii) psychiatric disorders. Non-limiting examples of some of these diseases, conditions, and injuries are provided below.

Examples of neurodegenerative diseases and conditions that can be prevented or treated according to the invention include amyotrophic lateral sclerosis (ALS), trigeminal neuralgia, glossopharyngeal neuralgia, Bell's Palsy, myasthenia gravis, muscular dystrophy, progressive muscular atrophy, primary lateral sclerosis (PLS), pseudobulbar palsy, progressive bulbar palsy, spinal muscular atrophy, progressive bulbar palsy, inherited muscular atrophy, invertebrate disk syndromes (e.g., herniated, ruptured, and prolapsed disk syndromes), cervical spondylosis, plexus disorders, thoracic outlet destruction syndromes, peripheral neuropathies, prophyria, mild cognitive impairment, Alzheimer's disease, Huntington's disease, Parkinson's disease, Parkinson's-plus diseases (e.g., multiple system atrophy, progressive supranuclear palsy, and corticobasal degeneration), dementia with Lewy bodies, frontotemporal dementia, demyelinating diseases (e.g., Guillain-Barre syndrome and multiple sclerosis), Charcot-Marie-Tooth disease (CMT; also known as Hereditary Motor and Sensory Neuropathy (HMSN), Hereditary Sensorimotor Neuropathy (HSMN), and Peroneal Muscular Atrophy), prion disease (e.g., Creutzfeldt-Jakob disease, Gerstmann-Straussler-Scheinker syndrome (GSS), fatal familial insomnia (FFI), and bovine spongiform encephalopathy (BSE, commonly known as mad cow disease)), Pick's disease, epilepsy, and AIDS demential complex (also known as HIV dementia, HIV encephalopathy, and HIV-associated dementia).

The methods of the invention can also be used in the prevention and treatment of ocular-related neurodegeneration and related diseases and conditions, such as glaucoma, lattice dystrophy, retinitis pigmentosa, age-related macular degeneration (AMD), photoreceptor degeneration associated with wet or dry AMD, other retinal degeneration, optic nerve drusen, optic neuropathy, and optic neuritis. Non-limiting examples of different types of glaucoma that can be prevented or treated according to the invention include primary glaucoma (also known as primary open-angle glaucoma, chronic open-angle glaucoma, chronic simple glaucoma, and glaucoma simplex), low-tension glaucoma, primary angle-closure glaucoma (also known as primary closed-angle glaucoma, narrow-angle glaucoma, pupil-block glaucoma, and acute congestive glaucoma), acute angle-closure glaucoma, chronic angle-closure glaucoma, intermittent angle-closure glaucoma, chronic open-angle closure glaucoma, pigmentary glaucoma, exfoliation glaucoma (also known as pseudoexfoliative glaucoma or glaucoma capsulare), developmental glaucoma (e.g., primary congenital glaucoma and infantile glaucoma), secondary glaucoma (e.g., inflammatory glaucoma (e.g., uveitis and Fuchs heterochromic iridocyclitis)), phacogenic glaucoma (e.g., angle-closure glaucoma with mature cataract, phacoanaphylactic glaucoma secondary to rupture of lens capsule, phacolytic glaucoma due to phacotoxic meshwork blockage, and subluxation of lens), glaucoma secondary to intraocular hemorrhage (e.g., hyphema and hemolytic glaucoma, also known as erythroclastic glaucoma), traumatic glaucoma (e.g., angle recession glaucoma, traumatic recession on anterior chamber angle, postsurgical glaucoma, aphakic pupillary block, and ciliary block glaucoma), neovascular glaucoma, drug-induced glaucoma (e.g., corticosteroid induced glaucoma and alpha-chymotrypsin glaucoma), toxic glaucoma, and glaucoma associated with intraocular tumors, retinal detachments, severe chemical burns of the eye, and iris atrophy.

Examples of types of pain that can be treated according to the methods of the invention include those associated with the following conditions: chronic pain, fibromyalgia, spinal pain, carpel tunnel syndrome, pain from cancer, arthritis, sciatica, headaches, pain from surgery, muscle spasms, back pain, visceral pain, pain from injury, dental pain, neuralgia, such as neuogenic or neuropathic pain, nerve inflammation or damage, shingles, herniated disc, torn ligament, and diabetes.

Certain diseases and conditions having primary effects outside of the nervous system can lead to damage to the nervous system, which can be treated according to the methods of the present invention. Examples of such conditions include peripheral neuropathy and neuralgia caused by, for example, diabetes, cancer, AIDS, hepatitis, kidney dysfunction, Colorado tick fever, diphtheria, HIV infection, leprosy, lyme disease, polyarteritis nodosa, rheumatoid arthritis, sarcoidosis, Sjogren syndrome, syphilis, systemic lupus erythematosus, and amyloidosis.

In addition, the methods of the invention can be used in the treatment of nerve damage, such as peripheral neuropathy, which is caused by exposure to toxic compounds, including heavy metals (e.g., lead, arsenic, and mercury) and industrial solvents, as well as drugs including chemotherapeutic agents (e.g., vincristine and cisplatin), dapsone, HIV medications (e.g., Zidovudine, Didanosine, Stavudine, Zalcitabine, Ritonavir, and Amprenavir), cholesterol lowering drugs (e.g., Lovastatin, Indapamid, and Gemfibrozil), heart or blood pressure medications (e.g., Amiodarone, Hydralazine, Perhexyline), and Metronidazole.

The methods of the invention can also be used to treat injury to the nervous system caused by physical, mechanical, or chemical trauma. Thus, the methods can be used in the treatment of peripheral nerve damage caused by physical injury (associated with, e.g., burns, wounds, surgery, and accidents), ischemia, prolonged exposure to cold temperature (e.g., frost-bite), as well as damage to the central nervous system due to, e.g., stroke or intracranial hemorrhage (such as cerebral hemorrhage).

Further, the methods of the invention can be used in the prevention or treatment of memory loss such as, for example, age-related memory loss. Types of memory that can be affected by loss, and thus treated according to the invention, include episodic memory, semantic memory, short-term memory, and long-term memory. Examples of diseases and conditions associated with memory loss, which can be treated according to the present invention, include mild cognitive impairment, Alzheimer's disease, Parkinson's disease, Huntington's disease, chemotherapy, stress, stroke, and traumatic brain injury (e.g., concussion).

The methods of the invention can also be used in the treatment of psychiatric disorders including, for example, schizophrenia, delusional disorder, schizoaffective disorder, schizopheniform, shared psychotic disorder, psychosis, paranoid personality disorder, schizoid personality disorder, borderline personality disorder, anti-social personality disorder, narcissistic personality disorder, obsessive-compulsive disorder, delirium, dementia, mood disorders, bipolar disorder, depression, stress disorder, panic disorder, agoraphobia, social phobia, post-traumatic stress disorder, anxiety disorder, and impulse control disorders (e.g., kleptomania, pathological gambling, pyromania, and trichotillomania).

In addition to the in vivo methods described above, the methods of the invention can be used to treat nerves ex vivo, which may be helpful in the context of nerve grafts or nerve transplants. Thus, the inhibitors described herein can be useful as components of culture media for use in culturing nerve cells in vitro.

Accordingly, in another aspect, the invention provides for a method for inhibiting or preventing degeneration of a central nervous system (CNS) neuron or a portion thereof, the method comprising administering to the CNS neuron a compound of formula I or an embodiment thereof.

In one embodiment, of the method for inhibiting or preventing degeneration of a central nervous system neuron or a portion thereof, the administering to the CNS neuron is performed in vitro.

In another embodiment, of the method for inhibiting or preventing degeneration of a central nervous system neuron or a portion thereof, the method further comprises grafting or implanting the CNS neuron into a human patient after administration of the agent.

In another embodiment, of the method for inhibiting or preventing degeneration of a central nervous system neuron or a portion thereof, the CNS neuron is present in a human patient.

In another embodiment, of the method for inhibiting or preventing degeneration of a central nervous system neuron or a portion thereof, the administering to the CNS neuron comprises administration of said compound of formula I or an embodiment thereof in a pharmaceutically acceptable carrier, diluent or excipient.

In another embodiment, of the method for inhibiting or preventing degeneration of a central nervous system neuron or a portion thereof, the administering to the CNS neuron is carried out by an administration route selected from the group consisting of parenteral, subcutaneous, intravenous, intraperitoneal, intracerebral, intralesional, intramuscular, intraocular, intraarterial interstitial infusion and implanted delivery device.

In another embodiment, of the method for inhibiting or preventing degeneration of a central nervous system neuron or a portion thereof, the method further comprises administering one or more additional pharmaceutical agents.

The inhibitors can be optionally combined with or administered in concert with each other or other agents known to be useful in the treatment of the relevant disease or condition. Thus, in the treatment of ALS, for example, inhibitors can be administered in combination with Riluzole (Rilutek), minocycline, insulin-like growth factor 1 (IGF-1), and/or methylcobalamin. In another example, in the treatment of Parkinson's disease, inhibitors can be administered with L-dopa, dopamine agonists (e.g., bromocriptine, pergolide, pramipexole, ropinirole, cabergoline, apomorphine, and lisuride), dopa decarboxylase inhibitors (e.g., levodopa, benserazide, and carbidopa), and/or MAO-B inhibitors (e.g., selegiline and rasagiline). In a further example, in the treatment of Alzheimer's disease, inhibitors can be administered with acetylcholinesterase inhibitors (e.g., donepezil, galantamine, and rivastigmine) and/or NMDA receptor antagonists (e.g., memantine). The combination therapies can involve concurrent or sequential administration, by the same or different routes, as determined to be appropriate by those of skill in the art. The invention also includes pharmaceutical compositions and kits comprising combinations as described herein.

In addition to the combinations noted above, other combinations included in the invention are combinations of inhibitors of degeneration of different neuronal regions. Thus, the invention includes combinations of agents that (i) inhibit degeneration of the neuron cell body, and (ii) inhibit axon degeneration. For example, inhibitors of GSK and transcription are found to prevent degeneration of neuron cell bodies, while inhibitors of EGFR and p38 MAPK are found to prevent degeneration of axons. Thus, the invention includes combinations of inhibitors of GSK and EGFR (and/or p38 MAPK), combinations of transcription inhibitors and EGF (and/or p38 MAPK), and further combinations of inhibitors of dual leucine zipper-bearing kinase (DLK), glycogen synthase kinase 3β (GSK3), p38 MAPK, EGFF, phosphoinositide 3-kinase (PI3K), cyclin-dependent kinase 5 (cdk5), adenylyl cyclase, c-Jun N-terminal kinase (JNK), BCL2-associated X protein (Bax), In channel, calcium/calmodulin-dependent protein kinase kinase (CaMKK), a G-protein, a G-protein coupled receptor, transcription factor 4 (TCF4), and β-catenin. The inhibitors used in these combinations can be any of those described herein, or other inhibitors of these targets as described in WO 2011/050192, incorporated herein by reference.

The combination therapy can provide "synergy" and prove "synergistic", i.e., the effect achieved when the active ingredients used together is greater than the sum of the effects that results from using the compounds separately. A synergistic effect can be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect can be attained when the compounds are administered or delivered sequentially, e.g., by different injections in separate syringes, separate pills or capsules, or in separate infusions. In general, during alternation therapy, an effective dosage of each active ingredient is administered sequentially, i.e., serially, whereas in combination therapy, effective dosages of two or more active ingredients are administered together.

F. Examples

The invention will be more fully understood by reference to the following examples. They should not, however, be construed as limiting the scope of the invention. These examples are not intended to limit the scope of the present invention, but rather to provide guidance to a skilled artisan to prepare and use the compounds, compositions, and methods of the present invention. While particular embodiments of the present invention are described, the skilled artisan will appreciate that various changes and modifications can be made without departing from the spirit and scope of the invention.

The chemical reactions in the Examples described can be readily adapted to prepare a number of other compounds of the invention, and alternative methods for preparing the compounds of this invention are deemed to be within the scope of this invention. For example, the synthesis of non-exemplified compounds according to the invention can be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention. Accordingly, the following examples are provided to illustrate but not limit the invention.

In the Examples described below, unless otherwise indicated all temperatures are set forth in degrees Celsius. Commercially available reagents were purchased from suppliers such as Aldrich Chemical Company, Lancaster, TCI or Maybridge, and were used without further purification unless otherwise indicated. The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried. Column chromatography was conducted on a Biotage system (Manufacturer: Dyax Corporation) having a silica gel column or on a silica SEP PAK® cartridge (Waters); or alternatively column chromatography was carried out using on an ISCO chromatography system (Manufacturer: Teledyne ISCO) having a silica gel column. $^1$H NMR spectra were recorded on a Varian instrument operating at 400 MHz. $^1$H NMR spectra were obtained in deuterated $CDCl_3$, $d_6$-DMSO, $CH_3OD$ or $d_6$-acetone solutions (reported in ppm), using tetramethylsilane (TMS) as the reference standard (0 ppm). When peak multiplicities are reported, the following abbreviations are used: s (singlet), d (doublet), t (triplet), q (quartet), m (multiplet), br (broadened), dd (doublet of doublets), dt (doublet of triplets). Coupling constants, when given, are reported in Hertz (Hz).

When possible, product formed in the reaction mixtures were monitored by LC/MS. High Pressure Liquid Chromatography-Mass Spectrometry (LCMS) experiments to performed either on an Agilent 1200 Series LC coupled to a 6140 quadrupole mass spectrometer using a Supelco Ascentis Express C18 column with a linear gradient of 5%-95% acetonitrile/water (with 0.1% trifluoroacetic acid in each mobile phase) within 1.4 minutes and held at 95% for 0.3 minute, or on a PE Sciex API 150 EX using a Phenomenex DNYC monolithic C18 column with a linear gradient of 5%-95% acetonitrile/water (with 0.1% trifluoroacetic acid in each mobile phase) within 5 minutes and held at 95% for 1 minute to determine retention times ($R_T$) and associated mass ions.

All abbreviations used to described reagents, reaction conditions, or equipment used are consistent with the definitions set forth in the "List of standard abbreviations and acronyms" published yearly by the Journal of Organic Chemistry (an American Chemical Society journal). The chemical names of discrete compounds of the invention were obtained using the structure naming feature ChemBioDraw Version 11.0 or from Accelrys' Pipeline Pilot IUPAC compound naming program.

Example 1

Method A

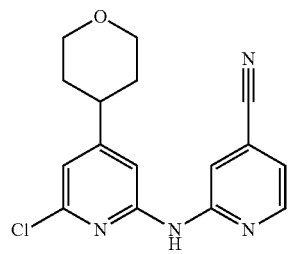 [SMILES: N#Cc1ccnc(Nc2cc(C3CCOCC3)cc(Cl)n2)c1]

Preparation of 2-((6-chloro-4-(tetrahydro-2H-pyran-4-yl)pyridin-2-yl)amino)isonicotinonitrile

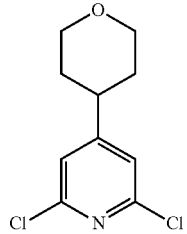 [SMILES: Clc1cc(C2CCOCC2)cc(Cl)n1]

Step 1:
2,6-dichloro-4-(tetrahydro-2H-pyran-4-yl)pyridine

To a 100 mL round-bottomed flask containing zinc dust (2.03 g, 31.0 mmol, 1.70 equiv) in N,N-dimethylacetamide (20 mL) was added chlorotrimethylsilane (0.473 mL, 3.65 mmol, 0.200 equiv) and 1,2-dibromoethane (0.318 mL, 3.65 mmol, 0.200 equiv) over 10 min. A solution of 4-bromotetrahydro-2H-pyran (2.88 mL, 25.6 mmol, 1.40 equiv) in N,N-dimethylacetamide (15 mL) was then added to the mixture. After 30 min, the reaction mixture was filtered over Celite and added to a round-bottomed flask containing [1,1'-bis(diphenylphosphino)ferrocene]dichloropalladium(II) (745 mg, 0.913 mmol, 0.0500 equiv), cuprous iodide (348 mg, 1.83 mmol, 0.100 equiv), and 2,6-dichloro-4-iodo-pyridine (5.00 g, 18.3 mmol, 1.00 equiv). The reaction was then heated to 80° C. for 16 h. After cooling to room temperature, the reaction mixture was filtered over Celite washing with ethyl acetate (3×10 mL) and concentrated to dryness. Purification by flash column chromatography (30:70 ethyl acetate/heptane) furnished the product as a white solid (3.00 g, 71% yield). $^1$H NMR (CDCl$_3$, 400 MHz), δ: 7.11 (s, 1H), 4.09 (dt, J=11.6, 3.3 Hz, 2H), 3.57-3.42 (m, 2H), 2.85-2.70 (m, 1H), 1.77 (tt, J=7.5, 3.7 Hz, 4H).

Step 2: 2-((6-chloro-4-(tetrahydro-2H-pyran-4-yl)pyridin-2-yl)amino)isonicotinonitrile To a 25 mL round-bottomed flask charged with 2,6-dichloro-4-(tetrahydro-2H-pyran-4-yl)pyridine (1.20 g, 5.20 mmol, 1.00 equiv), 2-aminopyridine-4-carbonitrile (620 mg, 5.20 mmol, 1.00 equiv), cesium carbonate (2.40 g, 7.20 mmol, 1.40 equiv), 2,2'-bis(diphenylphosphino)-1,1'-binaphthalene (170 mg, 0.260 mmol, 0.0500 equiv), and tris(dibenzylideneacetone)dipalladium(0) (120 mg 0.130 mmol, 0.0250 equiv) was added 1,4-dioxane (10 mL) under nitrogen atmosphere. The reaction was then heated to 80° C. for 16 h after which the mixture was cooled to room temperature, diluted with ethyl acetate (15 mL) and washed with water (2×15 mL). The organic layer was dried over anhydrous magnesium sulfate, filtered and concentrated. Purification by flash column chromatography (40:60 ethyl acetate/heptane) afforded the desired product as a yellow solid (892 mg, 51% yield). $^1$H NMR (400 MHz, DMSO-d$_6$), δ: 10.38 (s, 1H), 8.49 (d, J=5.3 Hz, 1H), 7.94 (s, 1H), 7.63 (s, 1H), 7.34-7.23 (dd, J=4.0, 2.0 Hz, 1H), 6.98 (d, J=1.1 Hz, 1H), 3.95 (dd, J=11.9, 4.0 Hz, 2H), 3.44 (td, J=11.9, 2.4 Hz, 2H), 2.82 (tt, J=12.0, 3.6 Hz, 1H), 1.77-1.70 (m, 2H), 1.69-1.61 (m, 2H).

Preparation of 2-((6-(3-fluoroazetidin-1-yl)-4-(tetrahydro-2H-pyran-4-yl)pyridin-2-yl)amino)isonicotinonitrile

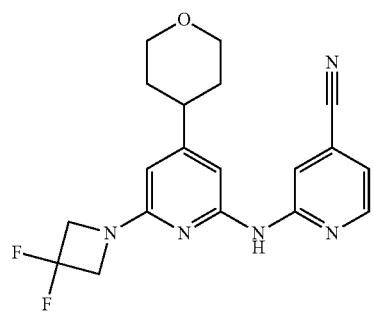 [SMILES: N#Cc1ccnc(Nc2cc(C3CCOCC3)cc(N3CC(F)(F)C3)n2)c1]

2-((6-Chloro-4-(tetrahydro-2H-pyran-4-yl)pyridin-2-yl)amino)isonicotinonitrile (50.0 mg, 0.159 mmol, 1.00 equiv), 3,3-difluoroazetidine hydrochloride (44.3 mg, 0.318 mmol, 2.00 equiv), sodium tert-butoxide (94.4 mg, 0.953 mmol, 6.00 equiv), 2-dicyclohexylphosphino-2',6'-diisopropoxybiphenyl (7.56 mg, 0.0159 mmol, 0.100 equiv), and chloro-(2-dicyclohexylphosphino-2',6'-diisopropoxy-1,1'-biphenyl)[2-(2-aminoethyl)phenyl]palladium(II)-methyl-t-butyl ether adduct (13.0 mg, 0.0159 mmol, 0.100 equiv) were added to a 2-dram vial. After purging the vial with nitrogen, dry tetrahydrofuran (1.50 mL) was added and the reaction mixture was left stirring at 80° C. for 14 h. The reaction mixture was then filtered over Celite washing with ethyl acetate (3×3 mL) and concentrated to dryness. Purification by reverse phase column chromatography (30:70 water/acetonitrile with 0.1% ammonium hydroxide) gave the desired product as a white solid (3.8 mg, 6.4% yield). $^1$H NMR (400 MHz, DMSO-d$_6$), δ: 9.87 (s, 1H), 8.42 (d, J=5.1 Hz, 1H), 8.26 (s, 1H), 7.21 (dd, J=5.2, 2.0 Hz, 1H), 6.88 (s, 1H), 6.04 (s, 1H), 4.49-4.26 (m, 4H), 4.02-3.86 (m, 2H), 3.52-3.35 (m, 2H), 2.76-2.58 (m, 1H), 1.73-1.59 (m, 4H).

The following examples were prepared similar as described for Method A above:

| Structure | $^1$H NMR | MS (m/z) |
|---|---|---|
| 2-((6-chloro-4-(tetrahydro-2H-pyran-4-yl)pyridin-2-yl)amino)isonicotinonitrile | (400 MHz, DMSO-d$_6$), δ: 10.38 (s, 1H), 8.49 (d, J = 5.3 Hz, 1H), 7.94 (s, 1H), 7.63 (s, 1H), 7.34-7.23 (dd, J = 4.0, 2.0 Hz, 1H), 6.98 (d, J = 1.1 Hz, 1H), 3.95 (dd, J = 11.9, 4.0 Hz, 2H), 3.44 (td, J = 11.9, 2.4 Hz, 2H), 2.82 (tt, J = 12.0, 3.6 Hz, 1H), 1.77-1.70 (m, 2H), 1.69-1.61 (m, 2H). | 415 |

| Structure | ¹H NMR | MS (m/z) |
|---|---|---|
| 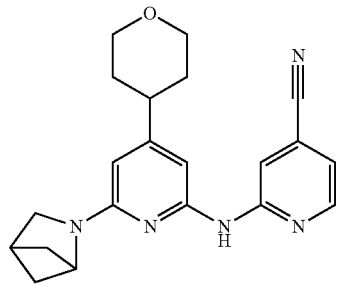 [SMILES: N#Cc1ccnc(Nc2cc(C3CCOCC3)cc(N3CC4CC3C4)n2)c1]<br>2-((6-(2-azabicyclo[2.1.1]hexan-2-yl)-4-(tetrahydro-2H-pyran-4-yl)pyridin-2-yl)amino) isonicotinonitrile | (400 MHz, DMSO-d6), δ: 9.71 (s, 1H), 8.45 (s, 1H), 8.40 (d, J = 5.1 Hz, 1H), 7.17 (dd, J = 5.2, 2.0 Hz, 1H), 6.55 (s, 1H), 6.08 (s, 1H), 4.69-4.61 (m, 1H), 3.98-3.89 (m, 2H), 3.47-3.36 (m, 4H), 2.99-2.91 (m, 1H), 2.68-2.57 (m, 1H), 2.00-1.93 (m, 2H), 1.71-1.56 (m, 4H), 1.40-1.29 (m, 2H). | 362 |
| 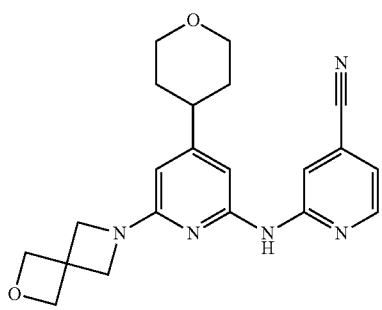 [SMILES: N#Cc1ccnc(Nc2cc(C3CCOCC3)cc(N3CC4(COC4)C3)n2)c1]<br>2-((6-(2-oxa-6-azaspiro[3.3]heptan-6-yl)-4-(tetrahydro-2H-pyran-4-yl)pyridin-2-yl)amino) isonicotinonitrile | (400 MHz, DMSO-d₆), δ: 9.78 (s, 1H), 8.44 (s, 1H), 8.40 (d, J = 5.0 Hz, 1H), 7.19 (dd, J = 5.2, 1.6 Hz, 1H), 6.66 (s, 1H), 5.84 (s, 1H), 4.74 (s, 4H), 4.11 (s, 4H), 3.98-3.88 (m, 2H), 3.47-3.35 (m, 2H), 2.70-2.57 (m, 1H), 1.71-1.54 (m, 4H). | 378 |
| 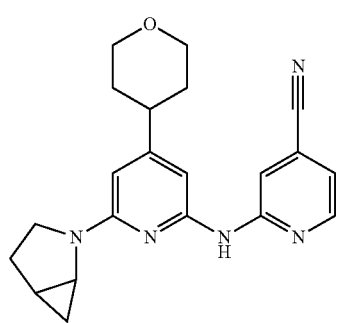 [SMILES: N#Cc1ccnc(Nc2cc(C3CCOCC3)cc(N3CCC4CC43)n2)c1]<br>2-((6-(2-azabicyclo[3.1.0]hexan-2-yl)-4-(tetrahydro-2H-pyran-4-yl)pyridin-2-yl)amino) isonicotinonitrile | (400 MHz, DMSO-d₆), δ: 9.78 (s, 1H), 8.44 (s, 1H), 8.40 (d, J = 5.0 Hz, 1H), 7.19 (dd, J = 5.2, 1.6 Hz, 1H), 6.66 (s, 1H), 5.84 (s, 1H), 4.74 (s, 4H), 4.11 (s, 4H), 3.98-3.86 (m, 2H), 3.50-3.35 (m, 2H), 2.72-2.56 (m, 1H), 1.71-1.47 (m, 4H). | 362 |

| Structure | ¹H NMR | MS (m/z) |
|---|---|---|
| 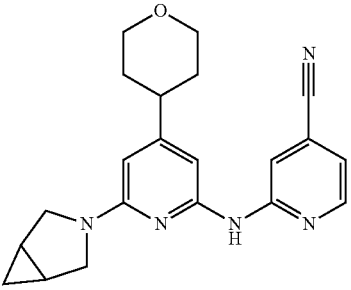 [SMILES: N#Cc1ccnc(Nc2cc(C3CCOCC3)cc(N3CC4CC4C3)n2)c1]<br>2-((6-(3-azabicyclo[3.1.0]hexan-3-yl)-4-(tetrahydro-2H-pyran-4-yl)pyridin-2-yl)amino) isonicotinonitrile | (400 MHz, DMSO-d$_6$), δ: 9.71 (s, 1H), 8.45 (s, 1H), 8.40 (d, J = 5.0 Hz, 1H), 7.18 (dd, J = 5.2, 1.9 Hz, 1H), 6.64 (s, 1H), 5.84 (s, 1H), 4.74 (s, 4H), 4.11 (s, 4H), 3.95-3.91 (m, 2H), 3.50-3.37 (m, 2H), 2.98-2.89 (m, 1H), 1.51-1.45 (m, 2H), 1.38-1.27 (m, 2H). | 362 |
| 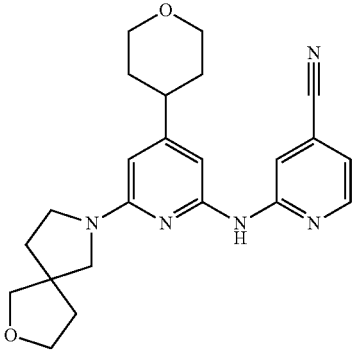 [SMILES: N#Cc1ccnc(Nc2cc(C3CCOCC3)cc(N3CCC4(CCOC4)C3)n2)c1]<br>2-((6-(2-oxa-7-azaspiro[4.4]nonan-7-yl)-4-(tetrahydro-2H-pyran-4-yl)pyridin-2-yl)amino) isonicotinonitrile | (400 MHz, DMSO-d$_6$), δ: 9.79 (s, 1H), 8.54 (s, 1H), 8.44 (d, J = 5.0 Hz, 1H), 7.23 (dd, J = 5.2, 2.0 Hz, 1H), 6.71 (s, 1H), 6.19 (s, 1H), 4.03-3.90 (m, 2H), 3.87-3.82 (m, 2H), 3.42-3.36 (m, 4H), 2.74-2.69 (m, 1H), 2.03-1.98 (m, 2H), 1.95-1.88 (m, 2H), 1.87-1.79 (m, 2H), 1.77-1.61 (m, 4H), 1.60-1.53 (m, 2H). | 406 |
| 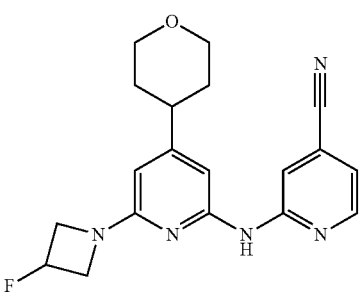 [SMILES: N#Cc1ccnc(Nc2cc(C3CCOCC3)cc(N3CC(F)C3)n2)c1]<br>2-((6-(3-fluoroazetidin-1-yl)-4-(tetrahydro-2H-pyran-4-yl)pyridin-2-yl)amino) isonicotinonitrile | (400 MHz, DMSO-d$_6$), δ: 9.86 (s, 1H), 8.40 (d, J = 5.0 Hz, 1H), 8.24 (s, 1H), 7.19 (dd, J = 5.0, 1.9 Hz, 1H), 6.76 (s, 1H), 5.99 (s, 1H), 4.41-4.35 (m, 4H), 4.15-4.05 (m, 2H), 3.79-3.73 (m, 1H), 3.58-3.49 (m, 2H), 2.74-2.56 (m, 1H), 1.76-1.57 (m, 4H). | 354 |

| Structure | ¹H NMR | MS (m/z) |
|---|---|---|
| 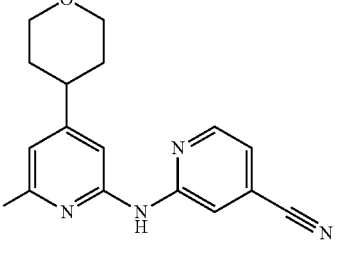<br>2-((6-(3-methoxyazetidin-1-yl)-4-(tetrahydro-2H-pyran-4-yl)pyridin-2-yl)amino)isonicotinonitrile | (400 MHz, DMSO-d₆), δ: 9.74 (s, 1H), 8.67 (s, 1H), 8.40 (d, J = 5.2 Hz, 1H), 7.19 (d, J = 5.0 Hz, 1H), 6.44 (s, 1H), 5.98 (s, 1H), 4.15-4.02 (m, 1H), 3.99-3.85 (m, 2H), 3.61-3.55 (m, 2H), 3.56-3.47 (m, 2H), 3.32 (s, 3H), 2.70-2.54 (m, 1H), 2.12-1.99 (m, 2H), 1.77-1.59 (m, 4H). | 366 |
| 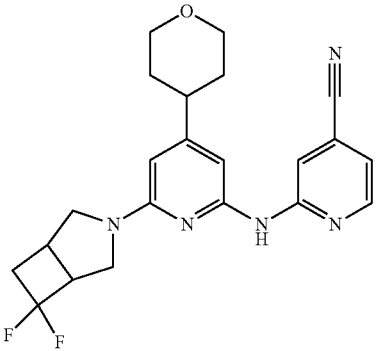 [SMILES: N#Cc1ccnc(Nc2cc(C3CCOCC3)cc(N3CC4CC(F)(F)C4C3)n2)c1]<br>2-((6-(6,6-difluoro-3-azabicyclo[3.2.0]heptan-3-yl)-4-(tetrahydro-2H-pyran-4-yl)pyridin-2-yl)amino)isonicotinonitrile | (400 MHz, DMSO-d₆), δ: 9.77 (s, 1H), 8.47 (s, 1H), 8.41 (d, J = 5.0 Hz, 1H), 7.19 (dd, J = 5.2, 2.0 Hz, 1H), 6.61 (s, 1H), 6.11 (s, 1H), 4.03 (d, J = 11.6 Hz, 1H), 3.98-3.90 (m, 2H), 3.73 (d, J = 10.5 Hz, 1H), 3.52-3.35 (m, 3H), 3.27-3.17 (m, 2H), 3.00-2.89 (s, 1H), 2.89-2.77 (s, 1H), 2.73-2.60 (m, 1H), 2.42-2.23 (m, 1H), 1.76-1.61 (m, 4H). | 412 |
| 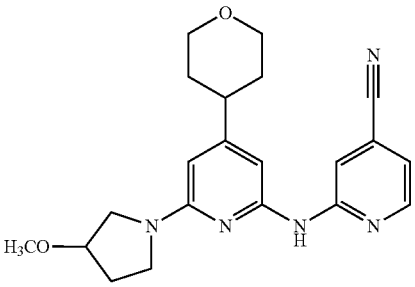 [SMILES: COC1CCN(c2cc(C3CCOCC3)cc(Nc3cc(C#N)ccn3)n2)C1]<br>2-((6-(3-methoxypyrrolidin-1-yl)-4-(tetrahydro-2H-pyran-4-yl)pyridin-2-yl)amino)isonicotinonitrile | (400 MHz, DMSO-d₆), δ: 9.72 (s, 1H), 8.64 (s, 1H), 8.39 (d, J = 5.2 Hz, 1H), 7.18 (d, J = 5.0 Hz, 1H), 6.45 (s, 1H), 5.90 (s, 1H), 4.16-4.04 (m, 1H), 4.00-3.88 (m, 2H), 3.59-3.53 (m, 1H), 3.53-3.45 (m, 2H), 3.45-3.37 (m, 3H), 3.29 (s, 3H), 2.72-2.56 (m, 1H), 2.16-2.02 (m, 2H), 1.75-1.56 (m, 4H). | 380 |

| Structure | ¹H NMR | MS (m/z) |
|---|---|---|
| 2-((6-(6-oxa-2-azaspiro[3.4]octan-2-yl)-4-(tetrahydro-2H-pyran-4-yl)pyridin-2-yl)amino)isonicotinonitrile | (400 MHz, DMSO-d₆), δ: 9.80 (s, 1H), 8.54 (s, 1H), 8.39 (d, J = 5.0 Hz, 1H), 7.20 (d, J = 5.2 Hz, 1H), 6.55 (s, 1H), 6.04 (s, 1H), 4.01-3.85 (m, 4H), 3.84-3.80 (m, 2H), 3.77-3.69 (m, 2H), 2.80-2.72 (m, 2H), 2.67-2.58 (m, 1H), 1.89-1.78 (m, 2H), 1.73-1.54 (m, 6H). | 392 |
| 2-((6-(5,5-difluoro-2-azaspiro[3.3]heptan-2-yl)-4-(tetrahydro-2H-pyran-4-yl)pyridin-2-yl)amino)isonicotinonitrile | (400 MHz, DMSO-d₆), δ: 9.81 (s, 1H), 8.47-8.30 (m, 2H), 7.19 (d, J = 6.0 Hz, 1H), 6.70 (s, 1H), 5.91 (s, 1H), 4.16 (d, J = 8.6 Hz, 2H), 3.98-3.82 (m, 4H), 3.49-3.35 (m, 2H), 2.71-2.60 (m, 1H), 2.60-2.51 (m, 2H), 2.13-2.04 (m, 2H), 1.72-1.56 (m, 4H). | 412 |
| 2-((6-(3,3-difluoroazetidin-1-yl)-4-(tetrahydro-2H-pyran-4-yl)pyridin-2-yl)amino)isonicotinonitrile | (400 MHz, DMSO-d6), δ: 9.87 (s, 1H), 8.42 (d, J = 5.1 Hz, 1H), 8.26 (s, 1H), 7.21 (dd, J = 5.2, 2.0 Hz, 1H), 6.88 (s, 1H), 6.04 (s, 1H), 4.49-4.26 (m, 4H), 4.02-3.86 (m, 2H), 3.52-3.35 (m, 2H), 2.76-2.58 (m, 1H), 1.73-1.59 (m, 4H). | 372 |

-continued

| Structure | ¹H NMR | MS (m/z) |
|---|---|---|
| 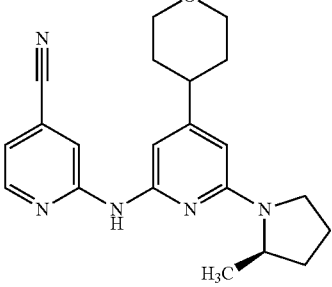<br>(R)-2-((6-(2-methylpyrrolidin-1-yl)-4-(tetrahydro-2H-pyran-4-yl)pyridin-2-yl)amino)isonicotinonitrile | 1H NMR (500 MHz, DMSO) δ 9.78 (s, 1H), 8.79 (s, 1H), 8.41 (d, J = 5.0 Hz, 1H), 7.21 (dd, J = 5.0, 1.3 Hz, 1H), 6.36 (s, 1H), 5.88 (s, 1H), 4.25-4.18 (m, 1H), 3.95 (dd, J = 10.4, 3.0 Hz, 2H), 3.49 (t, J = 7.8 Hz, 1H), 3.43 (td, J = 11.3, 3.0 Hz, 2H), 3.29-3.22 (m, 1H), 2.68-2.59 (m, 1H), 2.14-1.95 (m, 3H), 1.74-1.63 (m, 5H), 1.25 (d, J = 6.3 Hz, 3H). | 364 |
| 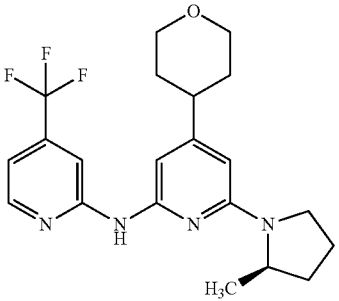 [SMILES: C[C@@H]1CCCN1c1cc(C2CCOCC2)cc(Nc2cc(C(F)(F)F)ccn2)n1]<br>(R)-6-(2-methylpyrrolidin-1-yl)-4-(tetrahydro-2H-pyran-4-yl)-N-(4-(trifluoromethyl)pyridin-2-yl)pyridin-2-amine | 1H NMR (400 MHz, DMSO) δ 9.74 (s, 1H), 8.82 (s, 1H), 8.41 (d, J = 5.1 Hz, 1H), 7.10 (d, J = 5.1 Hz, 1H), 6.32 (s, 1H), 5.85 (s, 1H), 4.21-4.11 (m, 1H), 3.93 (d, J = 10.3 Hz, 2H), 3.53-3.35 (m, 4H), 3.31-3.22 (m, 1H), 2.68-2.55 (m, 2H), 2.12-1.90 (m, 3H), 1.72-1.58 (m, 5H), 1.17 (d, J = 6.1 Hz, 3H). | 407 |

Example 2

Method B

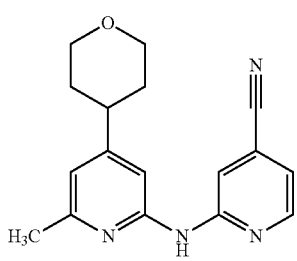

Preparation of 2-((4-(3,6-dihydro-2H-pyran-4-yl)-6-methylpyridin-2-yl)amino)isonicotinonitrile

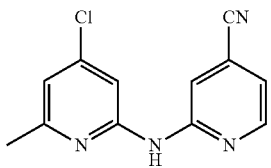 [SMILES: Cc1cc(Cl)cc(Nc2cc(C#N)ccn2)n1]

Step 1: 2-[(4-chloro-6-methyl-2-pyridyl)amino]pyridine-4-carbonitrile

A round-bottomed flask was charged with tris(dibenzylideneacetone)dipalladium(0) (534 mg, 5 mol %), 4,5-bis(diphenylphosphino)-9,9-dimethylxanthene (675 mg, 10 mol %) and cesium carbonate (5.16 g, 15.9 mmol). The flask was sealed with a septum and purged with nitrogen gas before injecting 2,4-dichloro-6-methyl-pyridine (1.83 g, 11.3 mmol) followed by anhydrous 1,4-dioxane (22.6 mL, 0.5 M). The reaction mixture was stirred at 70° C. for 18 hr before cooling to rt and filtering through Celite, rinsing with CH$_2$Cl$_2$. After concentration, flash column chromatography (100:0-95:5 CH$_2$Cl$_2$/MeOH) afforded 2-[(4-chloro-6-methyl-2-pyridyl)amino]pyridine-4-carbonitrile as a yellow solid (1.61 g, 58%); $^1$H NMR (400 MHz, CDCl$_3$) δ 8.39 (d, J=5.1 Hz, 1H), 8.04 (s, 1H), 7.41 (br s, 1H), 7.26 (s, 1H), 7.07 (d, J=5.1 Hz, 1H), 6.82 (s, 1H), 2.49 (s, 3H).

Step 2: 2-((4-(3,6-dihydro-2H-pyran-4-yl)-6-methylpyridin-2-yl)amino)isonicotinonitrile Into a vial was weighed 2-[(4-chloro-6-methyl-2-pyridyl)amino]pyridine-4-carbonitrile (282 mg, 1.15 mmol), [1,1-bis(diphenylphosphino)ferrocene]dichloropalladium(II) (85.1 mg, 10 mol %), 3,6-dihydro-2H-pyran-4-boronic acid pinacol ester (374 mg, 1.73 mmol) and potassium carbonate (478 mg, 3.46 mmol). After purging with nitrogen, the vial was charged with degassed 1,4-dioxane (2.3 mL) and degassed water (1 mL) and the reaction mixture was stirred at 80° C. overnight. The reaction was barely progressing at all as determined by RPLC and so bis(di-tert-butyl(4-dimethylaminophenyl)phosphine)dichloropalladium(II) (~50 mg) and more 3,6-dihydro-2H-pyran-4-boronic acid pinacol ester (374 mg, 1.73 mmol) was added and the reaction temperature was increased to 100° C. and stirred overnight again. After cooling to rt and filtration through Celite, rinsing with CH$_2$Cl$_2$, the mother liquor was washed with brine and dried over MgSO$_4$. Purification by flash column chromatography (100:0-95:5 CH$_2$Cl$_2$/MeOH) afforded 2-((4-(3,6-dihydro-2H-pyran-4-yl)-6-methylpyridin-2-yl)amino)isonicotinonitrile as a red solid (206 mg, 61%); $^1$H NMR (400 MHz, DMSO) δ 10.07 (br s, 1H), 8.44 (d, J=5.0 Hz, 1H), 8.21 (s, 1H), 7.51 (s, 1H), 7.23 (d, J=5.0 Hz, 1H), 6.93 (s, 1H), 6.45 (s, 1H), 4.25 (s, 2H), 3.83 (m, 2H), 2.43 (s, 3H), 2.41 (m, 2H); ESI-LRMS m/z [M+1]$^+$=293.

Example 3

Method C

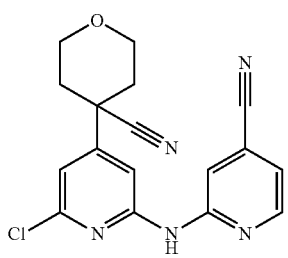 [SMILES: N#Cc1ccnc(Nc2cc(C3(C#N)CCOCC3)cc(Cl)n2)c1]

Preparation of 2-((6-chloro-4-(4-cyanotetrahydro-2H-pyran-4-yl)pyridin-2-yl)amino)isonicotinonitrile

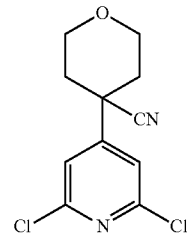 [SMILES: N#CC1(c2cc(Cl)nc(Cl)c2)CCOCC1]

Step 1: 4-(2,6-dichloro-4-pyridyl)tetrahydropyran-4-carbonitrile

To a stirring solution of 2,4,6-trichloropyridine (4.65 g, 24.7 mmol) and tetrahydropyran-4-carbonitrile (2.29 g, 20.6 mmol) in THF (100 mL, 0.2 M) and under nitrogen at −78° C. was added lithium bis(trimethylsilyl)amide (29 mL, 29 mmol, 1.0 M in THF) and after 5 min, the cooling bath was removed. After stirring a further 40 min, the reaction was quenched by the addition of sat. aq. NH$_4$Cl and then concentrated. The mixture was extracted with CH$_2$Cl$_2$ and organics dried over MgSO$_4$. Following concentration, the residue was purified by flash column chromatography (100:0-70:30 heptanes/EtOAc) but care needed to be taken to prevent compound precipitation on the column. After purification, 4-(2,6-dichloro-4-pyridyl)tetrahydropyran-4-carbonitrile was obtained a white solid (3.75 g, 71%); $^1$H NMR (400 MHz, CDCl$_3$) δ 7.39 (d, J=0.6 Hz, 2H), 4.17-4.05 (m, 2H), 3.93-3.84 (m, 2H), 2.15-1.99 (m, 4H).

Step 2: 2-((6-chloro-4-(4-cyanotetrahydro-2H-pyran-4-yl)pyridin-2-yl)amino)isonicotinonitrile A round-bottomed flask was charged with 4-(2,6-dichloro-4-pyridyl)tetrahydropyran-4-carbonitrile (1.50 g, 5.83 mmol), 2-amino-5-cyanopyridine (716 mg, 5.83 mmol), tris(dibenzylideneacetone)dipalladium(0) (138 mg, 2.5 mol %), 2,2'-bis(diphenylphosphino)-1,1'-binaphthyl (187 mg, 5 mol %) and cesium carbonate (2.66 g, 8.17 mmol). The flask was sealed with a septum and purged with nitrogen gas before injecting anhydrous 1,4-dioxane (23 mL, 0.25 M). The reaction mixture was stirred at 80° C. for 18 hr before cooling to rt and filtering through Celite, rinsing with CH$_2$Cl$_2$. After concentration, flash column chromatography (100:0-50:50 heptanes/EtOAc) afforded 2-((6-chloro-4-(4-cyanotetrahydro-2H-pyran-4-yl)pyridin-2-yl)amino)isonicotinonitrile as a colorless solid (880 mg, 44%); $^1$H NMR (400 MHz, CDCl$_3$) δ 8.44 (d, J=5.1 Hz, 1H), 7.82 (s, 1H), 7.67 (s, 1H), 7.52 (br s, 1H), 7.13 (d, J=5.1 Hz, 1H), 7.05 (s, 1H), 4.21-4.07 (m, 2H), 3.97-3.79 (m, 2H), 2.26-2.08 (m, 2H), 2.08-1.99 (m, 2H); ESI-LRMS m/z [M+1]$^+$=340.

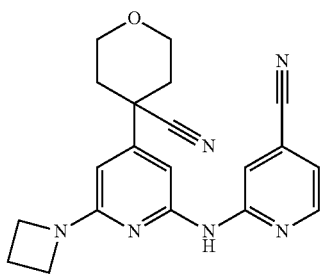 [SMILES: N#Cc1ccnc(Nc2cc(C3(C#N)CCOCC3)cc(N3CCC3)n2)c1]

Preparation of 2-((6-(azetidin-1-yl)-4-(4-cyanotetrahydro-2H-pyran-4-yl)pyridin-2-yl)amino)isonicotinonitrile Reaction of azetidine with 2-((6-chloro-4-(4-cyanotetrahydro-2H-pyran-4-yl)pyridin-2-yl)amino)isonicotinonitrile (50.0 mg, 0.147 mmol) following procedure of Method A afforded the target compound as a colorless solid (8.9 mg, 17%); $^1$H NMR (400 MHz, DMSO) δ 9.95 (br s, 1H), 8.48 (s, 1H), 8.42 (d, J=5.0 Hz, 1H), 7.23 (dd, J=5.0, 1.4 Hz, 1H), 6.89 (d, J=1.2 Hz, 1H), 5.99 (d, J=1.2 Hz, 1H), 4.06-3.98 (m, 6H), 3.70-3.59 (m, 2H), 2.41-2.28 (m, 2H), 2.08-1.96 (m, 4H); ESI-LRMS m/z [M+1]$^+$=361.

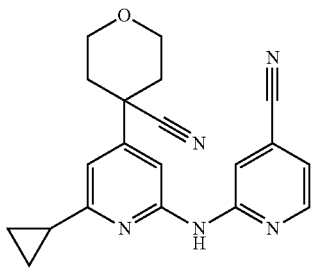 [SMILES: N#Cc1ccnc(Nc2cc(C3(C#N)CCOCC3)cc(C3CC3)n2)c1]

Preparation of 2-((4-(4-cyanotetrahydro-2H-pyran-4-yl)-6-cyclopropylpyridin-2-yl)amino)isonicotinonitrile General procedure for Suzuki-Miyaura reaction with ethyl or cyclopropyl trifluoroborate potassium salts:

A vial was charged with a 2-chloropyridine (1.0 equiv), palladium(II) acetate (10 mol %), butyldi-1-adamantylphosphine (15 mol %), the potassium trifluoroborate salt (1.2 equiv), and cesium carbonate (3 equiv) and purged under nitrogen before the addition of degassed toluene (0.2 M) and degassed water (2 M). The mixture was stirred at 110° C. overnight and then diluted with CH$_2$¬Cl$_2$, filtered through Celite, rinsing with CH$_2$¬Cl$_2$. The organics were dried over MgSO4 and concentrated to dryness. The reaction residue thus obtained was purified by RPLC to afford the target compound.

Preparation of 2-((4-(4-cyanotetrahydro-2H-pyran-4-yl)-6-cyclopropylpyridin-2-yl)amino)isonicotinonitrile Reaction of cyclopropyl trifluoroborate potassium salt with 2-((6-chloro-4-(4-cyanotetrahydro-2H-pyran-4-yl)pyridin-2-yl)amino)isonicotinonitrile (50.0 mg, 0.147 mmol) following general Suzuki-Miyaura procedure described above afforded the target compound as a colorless solid (8.1 mg, 16%); $^1$H NMR (400 MHz, DMSO) δ 10.12 (br s, 1H), 8.45 (d, J=5.0 Hz, 1H), 8.31 (s, 1H), 7.43 (d, J=1.4 Hz, 1H), 7.27 (dd, J=5.1, 1.2 Hz, 1H), 7.09 (d, J=1.4 Hz, 1H), 4.09-3.97 (m, 2H), 3.74-3.56 (m, 2H), 2.17-2.01 (m, 5H), 1.05-0.92 (m, 4H); ESI-LRMS m/z [M+1]$^+$=346.

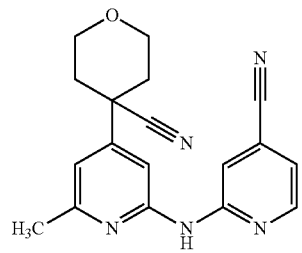 [SMILES: Cc1cc(C2(C#N)CCOCC2)cc(Nc2cc(C#N)ccn2)n1]

Preparation of 2-((4-(4-cyanotetrahydro-2H-pyran-4-yl)-6-methylpyridin-2-yl)amino)isonicotinonitrile A general procedure for Suzuki-Miyaura reaction with methylboronic acid:

A vial was charged with the 2-chloropyridine (1.0 equiv), [1,1-bis(diphenylphosphino)ferrocene]dichloropalladium (II) (20 mol %), methylboronic acid (2 equiv), and cesium carbonate (3 equiv) and purged under nitrogen before the addition of degassed toluene (0.2 M) and degassed water (2 M). The mixture was stirred at 110° C. overnight and then diluted with CH$_2$Cl$_2$, filtered through Celite, rinsing with CH$_2$Cl$_2$. The organics were dried over MgSO$_4$ and concentrated to dryness. The reaction residue thus obtained was purified by RPLC to afford the target compound.

Preparation of 2-((4-(4-cyanotetrahydro-2H-pyran-4-yl)-6-methylpyridin-2-yl)amino)isonicotinonitrile Reaction of 2-((6-chloro-4-(4-cyanotetrahydro-2H-pyran-4-yl)pyridin-2-yl)amino)isonicotinonitrile (50.0 mg, 0.147 mmol) following general Suzuki-Miyaura procedure described above afforded the target compound as a colorless solid (17.7 mg, 38%); $^1$H NMR (400 MHz, DMSO) δ 10.21 (br s, 1H), 8.45 (d, J=5.1 Hz, 1H), 8.17 (s, 1H), 7.72 (s, 1H), 7.26 (dd, J=5.1, 1.1 Hz, 1H), 7.03 (s, 1H), 4.07-3.98 (m, 2H), 3.72-3.57 (m, 2H), 2.47 (s, 3H), 2.09-2.01 (m, 5H); ESI-LRMS m/z [M+1]$^+$=320.

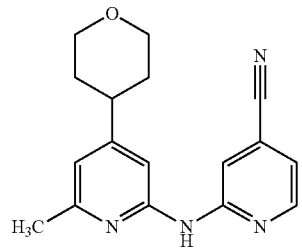 [SMILES: Cc1cc(C2CCOCC2)cc(Nc2cc(C#N)ccn2)n1]

Preparation of compound 2-((6-methyl-4-(tetrahydro-2H-pyran-4-yl)pyridin-2-yl)amino)isonicotinonitrile A vial was charged with 2-[(6-chloro-4-tetrahydropyran-4-yl-2-pyridyl)amino]pyridine-4-carbonitrile (51.1 mg, 0.162 mmol), [1,1-bis(diphenylphosphino)ferrocene]dichloropalladium(II) (13.5 mg, 10 mol %), methylboronic acid (20.0 mg, 0.325 mmol), and potassium carbonate (68 mg, 0.49 mmol) and purged under nitrogen before the addition of degassed 1,4-dioxane (1.6 mL) and degassed water (0.5 mL). The mixture was stirred at 100° C. for 19 hr and then diluted with CH$_2$Cl$_2$, filtered through Celite and washed with brine. The organics were dried over MgSO$_4$ and concentrated to dryness. The reaction residue thus obtained was purified by RPLC to afford 2-((6-methyl-4-(tetrahydro-2H-pyran-4-yl)pyridin-2-yl)amino)isonicotinonitrile as a white solid (4.1 mg, 9%); ESI-LRMS m/z [M+1]$^+$=295.

The following examples were prepared according to the methods of this Example:

| Structure | $^1$H NMR | MS (m/z) |
|---|---|---|
| 2-((6-chloro-4-(4-cyanotetrahydro-2H-pyran-4-yl)pyridin-2-yl)amino)isonicotinonitrile | $^1$H NMR (400 MHz, CDCl$_3$) δ 8.44 (d, J = 5.1 Hz, 1H), 7.82 (s, 1H), 7.67 (s, 1H), 7.52 (br s, 1H), 7.13 (d, J = 5.1 Hz, 1H), 7.05 (s, 1H), 4.21-4.07 (m, 2H), 3.97-3.79 (m, 2H), 2.26-2.08 (m, 2H), 2.08-1.99 (m, 2H); | 340 |
| 2-((4-(4-cyanotetrahydro-2H-pyran-4-yl)-6-(3,3-difluoropyrrolidin-1-yl)pyridin-2-yl)amino)isonicotinonitrile | | |
| 2-((4-(4-cyanotetrahydro-2H-pyran-4-yl)-6-cyclopropylpyridin-2-yl)amino)isonicotinonitrile | $^1$H NMR (400 MHz, DMSO) δ 10.12 (br s, 1H), 8.45 (d, J = 5.0 Hz, 1H), 8.31 (s, 1H), 7.43 (d, J = 1.4 Hz, 1H), 7.27 (dd, J = 5.1, 1.2 Hz, 1H), 7.09 (d, J = 1.4 Hz, 1H), 4.09-3.97 (m, 2H), 3.74-3.56 (m, 2H), 2.17-2.01 (m, 5H), 1.05-0.92 (m, 4H); | 346 |
| 2-((4-(4-cyanotetrahydro-2H-pyran-4-yl)-6-methylpyridin-2-yl)amino)isonicotinonitrile | $^1$H NMR (400 MHz, DMSO) δ 10.21 (br s, 1H), 8.45 (d, J = 5.1 Hz, 1H), 8.17 (s, 1H), 7.72 (s, 1H), 7.26 (dd, J = 5.1, 1.1 Hz, 1H), 7.03 (s, 1H), 4.07-3.98 (m, 2H), 3.72-3.57 (m, 2H), 2.47 (s, 3H), 2.09-2.01 (m, 5H); | 320 |

| Structure | ¹H NMR | MS (m/z) |
|---|---|---|
| 4-(2-chloro-6-((4-(difluoromethyl)pyridin-2-yl)amino)pyridin-4-yl)tetrahydro-2H-pyran-4-carbonitrile | ¹H NMR (400 MHz, CDCl₃) δ 8.42 (d, J = 5.2 Hz, 1H), 7.97 (s, 1H), 7.49 (br s, 1H), 7.42 (s, 1H), 7.04 (m, 2H), 6.62 (t, J = 55.7 Hz, 1H), 4.17-4.08 (m, 2H), 3.96-3.85 (m, 2H), 2.22-2.09 (m, 2H), 2.09-2.00 (m, 2H); | 365 |
| 2-((6-(3-azabicyclo[3.1.0]hexan-3-yl)-4-(4-cyanotetrahydro-2H-pyran-4-yl)pyridin-2-yl)amino)isonicotinonitrile | | |
| 2-((4-(4-cyanotetrahydro-2H-pyran-4-yl)-6-(6,6-difluoro-3-azabicyclo[3.2.0]heptan-3-yl)pyridin-2-yl)amino)isonicotinonitrile | 1H NMR (400 MHz, DMSO) δ 9.97 (br s, 1H), 8.43 (d, J = 4.9 Hz, 2H), 7.24 (dd, J = 4.9, 1.4 Hz, 1H), 6.92 (s, 1H), 6.29 (s, 1H), 4.11-3.99 (m, 3H), 3.81-3.76 (m, 1H), 3.69-3.62 (m, 2H), 3.54-3.42 (m, 1H), 3.36-3.31 (m, 1H), 3.02-2.79 (m, 2H), 2.40-2.28 (m, 1H), 2.15-2.00 (m, 5H); | 437 |
| (R)-2-((4-(4-cyanotetrahydro-2H-pyran-4-yl)-6-(2-methylpyrrolidin-1-yl)pyridin-2-yl)amino)isonicotinonitrile | 1H NMR (400 MHz, DMSO) δ 9.90 (br s, 1H), 8.71 (s, 1H), 8.42 (d, J = 5.0 Hz, 1H), 7.23 (dd, J = 5.0, 1.4 Hz, 1H), 6.64 (s, 1H), 6.05 (s, 1H), 4.29-4.20 (m, 1H), 4.07-3.96 (m, 2H), 3.69-3.58 (m, 2H), 3.57-3.47 (m, 1H), 2.13-1.95 (m, 8H), 1.76-1.68 (m, 1H), 1.25 (d, J = 6.2 Hz, 3H); | 389 |

| Structure | ¹H NMR | MS (m/z) |
|---|---|---|
| 2-((6-(azetidin-1-yl)-4-(4-cyanotetrahydro-2H-pyran-4-yl)pyridin-2-yl)amino)isonicotinonitrile | 1H NMR (400 MHz, DMSO) δ 9.95 (br s, 1H), 8.48 (s, 1H), 8.42 (d, J = 5.0 Hz, 1H), 7.23 (dd, J = 5.0, 1.4 Hz, 1H), 6.89 (d, J = 1.2 Hz, 1H), 5.99 (d, J = 1.2 Hz, 1H), 4.06-3.98 (m, 6H), 3.70-3.59 (m, 2H), 2.41-2.28 (m, 2H), 2.08-1.96 (m, 4H); | 361 |
| 2-((6-(3,3-difluoropyrrolidin-1-yl)-4-(tetrahydro-2H-pyran-4-yl)pyridin-2-yl)amino)isonicotinonitrile | 1H NMR (400 MHz, DMSO) δ 9.84 (s, 1H), 8.47 (s, 1H), 8.41 (d, J = 5.0 Hz, 1H), 7.21 (d, J = 5.0 Hz, 1H), 6.61 (s, 1H), 6.00 (s, 1H), 3.94 (d, J = 10.9 Hz, 2H), 3.86 (t, J = 13.2 Hz, 2H), 3.65 (t, J = 7.2 Hz, 2H), 3.47-3.38 (m, 2H), 2.70-2.52 (m, 3H), 1.71-1.62 (m, 4H). | 386 |
| 2-((6-methyl-4-(tetrahydro-2H-pyran-4-yl)pyridin-2-yl)amino)isonicotinonitrile | | 295 |
| N-(4-(difluoromethoxy)pyridin-2-yl)-6-(1-methyl-1H-pyrazol-4-yl)-4-(tetrahydro-2H-pyran-4-yl)pyridine-2-amine | 1H NMR (400 MHz, DMSO) δ 9.79 (s, 1H), 8.22 (d, J = 6.1 Hz, 2H), 8.05 (s, 1H), 7.98 (s, 1H), 7.47 (t, J = 73.1 Hz, 1H), 7.12 (d, J = 12.1 Hz, 2H), 6.70 (d, J = 5.6 Hz, 1H), 3.97 (d, J = 10.3 Hz, 2H), 3.88 (s, 3H), 3.59-3.37 (m, 2H), 2.72 (dt, J = 10.3, 5.6 Hz, 1H), 1.83-1.58 (m, 4H). | 402 |

-continued

| Structure | $^1$H NMR | MS (m/z) |
|---|---|---|
| 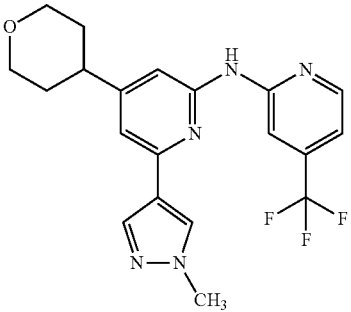 [SMILES: Cn1cc(-c2cc(C3CCOCC3)cc(Nc3cc(C(F)(F)F)ccn3)n2)cn1]<br>6-(1-methyl-1H-pyrazol-4-yl)-4-(tetrahydro-2H-pyran-4-yl)-N-(4-(trifluoromethyl)pyridin-2-yl)pyridin-2-amine | 1H NMR (400 MHz, DMSO) δ 10.09 (s, 1H), 8.70 (s, 1H), 8.49 (d, J = 5.1 Hz, 1H), 8.21 (s, 1H), 7.94 (s, 1H), 7.18 (s, 2H), 7.11 (s, 1H), 3.97 (d, J = 10.6 Hz, 2H), 3.89 (s, 3H), 3.54-3.39 (m, 2H), 2.87-2.63 (m, 2H), 1.82-1.57 (m, 4H). | 404 |

Example 4

Method D

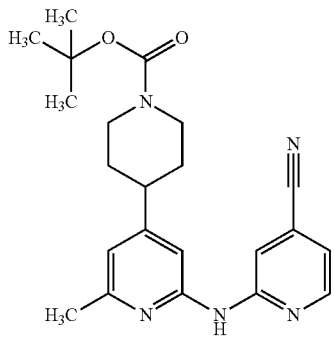 [SMILES: Cc1cc(C2CCN(C(=O)OC(C)(C)C)CC2)cc(Nc2cc(C#N)ccn2)n1]

Preparation of tert-Butyl 4-(2-((4-cyanopyridin-2-yl)amino)-6-methylpyridin-4-yl)piperidine-1-carboxylate

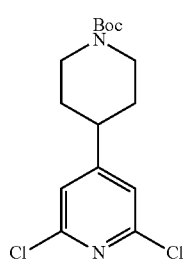 [SMILES: CC(C)(C)OC(=O)N1CCC(c2cc(Cl)nc(Cl)c2)CC1]

Step 1: tert-butyl 4-(2,6-dichloro-4-pyridyl)piperidine-1-carboxylate

Under a nitrogen atmosphere, zinc dust (4.06 g, 62.1 mmol) was suspended in N,N-dimethylacetamide (5 mL) and a mixture of trimethylsilylchloride (0.946 mL, 7.30 mmol) and 1,2-dibromoethane (0.636 mL, 7.30 mmol) was added cautiously over 10 min. After stirring for a further 15 min, a solution of N-(tert-butoxycarbonyl)-4-iodopiperidine (16.74 g, 51.11 mmol) in N,N-dimethylacetamide (20 mL) was added over 30 min and stirring was continued for an additional 30 min. In the open atmosphere, this mixture was filtered through Celite as quickly as possible, rinsing with a small amount of N,N-dimethylacetamide. The resulting yellow solution was injected into a separately prepared, nitrogen flushed suspension of [1,1-bis(diphenylphosphino)ferrocene]dichloropalladium(II) (1.35 g, 1.83 mmol), copper(I) iodide (695 mg, 3.65 mmol) and 2,6-dichloro-4-iodopyridine (10.0 g, 36.5 mmol) in N,N-dimethylacetamide (30 mL) and this mixture was stirred at 80° C. for 16.5 hr. After cooling to rt, the mixture was diluted with EtOAc and water and partitioned. Filtration through Celite was necessary to break the emulsion, following which, the organics were washed with water and then dried over MgSO$_4$. After being freed of volatiles, the resultant residue was purified by flash column chromatography (100:0-70:30 heptanes/EtOAc) to afford tert-butyl 4-(2,6-dichloro-4-pyridyl)piperidine-1-carboxylate as a white solid (7.49 g, 62%); $^1$H NMR (400 MHz, CDCl$_3$) δ 7.11 (s, 2H), 4.19 (m, 2H), 2.78 (m, 2H), 2.71 (m, 1H), 1.81 (m, 2H), 1.65 (m, 2H), 1.48 (s, 9H).

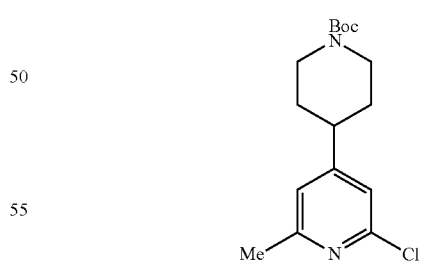

Step 2: tert-butyl 4-(2-chloro-6-methyl-4-pyridyl)piperidine-1-carboxylate

A round-bottomed flask was charged with tert-butyl 4-(2,6-dichloro-4-pyridyl)piperidine-1-carboxylate (1.01 g, 3.04 mmol), [1,1-bis(diphenylphosphino)ferrocene]dichloropalladium(II) (63 mg, 2.5 mol %), methylboronic acid (188 mg, 3.04 mmol), and potassium carbonate (1.27 g, 9.12 mmol)

and purged under nitrogen before the addition of degassed 1,4-dioxane (6.1 mL) and degassed water (2.1 mL). The mixture was stirred at 80° C. for 2 hr, 90° C. for 19 hr and then, after addition of an another aliquot of [1,1-bis(diphenylphosphino)ferrocene]dichloropalladium(II) (63 mg, 2.5 mol %), 90° C. for 28 hr. The mixture was then diluted with $CH_2Cl_2$ and washed with brine. The organics were dried over $MgSO_4$ and concentrated to dryness. The reaction residue thus obtained was purified by flash column chromatography (100:0-80:20 heptanes/EtOAc) to afford, along with recovered tert-butyl 4-(2,6-dichloro-4-pyridyl)piperidine-1-carboxylate which eluted first, tert-butyl 4-(2-chloro-6-methyl-4-pyridyl)piperidine-1-carboxylate as a white solid (345 mg, 37%); $^1$H NMR (400 MHz, $CDCl_3$) δ 6.98 (s, 1H), 6.90 (s, 1H), 4.17 (m, 2H), 2.78 (m, 2H), 2.60 (m, 1H), 2.51 (s, 3H), 1.81 (m, 2H), 1.65-1.57 (m, 2H), 1.48 (s, 9H).

Step 3: tert-butyl 4-(2-((4-cyanopyridin-2-yl)amino)-6-methylpyridin-4-yl)piperidine-1-carboxylate A vial was charged with tris(dibenzylideneacetone)dipalladium(0) (104 mg, 10 mol %), 4,5-bis(diphenylphosphino)-9,9-dimethylxanthene (65.8 mg, 10 mol %), cesium carbonate (503 mg, 1.54 mmol), 2-amino-5-cyanopyridine (163 mg, 1.32 mmol) and tert-butyl 4-(2-chloro-6-methyl-4-pyridyl)piperidine-1-carboxylate (343 mg, 1.10 mmol). After being purged with nitrogen, anhydrous 1,4-dioxane (2.2 mL, 0.5 M) was injected and the mixture stirred at 105° C. for 19 hr. After being concentrated to dryness, the reaction mixture was purified by flash column chromatography (100:0-65:35 heptanes/EtOAc) to afford tert-butyl 4-(2-((4-cyanopyridin-2-yl)amino)-6-methylpyridin-4-yl)piperidine-1-carboxylate as a white solid (280 mg, 64%); $^1$H NMR (400 MHz, $CDCl_3$) δ 8.36 (d, J=5.1 Hz, 1H), 8.24 (s, 1H), 7.39 (br s, 1H), 7.02 (d, J=5.1 Hz, 1H), 6.86 (s, 1H), 6.65 (s, 1H), 4.26 (m, 2H), 2.80 (m, 2H), 2.60 (m, 1H), 2.49 (s, 3H), 1.82 (m, 2H), 1.58 (m, 2H), 1.49 (s, 9H); ESI-LRMS m/z [M+1]$^+$=394.

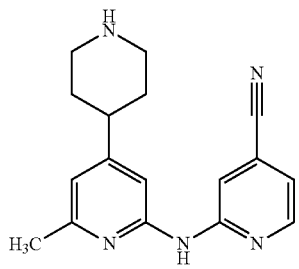 [SMILES: Cc1cc(C2CCNCC2)cc(Nc2cc(C#N)ccn2)n1]

Preparation of 2-((6-methyl-4-(piperidin-4-yl)pyridin-2-yl)amino)isonicotinonitrile To a solution of tert-butyl 4-(2-((4-cyanopyridin-2-yl)amino)-6-methylpyridin-4-yl)piperidine-1-carboxylate (216 mg, 0.550 mmol) in $CH_2Cl_2$ (2.2 mL) was added trifluoroacetic acid (1.1 mL) and stirring was maintained for 2 hr. Concentrated to dryness afforded 2-((6-methyl-4-(piperidin-4-yl)pyridin-2-yl)amino)isonicotinonitrile (1×TFA salt by $^1$H NMR) as a yellow solid (224 mg, >99%); $^1$H NMR (400 MHz, DMSO) δ 10.47 (br s, 1H), 8.65 (br s, 1H), 8.47 (d, J=5.1 Hz, 1H), 8.38 (br s, 1H), 8.07 (s, 1H), 7.36 (s, 1H), 7.32 (d, J=5.1 Hz, 1H), 6.80 (s, 1H), 3.40 (m, 2H), 3.02 (m, 2H), 2.93 (m, 1H), 2.47 (s, 3H), 1.96 (m, 2H), 1.76 (m, 2H); ESI-LRMS m/z [M+1]$^+$=294.

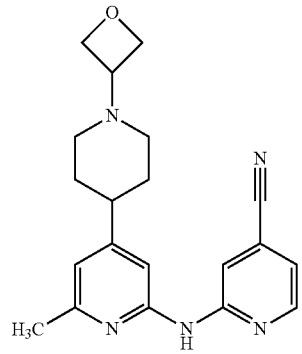 [SMILES: Cc1cc(C2CCN(C3COC3)CC2)cc(Nc2cc(C#N)ccn2)n1]

Preparation of 2-((6-methyl-4-(1-(oxetan-3-yl)piperidin-4-yl)pyridin-2-yl)amino)isonicotinonitrile To a suspension of 2-((6-methyl-4-(piperidin-4-yl)pyridin-2-yl)amino)isonicotinonitrile mono-TFA salt (33.8 mg, 0.0830 mmol) in anhydrous THF (0.8 mL) was added N,N-diisopropylethylamine (24 μL, 0.17 mmol) followed by 3-oxetanone (8.0 μL, 0.12 mmol) and the mixture was stirred for 15 min before the introduction of sodium triacetoxyborohydride (55 mg, 0.25 mmol). After stirring for a further 17 hr, the mixture was diluted with $CH_2Cl_2$ and washed with sat. aq. $NaHCO_3$ and the organics were dried over $MgSO_4$ and concentrated to dryness. The residue thus obtained was purified by RPLC to afford 2-((6-methyl-4-(1-(oxetan-3-yl)piperidin-4-yl)pyridin-2-yl)amino)isonicotinonitrile as a colorless solid (9.5 mg, 34%); $^1$H NMR (400 MHz, DMSO) δ 9.99 (br s, 1H), 8.44 (d, J=5.1 Hz, 1H), 8.18 (s, 1H), 7.36 (s, 1H), 7.21 (d, J=5.1 Hz, 1H), 6.75 (s, 1H), 4.54 (dd, J=6.5, 6.5 Hz, 2H), 4.45 (dd, J=6.5, 6.5 Hz, 2H), 3.42 (m, 1H), 2.80 (m, 2H), 2.44 (m, 1H), 2.40 (s, 3H), 1.86 (m, 2H), 1.76 (m, 2H), 1.63 (m, 2H); ESI-LRMS m/z [M+1]$^+$=350.

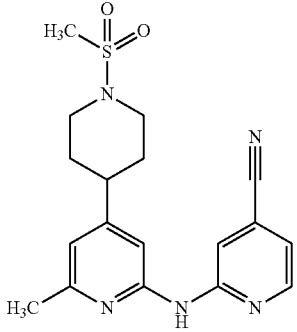 [SMILES: Cc1cc(C2CCN(S(C)(=O)=O)CC2)cc(Nc2cc(C#N)ccn2)n1]

Preparation of 2-((6-methyl-4-(1-(methylsulfonyl)piperidin-4-yl)pyridin-2-yl)amino)isonicotinonitrile General procedure for acylation/sulfonylation:
To a solution of 2-((6-methyl-4-(piperidin-4-yl)pyridin-2-yl)amino)isonicotinonitrile mono-TFA salt (34.9 mg, 0.0857 mmol) and 4-dimethylaminopyridine (1.0 mg, 10 mol %) in anhydrous $CH_2Cl_2$ (0.9 mL) was added triethylamine (36 μL, 0.26 mmol) followed by the acylation/sulfonylation anhydride (0.128 mmol). After stirring 2 hr, the reaction mixture was diluted with $CH_2Cl_2$ and washed with sat. aq. $NaHCO_3$ and the organics were dried over $MgSO_4$ and concentrated to dryness. The resultant residue was purified by RPLC to afford the title compound.

2-((6-methyl-4-(1-(methylsulfonyl)piperidin-4-yl)pyridin-2-yl)amino)isonicotinonitrile Submission to general acylation/sulfonylation procedure utilizing methanesulfonic anhydride (23 mg, 0.128 mmol) gave rise to 2-((6-methyl-4-(1-(methylsulfonyl)piperidin-4-yl)pyridin-2-yl)amino)isonicotinonitrile as a colorless solid (9.7 mg, 30%); $^1$H NMR (400 MHz, DMSO) δ 10.01 (br s, 1H), 8.43 (d, J=5.1 Hz, 1H), 8.18 (s, 1H), 7.38 (s, 1H), 7.21 (d, J=5.1 Hz, 1H), 6.78 (s, 1H), 3.68 (m, 2H), 2.90 (s, 3H), 2.83 (m, 2H), 2.60 (m, 1H), 2.41 (s, 3H), 1.89 (m, 2H), 1.65 (m, 2H); ESI-LRMS m/z $[M+1]^+=372$.

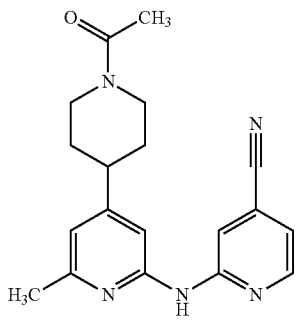 [SMILES: CC(=O)N1CCC(c2cc(C)nc(Nc3cc(C#N)ccn3)c2)CC1]

Preparation of 2-((4-(1-acetylpiperidin-4-yl)-6-methylpyridin-2-yl)amino)isonicotinonitrile Submission to general acylation/sulfonylation procedure described above utilizing acetic anhydride (13 μL, 0.128 mmol) provides 2-((4-(1-acetylpiperidin-4-yl)-6-methylpyridin-2-yl)amino)isonicotinonitrile as a colorless solid (10.9 mg, 38%); $^1$H NMR (400 MHz, DMSO) δ 9.99 (br s, 1H), 8.43 (d, J=5.1 Hz, 1H), 8.18 (s, 1H), 7.34 (s, 1H), 7.21 (d, J=5.1 Hz, 1H), 6.75 (s, 1H), 4.59-4.47 (m, 1H), 4.00-3.82 (m, 1H), 3.16-3.07 (m, 1H), 2.77-2.65 (m, 1H), 2.64-2.55 (m, 1H), 2.40 (s, 3H), 2.03 (s, 3H), 1.85-1.69 (m, 2H), 1.62-1.47 (m, 1H), 1.47-1.30 (m, 1H); ESI-LRMS m/z $[M+1]^+=336$.

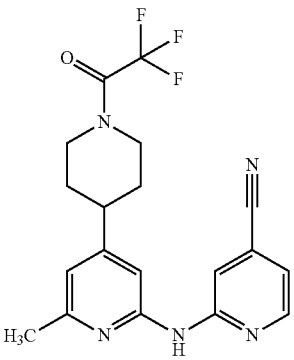 [SMILES: Cc1cc(C2CCN(C(=O)C(F)(F)F)CC2)cc(Nc2cc(C#N)ccn2)n1]

Preparation of 2-((6-methyl-4-(1-(2,2,2-trifluoroacetyl)piperidin-4-yl)pyridin-2-yl)amino)isonicotinonitrile Submission to general acylation/sulfonylation procedure described above utilizing trifluoroacetic anhydride (18 μL, 0.128 mmol) gave rise to 2-((6-methyl-4-(1-(2,2,2-trifluoroacetyl)piperidin-4-yl)pyridin-2-yl)amino)isonicotinonitrile as a colorless solid (11.5 mg, 35%); $^1$H NMR (400 MHz, DMSO) δ 10.00 (br s, 1H), 8.43 (d, J=5.1 Hz, 1H), 8.18 (s, 1H), 7.35 (s, 1H), 7.21 (d, J=5.1 Hz, 1H), 6.79 (s, 1H), 4.47-4.38 (m, 1H), 4.00-3.90 (m, 1H), 3.43-3.36 (m, 1H), 3.05-2.93 (m, 1H), 2.92-2.79 (m, 1H), 2.40 (s, 3H), 1.98-1.85 (m, 2H), 1.68-1.44 (m, 2H); ESI-LRMS m/z $[M+1]^+=390$.

The following examples were prepared according to the methods described in Example 4.

| Structure | $^1$H NMR | MS (m/z) |
|---|---|---|
| 2-((4-(1-acetylpiperidin-4-yl)-6-methylpyridin-2-yl)amino) isonicotinonitrile | $^1$H NMR (400 MHz, DMSO) δ 9.99 (br s, 1H), 8.43 (d, J = 5.1 Hz, 1H), 8.18 (s, 1H), 7.34 (s, 1H), 7.21 (d, J = 5.1 Hz, 1H), 6.75 (s, 1H), 4.59-4.47 (m, 1H), 4.00-3.82 (m, 1H), 3.16-3.07 (m, 1H), 2.77-2.65 (m, 1H), 2.64-2.55 (m, 1H), 2.40 (s, 3H), 2.03 (s, 3H), 1.85-1.69 (m, 2H), 1.62-1.47 (m, 1H), 1.47-1.30 (m, 1H). | 336 |

-continued

| Structure | ¹H NMR | MS (m/z) |
|---|---|---|
| 2-((6-methyl-4-(1-(methylsulfonyl)piperidin-4-yl)pyridin-2-yl)amino)isonicotinonitrile | ¹H NMR (400 MHz, DMSO) δ 10.01 (br s, 1H), 8.43 (d, J = 5.1 Hz, 1H), 8.18 (s, 1H), 7.38 (s, 1H), 7.21 (d, J = 5.1 Hz, 1H), 6.78 (s, 1H), 3.68 (m, 2H), 2.90 (s, 3H), 2.83 (m, 2H), 2.60 (m, 1H), 2.41 (s, 3H), 1.89 (m, 2H), 1.65 (m, 2H). | 372 |
| 2-((6-methyl-4-(1-(oxetan-3-yl)piperidin-4-yl)pyridin-2-yl)amino)isonicotinonitrile | ¹H NMR (400 MHz, DMSO) δ 9.99 (br s, 1H), 8.44 (d, J = 5.1 Hz, 1H), 8.18 (s, 1H), 7.36 (s, 1H), 7.21 (d, J = 5.1 Hz, 1H), 6.75 (s, 1H), 4.54 (dd, J = 6.5, 6.5 Hz, 2H), 4.45 (dd, J = 6.5, 6.5 Hz, 2H), 3.42 (m, 1H), 2.80 (m, 2H), 2.44 (m, 1H), 2.40 (s, 3H), 1.86 (m, 2H), 1.76 (m, 2H), 1.63 (m, 2H). | 350 |
| 2-((6-methyl-4-(piperidin-4-yl)pyridin-2-yl)amino)isonicotinonitrile | ¹H NMR (400 MHz, DMSO) δ 10.47 (br s, 1H), 8.65 (br s, 1H), 8.47 (d, J = 5.1 Hz, 1H), 8.38 (br s, 1H), 8.07 (s, 1H), 7.36 (s, 1H), 7.32 (d, J = 5.1 Hz, 1H), 6.80 (s, 1H), 3.40 (m, 2H), 3.02 (m, 2H), 2.93 (m, 1H), 2.47 (s, 3H), 1.96 (m, 2H), 1.76 (m, 2H). | 294 |

-continued

| Structure | ¹H NMR | MS (m/z) |
|---|---|---|
| 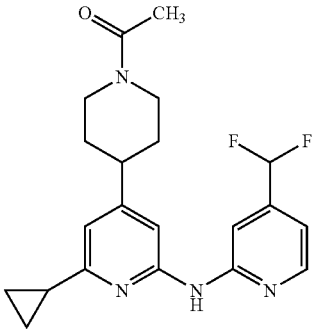 [SMILES: CC(=O)N1CCC(c2cc(Nc3cc(C(F)F)ccn3)nc(C3CC3)c2)CC1]<br>1-(4-(2-cyclopropyl-6-((4-(difluoromethyl)pyridin-2-yl)amino)pyridin-4-yl)piperidin-1-yl)ethanone | ¹H NMR (400 MHz, DMSO) δ 9.70 (br s, 1H), 8.33 (d, J = 5.1 Hz, 1H), 8.24 (s, 1H), 7.18-6.86 (m, 3H), 6.77 (s, 1H), 4.59-4.45 (m, 1H), 3.96-3.87 (m, 1H), 3.19-3.09 (m, 1H), 2.73-2.54 (m, 2H), 2.03 (s, 3H), 2.02-1.95 (m, 1H), 1.85-1.72 (m, 2H), 1.63-1.36 (m, 2H), 0.98-0.86 (m, 4H); | 387 |
| 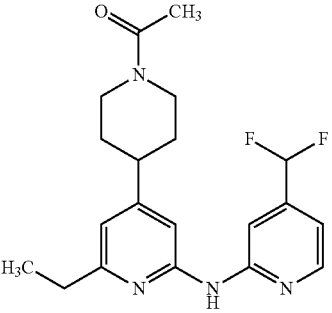 [SMILES: CCc1cc(C2CCN(C(C)=O)CC2)cc(Nc2cc(C(F)F)ccn2)n1]<br>1-(4-(2-((4-(difluoromethyl)pyridin-2-yl)amino)-6-ethylpyridin-4-yl)piperidin-1-yl)ethanone | ¹H NMR (400 MHz, DMSO) δ 9.78 (br s, 1H), 8.34 (d, J = 5.1 Hz, 1H), 8.19 (s, 1H), 7.29 (s, 1H), 7.18-6.86 (m, 2H), 6.71 (s, 1H), 4.57-4.46 (m, 1H), 3.97-3.84 (m, 1H), 3.19-3.07 (m, 1H), 2.77-2.54 (m, 4H), 2.03 (s, 3H), 1.86-1.73 (m, 2H), 1.61-1.35 (m, 2H), 1.25 (t, J = 7.6 Hz, 3H); | 375 |
| 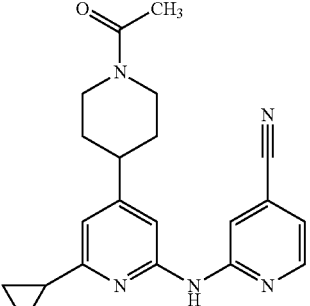<br>2-((4-(1-acetylpiperidin-4-yl)-6-cyclopropylpyridin-2-yl)amino)isonicotinonitrile | ¹H NMR (400 MHz, DMSO) δ 9.91 (s, 1H), 8.42 (d, J = 5.1 Hz, 1H), 8.34 (s, 1H), 7.22 (dd, J = 5.0, 1.3 Hz, 1H), 7.06 (s, 1H), 6.82 (s, 1H), 4.58-4.46 (m, 1H), 3.97-3.86 (m, 1H), 3.17-3.05 (m, 1H), 2.75-2.53 (m, 2H), 2.09-1.98 (m, 1H), 1.95 (s, 3H), 1.86-1.73 (m, 2H), 1.61-1.35 (m, 2H), 0.98-0.91 (m, 4H); | 362 |

-continued

| Structure | ¹H NMR | MS (m/z) |
|---|---|---|
| 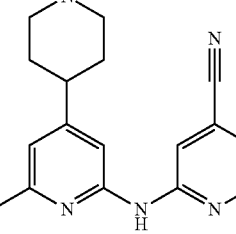<br>2-((4-(1-acetylpiperidin-4-yl)-6-ethylpyridin-2-yl)amino)isonicotinonitrile | ¹H NMR (400 MHz, DMSO) δ 9.99 (br s, 1H), 8.43 (d, J = 5.1 Hz, 1H), 8.34 (s, 1H), 7.26 (s, 1H), 7.22 (dd, J = 5.1, 1.3 Hz, 1H), 6.76 (s, 1H), 4.57-4.46 (m, 1H), 3.97-3.82 (m, 1H), 3.17-3.06 (m, 1H), 2.77-2.53 (m, 4H), 2.03 (s, 3H), 1.86-1.71 (m, 2H), 1.64-1.49 (m, 1H), 1.49-1.37 (m, 1H), 1.26 (t, J = 7.6 Hz, 3H); | 350 |
| 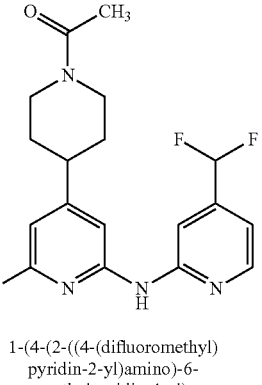<br>1-(4-(2-((4-(difluoromethyl)pyridin-2-yl)amino)-6-methylpyridin-4-yl)piperidin-1-yl)ethanone | ¹H NMR (400 MHz, DMSO) δ 9.80 (br s, 1H), 8.35 (d, J = 5.1 Hz, 1H), 7.97 (s, 1H), 7.43 (s, 1H), 7.18-6.87 (m, 2H), 6.71 (s, 1H), 4.58-4.45 (m, 1H), 3.96-3.85 (m, 1H), 3.19-3.08 (m, 1H), 2.77-2.64 (m, 1H), 2.63-2.55 (m, 1H), 2.38 (s, 3H), 2.03 (s, 3H), 1.84-1.73 (m, 2H), 1.48 (dtd, J = 56.2, 12.4, 8.3 Hz, 2H); | 361 |
| 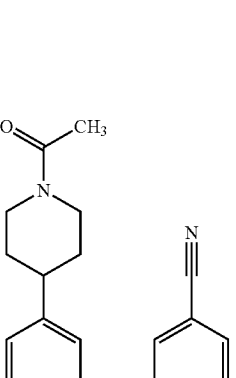<br>2-((4-(1-acetylpiperidin-4-yl)-6-chloropyridin-2-yl)amino)isonicotinonitrile | ¹H NMR (400 MHz, CDCl₃) δ 8.40 (d, J = 5.0 Hz, 1H), 7.90 (s, 1H), 7.39 (br s, 1H), 7.20 (s, 1H), 7.08 (d, J = 5.0 Hz, 1H), 6.81 (s, 1H), 4.87-4.78 (m, 1H), 4.00-3.92 (m, 1H), 3.22-3.13 (m, 1H), 2.79-2.70 (m, 1H), 2.68-2.57 (m, 1H), 2.14 (s, 3H), 1.99-1.86 (m, 2H), 1.69-1.58 (m, 2H); | 356 |

-continued

| Structure | ¹H NMR | MS (m/z) |
|---|---|---|
| 2-((6-methyl-4-(1-(2,2,2-trifluoroethyl)piperidin-4-yl)pyridin-2-yl)amino)isonicotinonitrile | ¹H NMR (400 MHz, DMSO) δ 9.97 (br s, 1H), 8.44 (d, J = 5.2 Hz, 1H), 8.19 (s, 1H), 7.34 (s, 1H), 7.21 (dd, J = 5.1, 1.4 Hz, 1H), 6.76 (s, 1H), 3.24-3.13 (m, 2H), 3.05-2.97 (m, 2H), 2.48-2.37 (m, 3H), 2.40 (s, 3H), 1.78-1.55 (m, 4H); | 376 |
| 1-(4-(2-chloro-6-((4-(difluoromethyl)pyridin-2-yl)amino)pyridin-4-yl)piperidin-1-yl)ethanone | ¹H NMR (400 MHz, CDCl₃) δ 8.39 (d, J = 5.0 Hz, 1H), 7.49 (s, 2H), 7.38 (br s, 1H), 7.01 (d, J = 5.1 Hz, 1H), 6.79-6.43 (m, 2H), 4.88-4.67 (m, 1H), 4.03-3.86 (m, 1H), 3.24-3.12 (m, 1H), 2.80-2.69 (m, 1H), 2.68-2.58 (m, 1H), 2.14 (s, 3H), 2.01-1.86 (m, 2H), 1.71-1.57 (m, 2H); | 381 |

Example 5

Method E

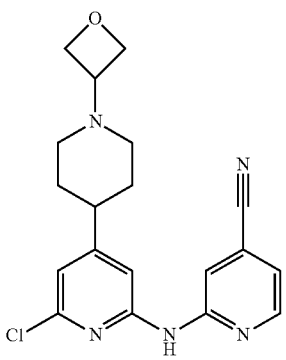 [SMILES: N#Cc1ccnc(Nc2cc(C3CCN(C4COC4)CC3)cc(Cl)n2)c1]

Preparation of 2-((6-chloro-4-(1-(oxetan-3-yl)piperidin-4-yl)pyridin-2-yl)amino)isonicotinonitrile

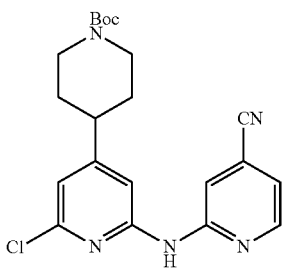 [SMILES: CC(C)(C)OC(=O)N1CCC(c2cc(Cl)nc(Nc3cc(C#N)ccn3)c2)CC1]

Step 1: tert-butyl 4-[2-chloro-6-[(4-cyano-2-pyridyl)amino]-4-pyridyl]piperidine-1-carboxylate A round-bottomed flask was charged with tert-butyl 4-(2,6-dichloro-4-pyridyl)piperidine-1-carboxylate (3.64 g, 11.0 mmol), 2-amino-4-cyanopyridine (1.35 g, 11.0 mmol), tris (dibenzylideneacetone)dipalladium(0) (259 mg, 2.5 mol %), 4,5-bis(diphenylphosphino)-9,9-dimethylxanthene (328 mg, 5 mol %) and potassium carbonate (2.13 g, 15.4 mmol). The flask was sealed with a septum and purged with nitrogen gas before injecting anhydrous 1,4-dioxane (22 mL, 0.5 M). The reaction mixture was stirred at 80° C. for 17 hr before cooling to rt and filtering through Celite, rinsing with $CH_2Cl_2$. After concentration, flash column chromatography (100:0-60:40 heptanes/EtOAc) afforded tert-butyl 4-[2-chloro-6-[(4-cyano-2-pyridyl)amino]-4-pyridyl]piperidine-1-carboxylate as a colorless film (1.745 g, 38%); $^1$H NMR (400 MHz, $CDCl_3$) δ 8.40 (d, J=5.1 Hz, 1H), 7.94 (s, 1H), 7.42 (br s, 1H), 7.17 (s, 1H), 7.08 (d, J=5.1 Hz, 1H), 6.81 (s, 1H), 4.41-4.09 (m, 2H), 2.87-2.72 (m, 2H), 2.71-2.60 (m, 1H), 1.88-1.80 (m, 2H), 1.67-1.58 (m, 2H), 1.49 (s, 9H).

Step 2: 2-((6-chloro-4-(1-(oxetan-3-yl)piperidin-4-yl)pyridin-2-yl)amino)isonicotinonitrile To a solution of tert-butyl 4-[2-chloro-6-[(4-cyano-2-pyridyl)amino]-4-pyridyl]piperidine-1-carboxylate (1.745 g, 4.216 mmol) in $CH_2Cl_2$ (17 mL) and at 0° C. was added trifluoroacetic acid (8.4 mL) and allowed to warm to room temperature. After stirring for 1 hr, the solution was concentrated to dryness to afford the TFA salt as a white solid which was re-suspended in anhydrous THF (17 mL) and submitted to the action of triethylamine (3.0 mL, 21 mmol) and 3-oxetanone (0.40 mL, 6.3 mmol). After stirring for 1 hr, sodium triacetoxyborohydride (2.82 g, 12.7 mmol) was added and stirring continued for 16.5 hr. The reaction mixture was a solid white mass at this point which was dissolved in $CH_2Cl_2$ and washed with half-saturated aq. $NaHCO_3$ and organics dried over $MgSO_4$. Following concentration, subjection to flash chromatographic purification (100:0-90:10 $CH_2Cl_2$/MeOH) gave rise to 2-((6-chloro-4-(1-(oxetan-3-yl)piperidin-4-yl)pyridin-2-yl)amino)isonicotinonitrile as a white solid (1.247 g, 80% over 2 steps); $^1$H NMR (400 MHz, DMSO) δ 10.38 (br s, 1H), 8.49 (d, J=5.1 Hz, 1H), 7.94 (s, 1H), 7.63 (s, 1H), 7.30 (d, J=5.1 Hz, 1H), 6.98 (s, 1H), 4.57-4.51 (m, 2H), 4.47-4.41 (m, 2H), 3.46-3.38 (m, 1H), 2.85-2.77 (m, 2H), 1.90-1.75 (m, 4H), 1.70-1.58 (m, 2H); ESI-LRMS m/z $[M+1]^+$=370.

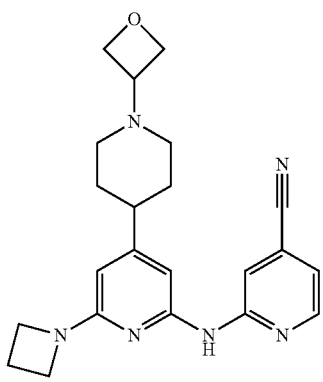 [SMILES: N#Cc1ccnc(Nc2cc(C3CCN(C4COC4)CC3)cc(N3CCC3)n2)c1]

Preparation of 2-((6-(azetidin-1-yl)-4-(1-(oxetan-3-yl)piperidin-4-yl)pyridin-2-yl)amino)isonicotinonitrile General procedure for Buchwald-Hartwig reaction of secondary amines:

Into a vial was weighed the 2-chloropyridine (1.0 equiv), the amine (usually as the HCl salt, 3 equiv), chloro(2-dicyclohexylphosphino-2',6'-di-i-propoxy-1,1'-biphenyl)[2-(2-aminoethylphenyl)]palladium(II) methyl-t-butylether adduct (10 mol %), 2-Dicyclohexylphosphino-2',6'-di-i-propoxy-1,1'-biphenyl (10 mol %) and sodium tert-butoxide (6 equiv), and purged under nitrogen before the addition of anhydrous THF (0.1 M). The mixture was stirred at 90° C. overnight before being filtered through Celite, rinsing with $CH_2Cl_2$. After being concentrated to dryness, the reaction residue was purified by RPLC to afford the final compound.

2-((6-(azetidin-1-yl)-4-(1-(oxetan-3-yl)piperidin-4-yl)pyridin-2-yl)amino)isonicotinonitrile Reaction of azetidine with 2-((6-chloro-4-(1-(oxetan-3-yl)piperidin-4-yl)pyridin-2-yl)amino)isonicotinonitrile (40 mg, 0.11 mmol) following general Buchwald-Hartwig procedure described above afforded the target compound as a colorless solid (19.8 mg, 47%); $^1$H NMR (400 MHz, DMSO) δ 9.76 (br s, 1H), 8.51 (s, 1H), 8.40 (d, J=5.1 Hz, 1H), 7.18 (d, J=5.1 Hz, 1H), 6.59 (s, 1H), 5.80 (s, 1H), 4.57-4.49 (m, 2H), 4.49-4.40 (m, 2H), 4.00-3.92 (m, 4H), 3.43-3.35 (m, 1H), 2.82-2.73 (m, 2H), 2.40-2.27 (m, 3H), 1.88-1.78 (m, 2H), 1.77-1.68 (m, 2H), 1.68-1.51 (m, 2H); ESI-LRMS m/z $[M+1]^+$=391.

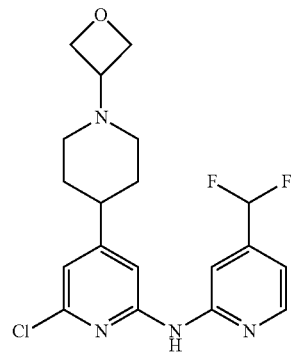 [SMILES: FC(F)c1ccnc(Nc2cc(C3CCN(C4COC4)CC3)cc(Cl)n2)c1]

Preparation of 6-chloro-N-(4-(difluoromethyl)pyridin-2-yl)-4-(1-(oxetan-3-yl)piperidin-4-yl)pyridin-2-amine

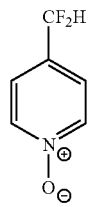

Step 1: 4-difluoromethyl-pyridine-N-oxide

To a stirring solution of 4-difluoromethylpyridine (5.00 g, 38.7 mmol) in $CH_2Cl_2$ (77 mL, 0.5 M) at 0° C. was added 77% meta-chloroperbenzoic acid (10.7 g, 46.5 mmol) and the ice bath was removed and stirring continued for 20.5 hr. The reaction mixture was concentrated to dryness and reaction residue purified by flash column chromatography (100:0-95:5 CH$_2$Cl$_2$/MeOH) to afford 4-difluoromethyl-pyridine-N-oxide as a colorless solid (5.62 g, >99%); $^1$H NMR (400 MHz, CDCl$_3$) δ 8.26 (d, J=6.4 Hz, 2H), 7.40 (d, J=6.4 Hz, 2H), 6.63 (t, J=55.7 Hz, 1H).

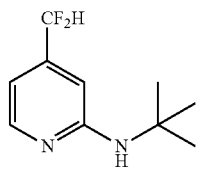

Step 2:
N-tert-butyl-4-(difluoromethyl)pyridin-2-amine

A suspension of 4-difluoromethyl-pyridine-N-oxide (4.95 g, 34.1 mmol), bromo-tris-pyrrolidino-phosphonium hexafluorophosphate (20.7 g, 44.3 mmol), triethylamine (15.6 mL, 111 mmol), and anhydrous tert-butylamine (4.6 mL, 43 mmol) in DCE (100 mL, 0.33 M) was sealed in pressure tube and stirred at 100° C. for 3.5 hr. After cooling to rt, the mixture was diluted with CH$_2$Cl$_2$ and washed with sat. aq. NaHCO$_3$. The organics were dried over MgSO$_4$ and following concentration, the reaction residue was purified by flash column chromatography (100:0-80:20 heptanes/EtOAc) to afford N-tert-butyl-4-(difluoromethyl)pyridin-2-amine as a yellow liquid (4.43 g, 65%); $^1$H NMR (400 MHz, CDCl$_3$) δ 8.15 (d, J=5.2 Hz, 1H), 6.65-6.28 (m, 3H), 4.62 (br s, 1H), 1.44 (s, 9H).

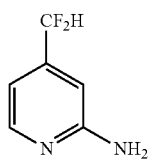

Step 3: 4-(difluoromethyl)pyridin-2-amine

A flask containing N-tert-butyl-4-(difluoromethyl)pyridin-2-amine (4.43 g, 22.1 mmol), triethylsilane (7.28 mL, 44.2 mmol) and trifluoroacetic acid (22.1 mL, 1 M) was fitted with a reflux condenser. The reaction mixture was stirred at 90° C. for 21 hr and then, after cooling to rt, concentrated to dryness and partitioned between CH$_2$Cl$_2$ and sat. aq. NaHCO$_3$. After separation of the phases, the aqueous layer was re-extracted with CH$_2$Cl$_2$ and the combined organics were dried over MgSO$_4$. Concentration afforded 4-(difluoromethyl)pyridin-2-amine as a light brown solid (3.16 g, >99%); $^1$H NMR (400 MHz, CDCl$_3$) δ 8.16 (d, J=5.3 Hz, 1H), 6.74 (d, J=5.3 Hz, 1H), 6.66-6.33 (m, 2H), 4.62 (br s, 2H).

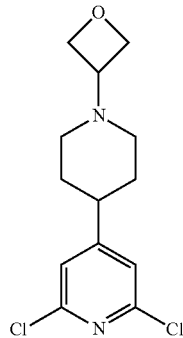 [SMILES: Clc1cc(C2CCN(C3COC3)CC2)cc(Cl)n1]

Step 4: 2,6-dichloro-4-[1-(oxetan-3-yl)-4-piperidyl]pyridine

To a solution of tert-butyl 4-(2,6-dichloro-4-pyridyl)piperidine-1-carboxylate (2.84 g, 8.57 mmol) in CH$_2$Cl$_2$ (17 mL) and at 0° C. was added trifluoroacetic acid (8.4 mL) and allowed to warm to room temperature. After stirring for 1 hr, the solution was concentrated to dryness to afford the TFA salt as a white solid which was re-suspended in anhydrous THF (34 mL) and submitted to the action of triethylamine (6.0 mL, 43 mmol) and 3-oxetanone (0.82 mL, 13 mmol). After stirring for 30 min, sodium triacetoxyborohydride (5.73 g, 25.7 mmol) was added and stirring continued for 2 hr. The reaction mixture was diluted with CH$_2$Cl$_2$ and washed with sat. aq. NaHCO$_3$ and organics dried over MgSO$_4$. Concentration gave sufficiently pure 2,6-dichloro-4-[1-(oxetan-3-yl)-4-piperidyl]pyridine as a beige solid (2.67 g, >99% over 2 steps); $^1$H NMR (400 MHz, CDCl$_3$) δ 7.13 (s, 2H), 4.73-4.63 (m, 4H), 3.60-3.52 (m, 1H), 3.00-2.88 (m, 2H), 2.60-2.48 (m, 1H), 2.05-1.94 (m, 2H), 1.93-1.78 (m, 4H).

Step 5: 6-chloro-N-(4-(difluoromethyl)pyridin-2-yl)-4-(1-(oxetan-3-yl)piperidin-4-yl)pyridin-2-amine A round-bottomed flask was charged with 2,6-dichloro-4-[1-(oxetan-3-yl)-4-piperidyl]pyridine (1.00 g, 3.48 mmol), 4-(difluoromethyl)pyridin-2-amine (502 mg, 3.48 mmol), tris(dibenzylideneacetone)dipalladium(0) (82.2 mg, 2.5 mol %), 4,5-bis(diphenylphosphino)-9,9-dimethylxanthene (125 mg, 6 mol %) and cesium carbonate (1.59 g, 4.87 mmol). The flask was sealed with a septum and purged with nitrogen gas before injecting anhydrous 1,4-dioxane (14 mL, 0.25 M). The reaction mixture was stirred at 80° C. for 22 hr before cooling to rt and filtering through Celite, rinsing with CH$_2$Cl$_2$. After concentration, flash column chromatography (100:0-95:5 CH$_2$Cl$_2$/MeOH) afforded 6-chloro-N-(4-(difluoromethyl)pyridin-2-yl)-4-(1-(oxetan-3-yl)piperidin-4-yl)pyridin-2-amine as a colorless solid (1.06 g, 77%); $^1$H NMR (400 MHz, CDCl$_3$) δ 8.38 (d, J=5.1 Hz, 1H), 7.53 (s, 1H), 7.46 (s, 1H), 7.34 (br s, 1H), 7.00 (d, J=5.1 Hz, 1H), 6.80 (s, 1H), 6.61 (t, J=55.8 Hz, 1H), 4.72-4.60 (m, 4H), 3.57-3.46 (m, 1H), 2.94-2.81 (m, 2H), 2.58-2.41 (m, 1H), 2.00-1.75 (m, 6H); ESI-LRMS m/z [M+1]⁺=395.

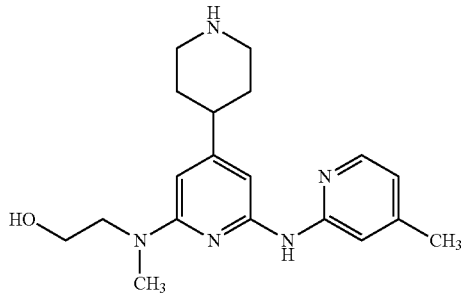 [SMILES: Cc1ccnc(Nc2cc(C3CCNCC3)cc(N(C)CCO)n2)c1]

Preparation of 2-(methyl(6-((4-methylpyridin-2-yl)amino)-4-(piperidin-4-yl)pyridin-2-yl)amino)ethanol

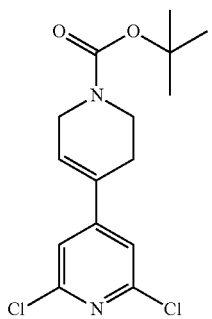 [SMILES: CC(C)(C)OC(=O)N1CC=C(c2cc(Cl)nc(Cl)c2)CC1]

Step 1: tert-butyl 4-(2,6-dichloropyridin-4-yl)-5,6-dihydropyridine-1(2H)-carboxylate To a mixture of 2,6-dichloro-4-iodo-pyridine (1.0 g, 3.7 mmol), tert-butyl 4-(4,4,5,5-tetramethyl-1,3,2-dioxaborolan-2-yl)-5,6-dihydro-2H-pyridine-1-carboxylate (1.4 g; 4.4 mmol), potassium carbonate (1.0 g, 7.3 mmol), and Pd(dppf)Cl₂ DCM (300 mg, 0.37 mmol) in 1,4-dioxane (12.0 mL) and water (3.0 mL) was capped in a large CEM microwave vial, de-gassed with N₂, and heated in an oil-bath at 90° C. for overnight. It was diluted with water (100 mL), extracted with EtOAc (2×100 mL). The combined EtOAc was washed with brine, dried over MgSO₄, filtered, and concentrated onto Celite. It was purified by column chromatography (ISCO0, 40 g column, eluded with 0-15% EtOAc/Heptane to give 670 mg (56%) of the title compound as a light yellow solid. ¹H NMR (400 MHz, CDCl₃) δ 7.21 (s, 2H), 6.32 (s, 1H), 4.12 (d, J=2.7 Hz, 2H), 3.63 (t, J=5.6 Hz, 2H), 2.45 (s, 2H), 1.49 (s, 9H). LC-MS: m/z=330 (M+H⁺).

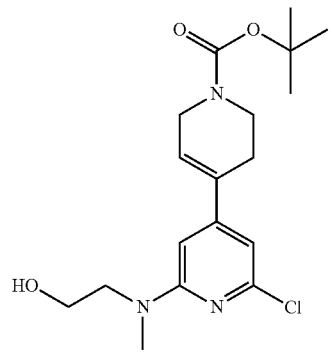 [SMILES: CN(CCO)c1cc(C2=CCN(C(=O)OC(C)(C)C)CC2)cc(Cl)n1]

Step 2: tert-butyl 4-(2-chloro-6-((2-hydroxyethyl)(methyl)amino)pyridin-4-yl)-5,6-dihydropyridine-1(2H)-carboxylate A solution of tert-butyl 4-(2,6-dichloro-4-pyridyl)-5,6-dihydro-2H-pyridine-1-carboxylate (395 mg, 1.20 mmol) and 2-(methylamino)ethanol (3.5 mL, 44 mmol) in a glass vial was heated in oil bath at 100° C. for 4 h. After cooled, it was diluted with water (50 mL), extracted with EtOAc (2×50 mL). The combined EtOAc were dried over Na₂SO₄, filtered, concentrated in vacuo, and dried under high vacuum to give orange syrup. It was carried on without further purification. LC-MS: m/z=367 (M+H⁺).

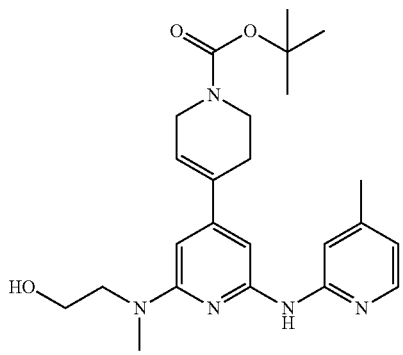 [SMILES: Cc1ccnc(Nc2cc(C3=CCN(C(=O)OC(C)(C)C)CC3)cc(N(C)CCO)n2)c1]

Step 3: tert-butyl 4-(2-((2-hydroxyethyl)(methyl)amino)-6-(4-methylpyridin-2-ylamino)pyridin-4-yl)-5,6-dihydropyridine-1(2H)-carboxylate To a mixture of tert-butyl 4-(2-chloro-6-(2-hydroxyethyl(methyl)amino)-4-pyridyl)-5,6-dihydro-2H-pyridine-1-carboxylate (220 mg, 0.60 mmol), 4-methylpyridin-2-amine (71.13 mg, 0.66 mmol), sodium tert-butoxide (86.2 mg, 0.90 mmol), 2-dicyclohexylphosphino-2',6'-diisopropoxybiphenyl (34.9 mg, 0.075 mmol), and RuPhos palladium(II) phenethylamine chloride (43.6 mg, 0.06 mmol) in 1,4-dioxane (3.0 mL) was capped in a small CEM microwave vial, de-gassed with N₂, and heated in microwave at 120° C. for 15 min. It was concentrated onto Celite, purified by column chromatography (ISCO), 12 g column, eluded with 0-5% MeOH/DCM to give 135 mg (51%) of the title compound as a yellow gum. LC-MS: m/z=440 (M+H$^+$).

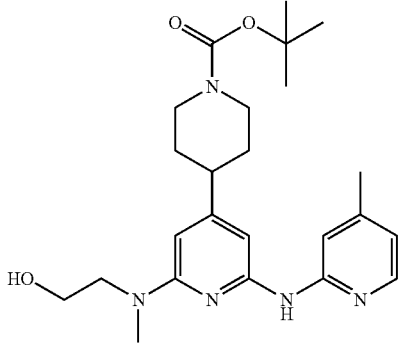 [SMILES: Cc1ccnc(Nc2cc(C3CCN(C(=O)OC(C)(C)C)CC3)cc(N(C)CCO)n2)c1]

Step 4: tert-butyl 4-(2-((2-hydroxyethyl)(methyl)amino)-6-(4-methylpyridin-2-ylamino)pyridin-4-yl)piperidine-1-carboxylate tert-butyl 4-(2-((2-hydroxyethyl)(methyl)amino)-6-(4-methylpyridin-2-yl)-5,6-dihydropyridine-1(2H)-carboxylate (130 mg, 0.29 mmol) was dissolved in MeOH (50 mL). The resulting solution was hydrogenated in H-Cube hydrogenation reactor, with 10% Pd/C cartridge under 40 bar, eluded 1 mL/min at 30° C. for two times. The resulting mixture was again hydrogenated under 50 bar, 1 mL/min at 30° C. for three times. The solution was concentrated in vacuo to give 100 mg (76%) of the title compound as a clear yellow gum. It was carried on as is. $^1$H NMR (400 MHz, CDCl$_3$) δ 8.09 (d, J=5.2 Hz, 1H), 7.35 (s, 1H), 6.96 (s, 1H), 6.65 (d, J=5.2 Hz, 1H), 6.61 (s, 1H), 5.92 (s, 1H), 4.30 (d, J=53.7 Hz, 2H), 3.87 (t, J=5.0 Hz, 2H), 3.75 (t, J=5.0 Hz, 2H), 3.07 (s, 3H), 2.78 (t, J=12.6 Hz, 2H), 2.59-2.51 (m, 1H), 2.31 (s, 3H), 1.82 (d, J=12.7 Hz, 2H), 1.70-1.56 (m, 2H), 1.49 (s, 9H). LC-MS: m/z=442 (M+H$^+$).

Step 5: 2-(methyl(6-(4-methylpyridin-2-ylamino)-4-(piperidin-4-yl)pyridin-2-yl)amino)ethanol To a solution of tert-butyl 4-(2-((2-hydroxyethyl)(methyl)amino)-6-(4-methylpyridin-2-ylamino)pyridin-4-yl)piperidine-1-carboxylate (100 mg, 0.22 mmol) in DCM (1.0 mL) was added hydrogen chloride (4 mol/L) in 1,4-dioxane (3.0 mL, 12 mmol). The resultant was stirred at room temperature for 3 h. It was purified by HPLC to give 37 mg (48%) of the title compound as a light yellow solid. $^1$H NMR (400 MHz, DMSO) δ 9.00 (s, 1H), 8.02 (d, J=5.1 Hz, 1H), 7.95 (s, 1H), 6.64 (d, J=5.1 Hz, 1H), 6.42 (s, 1H), 5.90 (s, 1H), 4.64 (s, 1H), 3.64-3.53 (m, 4H), 3.05-2.95 (m, 5H), 2.58-2.52 (m, 1H), 2.50-2.31 (m, 3H), 2.25 (s, 3H), 1.69-1.58 (m, 2H), 1.55-1.40 (m, 2H). LC-MS: m/z=342 (M+H$^+$).

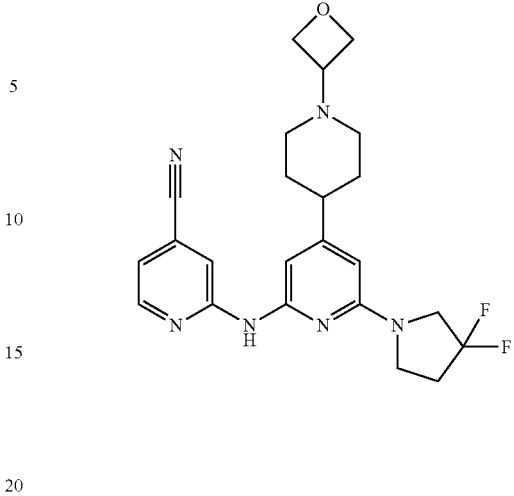

Preparation of 2-((6-(3,3-difluoropyrrolidin-1-yl)-4-(1-(oxetan-3-yl)piperidin-4-yl)pyridin-2-yl)amino)isonicotinonitrile

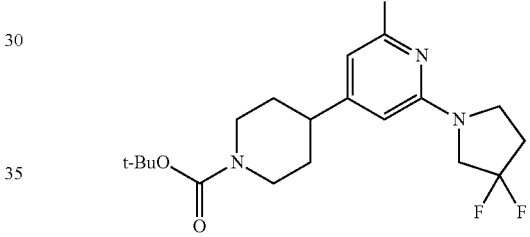

Step 1: tert-butyl 4-(2-chloro-6-(3,3-difluoropyrrolidin-1-yl)pyridin-4-yl)piperidine-1-carboxylate A solution of 3,3-difluoropyridine hydrochloride (533 mg, 3.72 mmol, 3.18 equiv), tert-butyl 4-(2,6-dichloropyridin-4-yl)piperidine-1-carboxylate (1.00 g, 1.17 mmol, 1 equiv), and N,N-diisopropylethylamine (1.23 mL, 7.03 mmol, 6.00 equiv) in N-methylpyrrolidinone (2.3 mL) was heated at 130° C. in the microwave (CEM) for 1.5 h. The reaction mixture was diluted with ethyl acetate (50 mL), and the resulting solution was washed with saturated aqueous ammonium chloride solution (2×20 mL). The aqueous washes were extracted with ethyl acetate (25 mL). The combined organic was washed with water (25 mL), dried over anhydrous sodium sulfate, filtered, and concentrated. Purification by flash column chromatography (4:1 heptane/ethyl acetate) provided product as a clear oil (220 mg, 47% yield). $^1$H NMR (400 MHz, CDCl$_3$): 6.51 (s, 1H), 6.03 (s, 1H), 4.25 (m, 2H), 3.83 (t, J=13.1 Hz, 2H), 3.67 (t, J=7.3 Hz, 2H), 2.77 (m, 2H), 2.42-2.58 (m, 3H), 1.78 (m, 2H), 1.53-1.62 (m, 2H), 1.48 (s, 9H).

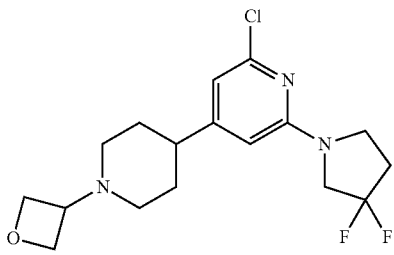 [SMILES: FC1(F)CCN(c2cc(C3CCN(C4COC4)CC3)cc(Cl)n2)C1]

Step 2: 2-chloro-6-(3,3-difluoropyrrolidin-1-yl)-4-(1-(oxetan-3-yl)piperidin-4-yl)pyridine To an ice-cooled solution of tert-butyl 4-(2-chloro-6-(3,3-difluoropyrrolidin-1-yl)pyridin-4-yl)piperidine-1-carboxylate (0.220 g, 0.547 mmol, 1 equiv) in dichloromethane (2 mL) was added trifluoroacetic acid (2 mL). After 2 h, the reaction mixture was concentrated in vacuo (25 mm Hg). The resulting residue was dissolved in dichloromethane (10 mL), and the solution was washed with saturated aqueous sodium bicarbonate solution (5 mL). The organic layer was dried over anhydrous sodium sulfate, filtered, and concentrated. The resulting residue was dissolved in tetrahydrofuran (2 mL). Oxetan-3-one (0.112 mL, 1.10 mmol, 2.00 equiv) and sodium triaetoxyborohydride (366 mg, 1.64 mmol, 3.00 equiv) were sequentially added to the solution at 24° C. After 35 min, the reaction mixture was partitioned between ethyl acetate (10 mL) and saturated aqueous ammonium chloride solution (10 mL). The organic was separated and the aqueous layer was further extracted with ethyl acetate (2×5 mL). The combined organic was dried over anhydrous sodium sulfate, filtered, and concentrated. Purification by flash column chromatography (98:2 dichloromethane/methanol+0.1% ammonium hydroxide) furnished product as a clear oil (166 mg, 85% yield). $^1$H NMR (CDCl$_3$, 400 MHz), δ: 6.54 (s, 1H), 6.07 (s, 1H), 4.67 (t, J=6.3 Hz, 2H), 4.63 (t, J=6.3 Hz, 2H), 3.82 (t, J=13.2 Hz, 2H), 3.66 (t, J=7.2 Hz, 2H), 3.50 (m, 1H), 2.86 (m, 2H), 2.38-2.52 (m, 3H), 1.72-1.94 (m, 6H).

Step 3: 2-((6-(3,3-difluoropyrrolidin-1-yl)-4-(1-(oxetan-3-yl)piperidin-4-yl)pyridin-2-yl)amino)isonicotinonitrile To a 50-mL recovery flask charged with 2-chloro-6-(3,3-difluoropyrrolidin-1-yl)-4-(1-(oxetan-3-yl)piperidin-4-yl)pyridine (216 mg, 0.603 mmol, 1 equiv), 2-amino-4-cyanopyridine (122 mg, 1.03 mmol, 1.70 equiv), cesium carbonate (399 mg, 1.22 mmol, 2.03 equiv) in 1,4-dioxane was added tris(dibenzylideneacetone)dipalladium(0) (28 mg, 0.031 mmol, 0.051 equiv). The reaction flask was fitted with a microreflux condenser, and the reaction mixture was heated at reflux under nitrogen for 13 h. After cooling to room temperature, the reaction mixture was diluted with ethyl acetate (20 mL) and washed with water (10 mL). The organic was separated and the aqueous wash was further extracted with ethyl acetate (2×10 mL). The combined organic was dried over anhydrous sodium sulfate, filtered, and concentrated. Purification by flash column chromatography (3% methanol in dichloromethane+0.1% ammonium hydroxide) provided product as a yellow solid (205 mg, 77% yield). $^1$H NMR (400 MHz, DMSO-d$_6$), δ: 9.72 (s, 1H), 8.46 (s, 1H), 8.41 (d, J=5.0 Hz, 1H), 7.20 (dd, J=5.1, 1.2 Hz, 1H), 6.60 (s, 1H), 6.00 (s, 1H), 4.54 (t, J=6.4 Hz, 2H), 4.44 (t, J=6.0 Hz, 2H), 3.85 (t, J=13.2 Hz, 2H), 3.65 (t, J=7.2 Hz, 2H), 3.40 (m, 1H), 2.80 (m, 2H), 2.56 (m, 2H), 2.39 (m, 1H), 1.84 (m, 2H), 1.61-1.76 (m, 4H). m/z (ESI-pos) M+1=441

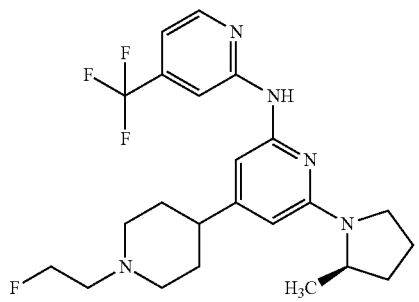 [SMILES: C[C@@H]1CCCN1c1cc(C2CCN(CCF)CC2)cc(Nc2cc(C(F)(F)F)ccn2)n1]

Preparation of (R)-4-(1-(2-fluoroethyl)piperidin-4-yl)-6-(2-methylpyrrolidin-1-yl)-N-(4-(trifluoromethyl) yridine-2-yl) yridine-2-amine To a mixture of 6-[(2R)-2-methylpyrrolidin-1-yl]-4-(4-piperidyl)-N-[4-(trifluoromethyl)-2-pyridyl]yridine-2-amine hydrochloride (90 mg, 0.203 mmol) and DIPEA (0.143 mL, 0.814 mmol, 4.0 equiv) in DMF (1.0 mL) was added 1-bromo-2-fluoroethane (0.022 mL, 0.305 mmol, 1.5 equiv), stirred @ rt o/n. More 1-bromo-2-fluoroethane (0.044 mL, 0.610 mmol, 3 equiv) and DIPEA (0.286 mL, 1.628 mmol, 8 equiv) were added, stirred at rt for another 48 h. It was purified by HPLC to afford 41.2 mg (44.8%) of product as off-white powder. 1H NMR (400 MHz, DMSO) δ 9.69 (s, 1H), 8.81 (s, 1H), 8.41 (d, J=5.1 Hz, 1H), 7.10 (d, J=5.1 Hz, 1H), 6.32 (s, 1H), 5.84 (s, 1H), 4.60 (t, J=4.9 Hz, 1H), 4.48 (t, J=4.9 Hz, 1H), 4.21-4.12 (m, 1H), 3.47 (t, J=8.7 Hz, 1H), 3.28-3.23 (m, 1H), 2.98 (d, J=11.5 Hz, 2H), 2.66 (t, J=4.9 Hz, 1H), 2.59 (t, J=5.0 Hz, 1H), 2.37-2.26 (m, 1H), 2.14-1.90 (m, 5H), 1.76-1.57 (m, 5H), 1.17 (d, J=6.2 Hz, 3H). LC-MS: m/z=452 (M+H$^+$).

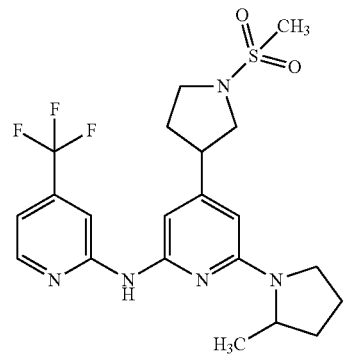 [SMILES: CC1CCCN1c1cc(C2CCN(S(C)(=O)=O)C2)cc(Nc2cc(C(F)(F)F)ccn2)n1]

Preparation of 6-(2-methylpyrrolidin-1-yl)-4-(1-(methylsulfonyl)pyrrolidin-3-yl)-N-(4-(trifluoromethyl)pyridin-2-yl)pyridin-2-amine

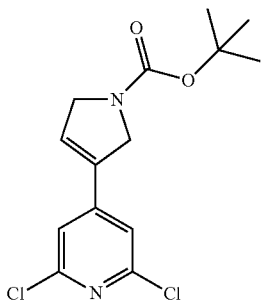 [SMILES: CC(C)(C)OC(=O)N1CC=C(c2cc(Cl)nc(Cl)c2)C1]

Step 1: tert-butyl 3-(2,6-dichloropyridin-4-yl)-2,5-dihydro-1H-pyrrole-1-carboxylate To a mixture of 2,6-dichloro-4-iodo-pyridine (500 mg, 1.826 mmol), tert-butyl 3-(4,4,5,5-tetramethyl-1,3,2-dioxaborolan-2-yl)-2,5-dihydropyrrole-1-carboxylate (646.7 mg, 2.191 mmol, 1.2 equiv.), potassium carbonate (510 mg, 3.651 mmol, 2 equiv.), and PD(dppf)Cl$_2$ DCM (223.6 mg, 0.274 mmol, 0.15 equiv.) in 1,4-dioxane (6 mL) and water (2 mL) was capped in a large CEM vial, de-gassed with N$_2$, heated in oil bath @ 65° C. o/n. It was diluted with water, extracted with EtOAc (2×50 mL), dried over Na$_2$SO$_4$, filtered, concentrated in vacuo. Purification by column chromatography (ISCO), 40 g column, eluded with 0-10% EtOAc/Heptane to afford 304 mg (52.8%) of product as white foam. $^1$H NMR (400 MHz, CDCl$_3$) δ 7.42 (s, 0.5H), 7.22 (s, 0.5H), 7.04 (s, 2H), 3.93 (s, 2H), 2.90 (s, 2H), 1.53 (s, 9H). LC-MS: m/z=316 (M+H$^+$).

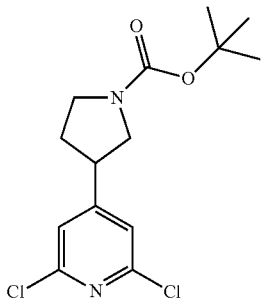 [SMILES: CC(C)(C)OC(=O)N1CCC(c2cc(Cl)nc(Cl)c2)C1]

Step 2: tert-butyl 3-(2,6-dichloropyridin-4-yl)pyrrolidine-1-carboxylate

A mixture of tert-butyl 3-(2,6-dichloro-4-pyridyl)-2,5-dihydropyrrole-1-carboxylate (126 mg, 0.399 mmol) and 5% Rh/C (20 mg) in absolute alcohol (12 mL) was purged with N$_2$, then primed with H$_2$ (balloon)/vacuum (3×), stirred under H$_2$ balloon for o/n. It was purged with N$_2$, filtered through Celite, washed the Celite with MeOH, concentrated in vacuo gave 121 mg (95.4%) of product as clear gum. It was carried on without further purification. LC-MS: m/z=318 (M+H$^+$).

Step 3: 6-(2-methylpyrrolidin-1-yl)-4-(1-(methylsulfonyl)pyrrolidin-3-yl)-N-(4-(trifluoromethyl)pyridin-2-yl)pyridin-2-amine The title compound was prepared by the general procedures as described in Example 4. 1H NMR (400 MHz, DMSO) δ 9.74 (s, 1H), 8.79 (s, 1H), 8.42 (d, J=5.1 Hz, 1H), 7.11 (d, J=5.2 Hz, 1H), 6.38 (s, 1H), 5.91 (s, 1H), 4.22-4.13 (m, 1H), 3.68 (t, J=8.5 Hz, 1H), 3.53-3.42 (m, 2H), 3.38-3.31 (m, 1H), 3.28-3.24 (m, 1H), 3.20-3.12 (m, 1H), 2.96 (s, 3H), 2.31-2.21 (m, 1H), 2.12-1.88 (m, 4H), 1.72-1.65 (m, 1H), 1.18 (d, J=6.2 Hz, 3H). LC-MS: m/z=470 (M+H$^+$).

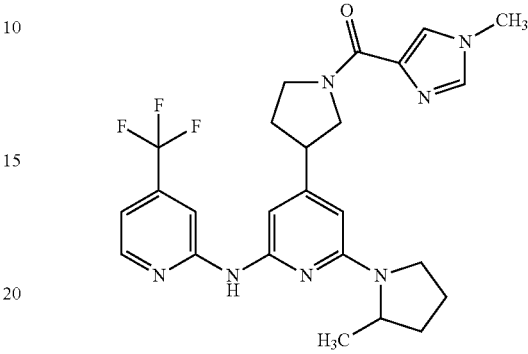

Preparation of (1-methyl-1H-imidazol-4-yl)(3-(2-(2-methylpyrrolidin-1-yl)-6-((4-(trifluoromethyl)pyridin-2-yl)amino)pyridin-4-yl)pyrrolidin-1-yl)methanone To a mixture of 1-methylimidazole-4-carboxylic acid (39.79 mg, 0.315 mmol, 1.5 equiv.), HOBT (57.42 mg, 0.420 mmol, 2.0 equiv.), and 1-(3-dimethylaminopropyl)-3-ethylcarbodiimide hydrochloride (81.46 mg; 0.420 mmol, 2.0 equiv.) in chloroform (3.0 mL) was added 6-[(2R)-2-methylpyrrolidin-1-yl]-4-pyrrolidin-3-yl-N-[4-(trifluoromethyl)-2-pyridyl]pyridin-2-amine hydrochloride (90 mg, 0.210 mmol) followed by DIPEA (0.148 mL, 0.841 mmol, 4.0 equiv.). The resulting mixture was stirred at rt for 2 h. It was diluted with DCM (10 mL), washed with 10% citric acid and 1 N NaHCO$_3$, dried over Na$_2$SO$_4$, filtered, concentrated in vacuo, and purified by HPLC to afford 16.1 mg (15.3%) of product as yellow solid. 1H NMR (400 MHz, DMSO) δ 9.74 (s, 1H), 8.80 (s, 1H), 8.41 (d, J=5.1 Hz, 1H), 7.68-7.60 (m, 2H), 7.10 (d, J=5.1 Hz, 1H), 6.39 (s, 1H), 5.90 (s, 1H), 4.48-4.09 (m, 3H), 3.94-3.73 (m, 2H), 3.69 (d, J=5.2 Hz, 3H), 3.56-3.43 (m, 2H), 3.25-3.18 (m, 1H), 2.31-2.13 (m, 1H), 2.12-1.86 (m, 4H), 1.73-1.63 (m, 1H), 1.17 (d, J=6.0 Hz, 3H). LC-MS: m/z=500 (M+H$^+$).

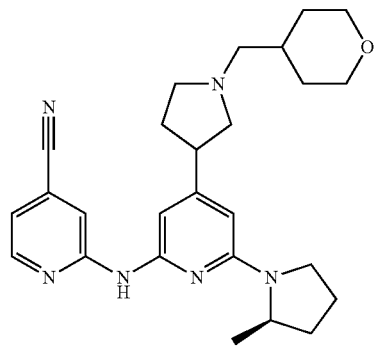 [SMILES: C[C@@H]1CCCN1c1cc(C2CCN(CC3CCOCC3)C2)cc(Nc2cc(C#N)ccn2)n1]

Preparation of 2-((6-((R)-2-methylpyrrolidin-1-yl)-4-(1-((tetrahydro-2H-pyran-4-yl)methyl)pyrrolidin-3-yl)pyridin-2-yl)amino)isonicotinonitrile

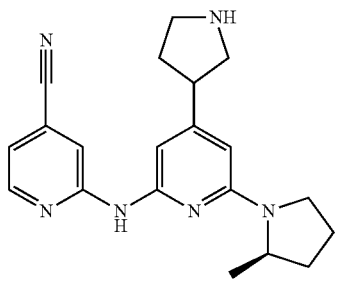 [SMILES: C[C@@H]1CCCN1c1cc(C2CCNC2)cc(Nc2cc(C#N)ccn2)n1]

Step 1: 2-((6-((R)-2-methylpyrrolidin-1-yl)-4-(pyrrolidin-3-yl)pyridin-2-yl)amino)isonicotinonitrile The title compound was prepared by the general procedures as described in the synthesis of [4-(1-Methanesulfonyl-pyrrolidin-3-yl)-6-(2-methyl-pyrrolidin-1-yl)-pyridin-2-yl]-(4-trifluoromethyl-pyridin-2-yl)-amine. LC-MS: m/z=349 (M+H$^+$).

Step 2: Synthesis of 2-((6-((R)-2-methylpyrrolidin-1-yl)-4-(1-((tetrahydro-2H-pyran-4-yl)methyl)pyrrolidin-3-yl)pyridin-2-yl)amino)isonicotinonitrile To a solution of 2-[[6-[(2R)-2-methylpyrrolidin-1-yl]-4-pyrrolidin-3-yl-2-pyridyl]amino]pyridine-4-carbonitrile hydrochloride (160 mg, 0.415 mmol) in methanol (3.0 mL) was added tetrahydropyran-4-carbaldehyde (0.086 mL, 0.831 mmol, 2.0 equiv.). It was heated @ 50° C. overnight. After cooling to room temperature, sodium triacetoxyborohydride (278.2 mg, 1.247 mmol, 3.0 equiv.) was added in portions. After 3 h, more sodium triacetoxyborohydride (278.2 mg, 1.247 mmol, 3.0 equiv.) was added, stirred @ rt for another o/n. It was quenched with 1N NaHCO$_3$, extracted with EtOAc (2×20 mL), dried over Na$_2$SO$_4$, filtered, concentrated in vacuo, and purified by HPLC to afford 15.5 mg (8.3%) of product as yellow gum. LC-MS: m/z=447 (M+H$^+$).

The following examples were prepared according to the methods described in Example 5:

| Structure | $^1$H NMR | MS (m/z) |
|---|---|---|
| 6-chloro-N-(4-(difluoromethyl)pyridin-2-yl)-4-(1-(oxetan-3-yl)piperidin-4-yl)pyridin-2-amine | $^1$H NMR (400 MHz, CDCl$_3$) δ 8.38 (d, J = 5.1 Hz, 1H), 7.53 (s, 1H), 7.46 (s, 1H), 7.34 (br s, 1H), 7.00 (d, J = 5.1 Hz, 1H), 6.80 (s, 1H), 6.61 (t, J = 55.8 Hz, 1H), 4.72-4.60 (m, 4H), 3.57-3.46 (m, 1H), 2.94-2.81 (m, 2H), 2.58-2.41 (m, 1H), 2.00-1.75 (m, 6H); | 395 |
| 2-((6-(3-methoxypyrrolidin-1-yl)-4-(1-(oxetan-3-yl)piperidin-4-yl)pyridin-2-yl)amino)isonicotinonitrile | $^1$H NMR (400 MHz, DMSO) δ 9.71 (br s, 1H), 8.64 (s, 1H), 8.39 (d, J = 5.1 Hz, 1H), 7.17 (d, J = 5.1 Hz, 1H), 6.44 (s, 1H), 5.90 (s, 1H), 4.58-4.49 (m, 2H), 4.49-4.41 (m, 2H), 4.13-4.05 (m, 1H), 3.59-3.40 (m, 5H), 3.29 (s, 3H), 2.84-2.75 (m, 2H), 2.42-2.29 (m, 1H), 2.13-2.05 (m, 2H), 1.88-1.79 (m, 2H), 1.78-1.56 (m, 4H); | 435 |

| Structure | ¹H NMR | MS (m/z) |
|---|---|---|
| 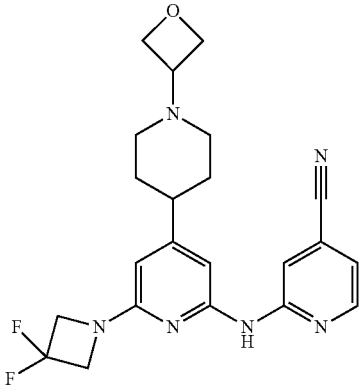 [SMILES: N#Cc1ccnc(Nc2cc(C3CCN(C4COC4)CC3)cc(N3CC(F)(F)C3)n2)c1]<br>2-((6-(3,3-difluoroazetidin-1-yl)-4-(1-(oxetan-3-yl)piperidin-4-yl)pyridin-2-yl)amino)isonicotinonitrile | ¹H NMR (400 MHz, DMSO) δ 9.86 (br s, 1H), 8.42 (d, J = 5.1 Hz, 1H), 8.25 (s, 1H), 7.20 (d, J = 5.1 Hz, 1H), 6.87 (s, 1H), 6.05 (s, 1H), 4.58-4.50 (m, 2H), 4.47-4.33 (m, 6H), 3.45-3.35 (m, 1H), 2.84-2.75 (m, 2H), 2.46-2.36 (m, 1H), 1.89-1.79 (m, 2H), 1.79-1.59 (m, 4H); | 427 |
| 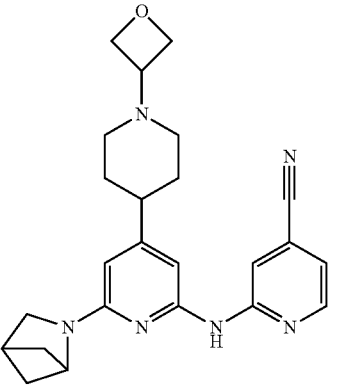 [SMILES: N#Cc1ccnc(Nc2cc(C3CCN(C4COC4)CC3)cc(N3CC4CC3C4)n2)c1]<br>2-((6-(2-azabicyclo[2.1.1]hexan-2-yl)-4-(1-(oxetan-3-yl)piperidin-4-yl)pyridin-2-yl)amino)isonicotinonitrile | ¹H NMR (400 MHz, DMSO) δ 9.70 (br s, 1H), 8.44 (s, 1H), 8.40 (d, J = 5.1 Hz, 1H), 7.17 (dd, J = 5.1, 1.3 Hz, 1H), 6.54 (s, 1H), 6.08 (s, 1H), 4.69-4.61 (m, 1H), 4.59-4.49 (m, 2H), 4.48-4.39 (m, 2H), 3.43-3.36 (m, 3H), 3.00-2.91 (m, 1H), 2.82-2.75 (m, 2H), 2.41-2.29 (m, 1H), 1.98-1.92 (m, 2H), 1.86-1.78 (m, 2H), 1.78-1.59 (m, 4H), 1.37-1.32 (m, 2H); | 417 |
| 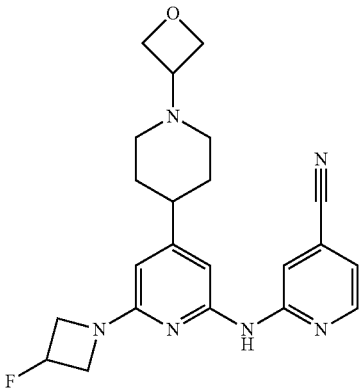 [SMILES: N#Cc1ccnc(Nc2cc(C3CCN(C4COC4)CC3)cc(N3CC(F)C3)n2)c1]<br>2-((6-(3-fluoroazetidin-1-yl)-4-(1-(oxetan-3-yl)piperidin-4-yl)pyridin-2-yl)amino)isonicotinonitrile | ¹H NMR (400 MHz, DMSO) δ 9.81 (br s, 1H), 8.44-8.36 (m, 2H), 7.19 (d, J = 5.1 Hz, 1H), 6.72 (s, 1H), 5.92 (s, 1H), 5.65-5.40 (m, 1H), 4.58-4.48 (m, 2H), 4.48-4.41 (m, 2H), 4.36-4.20 (m, 2H), 4.07-3.93 (m, 2H), 3.45-3.36 (m, 1H), 2.81-2.76 (m, 2H), 2.42-2.32 (m, 1H), 1.88-1.77 (m, 2H), 1.77-1.58 (m, 4H); | 409 |

| Structure | ¹H NMR | MS (m/z) |
|---|---|---|
| 2-((6-(3-azabicyclo[3.1.0]hexan-3-yl)-4-(1-(oxetan-3-yl)piperidin-4-yl)pyridin-2-yl)amino)isonicotinonitrile | ¹H NMR (400 MHz, DMSO) δ 9.70 (br s, 1H), 8.58 (s, 1H), 8.39 (d, J = 5.1 Hz, 1H), 7.18 (dd, J = 5.1, 1.2 Hz, 1H), 6.45 (s, 1H), 5.88 (s, 1H), 4.58-4.49 (m, 2H), 4.47-4.40 (m, 2H), 3.69-3.60 (m, 2H), 3.45-3.35 (m, 3H), 2.82-2.73 (m, 2H), 2.41-2.27 (m, 1H), 1.89-1.77 (m, 2H), 1.77-1.57 (m, 6H), 0.78-0.69 (m, 1H), 0.27-0.19 (m, 1H); | 417 |
| 2-((4-(1-(oxetan-3-yl)piperidin-4-yl)-6-(6-oxa-2-azaspiro[3.4]octan-2-yl)pyridin-2-yl)amino)isonicotinonitrile | ¹H NMR (400 MHz, DMSO) δ 9.77 (br s, 1H), 8.46 (s, 1H), 8.40 (d, J = 5.0 Hz, 1H), 7.18 (dd, J = 5.0, 1.3 Hz, 1H), 6.63 (s, 1H), 5.84 (s, 1H), 4.58-4.49 (m, 2H), 4.49-4.39 (m, 2H), 3.92 (s, 4H), 3.83 (s, 2H), 3.79-3.70 (m, 2H), 3.46-3.36 (m, 1H), 2.83-2.73 (m, 2H), 2.43-2.29 (m, 1H), 2.25-2.11 (m, 2H), 1.90-1.79 (m, 2H), 1.77-1.69 (m, 2H), 1.68-1.52 (m, 2H); | 447 |
| 2-((6-(5,5-difluoro-2-azaspiro[3.3]heptan-2-yl)-4-(1-(oxetan-3-yl)piperidin-4-yl)pyridin-2-yl)amino)isonicotinonitrile | ¹H NMR (400 MHz, DMSO) δ 9.80 (br s, 1H), 8.44-8.38 (m, 2H), 7.19 (dd, J = 5.0, 1.5 Hz, 1H), 6.69 (s, 1H), 5.91 (s, 1H), 4.59-4.49 (m, 2H), 4.49-4.38 (m, 2H), 4.21-4.11 (m, 2H), 3.93-3.83 (m, 2H), 3.44-3.34 (m, 1H), 2.83-2.74 (m, 2H), 2.59-2.51 (m, 2H), 2.43-2.28 (m, 1H), 2.14-2.02 (m, 2H), 1.88-1.78 (m, 2H), 1.78-1.69 (m, 2H), 1.69-1.52 (m, 2H); | 467 |

| Structure | ¹H NMR | MS (m/z) |
|---|---|---|
| 2-((4-(1-(oxetan-3-yl)piperidin-4-yl)-6-(2-oxa-7-azaspiro[4.4]nonan-7-yl)pyridin-2-yl)amino)isonicotinonitrile | ¹H NMR (400 MHz, DMSO) δ 9.71 (br s, 1H), 8.64 (s, 1H), 8.39 (d, J = 5.0 Hz, 1H), 7.17 (dd, J = 5.0, 1.4 Hz, 1H), 6.45 (s, 1H), 5.89 (s, 1H), 4.58-4.51 (m, 2H), 4.47-4.40 (m, 2H), 3.86-3.79 (m, 2H), 3.60 (s, 2H), 3.55-3.36 (m, 5H), 2.84-2.72 (m, 2H), 2.40-2.30 (m, 1H), 2.03-1.96 (m, 2H), 1.95-1.88 (m, 2H), 1.88-1.78 (m, 2H), 1.76-1.57 (m, 4H); | 461 |
| 2-((6-(3-methoxyazetidin-1-yl)-4-(1-(oxetan-3-yl)piperidin-4-yl)pyridin-2-yl)amino)isonicotinonitrile | ¹H NMR (400 MHz, DMSO) δ 9.77 (br s, 1H), 8.45 (s, 1H), 8.40 (d, J = 5.1 Hz, 1H), 7.18 (d, J = 5.1, 1H), 6.64 (s, 1H), 5.86 (s, 1H), 4.58-4.50 (m, 2H), 4.47-4.39 (m, 2H), 4.35 (m, 1H), 4.20-4.09 (m, 2H), 3.80-3.66 (m, 2H), 3.44-3.35 (m, 1H), 3.26 (s, 3H), 2.82-2.72 (m, 2H), 2.41-2.32 (m, 1H), 1.88-1.76 (m, 2H), 1.76-1.57 (m, 4H); | 421 |
| 2-((6-(6,6-difluoro-3-azabicyclo[3.2.0]heptan-3-yl)-4-(1-(oxetan-3-yl)piperidin-4-yl)pyridin-2-yl)amino)isonicotinonitrile | ¹H NMR (400 MHz, DMSO) δ 9.77 (br s, 1H), 8.47 (s, 1H), 8.41 (d, J = 5.0 Hz, 1H), 7.19 (dd, J = 5.0, 1.4 Hz, 1H), 6.61 (s, 1H), 6.11 (s, 1H), 4.58-4.51 (m, 2H), 4.47-4.41 (m, 2H), 4.06-3.99 (m, 1H), 3.76-3.71 (m, 1H), 3.50-3.37 (m, 2H), 3.27-3.17 (m, 2H), 2.98-2.89 (m, 2H), 2.82-2.75 (m, 3H), 2.43-2.26 (m, 2H), 1.89-1.79 (m, 2H), 1.79-1.60 (m, 5H); | 467 |

| Structure | ¹H NMR | MS (m/z) |
|---|---|---|
| 2-((4-(1-(oxetan-3-yl)piperidin-4-yl)-6-(2-oxa-6-azaspiro[3.3]heptan-6-yl)pyridin-2-yl)amino)isonicotinonitrile | ¹H NMR (400 MHz, DMSO) δ 9.77 (br s, 1H), 8.43 (s, 1H), 8.41 (d, J = 5.0 Hz, 1H), 7.19 (dd, J = 5.0, 1.4 Hz, 1H), 6.65 (s, 1H), 5.84 (s, 1H), 4.74 (s, 4H), 4.59-4.48 (m, 2H), 4.48-4.39 (m, 2H), 4.11 (s, 4H), 3.42-3.35 (m, 1H), 2.83-2.73 (m, 2H), 2.41-2.32 (m, 1H), 1.90-1.75 (m, 2H), 1.75-1.56 (m, 4H); | 433 |
| 2-((6-(2-azabicyclo[3.1.0]hexan-2-yl)-4-(1-(oxetan-3-yl)piperidin-4-yl)pyridin-2-yl)amino)isonicotinonitrile | ¹H NMR (400 MHz, DMSO) δ 9.75 (br s, 1H), 8.66 (s, 1H), 8.39 (d, J = 5.0 Hz, 1H), 7.17 (dd, J = 5.0, 1.4 Hz, 1H), 6.49 (s, 1H), 6.14 (s, 1H), 4.59-4.50 (m, 2H), 4.48-4.37 (m, 2H), 3.81-3.68 (m, 1H), 3.54-3.44 (m, 1H), 3.44-3.35 (m, 1H), 3.03-2.93 (m, 1H), 2.85-2.73 (m, 2H), 2.43-2.31 (m, 1H), 2.30-2.17 (m, 1H), 2.10-2.00 (m, 1H), 1.90-1.79 (m, 2H), 1.79-1.60 (m, 5H), 0.80-0.67 (m, 1H), 0.52-0.44 (m, 1H); | 417 |
| 2-((6-(azetidin-1-yl)-4-(1-(oxetan-3-yl)piperidin-4-yl)pyridin-2-yl)amino)isonicotinonitrile | ¹H NMR (400 MHz, DMSO) δ 9.76 (br s, 1H), 8.51 (s, 1H), 8.40 (d, J = 5.1 Hz, 1H), 7.18 (d, J = 5.1 Hz, 1H), 6.59 (s, 1H), 5.80 (s, 1H), 4.57-4.49 (m, 2H), 4.49-4.40 (m, 2H), 4.00-3.92 (m, 4H), 3.43-3.35 (m, 1H), 2.82-2.73 (m, 2H), 2.40-2.27 (m, 3H), 1.88-1.78 (m, 2H), 1.77-1.68 (m, 2H), 1.68-1.51 (m, 2H). | 391 |

| Structure | ¹H NMR | MS (m/z) |
|---|---|---|
| 2-((6-chloro-4-(1-(oxetan-3-yl)piperidin-4-yl)pyridin-2-yl)amino)isonicotinonitrile | ¹H NMR (400 MHz, DMSO) δ 10.38 (br s, 1H), 8.49 (d, J = 5.1 Hz, 1H), 7.94 (s, 1H), 7.63 (s, 1H), 7.30 (d, J = 5.1 Hz, 1H), 6.98 (s, 1H), 4.57-4.51 (m, 2H), 4.47-4.41 (m, 2H), 3.46-3.38 (m, 1H), 2.85-2.77 (m, 2H), 1.90-1.75 (m, 4H), 1.70-1.58 (m, 2H). | 370 |
| 2-((4-(1-(oxetan-3-yl)piperidin-4-yl)-6-(2-oxopyrrolidin-1-yl)pyridin-2-yl)amino)isonicotinonitrile | ¹H NMR (400 MHz, DMSO) δ 10.04 (br s, 1H), 8.45 (d, J = 5.0 Hz, 1H), 8.37 (s, 1H), 7.80 (s, 1H), 7.26 (dd, J = 5.0, 1.3 Hz, 1H), 7.04 (s, 1H), 4.58-4.50 (m, 2H), 4.48-4.42 (m, 2H), 4.09-4.01 (m, 2H), 3.45-3.37 (m, 1H), 3.20-3.12 (m, 1H), 2.84-2.74 (m, 2H), 2.62-2.55 (m, 2H), 2.13-2.00 (m, 2H), 1.92-1.83 (m, 2H), 1.82-1.70 (m, 2H), 1.69-1.59 (m, 2H); | 419 |
| (R)-N-(4-(difluoromethyl)pyridin-2-yl)-6-(2-methylpyrrolidin-1-yl)-4-(1-(oxetan-3-yl)piperidin-4-yl)pyridin-2-amine | ¹H NMR (400 MHz, DMSO) δ 9.45 (br s, 1H), 8.57 (s, 1H), 8.30 (d, J = 5.1 Hz, 1H), 7.15-6.82 (m, 2H), 6.34 (s, 1H), 5.81 (s, 1H), 4.58-4.50 (m, 2H), 4.49-4.40 (m, 2H), 4.24-4.12 (m, 1H), 3.52-3.44 (m, 1H), 3.44-3.35 (m, 1H), 2.82-2.74 (m, 2H), 2.38-2.27 (m, 1H), 2.11-1.56 (m, 11H), 1.18 (d, J = 6.2 Hz, 3H); | 444 |

| Structure | ¹H NMR | MS (m/z) |
|---|---|---|
| 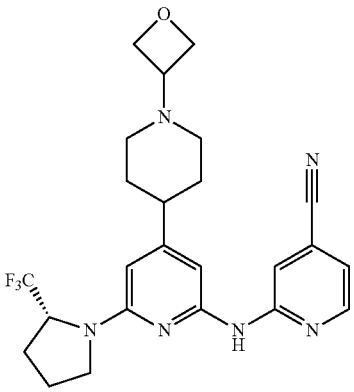 [SMILES: N#Cc1ccnc(Nc2cc(C3CCN(C4COC4)CC3)cc(N3CCC[C@@H]3C(F)(F)F)n2)c1]<br>(R)-2-((4-(1-(oxetan-3-yl)piperidin-4-yl)-6-(2-(trifluoromethyl)pyrrolidin-1-yl)pyridin-2-yl)amino)isonicotinonitrile | ¹H NMR (400 MHz, DMSO) δ 9.80 (br s, 1H), 8.48 (s, 1H), 8.41 (d, J = 5.1 Hz, 1H), 7.20 (dd, J = 5.1, 1.3 Hz, 1H), 6.57 (s, 1H), 6.14 (s, 1H), 5.06-4.93 (m, 1H), 4.58-4.48 (m, 2H), 4.47-4.40 (m, 2H), 3.70-3.59 (m, 1H), 3.43-3.32 (m, 2H), 2.84-2.74 (m, 2H), 2.45-2.34 (m, 1H), 2.16-2.00 (m, 4H), 1.89-1.81 (m, 2H), 1.79-1.61 (m, 4H); | 473 |
| 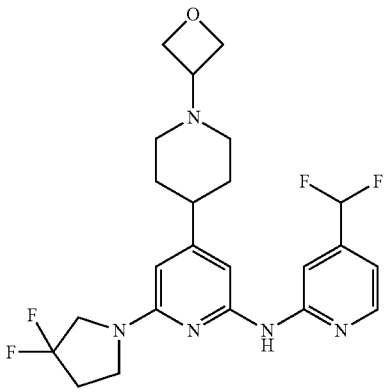 [SMILES: FC(F)c1ccnc(Nc2cc(C3CCN(C4COC4)CC3)cc(N3CCC(F)(F)C3)n2)c1]<br>N-(4-(difluoromethyl)pyridin-2-yl)-6-(3,3-difluoropyrrolidin-1-yl)-4-(1-(oxetan-3-yl)piperidin-4-yl)pyridin-2-amine | ¹H NMR (400 MHz, DMSO) δ 9.59 (br s, 1H), 8.44 (s, 1H), 8.32 (d, J = 5.1 Hz, 1H), 7.20-6.87 (m, 2H), 6.53 (s, 1H), 5.95 (s, 1H), 4.58-4.50 (m, 2H), 4.48-4.40 (m, 2H), 3.90-3.78 (m, 2H), 3.66-3.60 (m, 2H), 3.44-3.36 (m, 1H), 2.83-2.75 (m, 2H), 2.61-2.51 (m, 2H), 2.43-2.30 (m, 1H), 1.88-1.78 (m, 2H), 1.77-1.60 (m, 4H); | 466 |
| 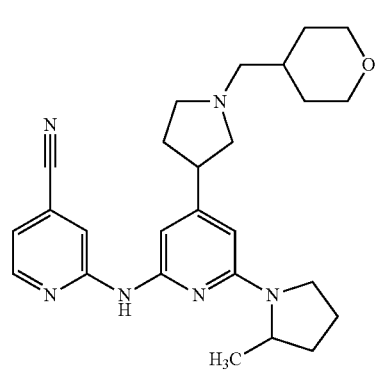 [SMILES: CC1CCCN1c1cc(C2CCN(CC3CCOCC3)C2)cc(Nc2cc(C#N)ccn2)n1]<br>2-((6-(2-methylpyrrolidin-1-yl)-4-(1-((tetrahydro-2H-pyran-4-yl)methyl)pyrrolidin-3-yl)pyridin-2-yl)amino)isonicotinonitrile | | 447 |

| Structure | ¹H NMR | MS (m/z) |
|---|---|---|
| 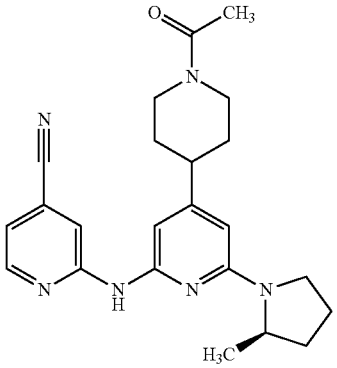 [SMILES: CC(=O)N1CCC(c2cc(Nc3cc(C#N)ccn3)nc(N3CCC[C@H]3C)c2)CC1]<br>(R)-2-((4-(1-acetylpiperidin-4-yl)-6-(2-methylpyrrolidin-1-yl)pyridin-2-yl)amino)isonicotinonitrile | 1H NMR (400 MHz, DMSO) δ 9.74 (s, 1H), 8.77 (s, 1H), 8.39 (d, J = 5.0 Hz, 1H), 7.19 (d, J = 5.0 Hz, 1H), 6.31 (s, 1H), 5.86 (s, 1H), 4.51 (d, J = 13.5 Hz, 1H), 4.24-4.15 (m, 1H), 3.91 (d, J = 13.9 Hz, 1H), 3.47 (t, J = 8.1 Hz, 1H), 3.28-3.21 (m, 1H), 3.11 (t, J = 12.7 Hz, 1H), 2.65-2.52 (m, 2H), 2.12-1.92 (m, 6H), 1.81-1.66 (m, 3H), 1.61-1.49 (m, 1H), 1.47-1.34 (m, 1H), 1.23 (d, J = 6.2 Hz, 3H). | 405 |
| 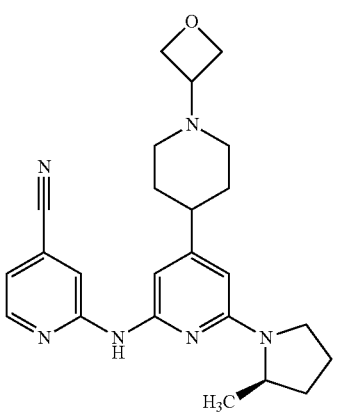 [SMILES: C[C@@H]1CCCN1c1cc(C2CCN(C3COC3)CC2)cc(Nc2cc(C#N)ccn2)n1]<br>(R)-2-((6-(2-methylpyrrolidin-1-yl)-4-(1-(oxetan-3-yl)piperidin-4-yl)pyridin-2-yl)amino)isonicotinonitrile | 1H NMR (400 MHz, DMSO) δ 9.75 (s, 1H), 8.77 (s, 1H), 8.40 (d, J = 5.0 Hz, 1H), 7.19 (d, J = 5.0 Hz, 1H), 6.33 (s, 1H), 5.86 (s, 1H), 4.54 (t, J = 6.4 Hz, 2H), 4.44 (t, J = 6.1 Hz, 2H), 4.24-4.14 (m, 1H), 3.48 (t, J = 8.2 Hz, 1H), 3.43-3.35 (m, 1H), 3.28-3.20 (m, 1H), 2.78 (d, J = 10.8 Hz, 2H), 2.39-2.30 (m, 1H), 2.13-1.92 (m, 3H), 1.82 (t, J = 11.0 Hz, 2H), 1.77-1.58 (m, 5H), 1.24 (d, J = 6.2 Hz, 3H). | 419 |
| 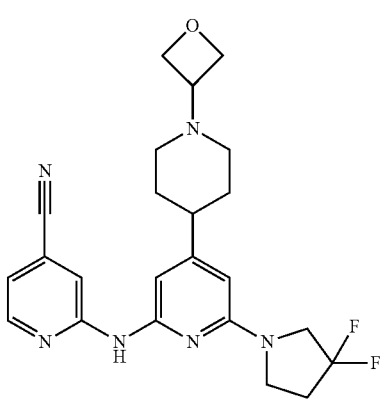 [SMILES: N#Cc1ccnc(Nc2cc(C3CCN(C4COC4)CC3)cc(N3CCC(F)(F)C3)n2)c1]<br>2-((6-(3,3-difluoropyrrolidin-1-yl)-4-(1-(oxetan-3-yl)piperidin-4-yl)pyridin-2-yl)amino)isonicotinonitrile | 1H NMR (400 MHz, DMSO) δ 9.83 (s, 1H), 8.47 (s, 1H), 8.42 (d, J = 5.0 Hz, 1H), 7.21 (d, J = 5.1 Hz, 1H), 6.60 (s, 1H), 6.00 (s, 1H), 4.54 (t, J = 6.4 Hz, 2H), 4.44 (t, J = 6.1 Hz, 2H), 3.86 (t, J = 13.2 Hz, 2H), 3.65 (t, J = 7.2 Hz, 2H), 3.46-3.38 (m, 1H), 2.79 (d, J = 10.9 Hz, 2H), 2.63-2.51 (m, 2H), 2.43-2.31 (m, 1H), 1.83 (t, J = 10.9 Hz, 2H), 1.78-1.59 (m, 4H). | 441 |

| Structure | ¹H NMR | MS (m/z) |
|---|---|---|
| 6-(2-methylpyrrolidin-1-yl)-4-(1-(methylsulfonyl)pyrrolidin-3-yl)-N-(4-(trifluoromethyl)pyridin-2-yl)pyridin-2-amine | 1H NMR (400 MHz, DMSO) δ 9.74 (s, 1H), 8.79 (s, 1H), 8.42 (d, J = 5.1 Hz, 1H), 7.11 (d, J = 5.2 Hz, 1H), 6.38 (s, 1H), 5.91 (s, 1H), 4.22-4.13 (m, 1H), 3.68 (t, J = 8.5 Hz, 1H), 3.53-3.42 (m, 2H), 3.38-3.31 (m, 1H), 3.28-3.24 (m, 1H), 3.20-3.12 (m, 1H), 2.96 (s, 3H), 2.31-2.21 (m, 1H), 2.12-1.88 (m, 4H), 1.72-1.65 (m, 1H), 1.18 (d, J = 6.2 Hz, 3H). | 470 |
| (1-methyl-1H-imidazol-4-yl)(3-(2-(2-methylpyrrolidin-1-yl)-6-((4-(trifluoromethyl)pyridin-2-yl)amino)pyridin-4-yl)pyrrolidin-1-yl)methanone | 1H NMR (400 MHz, DMSO) δ 9.74 (s, 1H), 8.80 (s, 1H), 8.41 (d, J = 5.1 Hz, 1H), 7.68-7.60 (m, 2H), 7.10 (d, J = 5.1 Hz, 1H), 6.39 (s, 1H), 5.90 (s, 1H), 4.48-4.09 (m, 3H), 3.94-3.73 (m, 2H), 3.69 (d, J = 5.2 Hz, 3H), 3.56-3.43 (m, 2H), 3.25-3.18 (m, 1H), 2.31-2.13 (m, 1H), 2.12-1.86 (m, 4H), 1.73-1.63 (m, 1H), 1.17 (d, J = 6.0 Hz, 3H). | 500 |
| (R)-N-(4-methylpyridin-2-yl)-6-(2-methylpyrrolidin-1-yl)-4-(1-(oxetan-3-yl)piperidin-4-yl)pyridin-2-amine | 1H NMR (400 MHz, DMSO) δ 9.00 (s, 1H), 8.14 (s, 1H), 8.02 (d, J = 5.1 Hz, 1H), 6.65 (d, J = 5.1 Hz, 1H), 6.37 (s, 1H), 5.76 (s, 1H), 4.54 (t, J = 6.5 Hz, 2H), 4.44 (t, J = 6.1 Hz, 2H), 4.23-4.15 (m, 1H), 3.47 (t, J = 8.5 Hz, 1H), 3.42-3.34 (m, 1H), 3.27-3.21 (m, 1H), 2.78 (d, J = 11.1 Hz, 2H), 2.37-2.27 (m, 1H), 2.25 (s, 3H), 2.10-1.91 (m, 3H), 1.83 (t, J = 10.7 Hz, 2H), 1.76-1.59 (m, 5H), 1.22 (d, J = 6.2 Hz, 3H). | 408 |

| Structure | ¹H NMR | MS (m/z) |
|---|---|---|
| (R)-N-(4-methylpyridin-2-yl)-6-(2-methylpyrrolidin-1-yl)-4-(1-(methylsulfonyl)piperidin-4-yl)pyridin-2-amine | 1H NMR (400 MHz, DMSO) δ 9.02 (s, 1H), 8.14 (s, 1H), 8.02 (d, J = 5.1 Hz, 1H), 6.65 (d, J = 5.1 Hz, 1H), 6.39 (s, 1H), 5.77 (s, 1H), 4.24-4.15 (m, 1H), 3.66 (d, J = 11.8 Hz, 2H), 3.47 (t, J = 8.5 Hz, 1H), 3.28-3.22 (m, 1H), 2.88 (s, 3H), 2.79 (t, J = 11.2 Hz, 2H), 2.48-2.41 (m, 1H), 2.25 (s, 3H), 2.09-1.91 (m, 3H), 1.85 (d, J = 12.1 Hz, 2H), 1.71-1.58 (m, 3H), 1.22 (d, J = 6.2 Hz, 3H). | 430 |
| (R)-4-(1-(2-fluoroethyl)piperidin-4-yl)-6-(2-methylpyrrolidin-1-yl)-N-(4-(trifluoromethyl)pyridin-2-yl)pyridin-2-amine | 1H NMR (400 MHz, DMSO) δ 9.69 (s, 1H), 8.81 (s, 1H), 8.41 (d, J = 5.1 Hz, 1H), 7.10 (d, J = 5.1 Hz, 1H), 6.32 (s, 1H), 5.84 (s, 1H), 4.60 (t, J = 4.9 Hz, 1H), 4.48 (t, J = 4.9 Hz, 1H), 4.21-4.12 (m, 1H), 3.47 (t, J = 8.7 Hz, 1H), 3.28-3.23 (m, 1H), 2.98 (d, J = 11.5 Hz, 2H), 2.66 (t, J = 4.9 Hz, 1H), 2.59 (t, J = 5.0 Hz, 1H), 2.37-2.26 (m, 1H), 2.14-1.90 (m, 5H), 1.76-1.57 (m, 5H), 1.17 (d, J = 6.2 Hz, 3H). | 452 |
| (R)-6-(2-methylpyrrolidin-1-yl)-4-(1-(methylsulfonyl)piperidin-4-yl)-N-(4-(trifluoromethyl)pyridin-2-yl)pyridin-2-amine | 1H NMR (400 MHz, DMSO) δ 9.72 (s, 1H), 8.80 (s, 1H), 8.42 (d, J = 5.1 Hz, 1H), 7.10 (d, J = 5.1 Hz, 1H), 6.33 (s, 1H), 5.86 (s, 1H), 4.22-4.13 (m, 1H), 3.67 (d, J = 11.8 Hz, 2H), 3.48 (t, J = 8.8 Hz, 1H), 3.29-3.23 (m, 1H), 2.89 (s, 3H), 2.80 (t, J = 11.2 Hz, 2H), 2.10-1.91 (m, 3H), 1.86 (d, J = 12.2 Hz, 2H), 1.73-1.59 (m, 3H), 1.17 (d, J = 6.2 Hz, 3H). | 484 |
| 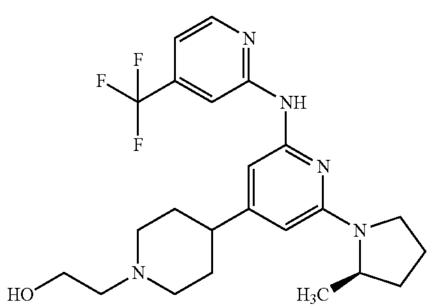 [SMILES: C[C@@H]1CCCN1c1cc(C2CCN(CCO)CC2)cc(Nc2cc(C(F)(F)F)ccn2)n1] | 1H NMR (400 MHz, DMSO) δ 9.70 (s, 1H), 8.81 (s, 1H), 8.42 (t, J = 4.8 Hz, 1H), 7.10 (dd, J = 5.1, 1.6 Hz, 1H), 6.31 (s, 1H), 5.83 (s, 1H), 4.39 (s, 1H), 4.20-4.12 (m, 1H), 3.52 (t, J = 6.3 Hz, 2H), 3.50-3.44 (m, 1H), 3.30-3.21 (m, 1H), 3.03-2.95 (m, 2H), 2.45 (t, J = 6.3 Hz, 2H), 2.39-2.28 (m, 1H), 2.14-1.90 (m, 5H), 1.75-1.59 (m, 5H), 1.17 (d, J = 6.3 Hz, 3H). | 450 |

| Structure | ¹H NMR | MS (m/z) |
|---|---|---|
| (R)-2-(4-(2-(2-methylpyrrolidin-1-yl)-6-((4-(trifluoromethyl)pyridin-2-yl)amino)pyridin-4-yl)piperidin-1-yl)ethanol | | |
| 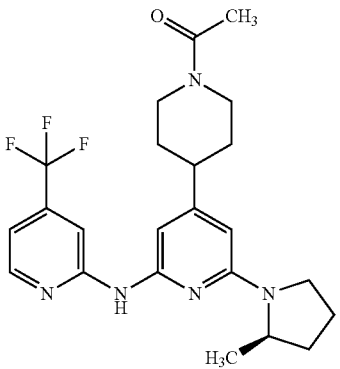 [SMILES: CC(=O)N1CCC(c2cc(Nc3cc(C(F)(F)F)ccn3)nc(N3CCC[C@H]3C)c2)CC1]<br>(R)-1-(4-(2-(2-methylpyrrolidin-1-yl)-6-((4-(trifluoromethyl)pyridin-2-yl)amino)pyridin-4-yl)piperidin-1-yl)ethanone | 1H NMR (400 MHz, DMSO) δ 9.69 (s, 1H), 8.80 (s, 1H), 8.41 (d, J = 5.1 Hz, 1H), 7.10 (d, J = 5.1 Hz, 1H), 6.30 (s, 1H), 5.85 (s, 1H), 4.51 (d, J = 13.5 Hz, 1H), 4.21-4.11 (m, 1H), 3.91 (d, J = 13.6 Hz, 1H), 3.51-3.43 (m, 1H), 3.25 (d, J = 8.8 Hz, 1H), 3.11 (t, J = 12.6 Hz, 1H), 2.65-2.52 (m, 2H), 2.12-1.91 (m, 6H), 1.82-1.62 (m, 3H), 1.62-1.48 (m, 1H), 1.49-1.34 (m, 1H), 1.17 (d, J = 6.2 Hz, 3H). | 448 |
| 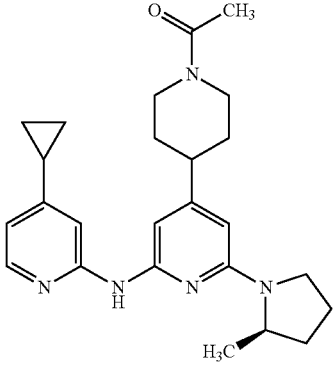 [SMILES: CC(=O)N1CCC(c2cc(Nc3cc(C4CC4)ccn3)nc(N3CCC[C@H]3C)c2)CC1]<br>(R)-1-(4-(2((4-cyclopropylpyridin-2-yl)amino)-6-(2-methylpyrrolidin-1-yl)pyridin-4-yl)piperidin-1-yl)ethanone | 1H NMR (400 MHz, DMSO) δ 8.93 (s, 1H), 7.97 (d, J = 5.3 Hz, 1H), 7.96 (s, 1H), 6.52 (d, J = 5.2 Hz, 1H), 6.37 (s, 1H), 5.76 (s, 1H), 4.51 (d, J = 12.9 Hz, 1H), 4.22-4.11 (m, 1H), 3.90 (d, J = 13.4 Hz, 1H), 3.48 (t, J = 8.1 Hz, 1H), 3.10 (t, J = 12.4 Hz, 1H), 2.63-2.52 (m, 2H), 2.07-2.00 (m, 5H), 1.98-1.90 (m, 1H), 1.87-1.62 (m, 4H), 1.61-1.47 (m, 1H), 1.47-1.33 (m, 1H), 1.20 (d, J = 6.2 Hz, 3H), 1.02 (dd, J = 8.2, 2.3 Hz, 2H), 0.74 (dd, J = 4.8, 1.7 Hz, 2H). | 420 |
| 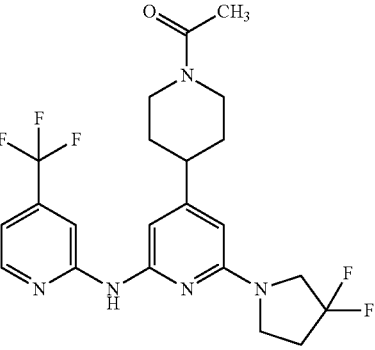<br>1-(4-(2-(3,3-difluoropyrrolidin-1-yl)-6-((4-(trifluoromethyl)pyridin-2-yl)amino)pyridin-4-yl)piperidin-1-yl)ethanone | 1H NMR (400 MHz, DMSO) δ 9.82 (s, 1H), 8.67 (s, 1H), 8.43 (d, J = 5.1 Hz, 1H), 7.13 (d, J = 5.2 Hz, 1H), 6.50 (s, 1H), 5.98 (s, 1H), 4.52 (d, J = 13.2 Hz, 1H), 3.91 (d, J = 13.5 Hz, 1H), 3.83 (t, J = 13.3 Hz, 2H), 3.63 (t, J = 7.2 Hz, 2H), 3.12 (t, J = 12.2 Hz, 1H), 2.69-2.53 (m, 3H), 2.03 (s, 3H), 1.77 (t, J = 13.8 Hz, 2H), 1.64-1.51 (m, 1H), 1.50-1.33 (m, 2H). | 470 |

| Structure | ¹H NMR | MS (m/z) |
|---|---|---|
| 2-(methyl(6-((4-methylpyridin-2-yl)amino)-4-(piperidin-4-yl)pyridin-2-yl)amino) ethanol | ¹H NMR (400 MHz, DMSO) δ 9.00 (s, 1H), 8.02 (d, J = 5.1 Hz, 1H), 7.95 (s, 1H), 6.64 (d, J = 5.1 Hz, 1H), 6.42 (s, 1H), 5.90 (s, 1H), 4.64 (s, 1H), 3.64-3.53 (m, 4H), 3.05-2.95 (m, 5H), 2.58-2.52 (m, 1H), 2.50-2.31 (m, 3H), 2.25 (s, 3H), 1.69-1.58 (m, 2H), 1.55-1.40 (m, 2H). | 342 |

Example 6

Method F

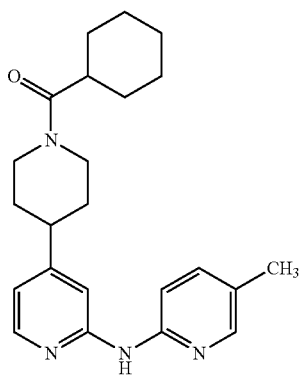 [SMILES: Cc1ccc(Nc2cc(C3CCN(C(=O)C4CCCCC4)CC3)ccn2)nc1]

Preparation of Cyclohexyl(4-(2-((5-methylpyridin-2-yl)amino)pyridin-4-yl)piperidin-1-yl)methanone

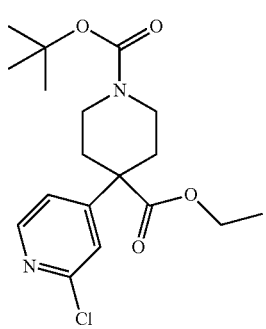 [SMILES: CCOC(=O)C1(c2ccnc(Cl)c2)CCN(C(=O)OC(C)(C)C)CC1]

Step 1: 1-tert-butyl 4-ethyl 4-(2-chloropyridin-4-yl)piperidine-1,4-dicarboxylate A solution of piperidine-1,4-dicarboxylic acid 1-tert-butylester 4-ethyl ester (200 g, 0.78 mol, 1 equiv.) in dry tetrahydrofuran (350 mL) was added a 1M solution of sodium bis(trimethylsilyl)amide (1010 mL, 1.01 mol, 1.3 equiv.) dropwise at 0° C. under nitrogen atmosphere. The reaction mixture was stirred for 1.5 h at 0° C. and added to a solution of 2-chloro-4-iodopyridine (199.2 g, 0.83 mol) in dry tetrahydrofuran (350 mL) at 0° C. under nitrogen atmosphere. The reaction mixture was kept at 0° C. for 3 hours, and was monitored by TLC (ethyl acetate/petroleum ether; 1/5). A solution of ammonium chloride (34.8 g) in water (260 mL) was added cautiously. The formed two layers were separated in a separation funnel. The organic layer was extracted, dried over anhydrous sodium sulfate and concentrated. The resulting dark oil was purified by flash chromatography on silica gel to obtain the oil 1-tert-butyl 4-ethyl 4-(2-chloropyridin-4-yl)piperidine-1,4-dicarboxylate (90 g, 32% yield).

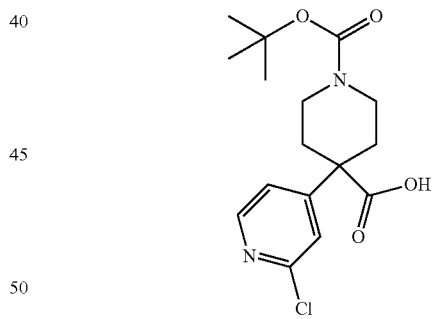

Step 2: 1-(tert-butoxycarbonyl)-4-(2-chloropyridin-4-yl)piperidine-4-carboxylic acid To a mixture of the compound 1-tert-butyl 4-ethyl 4-(2-chloropyridin-4-yl)piperidine-1,4-dicarboxylate (50 g, 0.14 mols, 1 equiv.) in ethanol (75 mL) was added 500 mL of a 10% solution of NaOH. The mixture was refluxed for 2 h. The reaction was monitored by TLC (ethyl acetate/petroleum ether; 1/5), cooled, concentrated to a half of the primary volume and extracted with methyltertiarybutyl ether (3×150 mL). The aqueous layer was acidified with 3M hydrochloric acid to pH=4 and extracted with dichloromethane (2×350 mL). The combined organic layers were dried over anhydrous sodium sulfate. The organic was concentrated to give crude product 1-(tert-butoxycarbonyl)-4-(2-chloropyridin-4-yl)piperidine-4-carboxylic acid (42 g, 91% crude). The crude was used as is in Step C.

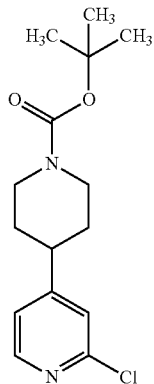

Step 3: tert-butyl 4-(2-chloropyridin-4-yl)piperidine-1-carboxylate

The pure compound 1-(tert-butoxycarbonyl)-4-(2-chloropyridin-4-yl)piperidine-4-carboxylic acid (42 g, 0.12 mols, 1 equiv.) from Step B was dissolved in toluene (250 mL) and heated at 110° for 4 hours. The reaction was monitored by TLC (ethyl acetate/petroleum ether; 1/5). Once complete, the mixture was concentrated and purified by flash chromatography using silica gel (ethyl acetate/petroleum ether; 1/20) to give tert-butyl 4-(2-chloropyridin-4-yl)piperidine-1-carboxylate (31 g, 87%)

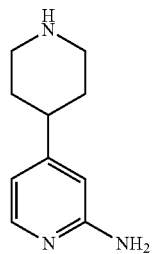 [SMILES: Nc1cc(C2CCNCC2)ccn1]

Step 4: 4-(piperidin-4-yl)pyridin-2-amine

To a stirred solution of tert-butyl 4-(2-chloropyridin-4-yl)piperidine-1-carboxylate (24 g, 0.08 mol, 1 equiv) in ammonia (250 mL) was added copper(I) oxide (5 g, 0.03 mols, 0.4 equiv.) and stirred 10 h at 200° C. under 2.2 MPa of ammonia. The reaction was monitored by LC-MS to completion. The mixture was cooled, extracted with dichloromethane (5×250 mL), dried over $Na_2SO_4$, then concentrated to obtain compound 4-(piperidin-4-yl)pyridin-2-amine (8.5 g, 36%).

Step 5: tert-butyl 4-(2-aminopyridin-4-yl)piperidine-1-carboxylate

To a solution of compound 4-(piperidin-4-yl)pyridin-2-amine (8.5 g, 0.05 mols, 1 equiv.) in tetrahydrofuran (100 mL) was added triethylamine (5 g, 0.05 mols, 1 equiv.)) and di-tert-butyl dicarbonate (5.3 g, 0.025 mols, 0.5 equiv.)). The mixture was stirred at r.t. for 1 h The reaction was monitored to completion by TLC (dichloromethane/methanol; 10/1), concentrated and purified by flash chromatography using silica gel (ethyl acetate/dichloromethane; 10/1) to obtained tert-butyl 4-(2-aminopyridin-4-yl)piperidine-1-carboxylate (5.2 g, 38% yield).

Step 6: cyclohexyl(4-(2-((5-methylpyridin-2-yl)amino)pyridin-4-yl)piperidin-1-yl)methanone To a 20 ml screw cap vial was charged 2-bromo-5-methylpyridine (50 mg, 0.3 mmols, 1 equiv.), (tert-butyl 4-(2-aminopyridin-4-yl)piperidine-1-carboxylate (113 mg, 0.4 mmols, 1.4 equiv.), sodium tert-butoxide (40.3 mg, 0.40 mMols, 1.4 equiv.), 4,5-bis(diphenylphosphino)-9,9-dimethylxanthene (25.7 mg, 0.045 mmols, 0.15 equiv.) and tris(dibenzylideneacetone)dipalladium(0 (26.8 mg, 0.03 mmols, 0.1 equiv.). The contents were dissolved in 5 ml of anhydrous dioxane, capped, vortexed for 10 seconds and shaken at 80° C. for 18 h. The crude was filtered, concentrated and dissolved in ethyl acetate (10 ml), washed with water (once), brine (once) and dried over sodium sulfate. The organic was concentrated, dissolved in dichloromethane (10 ml) and hydrogen chloride gas was bubbled through for 30 seconds and capped. The reaction was shaken until complete (45 mins) and concentrated. To a solution of the crude in anhydrous dimethylformamide (3 ml) was added cyclohexanecarboxylic acid (44.7 mg, 0.36 mmols, 1.2 equiv.), triethylamine (91 mg, 0.9 mmols, 3 equiv.) and finally O-Benzotriazole-N,N,N',N'-tetramethyl-uronium-hexafluoro-phosphate (167 mg, 0.42 mmols, 1.4 equiv.). The vial was capped and shaken at 45° C. for 18 h. The mixture was concentrated, dissolved in ethyl acetate (10 ml) and washed with 1N sodium hydroxide (once), water (once), brine (once), dried over sodium sulfate and concentrated. The crude was evaporated to dryness, dissolved into dimethylformamide (1 ml) and purified by reverse phase HPLC (basic conditions) to give cyclohexyl(4-(2-((5-methylpyridin-2-yl)amino)pyridin-4-yl)piperidin-1-yl)methanone (47.4 mg, 42% yield). 1H NMR (400 MHz, DMSO-d6) δ 9.43 (d, J=3.2 Hz, 1H), 8.10-8.03 (m, 2H), 7.57 (d, J=5.8 Hz, 2H), 6.75-6.72 (m, 3H), 4.65-3.69 (m, 3H), 3.07-2.58 (m, 5H), 1.93-1.24 (m, 11H).

The following examples were prepared according to the method described in this Example:

| Structure | $^1$H NMR | MS (m/z) |
|---|---|---|
| cyclohexyl(4-(2-((5-methylpyridin-2-yl)amino)pyridin-4-yl)piperidin-1-yl)methanone | 1H NMR (400 MHz, DMSO-d6) δ 9.43 (d, J = 3.2 Hz, 1H), 8.10-8.03 (m, 2H), 7.57 (d, J = 5.8 Hz, 2H), 6.75-6.72 (m, 3H), 4.65-3.69 (m, 3H), 3.07-2.58 (m, 5H), 1.93-1.24 (m, 11H). | 379 |
| (S)-piperidin-2-yl(4-(2-(pyridin-2-yl-amino)pyridin-4-yl)piperidin-1-yl)methanone | 1H NMR (400 MHz, DMSO-d6) δ 9.53 (d, J = 10.4 Hz, 1H), 8.27-8.05 (m, 2H), 7.76 (d, J = 8.6 Hz, 1H), 7.68-7.53 (m, 2H), 6.90-6.71 (m, 2H), 4.60-3.74 (m, 3H), 3.11-2.64 (m, 4H), 1.93-1.24 (m, 11H). | 366 |
| (S)-(4-(2-((4-methylpyridin-2-yl)amino)pyridin-4-yl)piperidin-1-yl)(piperidin-2-yl)methanone | 1H NMR (400 MHz, DMSO-d6) δ 9.43 (d, J = 3.2 Hz, 1H), 8.14-8.04 (m, 2H), 7.57 (d, J = 5.8 Hz, 2H), 6.8-6.75 (m, 3H), 4.65-3.69 (m, 3H), 3.07-2.58 (m, 5H), 1.93-1.24 (m, 11H). | 380 |
| 4-(1-(oxetan-3-yl)piperidin-4-yl)-N-(4- | 1H NMR (400 MHz, DMSO) δ 10.08 (s, 1H), 8.48 (d, J = 5.1 Hz, 1H), 8.27 (s, 1H), 8.18 (d, J = 5.2 Hz, 1H), 7.49 (s, 1H), 7.16 (d, J = 5.2 Hz, 1H), 6.87 (d, J = 5.2 Hz, 1H), 4.55 (t, J = 6.4 Hz, 2H), 4.45 (t, J = 6.1 Hz, 2H), 3.45-3.37 (m, 1H), 2.81 (d, J = 11.0 Hz, 2H), 2.48-2.44 (m, 1H), 1.87 (t, J = 11.3 Hz, 2H), 1 78 (d, J = 11.9 Hz, 2H), 1.70-1.58 (m, 2H). | 379 |

| Structure | ¹H NMR | MS (m/z) |
|---|---|---|

(trifluoromethyl)pyridin-2-yl)pyridin-2-amine

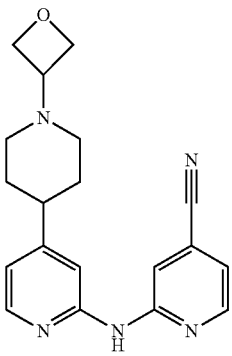 [SMILES: N#Cc1ccnc(Nc2cc(C3CCN(C4COC4)CC3)ccn2)c1]

2-((4-(1-(oxetan-3-yl)piperidin-4-yl)
pyridin-2-yl)amino)isonicotinonitrile

1H NMR (400 MHz, DMSO) δ 10.09 (s, 1H), 8.45 (d, J = 5.1 Hz, 1H), 8.31 (s, 1H), 8.19 (d, J = 5.2 Hz, 1H), 7.41 (s, 1H), 7.25 (d, J = 5.1 Hz, 1H), 6.89 (d, J = 5.2 Hz, 1H), 4.55 (t, J = 6.5 Hz, 2H), 4.45 (t, J = 6.1 Hz, 2H), 3.45-3.36 (m, 1H), 2.80 (d, J = 11.1 Hz, 2H), 2.49-2.43 (m, 1H), 1.86 (t, J = 11.2 Hz, 2H), 1.78 (d, J = 12.1 Hz, 2H), 1.63 (dt, J = 12.2, 9.3 Hz, 2H).

336

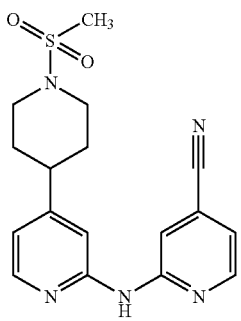 [SMILES: CS(=O)(=O)N1CCC(c2ccnc(Nc3cc(C#N)ccn3)c2)CC1]

2-((4-(1-(methylsulfonyl)piperidin-4-yl)
pyridin-2-yl)amino)isonicotinonitrile

1H NMR (400 MHz, DMSO) δ 10.11 (s, 1H), 8.46 (d, J = 5.1 Hz, 1H), 8.31 (s, 1H), 8.22 (d, J = 5.2 Hz, 1H), 7.43 (s, 1H), 7.25 (d, J = 5.1 Hz, 1H), 6.92 (d, J = 5.3 Hz, 1H), 3.68 (d, J = 11.8 Hz, 2H), 2.90 (s, 3H), 2.83 (t, J = 11.4 Hz, 2H), 2.64 (t, J = 12.1 Hz, 1H), 1.90 (d, J = 12.5 Hz, 2H), 1.65 (qd, J = 12.5, 3.8 Hz, 2H).

358

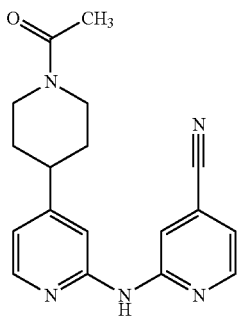 [SMILES: CC(=O)N1CCC(c2ccnc(Nc3cc(C#N)ccn3)c2)CC1]

2-((4-(1-acetylpiperidin-4-yl)pyridin-2-
yl)amino)isonicotinonitrile

1H NMR (400 MHz, DMSO) δ 10.10 (s, 1H), 8.45 (d, J = 5.1 Hz, 1H), 8.31 (s, 1H), 8.20 (d, J = 5.2 Hz, 1H), 7.40 (s, 1H), 7.25 (d, J = 5.1 Hz, 1H), 6.89 (d, J = 5.3 Hz, 1H), 4.53 (d, J = 12.7 Hz, 1H), 3.92 (d, J = 13.3 Hz, 1H), 3.14 (t, J = 12.5 Hz, 1H), 2.76 (t, J = 12.0 Hz, 1H), 2.60 (t, J = 12.2 Hz, 1H), 2.03 (s, 3H), 1.81 (t, J = 13.2 Hz, 2H), 1.55 (dt, J = 12.7, 8.6 Hz, 1H), 1.41 (dt, J = 12.3, 8.3 Hz, 1H).

322

Example 7

Method G

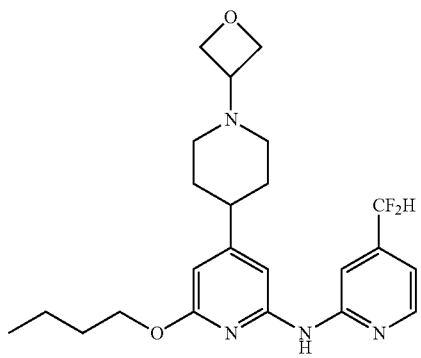 [SMILES: CCCCOc1cc(C2CCN(C3COC3)CC2)cc(Nc2cc(C(F)F)ccn2)n1]

Preparation of 6-butoxy-N-[4-(difluoromethyl)-2-pyridyl]-4-[1-(oxetan-3-yl)-4-piperidyl]pyridin-2-amine General procedure for Beller etherification with aliphatic alcohols:

A vial was charged with the 2-chloropyridine (1.0 equiv), palladium(II) acetate (5 mol %), 5-di(1-adamantylphosphino)-1-(1,3,5-triphenyl-1H-pyrazol-4-yl)-1H-pyrazole (10 mol %), and cesium carbonate (1.5 equiv) and purged under nitrogen before the addition of anhydrous degassed aliphatic alcohol (3 equiv or excess) and degassed toluene (0.25 M). The mixture was stirred at 110° C. overnight and then diluted with $CH_2Cl_2$, filtered through Celite, rinsing with $CH_2Cl_2$. The organics were dried over $MgSO_4$ and concentrated to dryness. The reaction residue thus obtained was purified by RPLC to afford the target compound.

6-butoxy-N-[4-(difluoromethyl)-2-pyridyl]-4-[1-(oxetan-3-yl)-4-piperidyl]pyridin-2-amine Reaction of n-butanol (3 equiv) with 6-chloro-N-(4-(difluoromethyl)pyridin-2-yl)-4-(1-(oxetan-3-yl)piperidin-4-yl)pyridin-2-amine (50.0 mg, 0.127 mmol) following general Beller etherification procedure afforded the target compound as a colorless solid (17.0 mg, 31%); $^1$H NMR (400 MHz, DMSO) δ 9.77 (s, 1H), 8.35 (d, J=5.1 Hz, 1H), 8.22 (s, 1H), 7.19-6.86 (m, 3H), 6.18 (s, 1H), 4.57-4.51 (m, 2H), 4.48-4.42 (m, 2H), 4.25 (t, J=6.8 Hz, 2H), 3.45-3.36 (m, 1H), 2.83-2.75 (m, 2H), 2.46-2.37 (m, 1H), 1.90-1.79 (m, 2H), 1.78-1.55 (m, 6H), 1.49-1.38 (m, 2H), 0.93 (t, J=7.4 Hz, 3H); ESI-LRMS m/z $[M+1]^+$=433.

The following examples were prepared according to the method described in this Example:

| Structure | $^1$H NMR | MS (m/z) |
|---|---|---|
| 6-butoxy-N-[4-(difluoromethyl)-2-pyridyl]-4-[1-(oxetan-3-yl)-4-piperidyl]pyridin-2-amine | $^1$H NMR (400 MHz, DMSO) δ 9.77 (s, 1H), 8.35 (d, J = 5.1 Hz, 1H), 8.22 (s, 1H), 7.19-6.86 (m, 3H), 6.18 (s, 1H), 4.57-4.51 (m, 2H), 4.48-4.42 (m, 2H), 4.25 (t, J = 6.8 Hz, 2H), 3.45-3.36 (m, 1H), 2.83-2.75 (m, 2H), 2.46-2.37 (m, 1H), 1.90-1.79 (m, 2H), 1.78-1.55 (m, 6H), 1.49-1.38 (m, 2H), 0.93 (t, J = 7.4 Hz, 3H) | 433 |
| 2-[[4-(1-acetyl-4-piperidyl)-6-isopropoxy-2-pyridyl]amino]pyridine-4-carbonitrile | $^1$H NMR (400 MHz, DMSO) δ 9.95 (s, 1H), 8.44 (d, J = 5.1 Hz, 1H), 8.30 (s, 1H), 7.24 (d, J = 5.0 Hz, 1H), 6.88 (s, 1H), 6.19 (s, 1H), 5.24-5.11 (m, 1H), 4.57-4.44 (m, 1H), 3.95-3.83 (m, 1H), 3.16-3.05 (m, 1H), 2.73-2.64 (m, 1H), 2.63-2.56 (m, 1H), 2.02 (s, 3H), 1.85-1.70 (m, 2H), 1.60-1.47 (m, 1H), 1.36 (m, 1H), 1.35 (d, J = 6.0 Hz, 6H) | 380 |

| Structure | ¹H NMR | MS (m/z) |
|---|---|---|
| 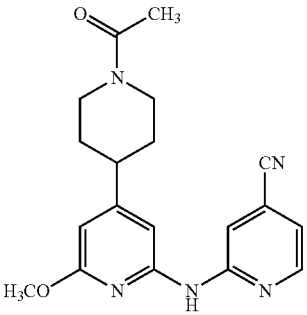 [SMILES: COc1cc(C2CCN(C(C)=O)CC2)cc(Nc2cc(C#N)ccn2)n1]<br>2-[[4-(1-acetyl-4-piperidyl)-6-methoxy-2-pyridyl]amino]pyridine-4-carbonitrile | ¹H NMR (400 MHz, DMSO) δ 9.98 (s, 1H), 8.44 (d, J = 4.9 Hz, 1H), 8.28 (s, 1H), 7.24 (dd, J = 5.1, 1.4 Hz, 1H), 6.98 (s, 1H), 6.28 (s, 1H), 4.58-4.45 (m, 1H), 3.89 (m, 1H), 3.88 (s, 3H), 3.17-3.06 (m, 1H), 2.77-2.63 (m, 1H), 2.63-2.52 (m, 1H), 2.02 (s, 3H), 1.84-1.73 (m, 2H), 1.61-1.32 (m, 2H) | 352 |

Example 8

Method H

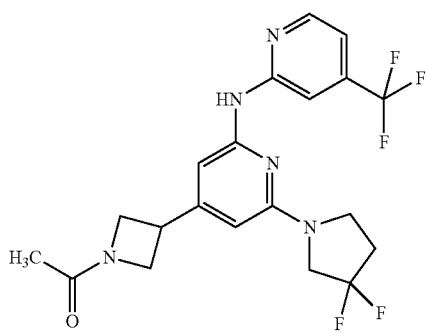 [SMILES: CC(=O)N1CC(c2cc(Nc3cc(C(F)(F)F)ccn3)nc(N3CCC(F)(F)C3)c2)C1]

Preparation of 1-(3-(2-(3,3-difluoropyrrolidin-1-yl)-6-((4-(trifluoromethyl)pyridin-2-yl)amino)pyridin-4-yl)azetidin-1-yl)ethanone

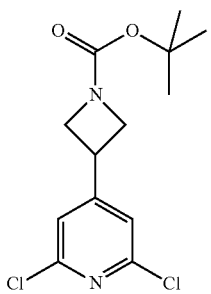 [SMILES: CC(C)(C)OC(=O)N1CC(c2cc(Cl)nc(Cl)c2)C1]

Step 1: tert-butyl 3-(2,6-dichloropyridin-4-yl)azetidine-1-carboxylate

To a suspension of zinc (3.56 g, 3.0 equiv., 53.1 mmol) in DMA (8.3 mL, 88.5 mmol) was added 1,2-dibromoethane (0.37 mL, 0.24 equiv., 4.25 mmol), followed by TMS chloride (0.55 mL, 0.24 equiv., 4.25 mmol). After the reaction ceased down, a solution of 1-boc-3-(iodo)azetidine (11.3 g, 2.2 equiv., 39.0 mmol) in DMA (6.6 mL, 70.8 mmol) was added dropwise. After 30 min at 25° C. and then 2 h at 50° C., LCMS showed no m/z 228 peak. The mixture was transferred dropwise into a suspension of 2,6-dichloro-4-iodopyridine (5.00 g, 17.7 mmol), [1,1'-bis(diphenylphosphino)ferrocene]palladium(ii) dichloride dichloromethane adduct (738 mg, 0.050 equiv., 0.885 mmol) and cuprous iodide (337 mg, 0.10 equiv., 1.77 mmol) in DMA (16.5 mL, 177 mmol). DMA (16.5 mL, 177 mmol)) was used to rinse the flask. The whole reaction mixture was kept at 80° C. in oil-bath for 4 h. DMA was removed at 60° C. under vacuum, and the crude was purified via silica gel chromatography (0-50% EtOAc/Heptanes) to yield 1.73 g (54% based on the conversion) of the title compound. ¹H NMR (400 MHz, CDCl₃) δ (delta) 7.23 (s, 2H), 4.35 (t, J=8.7 Hz, 2H), 3.92 (dd, J=8.7, 5.6 Hz, 2H), 3.73-3.61 (m, 1H), 1.47 (s, 9H). ¹³C NMR (101 MHz, CDCl₃) δ (delta) 157.03, 156.08, 151.09, 121.24, 80.24, 55.31, 32.48, 28.32. LCMS: m/z 303 (M+H).

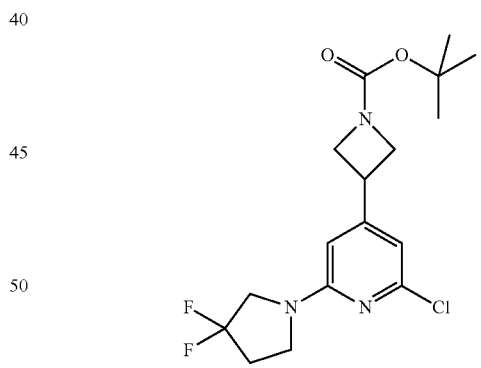

Step 2: tert-butyl 3-(2-chloro-6-(3,3-difluoropyrrolidin-1-yl)pyridin-4-yl)azetidine-1-carboxylate To a suspension of tert-butyl 3-(2,6-dichloro-4-pyridyl) azetidine-1-carboxylate (1-a, 472 mg, 1.557 mmol), 3,3-difluoropyrrolidine hydrochloride (1.12 g, 5.0 equiv., 7.784 mmol) in NMP (3.0 mL, 31 mmol) in a microwave vial was added DIPEA (1.90 mL, 7.0 equiv., 10.90 mmol)), and the reaction was maintained at 140° C. for 30 min and then at 150° C. for 30 min in the microwave machine. LCMS showed more than 95% conversion. The crude was used without further treatment. LCMS: m/z 374 (M+H).

Step 3: tert-butyl 3-(2-(3,3-difluoropyrrolidin-1-yl)-6-((4-(trifluoromethyl)pyridin-2-yl)amino)pyridin-4-yl)azetidine-1-carboxylate

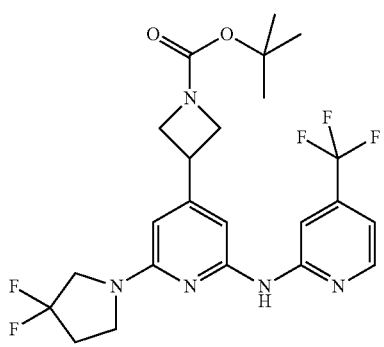 [SMILES: CC(C)(C)OC(=O)N1CC(c2cc(Nc3cc(C(F)(F)F)ccn3)nc(N3CCC(F)(F)C3)c2)C1]

To a solution of tert-butyl 3-[2-chloro-6-(3,3-difluoropyrrolidin-1-yl)-4-pyridyl]azetidine-1-carboxylate (1-b, 582 mg, 1.557 mmol), Pd2(dba)3 (147 mg, 0.10 equiv., 0.1557 mmol), XantPhos (186 mg, 0.20 equiv., 0.3114 mmol), 2-amino-4-(trifluoromethyl)pyridine (765 mg, 3.0 equiv., 4.671 mmol) in 1,4-dioxane (5.3 mL, 62.28 mmol) was added cesium carbonate (2.03 g, 4.0 equiv., 6.228 mmol), and the reaction was kept at 150° C. for 60 min. The crude was purified by silica gel chromatography (0-60% EtOAc/Heptane) to yield 917 mg yellow powder (contaminated by 2-amino-4-(trifluoromethyl)pyridine). $^1$H NMR (400 MHz, CDCl$_3$) δ (delta) 8.57 (s, 1H), 8.36 (d, J=5.1 Hz, 1H), 7.04 (d, J=5.2 Hz, 1H), 6.29 (s, 1H), 5.87 (s, 1H), 4.30 (t, J=8.6 Hz, 2H), 4.02-3.93 (m, 2H), 3.87 (t, J=13.1 Hz, 2H), 3.74 (t, J=7.2 Hz, 2H), 3.67-3.54 (m, 1H), 2.60-2.43 (m, 2H), 1.47 (s, 9H). LCMS: m/z 500 (M+H).

Step 4: 4-(azetidin-3-yl)-6-(3,3-difluoropyrrolidin-1-yl)-N-(4-(trifluoromethyl)pyridin-2-yl)pyridin-2-amine

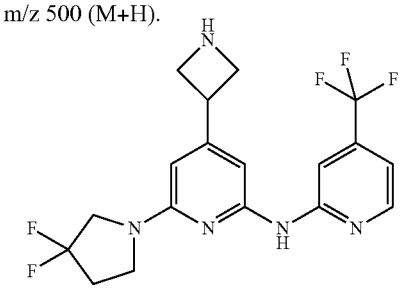

To a solution of tert-butyl 3-[2-(3,3-difluoropyrrolidin-1-yl)-6-[[4-(trifluoromethyl)-2-pyridyl]amino]-4-pyridyl]azetidine-1-carboxylate (1-c, 918 mg, 1.562 mmol) in dioxane (6.0 ml, 70.30 mmol) was added hydrogen chloride (4.0 mol/l) in dioxane (16.0 mL, 40 equiv., 62.49 mmol), and the reaction was kept at 25° C. for 4 h. The reaction was neutralized by NaHCO$_3$ to pH 9, and the aqueous layer was extracted by EtOAc. After evaporation of the organic layer, the crude was used without further purification. LCMS: m/z 400 (M+H).

Step 5: 1-(3-(2-(3,3-difluoropyrrolidin-1-yl)-6-((4-(trifluoromethyl)pyridin-2-yl)amino)pyridin-4-yl)azetidin-1-yl)ethanone To a solution of 4-(azetidin-3-yl)-6-(3,3-difluoropyrrolidin-1-yl)-N-[4-(trifluoromethyl)-2-pyridyl]pyridin-2-amine (1-d, 180 mg, 0.4507 mmol) and DMAP (5.6 mg, 0.1 equiv., 0.04507 mmol) in dichloromethane (2 mL, 31.0 mmol) and N-ethyldiisopropylamine (0.47 mL, 6.0 equiv., 2.704 mmol) was added acetic anhydride (0.22 mL, 5.0 equiv., 2.253 mmol), and the brown solution was stirred at 25° C. for 2 h. DCM was removed, and the crude was submitted for HPLC purification to yield 9.5 mg (4.8%) off-white powder. $^1$H NMR (400 MHz, DMSO) δ (delta) 9.99-9.83 (s, 1H), 8.74-8.62 (s, 1H), 8.48-8.40 (d, J=5.1 Hz, 1H), 7.21-7.11 (d, J=5.2 Hz, 1H), 6.66-6.55 (s, 1H), 6.15-5.96 (s, 1H), 4.53-4.39 (t, J=8.6 Hz, 1H), 4.27-4.15 (t, J=9.2 Hz, 1H), 4.14-4.07 (dd, J=8.3, 6.1 Hz, 1H), 3.94-3.78 (m, 3H), 3.77-3.61 (m, 3H), 2.64-2.52 (dt, J=14.1, 7.0 Hz, 2H), 1.85-1.75 (s, 3H). LCMS: m/z 442 (M+H).

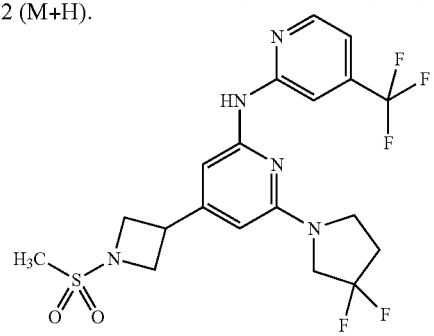

Preparation of 6-(3,3-difluoropyrrolidin-1-yl)-4-(1-(methylsulfonyl)azetidin-3-yl)-N-(4-(trifluoromethyl) yridine-2-yl) yridine-2-amine To a solution of 4-(azetidin-3-yl)-6-(3,3-difluoropyrrolidin-1-yl)-N-[4-(trifluoromethyl)-2-pyridyl]yridine-2-amine (1-d, 210 mg, 0.5258 mmol) and DMAP (6.5 mg, 0.1 equiv., 0.05258 mmol)) in dichloromethane (2 mL, 31.0 mmol) and N-ethyldiisopropylamine (0.55 mL, 6.0 equiv., 3.155 mmol) was added MESYL CHLORIDE (0.125 mL, 3.0 equiv., 1.577 mmol) dropwise, and the dark brown solution was stirred at 25° C. for 2 h. DCM was removed, and the crude was submitted for HPLC purification to yield 17.5 mg (7.0%) yellow powder. $^1$H NMR (400 MHz, DMSO) δ (delta) 10.02-9.89 (s, 1H), 8.75-8.60 (s, 1H), 8.55-8.33 (d, J=5.2 Hz, 1H), 7.31-7.04 (d, J=5.2 Hz, 1H), 6.69-6.52 (s, 1H), 6.30-5.92 (s, 1H), 4.38-4.07 (t, J=8.4 Hz, 2H), 4.05-3.81 (m, 4H), 3.81-3.70 (p, J=7.9 Hz, 1H), 3.69-3.61 (t, J=7.3 Hz, 2H), 3.18-2.94 (s, 3H), 2.68-2.48 (m, 1H). LCMS: m/z 478 (M+H).

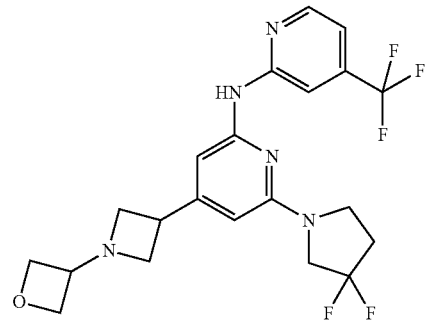 [SMILES: FC1(F)CCN(c2cc(C3CN(C4COC4)C3)cc(Nc3cc(C(F)(F)F)ccn3)n2)C1]

Preparation of 6-(3,3-difluoropyrrolidin-1-yl)-4-(1-(oxetan-3-yl)azetidin-3-yl)-N-(4-(trifluoromethyl)pyridin-2-yl)pyridin-2-amine To a solution of 4-(azetidin-3-yl)-6-(3,3-difluoropyrrolidin-1-yl)-N-[4-(trifluoromethyl)-2-pyridyl]pyridin-2-amine (1-d, 200 mg, 0.5008 mmol) in 1,4-dioxane (3.0 mL, 35 mmol) and N-ethyldiisopropylamine (0.26 mL, 3.0 equiv., 1.502 mmol) was added 3-oxetanone (219 mg, 6.0 equiv., 3.005 mmol), and the reaction was stirred at 50° C. for 1.5 h. After the reaction was cooled down, sodium triacetoxyborohydride (447 mg, 4.0 equiv., 2.003 mmol) was added in portions. The reaction was stirred at 25° C. overnight. The crude was submitted for HPLC purification to yield 7.5 mg (3.3%) white powder. $^1$H NMR (400 MHz, DMSO-d6) δ (delta) 9.91 (s, 1H), 8.70 (s, 1H), 8.44 (d, J=5.4 Hz, 1H), 7.14 (d, J=5.3 Hz, 1H), 6.62 (s, 1H), 6.00 (s, 1H), 4.58 (t, J=6.7 Hz, 2H), 4.41 (t, J=5.9 Hz, 2H), 3.85 (t, J=13.2 Hz, 2H), 3.75 (p, J=6.2 Hz, 1H), 3.63 (q, J=6.4, 6.0 Hz, 4H), 3.54 (p, J=7.7, 7.1 Hz, 1H), 3.20 (t, J=6.6 Hz, 2H), 2.58 (td, J=14.5, 7.3 Hz, 2H). LCMS: m/z 456 (M+H).

The following examples were prepared similarly to the methods described in this Example:

| Structure | $^1$H NMR | MS (m/z) |
|---|---|---|
| 4-(azetidin-3-yl)-N2,N6-bis(4-(trifluoromethyl)pyridin-2-yl)pyridine-2,6-diamine | NMR (400 MHz, DMSO-d6) δ (delta) 9.91 (s, 2H), 8.46 (d, J = 5.2 Hz, 2H), 8.08 (s, 2H), 7.13 (d, J = 5.4 Hz, 2H), 6.98 (s, 2H), 3.78 (m, 3H), 3.59 (s, 2H). | |
| 6-(3,3-difluoropyrrolidin-1-yl)-4-(1-(oxetan-3-yl)azetidin-3-yl)-N-(4-(trifluoromethyl)pyridin-2-yl)pyridin-2-amine | (400 MHz, DMSO-d6) δ (delta) 9.91 (s, 1H), 8.70 (s, 1H), 8.44 (d, J = 5.4 Hz, 1H), 7.14 (d, J = 5.3 Hz, 1H), 6.62 (s, 1H), 6.00 (s, 1H), 4.58 (t, J = 6.7 Hz, 2H), 4.41 (t, J = 5.9 Hz, 2H), 3.85 (t, J = 13.2 Hz, 2H), 3.75 (p, J = 6.2 Hz, 1H), 3.63 (q, J = 6.4, 6.0 Hz, 4H), 3.54 (p, J = 7.7, 7.1 Hz, 1H), 3.20 (t, J = 6.6 Hz, 2H), 2.58 (td, J = 14.5, 7.3 Hz, 2H). | 456 |
| 6-(3,3-difluoropyrrolidin-1-yl)-4-(1-(methylsulfonyl)azetidin-3-yl)-N-(4-(trifluoromethyl)pyridin-2-yl)pyridin-2-amine | (400 MHz, DMSO) δ (delta) 10.02-9.89 (s, 1H), 8.75-8.60 (s, 1H), 8.55-8.33 (d, J = 5.2 Hz, 1H), 7.31-7.04 (d, J = 5.2 Hz, 1H), 6.69-6.52 (s, 1H), 6.30-5.92 (s, 1H), 4.38-4.07 (t, J = 8.4 Hz, 2H), 4.05-3.81 (m, 4H), 3.81-3.70 (p, J = 7.9 Hz, 1H), 3.69-3.61 (t, J = 7.3 Hz, 2H), 3.18-2.94 (s, 3H), 2.68-2.48 (m, 1H). | 478 |

-continued

| Structure | ¹H NMR | MS (m/z) |
|---|---|---|
| 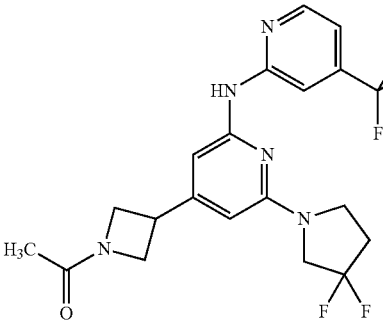<br>1-(3-(2-(3,3-difluoropyrrolidin-1-yl)-6-((4-(trifluoromethyl)pyridin-2-yl)amino)pyridin-4-yl)azetidin-1-yl)ethanone | (400 MHz, DMSO) δ (delta) 9.99-9.83 (s, 1H), 8.74-8.62 (s, 1H), 8.48-8.40 (d, J = 5.1 Hz, 1H), 7.21-7.11 (d, J = 5.2 Hz, 1H), 6.66-6.55 (s, 1H), 6.15-5.96 (s, 1H), 4.53-4.39 (t, J = 8.6 Hz, 1H), 4.27-4.15 (t, J = 9.2 Hz, 1H), 4.14-4.07 (dd, J = 8.3, 6.1 Hz, 1H), 3.94-3.78 (m, 3H), 3.77-3.61 (m, 3H), 2.64-2.52 (dt, J = 14.1, 7.0 Hz, 2H), 1.85-1.75 (s, 3H). | 442 |

Example 9

Method I

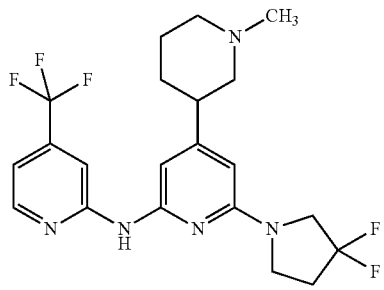 [SMILES: CN1CCCC(c2cc(Nc3cc(C(F)(F)F)ccn3)nc(N3CCC(F)(F)C3)c2)C1]

Preparation of 6-(3,3-difluoropyrrolidin-1-yl)-4-(1-methylpiperidin-3-yl)-N-(4-(trifluoromethyl)pyridin-2-yl)pyridin-2-amine

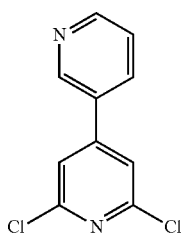 [SMILES: Clc1cc(-c2cccnc2)cc(Cl)n1]

Step 1: 2',6'-dichloro-3,4'-bipyridine 2,6-dichloro-4-iodopyridine (500 mg, 1.77082 mmol), 3-pyridylboronic acid pinacol ester (487 mg, 1.3 equiv., 2.30207 mmol), PCy3 (112 mg, 0.22 equiv., 0.389581 mmol), and Pd2(dba)3 (84 mg, 0.050 equiv., 0.0885411 mmol) were mixed in acetonitrile (13 mL, 140 equiv., 247.915 mmol) and K₃PO₄ (1.27 M, 1.95 mL, 1.4 equiv., 2.47915 mmol), and the reaction was kept at 110° C. for 2 h. Brine and 10% citric acid was used to adjust the pH around 8. The mixture was extracted with EtOAc three times. After evaporation of the organic layers, the residue was purified via chromatography (0-70% EtOAc/Heptane) to yield 367 mg yellow powder ¹H NMR (400 MHz, CDCl₃) δ (delta) 8.86 (d, J=2.4 Hz, 1H), 8.74 (dd, J=4.8, 1.6 Hz, 1H), 7.92-7.86 (m, 1H), 7.47 (s, 2H), 7.45 (dd, J=7.9, 4.8 Hz, 1H). ¹³C NMR (101 MHz, CDCl₃) δ (delta) 151.45, 151.24, 150.72, 148.02, 134.40, 131.63, 123.96, 120.75. LCMS: m/z 225 (M+H).

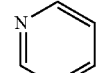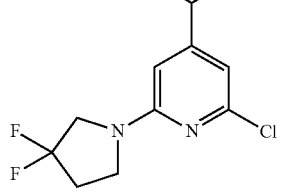

Step 2: 2'-chloro-6'-(3,3-difluoropyrrolidin-1-yl)-3,4'-bipyridine

To a solution of 2,6-dichloro-4-(3-pyridyl)pyridine (48 mg, 0.21327 mmol) and 3,3-difluoropyrrolidine hydrochloride (153 mg, 5.0 equiv., 1.0663 mmol) in NMP (1.0 mL, 10 mmol) in a microwave vial was added DIPEA (0.26 mL, 7.0 equiv., 1.4929 mmol), and the reaction was maintained at 140° C. for 60 min then at 150° C. for 20 min in the microwave machine, while LCMS indicated the conversion was more than 95%. The crude was used without further treatment. LCMS: m/z 296 (M+H).

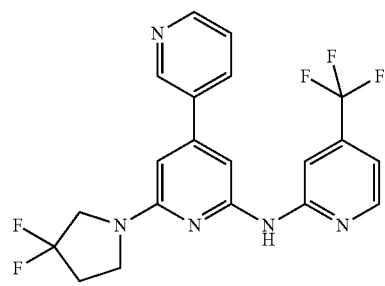 [SMILES: FC1(F)CCN(c2cc(-c3cccnc3)cc(Nc3cc(C(F)(F)F)ccn3)n2)C1]

Step 3: 6'-(3,3-difluoropyrrolidin-1-yl)-N-(4-(trifluoromethyl)pyridin-2-yl)-[3,4'-bipyridin]-2'-amine To a mixture of 2-chloro-6-(3,3-difluoropyrrolidin-1-yl)-4-(3-pyridyl)pyridine (2-b, 63 mg, 0.2131 mmol), 2-amino-4-(trifluoromethyl)PYRIDINE (70 mg, 2.0 equiv., 0.4261 mmol), XantPhos (25 mg, 0.20 equiv., 0.04261 mmol), Pd2(dba)3 (20 mg, 0.10 equiv., 0.02131 mmol) in 1,4-dioxane (2.4 mL, 130 equiv., 27.70 mmol) was added cesium carbonate (208 mg, 3.0 equiv., 0.6392 mmol), and the reaction was maintained at 180° C. for 90 min. The crude was diluted with water, and extraction was done with EtOAc. After evaporation of the organic layers, the crude was purified via silica gel chromatography (0-100% EtOAc/Heptane) to 60 mg (67% after two steps) brown solid. $^1$H NMR (400 MHz, CDCl$_3$) δ (delta) 8.86 (s, 1H), 8.66 (d, J=4.8 Hz, 1H), 8.58 (s, 1H), 8.38 (d, J=5.2 Hz, 1H), 7.89 (d, J=7.9 Hz, 1H), 7.46 (s, 1H), 7.43-7.35 (m, 1H), 7.05 (d, J=5.2 Hz, 1H), 6.55 (s, 1H), 6.10 (s, 1H), 3.93 (t, J=13.1 Hz, 2H), 3.79 (t, J=7.3 Hz, 2H), 2.62-2.47 (m, 2H). LCMS: m/z 422 (M+H).

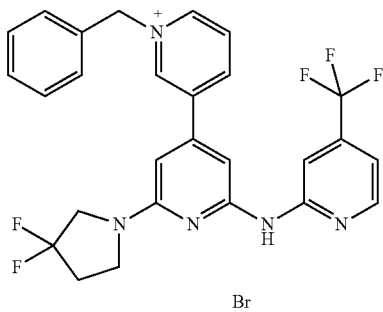

Br

Step 4: 1-benzyl-2'-(3,3-difluoropyrrolidin-1-yl)-6'-((4-(trifluoromethyl)pyridin-2-yl)amino)-[3,4'-bipyridin]-1-ium bromide To a suspension of 6-(3,3-difluoropyrrolidin-1-yl)-4-(3-pyridyl)-N-[4-(trifluoromethyl)-2-pyridyl]pyridin-2-amine (2-c, 320 mg, 0.7594 mmol) in methanol (5 ml, 100 mmol) was added benzyl bromide (0.46 ml, 5.0 equiv., 3.797 mmol), and the reaction was kept at 60° C. overnight. MeOH was removed as much as possible. Ethyl ether (3×10 mL) was used to wash away the excess BnBr. The leftover solid was used without further treatment. LCMS: m/z 512 (M$^+$).

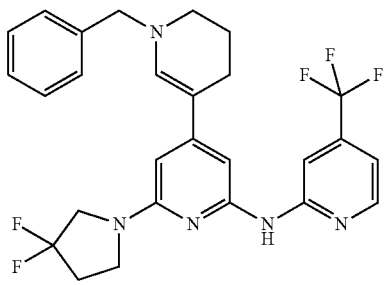 [SMILES: FC1(F)CCN(c2cc(C3=CN(Cc4ccccc4)CCC3)cc(Nc3cc(C(F)(F)F)ccn3)n2)C1]

Step 5: 1-benzyl-6'-(3,3-difluoropyrrolidin-1-yl)-N-(4-(trifluoromethyl)pyridin-2-yl)-1,4,5,6-tetrahydro-[3,4'-bipyridin]-2'-amine To a solution of 4-(1-benzylpyridin-1-ium-3-yl)-6-(3,3-difluoropyrrolidin-1-yl)-N-[4-(trifluoromethyl)-2-pyridyl]pyridin-2-amine (2-d, 500 mg, 0.9756 mmol) in methyl alcohol (12 ml, 300 equiv., 292.7 mmol) was added sodium borohydride (225 mg, 6.0 equiv., 5.853 mmol) in three portions with the interval of 30 min each, and the reaction was stirred at 25° C. for 4 h. The reaction was quenched by citric acid (10% aq.), and extracted EtOAc three times. After evaporation of the organic layers, the crude brown solid was used without further purification. LCMS: m/z 516 (M+H).

Step 6: 6-(3,3-difluoropyrrolidin-1-yl)-4-(1-methylpiperidin-3-yl)-N-(4-(trifluoromethyl)pyridin-2-yl)pyridin-2-amine A suspension of 4-(1-benzyl-3,4-dihydro-2H-pyridin-5-yl)-6-(3,3-difluoropyrrolidin-1-yl)-N-[4-(trifluoromethyl)-2-pyridyl]pyridin-2-amine (250 mg, 0.4850 mmol) and palladium hydroxide on activated charcoal (85 mg, 0.25 equiv., 0.1212 mmol) in methanol (20 ml, 500 mmol) and ethyl acetate (20 ml, 204 mmol) was charged with H$_2$ balloon. The reaction was kept stirring for 48 h, while LCMS indicated olefin was reduced. The catalyst was filtered off, and new portion of catalyst was refilled, followed by addition of acetic acid (0.556 mL, 20 equiv., 9.699 mmol). The reaction was stirred with H$_2$ balloon overnight. LCMS showed both m/z 442 and 456. The catalyst was filtered off, and the solvent was evaporated to dryness. The residue was submitted for HPLC purification to yield 4.7 mg (4.4%) off-white powder. LCMS: m/z 442 (M+H).

The following examples were prepared similarly to the methods described in this Example:

| Structure | $^1$H NMR | MS (m/z) |
|---|---|---|
| 6-(3,3-difluoropyrrolidin-1-yl)-4-(1-methyl-piperidin-3-yl)-N-(4-(trifluoromethyl)pyridin-2-yl)pyridin-2-amine | | 442 |

Example 10

DLK TR-FRET assay: DLK kinase reactions (20 μL) containing 5 nM N-terminally GST-tagged DLK (catalytic domain amino acid 1-520) (Carna Bioscience), 40 nM N-terminally HIS-tagged MKK4 K131M substrate, and 30 μM ATP in kinase reaction buffer (50 mM HEPES, pH 7.5, 0.01% Triton X-100, 0.01% Bovine γ-Globulins, 2 mM DTT, 10 mM MgCl$_2$ and 1 mM EGTA), and testing compound 1:3 serial diluted starting at 20 uM were incubated at ambient temperature for 60 minutes in 384 well OptiPlate (Perkin Elmer). To quench kinase reactions and detect phosphorylated MKK4, 15 μL of TR-FRET antibody mixture containing 2 nM anti-phosphorylated MKK4 labeled with Europium cryptate (Cisbio) and 23 nM anti-HIS labeled with D2 (Cisbio) in detection buffer (25 mM Tris pH 7.5, 100 mM NaCl, 100 mM EDTA, 0.01% Tween-20, and 200 mM KF) was added to the reaction mixture. The detection mixture was incubated for 3 hours at ambient temperature and the TR-FRET was detected with an EnVision multilabel plate reader (Perkin-Elmer) using the LANCE/DELFIA Dual Enh label from Perkin-Elmer (excitation filter: UV2 (TRF) 320 and emission filters: APC 665 and Europium 615). Compounds of formula I as set forth in Table 1 inhibited the DLK kinase with the $K_i$s as provided in Table B below.

TABLE 2

| No. | DLK (KI) [µM] |
|---|---|
| 1 | |
| 2 | |
| 3 | |
| 4 | |
| 5 | |
| 6 | |
| 7 | |
| 8 | |
| 9 | |
| 10 | |
| 11 | |
| 12 | |
| 13 | |
| 14 | |
| 15 | |
| 16 | |
| 17 | |
| 18 | |
| 19 | 0.0051 |
| 20 | 0.11 |
| 21 | 0.012 |
| 22 | 0.0022 |
| 23 | 0.00032 |
| 24 | 0.14 |
| 25 | 0.00084 |
| 26 | 0.021 |
| 27 | 0.10 |
| 28 | 0.0014 |
| 29 | 0.018 |
| 30 | 0.00017 |
| 31 | 0.00017 |
| 32 | 0.22 |
| 33 | 0.00017 |
| 34 | 0.0019 |
| 35 | 0.0008 |
| 36 | 0.00017 |
| 37 | 0.0025 |
| 38 | 0.0022 |
| 39 | 0.00017 |
| 40 | 0.00017 |
| 41 | 0.056 |
| 42 | 0.0064 |
| 43 | 0.0038 |
| 44 | 0.0068 |
| 45 | 0.048 |
| 46 | 0.013 |
| 47 | 0.040 |
| 48 | 0.021 |
| 49 | 0.019 |
| 50 | 0.0010 |
| 51 | 0.0024 |
| 52 | 0.0020 |
| 53 | 0.024 |
| 54 | 0.021 |
| 55 | 0.0089 |
| 56 | 0.0021 |
| 57 | 0.0035 |
| 58 | 0.064 |
| 59 | 0.0015 |
| 60 | 0.028 |
| 61 | 0.0047 |
| 62 | 0.17 |
| 63 | 0.0086 |
| 64 | 0.17 |
| 65 | 0.03 |
| 66 | 0.043 |

TABLE 2-continued

| No. | DLK (KI) [µM] |
|---|---|
| 67 | 0.0004 |
| 68 | 0.0003 |
| 69 | 0.004 |
| 70 | 0.0018 |
| 71 | 0.00036 |
| 72 | 0.15 |
| 73 | |
| 74 | 0.0002 |
| 75 | 0.013 |
| 76 | 0.016 |
| 77 | 0.19 |
| 78 | 0.0031 |
| 79 | 0.035 |
| 80 | 0.058 |
| 81 | 0.0114 |
| 82 | 0.10 |
| 83 | 0.0046 |
| 84 | 0.0016 |
| 85 | 0.015 |
| 86 | 0.0119 |
| 87 | 0.051 |
| 88 | 0.0028 |
| 89 | 0.0080 |
| 90 | 0.0019 |
| 91 | 0.0067 |
| 92 | 0.0007 |
| 93 | 0.020 |
| 94 | 0.0041 |
| 95 | 0.0073 |
| 96 | 0.018 |
| 97 | 0.0006 |
| 98 | 0.0422 |
| 99 | 0.0009 |
| 100 | 0.011 |
| 101 | 0.038 |
| 102 | 0.088 |
| 103 | 0.016 |
| 104 | 0.0126 |
| 105 | 0.007 |
| 106 | 0.010 |
| 107 | 0.12 |
| 108 | 0.093 |
| 109 | 0.14 |
| 110 | 0.093 |
| 111 | 0.089 |
| 112 | 0.22 |
| 113 | 1.6 |
| 114 | |
| 115 | 0.00009 |
| 116 | 0.215 |
| 117 | 0.00094 |
| 118 | 0.004 |
| 119 | 0.0002 |
| 120 | 0.17 |
| 121 | 0.0002 |
| 122 | 0.00040 |
| 123 | 0.0002 |
| 124 | 0.71 |
| 125 | 0.0031 |
| 126 | 0.0066 |
| 127 | 0.0029 |
| 128 | 0.45 |
| 129 | 0.51 |
| 130 | 0.00088 |
| 131 | 0.00044 |
| 132 | 0.00212 |
| 133 | 0.00066 |
| 134 | 0.03 |
| 135 | 0.021 |
| 136 | 0.025 |
| 137 | 0.00017 |
| 138 | 0.00017 |
| 139 | 0.0066 |
| 140 | 0.00017 |
| 141 | 0.0020 |
| 142 | 0.022 |
| 143 | 0.0012 |

TABLE 2-continued

| No. | DLK (KI) [μM] |
|---|---|
| 144 | 0.061 |
| 145 | 3.6 |
| 146 | 2.1 |
| 147 | 1.2 |

The invention claimed is:

1. A compound of formula (I):

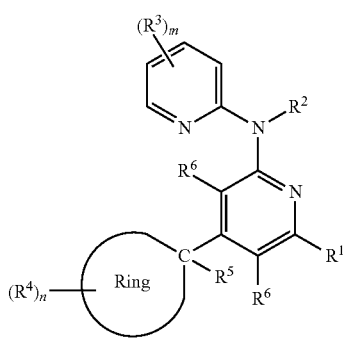

(I)

wherein $R^1$ is selected from the group consisting of $C_{1-6}$ alkyl, $C_{1-6}$ haloalkyl, $C_{1-6}$ heteroalkyl, —$OR^{1a}$, —$SR^{1a}$, —N(H)($R^{1a}$), and —N($R^{1a}$)($R^{1b}$), methyl, ethyl, propyl, isopropyl, butyl, sec-butyl, tert-butyl, cyclopropane, cyclobutane, cyclopentane, cyclohexane, cycloheptane, morpholine, homomorpholine, piperidine, homopiperidine, piperazine, homopiperazine, azetidine, pyrrolidine, benzene, pyrrole, pyrazole, imidazole, triazole, tetrazole, pyridine, pyrimidine, pyrazine, pyridazine, oxetane, tetrahydrofuran, tetrahydropyran, azabicyclo[2.2.1]heptane, 2-oxa-6-azaspiro[3.3]heptane, 8-oxa-3-azabicyclo[3.2.1]octane, 3-oxa-8-azabicyclo[3.2.1]octane, 7-oxabicyclo[2.2.1]heptane, 7-azabicyclo[2.2.1]heptane, nonbornane, bicyclo[2.2.2]octane, 2-azabicyclo[2.2.2]octane, 2-oxabicyclo[2.2.2]octane, 2-oxa-5-azabicyclo[2.2.2]octane and 2,5-diazabicyclo[2.2.2]octane, 5,6,7,8-tetrahydroimidazo[1,2-a]pyrazine, 4,5,6,7-tetrahydro-3H-imidazo[4,5-c]pyridine, wherein $R^{1a}$ and $R^{1b}$ are each independently selected from the group consisting of $C_{1-6}$ alkyl, $C_{1-6}$ haloalkyl, $C_{1-6}$ heteroalkyl, 3-10 membered cycloalkyl and 3-10 membered heterocycloalkyl, and wherein the aliphatic and aromatic portions of $R^1$ are independently further substituted with 0 to 5 $R^{41}$ substituents selected from the group consisting of —F, —Cl, —Br, I, —CN, —$NO_2$, —$SF_5$, —OH, —$NH_2$, —$CF_3$, =O, $C_{1-4}$ alkyl, $C_{1-4}$ haloalkyl, $C_{1-4}$ heteroalkyl, $C_{1-4}$ alkoxy, $C_{1-4}$ alkylthio, $C_{1-4}$ alkylamino, $C_{1-4}$ dialkylamino, $R^{1c}$—C(=O)—, —$R^{1c}$—C(=O)N(H)—, $R^{1c}$—C(=O)N($R^{1d}$)—, $R^{1c}$—C(=O)O—, $R^{1c}$—S(O)$_{1-2}$, $R^{1c}$—S(O)$_{1-2}$N($R^{1d}$)—, $R^{1c}$—S(O)$_{1-2}$N(H)—, 3-6 membered cycloalkyl, phenyl, 5-6 membered heteroaryl and 3-7 membered heterocycloalkyl, wherein $R^{1c}$ is selected from the group consisting of $C_{1-6}$ alkyl, $C_{1-6}$ haloalkyl, $C_{5-6}$ heteraryl, 3-7 membered heterocycloalkyl, phenyl and 3-6 membered cycloalkyl, $R^{1d}$ is selected from the group consisting of hydrogen, $C_{1-3}$ alkyl and $C_{1-3}$ haloalkyl, and wherein said 5-6 membered heteraryl, phenyl, 3-6 membered heteroaryl, 3-6 membered cycloalkyl and 3-7 membered heterocycloalkyl of the $R^{41}$ substituent are substituted with from 0-4 substituents selected from —F, —Cl, —Br, I, —CN, —$NO_2$, —$SF_5$, —OH, —$NH_2$, —$CF_3$, $C_{1-4}$ alkyl, $C_{1-4}$ haloalkyl, $C_{1-4}$ alkoxy, $C_{1-4}$ alkylthio, $C_{1-4}$ alkylamino and $C_{1-4}$ dialkylamino;

$R^2$ is selected from the group consisting of hydrogen, $C_{1-6}$ alkyl and $C_{1-6}$ haloalkyl;

$R^3$ is selected from the group consisting of —F, —Cl, —Br, —I, —$(X^3)_{0-1}$—CN, —$(X^3)_{0-1}$—$NO_2$, —$(X^3)_{0-1}$—$SF_5$, —$(X^3)_{0-1}$OH, —$(X^3)_{0-1}$-$NH_2$, —$(X^3)_{0-1}$-N(H)($R^{3a}$), —$(X^3)_{0-1}$-N($R^{3b}$)($R^{3a}$), —$(X^3)_{0-1}$-$CF_3$, —S-(Phenyl), $C_{1-6}$ alkyl, $C_{1-6}$ haloalkyl, $C_{1-6}$ heteroalkyl, $C_{1-6}$ alkoxy, $C_{1-6}$ alkylthio, —$(X^3)_{0-1}$-3-7 membered cycloalkyl, —$(X^3)_{0-1}$-3-7 membered heterocycloalkyl, —$(X^3)_{0-1}$-5-6 membered heteroaryl, —$(X^3)_{0-1}$-$C_6$ aryl, —$(X^3)_{0-1}$-C(=$Y^3$)N(H)($R^{3a}$), —$(X^3)_{0-1}$—C(=$Y^3$)$NH_2$, —$(X^3)_{0-1}$—C(=$Y^3$)N($R^{3a}$)($R^{3b}$), —$(X^3)_{0-1}$-C(=$Y^3$)$OR^{3a}$, —$(X^3)_{0-1}$-C(=$Y^3$)OH, —$(X^3)_{0-1}$-N(H)C(=$Y^3$)($R^{3a}$), —$(X^3)_{0-1}$—N($R^{3b}$)C(=$Y^3$)($R^{3a}$), —$(X^3)_{0-1}$—N(H)C(=$Y^3$)$OR^{3a}$, —$(X^3)_{0-1}$-N($R^{3b}$)C(=$Y^3$)$OR^{3a}$, —$(X^3)_{0-1}$S(=$Y^3$)$_{1-2}R^{3a}$, —$(X^3)_{0-1}$-N(H)S(=$Y^3$)$_{1-2}R^{3a}$, —$(X^3)_{0-1}$-N($R^{3b}$)S(=$Y^3$)$_{1-2}R^{3a}$, —$(X^3)_{0-1}$—S(=$Y^3$)$_{1-2}$N(H)($R^{3a}$), —$(X^3)_{0-1}$—S(=$Y^3$)$_{1-2}$N($R^{3b}$)($R^{3a}$), —$(X^3)_{0-1}$—S(=$Y^3$)$_{1-2}NH_2$, —$(X^3)_{0-1}$—C(=$Y^3$)$R^{3a}$, —$(X^3)_{0-1}$-C(=$Y^3$)H, —$(X^3)_{0-1}$—C(=NOH)$R^{3a}$, —$(X^3)_{0-1}$-C(=$NOR^{3b}$)$R^{3a}$, —$(X^3)_{0-1}$—NHC(=$Y^3$)N(H)($R^{3a}$), —$(X^3)_{0-1}$-NHC(=$Y^3$)$NH_2$, —$(X^3)_{0-1}$-NHC(=$Y^3$)N($R^{3b}$)($R^{3a}$), —$(X^3)_{0-1}$—N($R^{3a}$)C(=$Y^3$)N(H)($R^{3a}$), —$(X^3)_{0-1}$—N($R^{3a}$)C(=$Y^3$)$NH_2$, —$(X^3)_{0-1}$-OC(=$Y^3$)$R^{3a}$, —$(X^3)_{0-1}$-OC(=$Y^3$)H, —$(X^3)_{0-1}$-OC(=$Y^3$)$OR^{3a}$, —$(X^3)_{0-1}$-OP(=$Y^3$)($OR^{3a}$)($OR^{3b}$), —$(X^3)$—SC(=$Y^3$)$OR^{3a}$ and —$(X^3)$—SC(=$Y^3$)N($R^{3a}$)($R^{3b}$) wherein $X^3$ is selected from the group consisting of $C_{1-4}$ alkylene, $C_{1-4}$ haloalkylene, $C_{1-4}$ heteroalkylene, $C_{2-4}$ alkenylene, and $C_{2-4}$ alkynylene, $R^{3a}$ and $R^{3b}$ are each independently selected from the group consisting of $C_{1-6}$ alkyl, $C_{1-6}$ haloalkyl, $C_{1-6}$ heteroalkyl, 3-7 membered cycloalkyl, 3-7 membered cycloalkyl-$C_{1-4}$ alkyl, 3-7 membered heterocycloalkyl, 3-7 membered heterocycloalkyl-$C_{1-4}$ alkyl, 5-6 membered heteroaryl, 5-6 membered heteroaryl-$C_{1-4}$ alkyl, $C_6$ aryl, $C_6$ aryl-$C_{1-4}$ alkyl and benzyl; $Y^3$ is O, $NR^{3d}$ or S wherein $R^{3d}$ is hydrogen or $C_{1-6}$ alkyl; wherein aliphatic or aromatic portion of $R^3$ is independently further substituted with from 0 to 4 $R^{43}$ substituents selected from the group consisting of —F, —Cl, —Br, —I, —CN, —$NO_2$, —$SF_5$, —OH, —$NH_2$, —$CF_3$, =O, $C_{1-6}$ alkyl, $C_{1-6}$ haloalkyl, $C_{1-6}$ heteroalkyl, $C_{1-6}$ alkoxy, $C_{1-6}$ alkylthio, 3-6 membered cycloalkyl, 3-6 membered heterocycloalkyl, —C(=O)N(H)($C_{1-6}$ alkyl), —C(=O)N($C_{1-6}$ alkyl)$_2$, —C(=O)$NH_2$, —C(=O)O$C_{1-6}$ alkyl, —C(=O)OH, —N(H)C(=O)($C_{1-6}$ alkyl), —N($C_{1-6}$ alkyl)C(=O)($C_{1-6}$ alkyl), —N(H)C(=O)O$C_{1-6}$ alkyl, —N($C_{1-6}$ alkyl)C(=O)O$C_{1-6}$ alkyl, —S(O)$_{1-2}C_{1-6}$ alkyl, —N(H)S(O)$_{1-2}C_{1-6}$ alkyl, —N($C_{1-6}$ alkyl)S(O)$_{1-2}C_{1-6}$ alkyl, —S(O)$_{0-1}$N(H)($C_{1-6}$ alkyl), —S(O)$_{0-1}$N($C_{1-6}$ alkyl)$_2$, —S(O)$_{0-1}NH_2$, —C(=O)$C_{1-6}$ alkyl, —C(=NOH)$C_{1-6}$ alkyl, —C(=NO$C_{1-6}$ alkyl)$C_{1-6}$ alkyl, —NHC(=O)N(H)

(C$_{1-6}$ alkyl), —NHC(=O)N(C$_{1-6}$ alkyl)$_2$, —NHC(=O)NH$_2$, —N(C$_{1-6}$ alkyl)C(=O)N(H)(C$_{1-6}$ alkyl), —N(C$_{1-6}$ alkyl)C(=O)NH$_2$, —OC(=O)C$_{1-6}$ alkyl, —OC(=O)OC$_{1-6}$ alkyl, —OP(=O)(OC$_{1-6}$ alkyl)$_2$, —SC(=O)OC$_{1-6}$ alkyl and —SC(=O)N(C$_{1-6}$ alkyl)$_2$; the ring represented by the structure

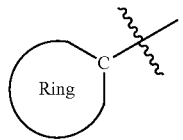

is an optionally substituted C-linked 4 to 10 membered heterocyclic ring selected from the group consisting of morpholine, morpholinone, piperazine, piperazinone, thiomorpholine, thiomorpholinone, homopiperidine, homopiperidinone, piperidine, valerolactam, pyrrolidine, butyrolactam, azetidine, azetidinone, thiazepane-1,1-dioxide, thiazinane-1,1-dioxide, isothiazolidine-1,1-dioxide, pyridinone, tetrahydropyran, oxetane and tetrahydrofuran attached to the remainder of the compound represented by formula I;

R$^4$ is selected from the group consisting of —F, —Cl, —Br, —I, —(X$^4$)$_{0-1}$-CN, —(X$^4$)$_{0-1}$-NO$_2$, —(X$^4$)$_{0-1}$—SF$_5$, —(X$^4$)$_{0-1}$-OH, —(X$^4$)$_{0-1}$-NH$_2$, —(X$^4$)$_{0-1}$-N(H)(R$^{4a}$), —(X$^4$)$_{0-1}$-N(R$^{4b}$)(R$^{4a}$), —(X$^4$)$_{0-1}$-CF$_3$, C$_{1-6}$ alkyl, C$_{1-6}$ haloalkyl, C$_{1-6}$ heteroalkyl, C$_{1-6}$ alkoxy, C$_{1-6}$ alkylthio, —(X$^4$)$_{0-1}$-(3-10 membered heterocycloalkyl), —(X$^4$)$_{0-1}$-(5-10 membered heteroaryl), —(X$^4$)$_{0-1}$-(3-7 membered cycloalkyl), —(X$^4$)$_{0-1}$-(6-10 membered aryl), —(X$^4$)$_{0-1}$-C(=Y$^4$)N(H)(R$^{4a}$), —(X$^4$)$_{0-1}$—C(=Y$^4$)NH$_2$, —(X$^4$)$_{0-1}$—C(=Y$^4$)N(R$^{4a}$)(R$^{4b}$), —(X$^4$)$_{0-1}$-C(=Y$^4$)OR$^{4a}$, —(X$^4$)$_{0-1}$-C(=Y$^4$)OH, —(X$^4$)$_{0-1}$-N(H)C(=Y$^4$)(R$^{4a}$), —(X$^4$)$_{0-1}$—N(R$^{4b}$)C(=Y$^4$)(R$^{4a}$), —(X$^4$)$_{0-1}$—N(H)C(=Y$^4$)OR$^{4a}$, —(X$^4$)$_{0-1}$-N(R$^{4b}$)C(=Y$^4$)OR$^4$, —(X$^4$)$_{0-1}$—S(=Y$^4$)$_{1-2}$R$^{4a}$, —(X$^4$)$_{0-1}$-N(H)S(=Y$^4$)$_{1-2}$R$^{4a}$, —(X$^4$)$_{0-1}$-N(R$^{4b}$)S(=Y$^4$)$_{1-2}$R$^{4a}$, —(X$^4$)$_{0-1}$—S(=Y$^4$)$_{1-2}$N(H)(R$^{4a}$), —(X$^4$)$_{0-1}$—S(=Y$^4$)$_{1-2}$N(R$^{4b}$)(R$^{4a}$), —(X$^4$)$_{0-1}$—S(=Y$^4$)$_{1-2}$NH$_2$, —(X$^4$)$_{0-1}$—C(=Y$^4$)R$^{4a}$, —(X$^4$)$_{0-1}$—C(=Y$^4$)H, —(X$^4$)$_{0-1}$—C(=NOH)R$^{4a}$, —(X$^4$)$_{0-1}$—C(=NOR$^{4b}$)R$^{4a}$, —(X$^4$)$_{0-1}$—NHC(=Y$^4$)N(H)(R$^{4a}$), —(X$^4$)$_{0-1}$-NHC(=Y$^4$)NH$_2$, —(X$^4$)$_{0-1}$-NHC(=Y$^4$)N(R$^{4b}$)(R$^{4a}$), —(X$^4$)$_{0-1}$-NR$^{4a}$C(=Y$^4$)N(H)(R$^{4a}$), —(X$^4$)$_{0-1}$—N(R$^{4a}$)C(=Y$^4$)NH$_2$, —(X$^4$)$_{0-1}$-OC(=Y$^4$)R$^{4a}$, —(X$^4$)$_{0-1}$-OC(=Y$^4$)H, —(X$^4$)$_{0-1}$-OC(=Y$^4$)OR$^{4a}$, —(X$^4$)$_{0-1}$-OP(=Y$^4$)(OR$^{4a}$)(OR$^{4b}$), —SC(=Y$^4$)OR$^{4a}$ and —SC(=Y$^4$)N(R$^{4a}$)(R$^{4b}$) wherein R$^{4a}$ and R$^{4b}$ at each occurrence are each independently selected from the group consisting of C$_{1-6}$ alkyl, C$_{1-6}$ haloalkyl, C$_{1-6}$ heteroalkyl, 6-10 membered aryl, 3-7 membered cycloalkyl, 5-10 membered heteroaryl, 3-7 membered heterocycloalkyl, 6-10 membered aryl-C$_{1-4}$ alkyl, 3-7 membered cycloalkyl-C$_{1-4}$ alkyl, 5-10 membered heteroaryl-C$_{1-4}$ alkyl and 3-7 membered heterocycloalkyl-C$_{1-4}$ alkyl, and X$^4$ is selected from the group consisting of C$_{1-4}$ alkylene, C$_{1-4}$ haloalkylene, C$_{1-4}$ heteroalkylene, C$_{2-4}$ alkenylene and C$_{2-4}$ alkynylene; Y$^4$ is O, NR$^{4c}$ or S wherein R$^{4c}$ is hydrogen or C$_{1-6}$ alkyl; wherein the aromatic and aliphatic portions of R$^4$ is independently further substituted with 0 to 4 R$^{44}$ substituents selected from the group consisting of —F, —Cl, —Br, I, —CN, —NO$_2$, —SF$_5$, —OH, —NH$_2$, —CF$_3$, =O, C$_{1-6}$ alkyl, C$_{1-6}$ haloalkyl, C$_{1-6}$ heteroalkyl, C$_{1-6}$ alkoxy, C$_{1-6}$ alkylthio, 3-6 membered cycloalkyl, 3-6 membered heterocycloalkyl, —C(=O)N(H)(C$_{1-6}$ alkyl), —C(=O)N(C$_{1-6}$ alkyl)$_2$, —C(=O)NH$_2$, —C(=O)OC$_{1-6}$ alkyl, —C(=O)OH, —N(H)C(=O)(C$_{1-6}$ alkyl), —N(C$_{1-6}$ alkyl)C(=O)(C$_{1-6}$ alkyl), —N(H)C(=O)OC$_{1-6}$ alkyl, —N(C$_{1-6}$ alkyl)C(=O)OC$_{1-6}$ alkyl, —S(O)$_{1-2}$C$_{1-6}$ alkyl, —N(H)S(O)$_{1-2}$C$_{1-6}$ alkyl, —N(C$_{1-6}$ alkyl)S(O)$_{1-2}$C$_{1-6}$ alkyl, —S(O)$_{0-1}$N(H)(C$_{1-6}$ alkyl), —S(O)$_{0-1}$N(C$_{1-6}$ alkyl)$_2$, —S(O)$_{0-1}$NH$_2$, —C(=O)C$_{1-6}$ alkyl, —C(=NOH)C$_{1-6}$ alkyl, —C(=NOC$_{1-6}$ alkyl)C$_{1-6}$ alkyl, —NHC(=O)N(H)(C$_{1-6}$ alkyl), —NHC(=O)N(C$_{1-6}$ alkyl)$_2$, —NHC(=O)NH$_2$, —N(C$_{1-6}$ alkyl)C(=O)N(H)(C$_{1-6}$ alkyl), —N(C$_{1-6}$ alkyl)C(=O)NH$_2$, —OC(=O)C$_{1-6}$ alkyl, —OC(=O)OC$_{1-6}$ alkyl, —OP(=O)(OC$_{1-6}$ alkyl)$_2$, —SC(=O)OC$_{1-6}$ alkyl and —SC(=O)N(C$_{1-6}$ alkyl)$_2$;

m is an integer from 0 to 4;

n is an integer from 0 to 5;

R$^5$ is absent or is selected from the group consisting of hydrogen, C$_{1-6}$ alkyl, C$_{1-6}$ haloalkyl, —OH, OR$^{5a}$, —CN and halogen, wherein R$^{5a}$ is selected from the group consisting of C$_{1-6}$ alkyl, C$_{1-6}$ haloalkyl and C$_{1-6}$ heteroalkyl; or optionally R$^4$ and R$^5$ are optionally combined to form a 5-7 membered cycloalkyl or heterocycloalkyl and is independently further substituted with 0-4 R$^{44}$ substituents;

R$^6$ is independently selected from the group consisting of hydrogen, —F, Cl, Br, I, C$_{1-3}$ alkyl, C$_{1-3}$ haloalkyl.

2. The compound of claim 1, wherein said compound of formula I has the subformula selected from the group consisting of:

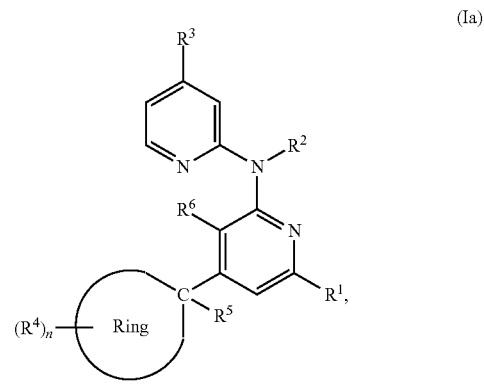

(Ia)

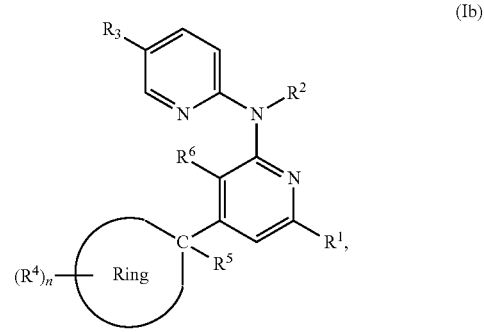

(Ib)

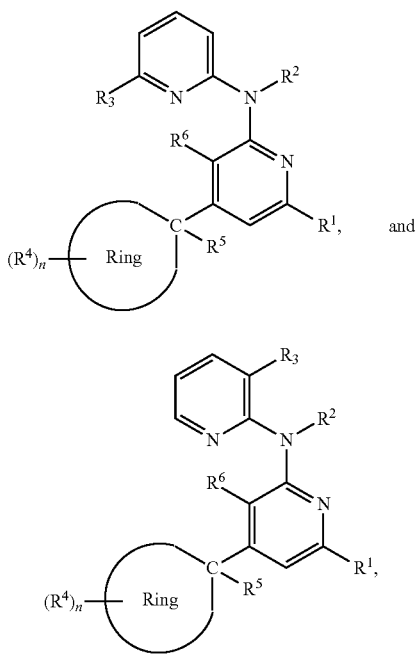
wherein R¹, R², R³, R³$^a$, R⁴, R⁵, R⁶, ring and n are defined according to claim 1.
3. The compound of claim 1, wherein the ring represented by the structure
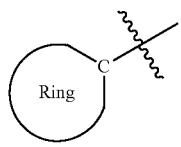 [SMILES: *C(C)C]
is selected from the group consisting of:
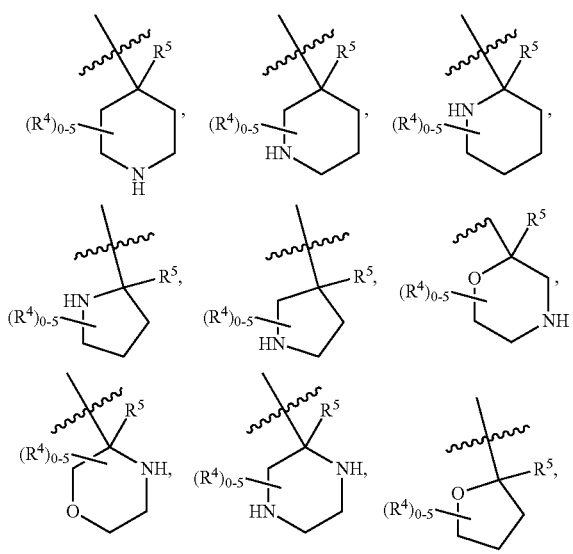
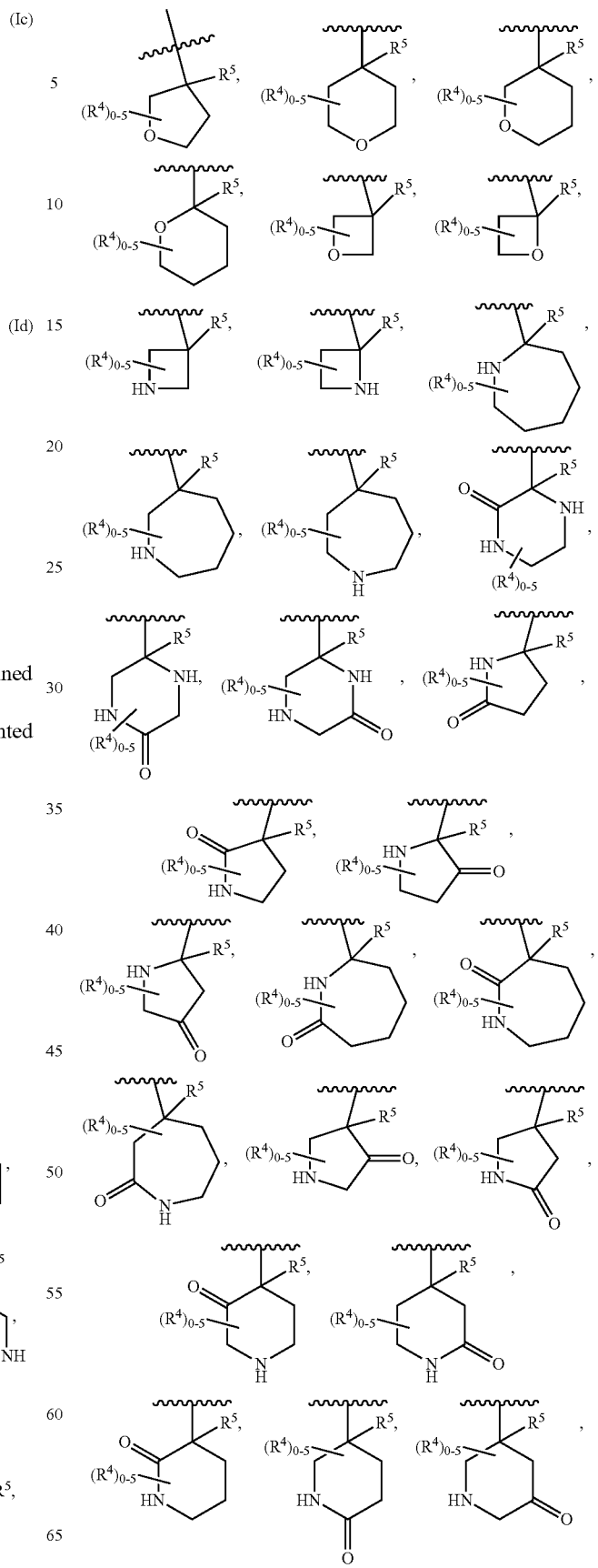

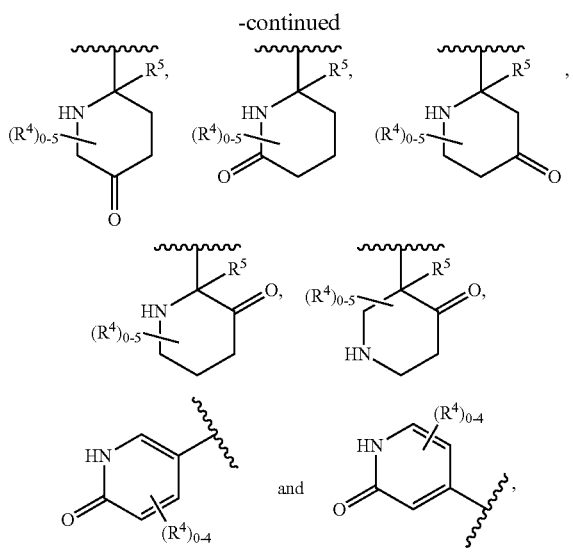
wherein R⁴ and R⁵ are defined according to claim 1, and wherein a R⁴ substituent, if present, replaces a hydrogen atom that is attached to a carbon or nitrogen atom in said ring.
4. The compound of claim 1, wherein the ring
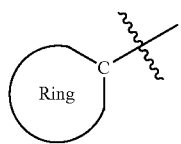 [SMILES: *C(C)C]
is selected from the group consisting of:
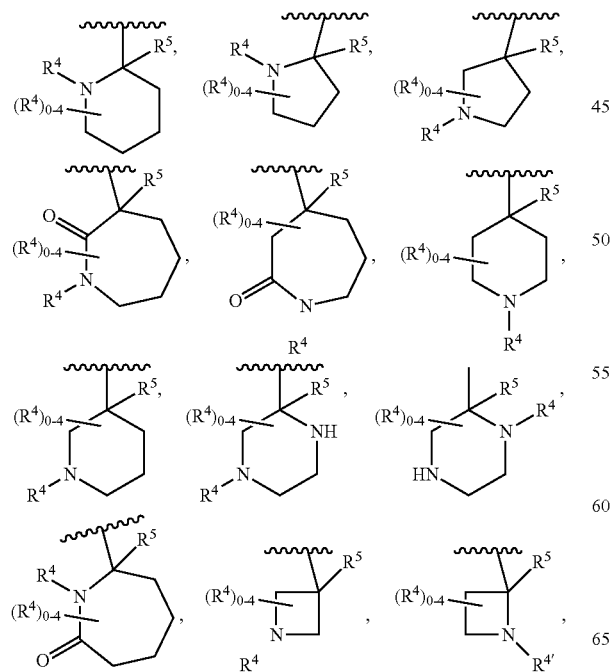
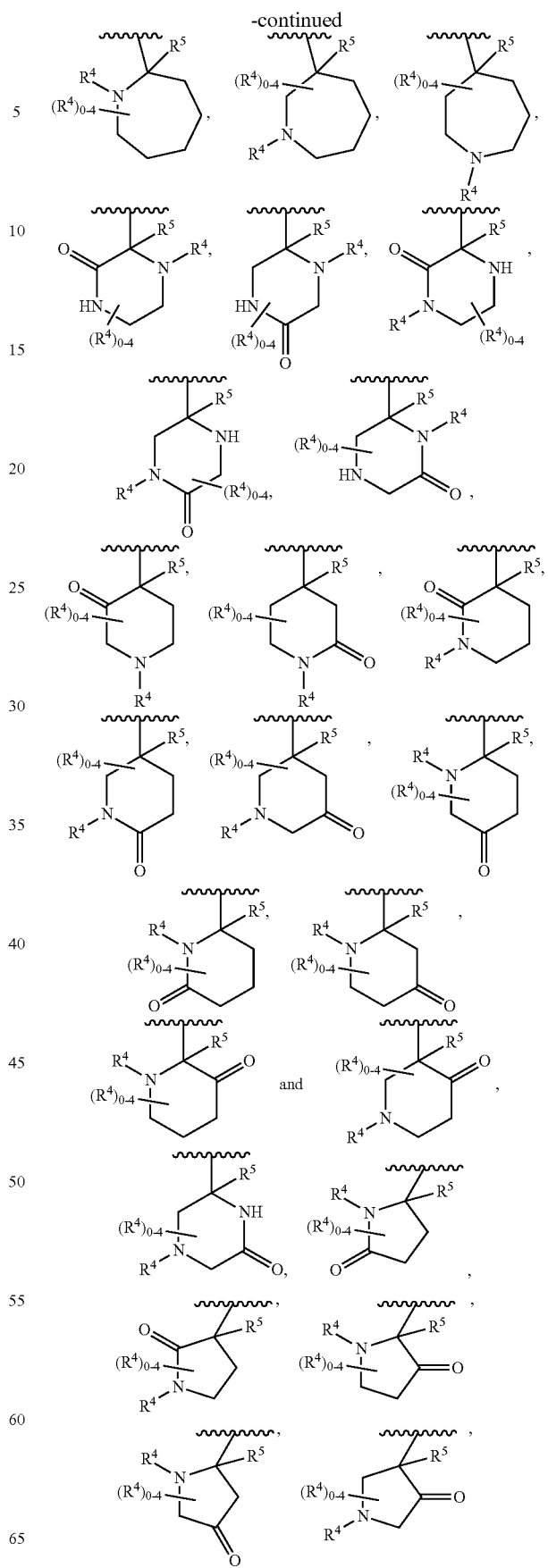

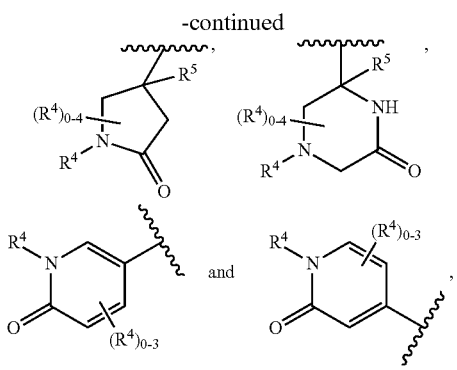

wherein R⁴ and R⁵ are defined according to claim 1, and wherein

R⁴ attached to the nitrogen atom of said ring is selected from the group consisting of —(X⁴)₀₋₁-CN, —(X⁴)₀₋₁-NO₂, —(X⁴)₀₋₁-SF₅, —(X⁴)₀₋₁-OH, —(X⁴)₀₋₁-NH₂, —(X⁴)₀₋₁—N(H)(R⁴ᵃ), —(X⁴)₀₋₁, N(R⁴ᵇ)(R⁴ᵃ), —(X⁴)₀₋₁-CF₃, C₁₋₆ alkyl, C₁₋₆ haloalkyl, C₁₋₆ heteroalkyl, C₁₋₆ alkoxy, C₁₋₆ alkylthio, —(X⁴)₀₋₁-(3-10 membered heterocycloalkyl), —(X⁴)₀₋₁-(5-10 membered heteroaryl), —(X⁴)₀₋₁-(3-7 membered cycloalkyl), —(X⁴)₀₋₁-C(=Y⁴)N(H)(R⁴ᵃ), —(X⁴)₀₋₁-C(=Y⁴)NH₂, —(X⁴)₀₋₁—C(=Y⁴)N(R⁴ᵃ)(R⁴ᵇ), —(X⁴)₀₋₁-C(=Y⁴)OR⁴ᵃ, —(X⁴)₀₋₁-C(=Y⁴)OH, —(X⁴)₀₋₁-N(H)C(=Y⁴)(R⁴ᵃ), —(X⁴)₀₋₁—N(R⁴ᵇ)C(=Y⁴)(R⁴ᵃ), —(X⁴)₀₋₁-N(H)C(=Y⁴)OR⁴ᵃ, —(X⁴)₀₋₁-N(R⁴ᵇ)C(=Y⁴)OR⁴, —(X⁴)₀₋₁—S(O)₁₋₂R⁴ᵃ, —(X⁴)₀₋₁-N(H)S(O)₁₋₂R⁴ᵃ, —(X⁴)₀₋₁—N(R⁴ᵇ)S(O)₁₋₂R⁴ᵃ, —(X⁴)₀₋₁—S(O)₀₋₁N(H)(R⁴ᵃ), —(X⁴)₀₋₁—S(O)₀₋₁N(R⁴ᵇ)(R⁴ᵃ), —(X⁴)₀₋₁—S(O)₀₋₁NH₂, —(X⁴)₀₋₁—S(=O)(=NR⁴ᵇ)R⁴ᵃ, —(X⁴)₀₋₁-C(=Y⁴)R⁴ᵃ, —(X⁴)₀₋₁—C(=Y⁴)H, —(X⁴)₀₋₁-C(=NOH)R⁴ᵃ, —(X⁴)₀₋₁-C(=NOR⁴ᵇ)R⁴ᵃ, —(X⁴)₀₋₁-NHC(=Y⁴)N(H)(R⁴ᵃ), —(X⁴)₀₋₁—NHC(=Y⁴)NH₂, —(X⁴)₀₋₁-NHC(=Y⁴)N(R⁴ᵇ)(R⁴ᵃ), —(X⁴)₀₋₁-NR⁴ᵃC(=Y⁴)N(H)(R⁴ᵃ), —(X⁴)₀₋₁—N(R⁴ᵃ)C(=Y⁴)NH₂, —(X⁴)₀₋₁-OC(=Y⁴)R⁴ᵃ, —(X⁴)₀₋₁-OC(=Y⁴)H, —(X⁴)₀₋₁—OC(=Y⁴)OR⁴ᵃ, —(X⁴)₀₋₁—OP(=Y⁴)(OR⁴ᵃ)(OR⁴ᵇ), —SC(=Y⁴)OR⁴ᵃ and —SC(=Y⁴)N(R⁴ᵃ)(R⁴ᵇ) wherein R⁴ᵃ and R⁴ᵇ at each occurrence are each independently selected from the group consisting of C₁₋₆ alkyl, C₁₋₆ haloalkyl, C₁₋₆ heteroalkyl, 6-10 membered aryl, 3-7 membered cycloalkyl, 5-10 membered heteroaryl, 3-7 membered heterocycloalkyl, 6-10 membered aryl-C₁₋₄ alkyl, 3-7 membered cycloalkyl-C₁₋₄ alkyl, 5-10 membered heteroaryl-C₁₋₄ alkyl and 3-7 membered heterocycloalkyl-C₁₋₄ alkyl, and X⁴ is selected from the group consisting of C₁₋₄ alkylene, C₁₋₄ haloalkylene, C₁₋₄ heteroalkylene, C₂₋₄ alkenylene and C₂₋₄ alkynylene; Y⁴ is O, NR⁴ᶜ or S wherein R⁴ᶜ is hydrogen or C₁₋₆ alkyl; wherein the aromatic and aliphatic portions of R⁴ is independently further substituted with 0 to 4 R⁴⁴ substituents selected from the group consisting of —Cl, —Br, I, —CN, —NO₂, —SF₅, —OH, —NH₂, —CF₃, =O, C₁₋₆ alkyl, C₁₋₆ haloalkyl, C₁₋₆ heteroalkyl, C₁₋₆ alkoxy, C₁₋₆ alkylthio, 3-6 membered cycloalkyl, 3-6 membered heterocycloalkyl, —C(=O)N(H)(C₁₋₆ alkyl), —C(=O)N(C₁₋₆ alkyl)₂, —C(=O)NH₂, —C(=O)OC₁₋₆ alkyl, —C(=O)OH, —N(H)C(=O)(C₁₋₆ alkyl), —N(C₁₋₆ alkyl)C(=O)(C₁₋₆ alkyl), —N(H)C(=O)OC₁₋₆ alkyl, —N(C₁₋₆ alkyl)C(=O)OC₁₋₆ alkyl, —S(O)₁₋₂C₁₋₆ alkyl, —N(H)S(O)₁₋₂C₁₋₆ alkyl, —N(C₁₋₆ alkyl)S(O)₁₋₂C₁₋₆ alkyl, —S(O)₀₋₁N(H)C₁₋₆ alkyl), —S(O)₀₋₁N(C₁₋₆ alkyl)₂, —S(O)₀₋₁NH₂, —C(=O)C₁₋₆ alkyl, —C(=NOH)C₁₋₆ alkyl, —C(=NOC₁₋₆ alkyl)C₁₋₆ alkyl, —NHC(=O)N(H)(C₁₋₆ alkyl), —NHC(=O)N(C₁₋₆ alkyl)₂, —NHC(=O)NH₂, —N(C₁₋₆ alkyl)C(=O)N(H)(C₁₋₆ alkyl), —N(C₁₋₆ alkyl)C(=O)NH₂, —OC(=O)C₁₋₆ alkyl, —OC(=O)OC₁₋₆ alkyl, —OP(=O)(OC₁₋₆ alkyl)₂, —SC(=O)OC₁₋₆ alkyl and —SC(=O)N(C₁₋₆ alkyl)₂; and the remainder R⁴, if present on said ring, is each independently selected from the group consisting of —F, —Cl, —Br, I, —(X⁴)₀₋₁-CN, —(X⁴)₀₋₁-NO₂, —(X⁴)₀₋₁—SF₅, —(X⁴)₀₋₁-OH, —(X⁴)₀₋₁-NH₂, —(X⁴)₀₋₁-N(H)(R⁴ᵃ), —(X⁴)₀₋₁-N(R⁴ᵇ)(R⁴ᵃ), —(X⁴)₀₋₁-CF₃, —(X⁴)₀₋₁-C(=Y⁴)R⁴ᵃ, —(X⁴)₀₋₁-C(=Y⁴)H, C₁₋₆ alkyl, C₁₋₆ haloalkyl, C₁₋₆ heteroalkyl, C₁₋₆ alkoxy and C₁₋₆ alkylthio wherein X⁴ is selected from the group consisting of C₁₋₄ alkylene, C₁₋₄ haloalkylene, C₁₋₄ heteroalkylene, C₂₋₄ alkenylene and C₂₋₄ alkynylene and R⁴ᵃ and R⁴ᵇ is each independently selected from the group consisting of: C₁₋₆ alkyl, C₁₋₆ haloalkyl and C₁₋₆ heteroalkyl.

5. The compound of claim 1, wherein the ring

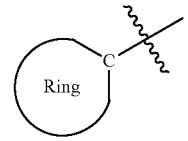

is selected from the group consisting of:

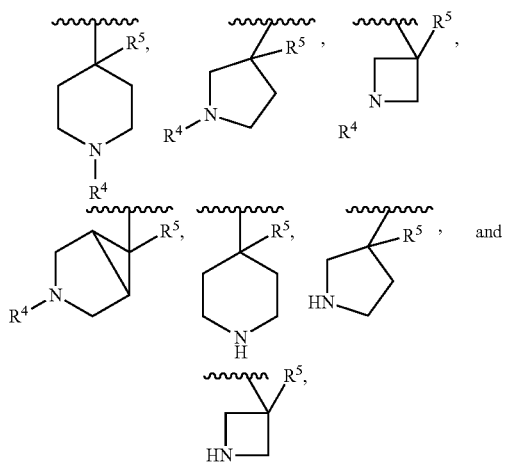

wherein R⁵ is defined according to claim 1.

6. The compound of claim 1, wherein said

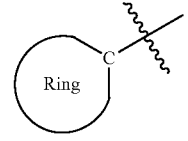 [SMILES: *C(C)C]

is selected from the group consisting of:

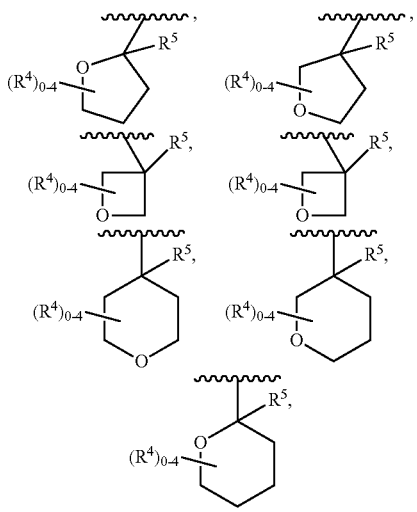

wherein R⁵ is defined according to claim 1, and wherein R⁴ is selected from the group consisting of: —F, —Cl, —Br, —I, —(X⁴)₀₋₁-CN, —(X⁴)₀₋₁—NO₂, —(X⁴)₀₋₁—SF₅, —(X⁴)₀₋₁—OH, —(X⁴)₀₋₁-NH₂, —(X⁴)₀₋₁—N(H)(R⁴ᵃ), —(X⁴)₀₋₁-N(R⁴ᵇ)(R⁴ᵃ), —(X⁴)₀₋₁—CF₃, $C_{1-6}$ alkyl, $C_{1-6}$ haloalkyl, $C_{1-6}$ heteroalkyl, $C_{1-6}$ alkoxy and $C_{1-6}$ alkylthio wherein X⁴ is selected from the group consisting of $C_{1-4}$ alkylene, $C_{1-4}$ haloalkylene, $C_{1-4}$ heteroalkylene, $C_{2-4}$ alkenylene and $C_{2-4}$ alkynylene and R⁴ᵃ and R⁴ᵇ is each independently selected from the group consisting of: $C_{1-6}$ alkyl, $C_{1-6}$ haloalkyl and $C_{1-6}$ heteroalkyl.

7. The compound of claim 1, wherein R⁵ is selected from the group consisting of hydrogen, $C_{1-4}$ alkyl, $C_{1-4}$ haloalkyl, hydroxy, OR⁵ᵃ, —CN, —F, —Cl, —Br and —I.

8. The compound of claim 1, wherein R¹ is selected from the group consisting of pyrrolidin-1-yl, phenyl, piperidin-1-yl, pyrrol-1-yl, azetidin-1-yl, morpholin-4-yl, homomorpholin-4-yl, 2-oxa-5-azabicyclo[2.2.1]hept-5-yl, 3-oxa-8-azabicyclo[3.2.1]oct-8-yl, 2-oxa-6-azaspiro[3.3]hept-6-yl, -8-oxa-3-azabicyclo[3.2.1]octane, methyl, isopropyl, isobutyl, cyclopropyl, pyrazol-1-yl, 4,5,6,7-tetrahydro-1H-imidazo[4,5-c]pyridin-5-yl, 3,5,6,7,8,8a-hexahydroimidazo[1,2-a]pyrazin-7-yl, 3-azabicyclo[3.2.0]heptan-3-yl, 3-azabicyclo[3.1.0]hexan-3-yl, 2-azabicyclo[2.1.1]hexan-2-yl, 2-azabicyclo[3.1.0]hexan-2-yl, 2-oxa-7-azaspiro[4.4]nonan-7-yl, 2-oxa-6-azaspiro[3.4]octan-6-yl, —N(H)R¹ᵃ, and —N(R¹ᵃ)(R¹ᵇ).

9. The compound of claim 1, wherein R² is hydrogen.
10. The compound of claim 1, wherein m is 0.
11. The compound of claim 1, wherein m is 1.
12. The compound of claim 1, wherein n is 0.
13. The compound of claim 1, wherein n is 1.
14. The compound of claim 1, wherein R⁴ is selected from the group consisting of $C_{1-6}$ alkyl, $C_{1-6}$ haloalkyl, —(X⁴)₀₋₁-(3-10 membered heterocycloalkyl), —(X⁴)₀₋₁—C(=Y⁴)OR⁴ᵃ, —(X⁴)₀₋₁—S(=Y⁴)₁₋₂R⁴ᵃ and —(X⁴)₀₋₁-C(=Y⁴)R⁴ᵃ, wherein R⁴ᵃ is selected from the group consisting of $C_{1-6}$ alkyl, $C_{1-6}$ haloalkyl, 3-7 membered cycloalkyl, 5-10 membered heteroaryl, and 3-7 membered heterocycloalkyl, and X⁴ is CH₂, and Y⁴ is O; wherein the aromatic and aliphatic portions of R⁴ is independently further substituted with 0 to 4 R⁴⁴ substituents selected from the group consisting of —OH, and $C_{1-6}$ alkyl.

15. The compound of claim 1, wherein R⁶ is hydrogen.
16. The compound of claim 1, selected from the group of compounds in Table 1:

TABLE 1

| No. | Structure | Name |
|---|---|---|
| 1 | 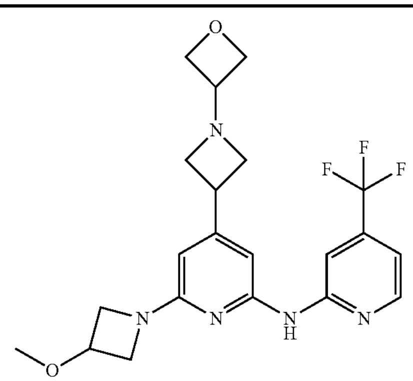 | [6-(3-Methoxy-azetidin-1-yl)-4-(1-oxetan-3-yl-azetidin-3-yl)-pyridin-2-yl]-(4-trifluoromethyl-pyridin-2-yl)-amine |
| 2 | 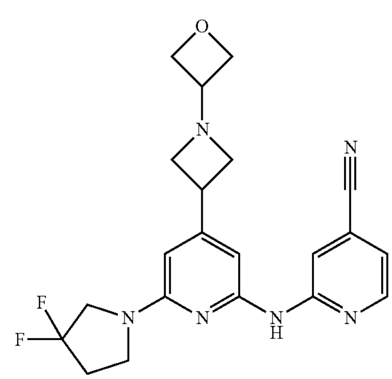 [SMILES: N#Cc1ccnc(Nc2cc(C3CN(C4COC4)C3)cc(N3CCC(F)(F)C3)n2)c1] | 2-[6-(3,3-Difluoro-pyrrolidin-1-yl)-4-(1-oxetan-3-yl-azetidin-3-yl)-pyridin-2-ylamino]-isonicotinonitrile |

TABLE 1-continued

| No. | Structure | Name |
|---|---|---|
| 3 | 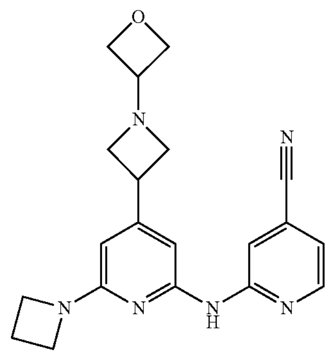 [SMILES: N#Cc1ccnc(Nc2cc(C3CN(C4COC4)C3)cc(N3CCC3)n2)c1] | 2-[6-Azetidin-1-yl-4-(1-oxetan-3-yl-azetidin-3-yl)-pyridin-2-ylamino]-isonicotinonitrile |
| 4 | 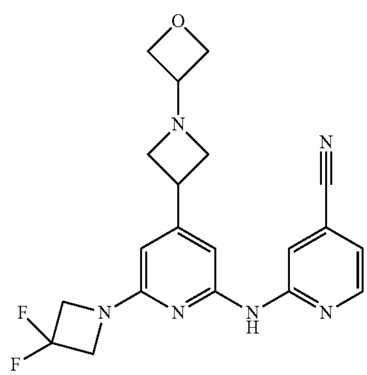 [SMILES: N#Cc1ccnc(Nc2cc(C3CN(C4COC4)C3)cc(N3CC(F)(F)C3)n2)c1] | 2-[6-(3,3-Difluoro-azetidin-1-yl)-4-(1-oxetan-3-yl-azetidin-3-yl)-pyridin-2-ylamino]-isonicotinonitrile |
| 5 | 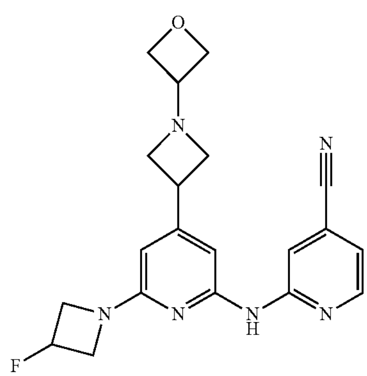 [SMILES: N#Cc1ccnc(Nc2cc(C3CN(C4COC4)C3)cc(N3CC(F)C3)n2)c1] | 2-[6-(3-Fluoro-azetidin-1-yl)-4-(1-oxetan-3-yl-azetidin-3-yl)-pyridin-2-ylamino]-isonicotinonitrile |
| 6 | 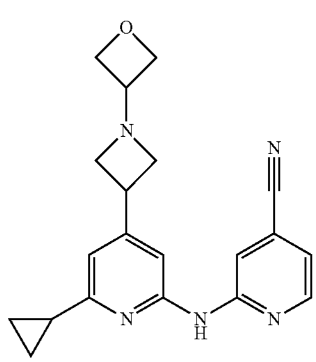 [SMILES: N#Cc1ccnc(Nc2cc(C3CN(C4COC4)C3)cc(C3CC3)n2)c1] | 2-[6-Cyclopropyl-4-(1-oxetan-3-yl-azetidin-3-yl)-pyridin-2-ylamino]-isonicotinonitrile |

TABLE 1-continued

| No. | Structure | Name |
|---|---|---|
| 7 | 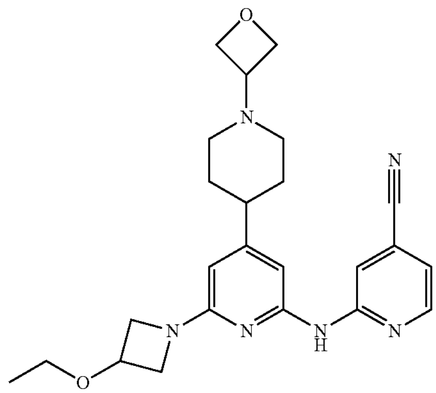 [SMILES: CCOC1CN(c2cc(C3CCN(C4COC4)CC3)cc(Nc3cc(C#N)ccn3)n2)C1] | 2-[6-(3-Ethoxy-azetidin-1-yl)-1'-oxetan-3-yl-1',2',3',4',5',6'-hexahydro-[4,4']bipyridin-yl-2-ylamino]-isonicotino-nitrile |
| 8 | 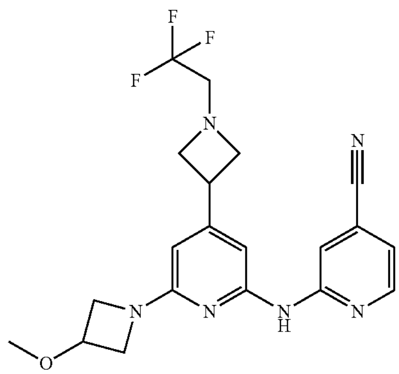 [SMILES: COC1CN(c2cc(C3CN(CC(F)(F)F)C3)cc(Nc3cc(C#N)ccn3)n2)C1] | 2-{6-(3-Methoxy-azetidin-1-yl)-4-[1-(2,2,2-trifluoro-ethyl)-azetidin-3-yl]-pyridin-2-ylamino}-isonicotinonitrile |
| 18 | 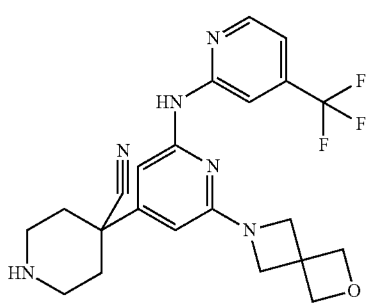 [SMILES: N#CC1(c2cc(Nc3cc(C(F)(F)F)ccn3)nc(N3CC4(COC4)C3)c2)CCNCC1] | 6'-(2-Oxa-6-aza-spiro[3.3]hept-6-yl)-2'-(4-trifluoromethyl-pyridin-2-ylamino)-2,3,5,6-tetrahydro-1H-[4,4']bipyridin-yl-4-carbonitrile |
| 19 | 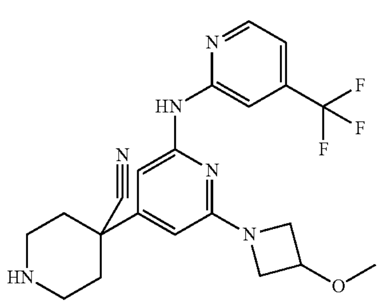 [SMILES: COC1CN(c2cc(C3(C#N)CCNCC3)cc(Nc3cc(C(F)(F)F)ccn3)n2)C1] | 6'-(3-Methoxy-azetidin-1-yl)-2'-(4-trifluoromethyl-pyridin-2-ylamino)-2,3,5,6-tetrahydro-1H-[4,4']bipyridinyl-4-carbonitrile |

TABLE 1-continued

| No. | Structure | Name |
|---|---|---|
| 21 | 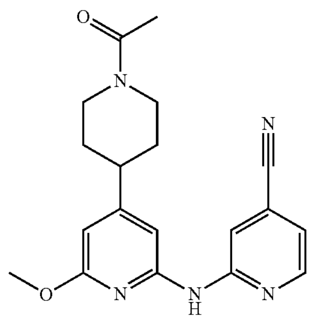 [SMILES: COc1cc(C2CCN(C(C)=O)CC2)cc(Nc2cc(C#N)ccn2)n1] | 2-(1'-Acetyl-6-methoxy-1',2',3',4',5',6'-hexahydro-[4,4']bipyridinyl-2-ylamino)-isonicotinonitrile |
| 22 | 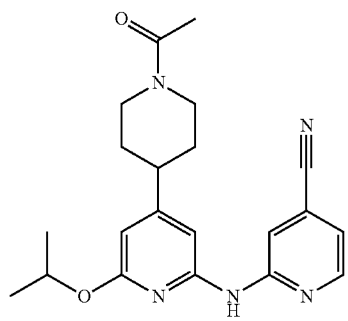 [SMILES: CC(=O)N1CCC(c2cc(Nc3cc(C#N)ccn3)nc(OC(C)C)c2)CC1] | 2-(1'-Acetyl-6-isopropoxy-1',2',3',4',5',6'-hexahydro-[4,4']bipyridinyl-2-ylamino)-isonicotinonitrile |
| 23 | 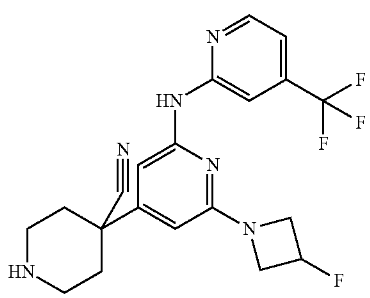 [SMILES: N#CC1(c2cc(Nc3cc(C(F)(F)F)ccn3)nc(N3CC(F)C3)c2)CCNCC1] | 6'-(3-Fluoro-azetidin-1-yl)-2'-(4-trifluoromethyl-pyridin-2-ylamino)-2,3,5,6-tetrahydro-1H-[4,4']bipyridinyl-4-carbonitrile |
| 25 | 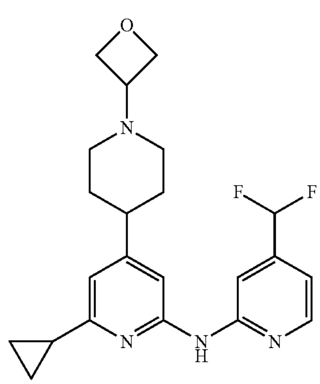 [SMILES: FC(F)c1ccnc(Nc2cc(C3CCN(C4COC4)CC3)cc(C3CC3)n2)c1] | (6-Cyclopropyl-1'-oxetan-3-yl-1',2',3',4',5',6'-hexahydro-[4,4']bipyridinyl-2-yl)-(4-difluoromethyl-pyridin-2-yl)-amine |

TABLE 1-continued

| No. | Structure | Name |
|---|---|---|
| 26 | 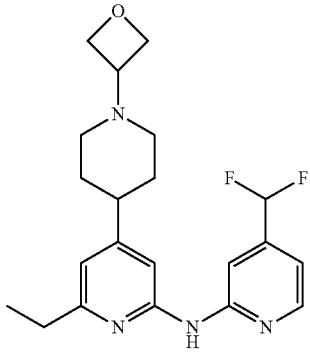 [SMILES: CCc1cc(C2CCN(C3COC3)CC2)cc(Nc2cc(C(F)F)ccn2)n1] | (4-Difluoromethyl-pyridin-2-yl)-(6-ethyl-1'-oxetan-3-yl-1',2',3',4',5',6'-hexahydro-[4,4']bipyridinyl-2-yl)-amine |
| 27 | 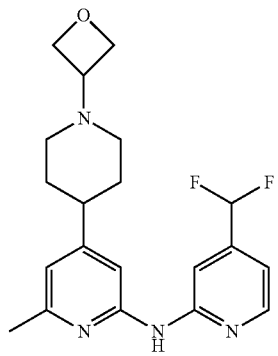 [SMILES: Cc1cc(C2CCN(C3COC3)CC2)cc(Nc2cc(C(F)F)ccn2)n1] | (4-Difluoromethyl-pyridin-2-yl)-(6-methyl-1'-oxetan-3-yl-1',2',3',4',5',6'-hexahydro-[4,4']bipyridinyl-2-yl)-amine |
| 28 | 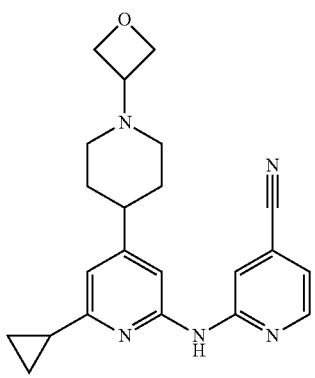 [SMILES: N#Cc1ccnc(Nc2cc(C3CCN(C4COC4)CC3)cc(C3CC3)n2)c1] | 2-(6-Cyclopropyl-1'-oxetan-3-yl-1',2',3',4',5',6'-hexahydro-[4,4']bipyridinyl-2-ylamino)-isonicotinonitrile |
| 29 | 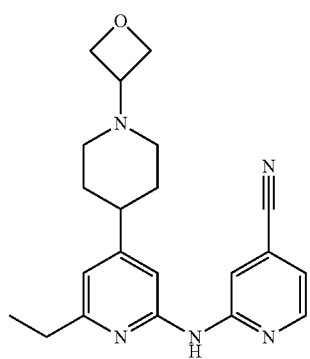 [SMILES: CCc1cc(C2CCN(C3COC3)CC2)cc(Nc2cc(C#N)ccn2)n1] | 2-(6-Ethyl-1'-oxetan-3-yl-1',2',3',4',5',6'-hexahydro-[4,4']bipyridinyl-2-ylamino)-isonicotinonitrile |

TABLE 1-continued

| No. | Structure | Name |
|---|---|---|
| 30 | 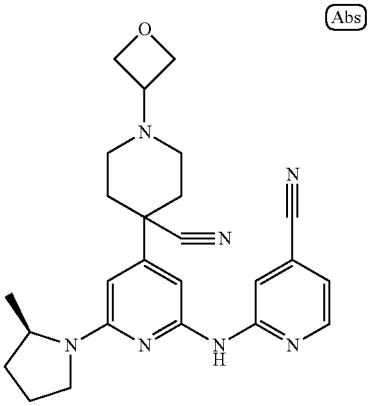 [SMILES: C[C@@H]1CCCN1c1cc(C2(C#N)CCN(C3COC3)CC2)cc(Nc2cc(C#N)ccn2)n1] (Abs) | 2'-(4-Cyano-pyridin-2-ylamino)-6'-((R)-2-methyl-pyrrolidin-1-yl)-1-oxetan-3-yl-2,3,5,6-tetrahydro-1 H-[4,4']bipyridinyl-4-carbonitrile |
| 31 | 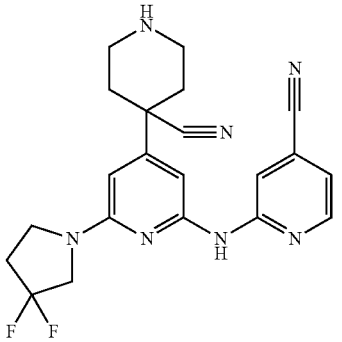 [SMILES: N#Cc1ccnc(Nc2cc(C3(C#N)CCNCC3)cc(N3CCC(F)(F)C3)n2)c1] | 2'-(4-Cyano-pyridin-2-ylamino)-6'-(3,3-difluoro-pyrrolidin-1-yl)-2,3,5,6-tetrahydro-1H-[4,4']bipyridinyl-4-carbonitrile |
| 33 | 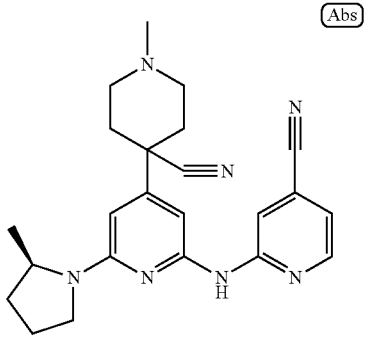 [SMILES: C[C@@H]1CCCN1c1cc(C2(C#N)CCN(C)CC2)cc(Nc2cc(C#N)ccn2)n1] (Abs) | 2'-(4-Cyano-pyridin-2-ylamino)-1-methyl-6'-((R)-2-methyl-pyrrolidin-1-yl)-2,3,5,6-tetrahydro-1H-[4,4']bipyridinyl-4-carbonitrile |
| 34 | 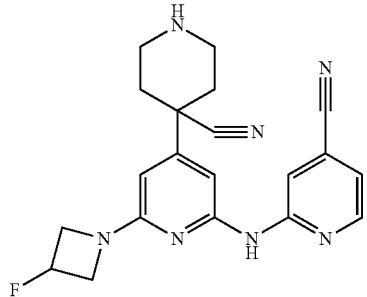 [SMILES: N#Cc1ccnc(Nc2cc(C3(C#N)CCNCC3)cc(N3CC(F)C3)n2)c1] | 2'-(4-Cyano-pyridin-2-ylamino)-6'-(3-fluoro-azetidin-1-yl)-2,3,5,6-tetrahydro-1H-[4,4']bipyridinyl-4-carbonitrile |

TABLE 1-continued

| No. | Structure | Name |
|---|---|---|
| 35 | 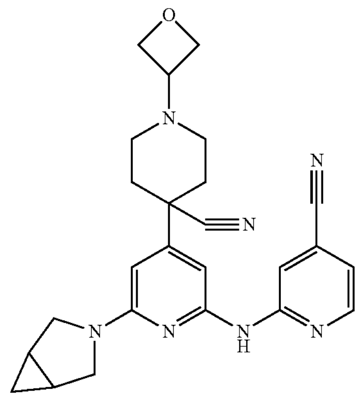 [SMILES: N#Cc1ccnc(Nc2cc(C3(C#N)CCN(C4COC4)CC3)cc(N3CC4CC4C3)n2)c1] | 6'-(3-Aza-bicyclo[3.1.0]hex-3-yl)-2'-(4-cyano-pyridin-2-ylamino)-1-oxetan-3-yl-2,3,5,6-tetrahydro-1H-[4,4']bipyridinyl-4-carbonitrile |
| 36 | 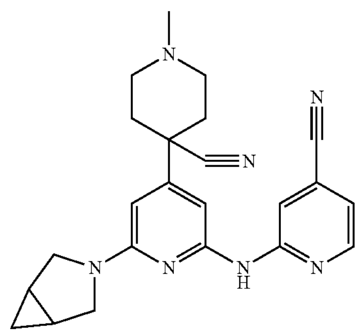 [SMILES: CN1CCC(C#N)(c2cc(Nc3cc(C#N)ccn3)nc(N3CC4CC4C3)c2)CC1] | 6'-(3-Aza-bicyclo[3.1.0]hex-3-yl)-2'-(4-cyano-pyridin-2-ylamino)-1-methyl-2,3,5,6-tetrahydro-1H-[4,4']bipyridinyl-4-carbonitrile |
| 37 | 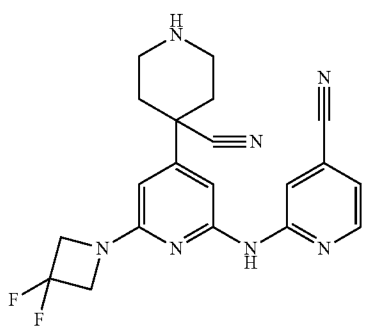 [SMILES: N#Cc1ccnc(Nc2cc(C3(C#N)CCNCC3)cc(N3CC(F)(F)C3)n2)c1] | 2'-(4-Cyano-pyridin-2-ylamino)-6'-(3,3-difluoro-azetidin-1-yl)-2,3,5,6-tetrahydro-1H-[4,4']bipyridinyl-4-carbonitrile |
| 38 | 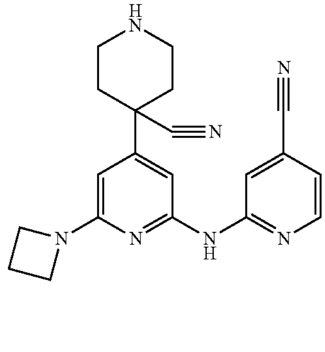 [SMILES: N#Cc1ccnc(Nc2cc(C3(C#N)CCNCC3)cc(N3CCC3)n2)c1] | 6'-Azetidin-1-yl-2'-(4-cyano-pyridin-2-ylamino)-2,3,5,6-tetrahydro-1H-[4,4']bipyridinyl-4-carbonitrile |

TABLE 1-continued

| No. | Structure | Name |
|---|---|---|
| 39 | 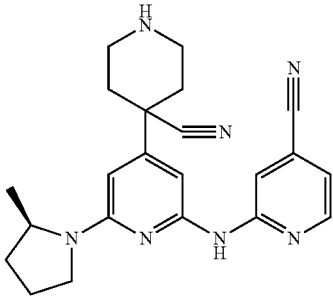 (Abs) | 2'-(4-Cyano-pyridin-2-ylamino)-6'-((R)-2-methyl-pyrrolidin-1-yl)-2,3,5,6-tetrahydro-1H-[4,4']bipyridinyl-4-carbonitrile |
| 40 | 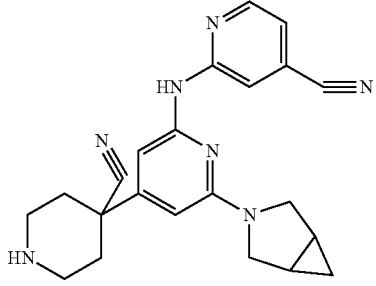 [SMILES: N#Cc1ccnc(Nc2cc(C3(C#N)CCNCC3)cc(N3CC4CC4C3)n2)c1] | 6'-(3-Aza-bicyclo[3.1.0]hex-3-yl)-2'-(4-cyano-pyridin-2-ylamino)-2,3,5,6-tetrahydro-1H-[4,4']bipyridinyl-4-carbonitrile |
| 42 | 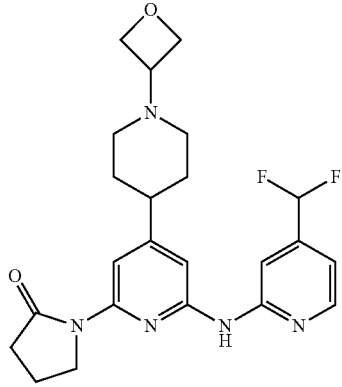 [SMILES: O=C1CCCN1c1cc(C2CCN(C3COC3)CC2)cc(Nc2cc(C(F)F)ccn2)n1] | 1-[6-(4-Difluoromethyl-pyridin-2-ylamino)-1'-oxetan-3-yl-1',2',3',4',5',6'-hexahydro-[4,4']bipyridinyl-2-yl]-pyrrolidin-2-one |
| 43 | 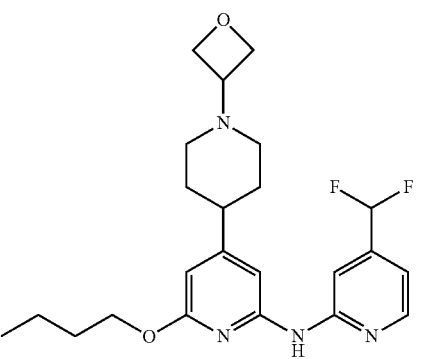 [SMILES: CCCCOc1cc(C2CCN(C3COC3)CC2)cc(Nc2cc(C(F)F)ccn2)n1] | (6-Butoxy-1'-oxetan-3-yl-1',2',3',4',5',6'-hexahydro-[4,4']bipyridinyl-2-yl)-(4-difluoromethyl-pyridin-2-yl)-amine |

TABLE 1-continued

| No. | Structure | Name |
|---|---|---|
| 44 | 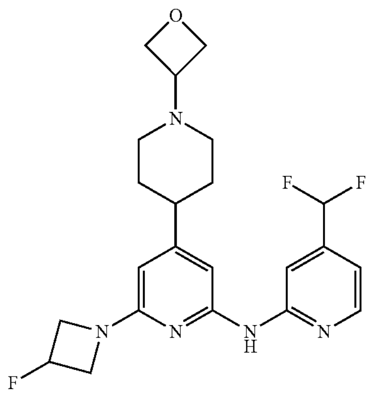 [SMILES: FC1CN(c2cc(C3CCN(C4COC4)CC3)cc(Nc3cc(C(F)F)ccn3)n2)C1] | (4-Difluoromethyl-pyridin-2-yl)-[6-(3-fluoro-azetidin-1-yl)-1'-oxetan-3-yl-1',2',3',4',5',6'-hexahydro-[4,4']bipyridin-yl-2-yl]-amine |
| 46 | 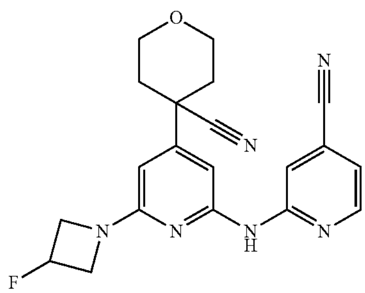 [SMILES: N#Cc1ccnc(Nc2cc(C3(C#N)CCOCC3)cc(N3CC(F)C3)n2)c1] | 2-[4-(4-Cyano-tetrahydro-pyran-4-yl)-6-(3-fluoro-azetidin-1-yl)-pyridin-2-ylamino]-isonicotinonitrile |
| 47 | 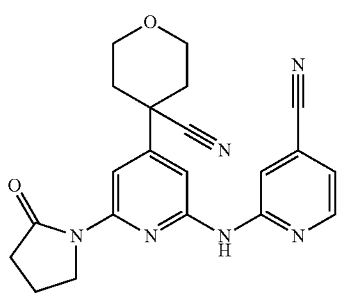 [SMILES: N#Cc1ccnc(Nc2cc(C3(C#N)CCOCC3)cc(N3CCCC3=O)n2)c1] | 2-[4-(4-Cyano-tetrahydro-pyran-4-yl)-6-(2-oxo-pyrrolidin-1-yl)-pyridin-2-ylamino]-isonicotinonitrile |
| 48 | 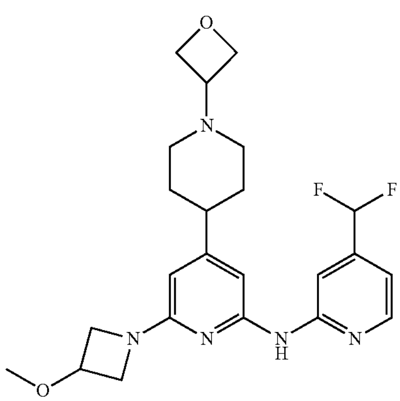 [SMILES: COC1CN(c2cc(C3CCN(C4COC4)CC3)cc(Nc3cc(C(F)F)ccn3)n2)C1] | (4-Difluoromethyl-pyridin-2-yl)-[6-(3-methoxy-azetidin-1-yl)-1'-oxetan-3-yl-1',2',3',4',5',6'-hexahydro-[4,4']bipyridinyl-2-yl]-amine |

TABLE 1-continued

| No. | Structure | Name |
|---|---|---|
| 49 | 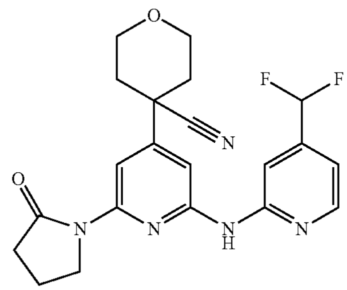 [SMILES: N#CC1(c2cc(Nc3cc(C(F)F)ccn3)nc(N3CCCC3=O)c2)CCOCC1] | 4-[2-(4-Difluoromethyl-pyridin-2-ylamino)-6-(2-oxo-pyrrolidin-1-yl)-pyridin-4-yl]-tetrahydro-pyran-4-carbonitrile |
| 50 | 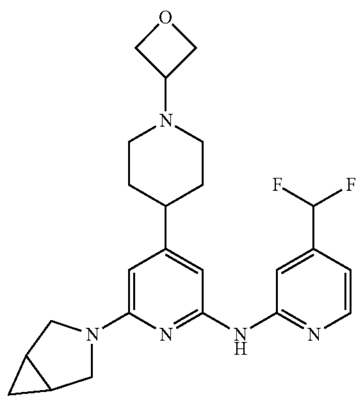 [SMILES: FC(F)c1ccnc(Nc2cc(C3CCN(C4COC4)CC3)cc(N3CC4CC4C3)n2)c1] | [6-(3-Aza-bicyclo[3.1.0]hex-3-yl)-1'-oxetan-3-yl-1',2',3',5',6'-hexahydro-[4,4']bi-pyridinyl-2-yl]-(4-difluoromethyl-pyridin-2-yl)-amine |
| 51 | 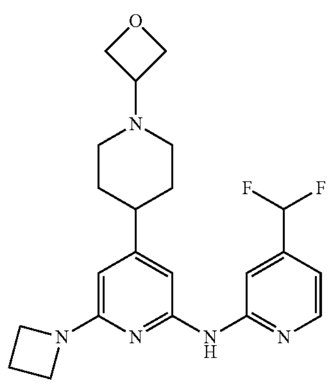 [SMILES: FC(F)c1ccnc(Nc2cc(C3CCN(C4COC4)CC3)cc(N3CCC3)n2)c1] | (6-Azetidin-1-yl-1'-oxetan-3-yl-1',2',3',4',5',6'-hexahydro-[4,4']bipyridinyl-2-yl)-(4-difluoromethyl-pyridin-2-yl)-amine |
| 52 | 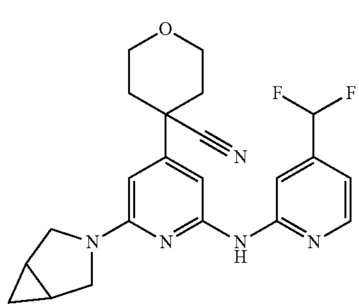 [SMILES: N#CC1(c2cc(Nc3cc(C(F)F)ccn3)nc(N3CC4CC4C3)c2)CCOCC1] | 4-[2-(3-Aza-bicyclo[3.1.0]hex-3-yl)-6-(4-difluoromethyl-pyridin-2-ylamino)-pyridin-4-yl]-tetrahydro-pyran-4-carbonitrile |

TABLE 1-continued

| No. | Structure | Name |
|---|---|---|
| 53 | 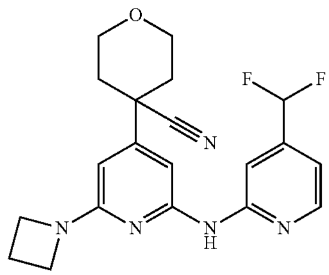 [SMILES: N#CC1(c2cc(Nc3cc(C(F)F)ccn3)nc(N3CCC3)c2)CCOCC1] | 4-[2-Azetidin-1-yl-6-(4-difluoromethyl-pyridin-2-ylamino)-pyridin-4-yl]-tetrahydro-pyran-4-carbonitrile |
| 54 | 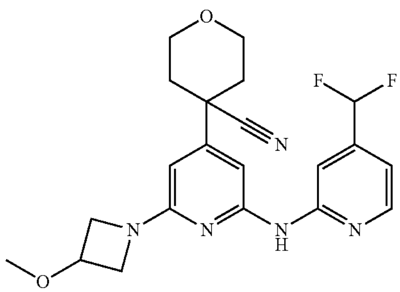 [SMILES: COC1CN(c2cc(C3(C#N)CCOCC3)cc(Nc3cc(C(F)F)ccn3)n2)C1] | 4-[2-(4-Difluoromethyl-pyridin-2-ylamino)-6-(3-methoxy-azetidin-1-yl)-pyridin-4-yl]-tetrahydro-pyran-4-carbonitrile |
| 55 | 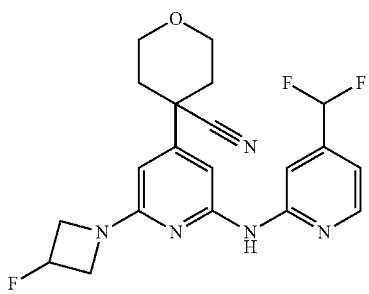 [SMILES: N#CC1(c2cc(Nc3cc(C(F)F)ccn3)nc(N3CC(F)C3)c2)CCOCC1] | 4-[2-(4-Difluoromethyl-pyridin-2-ylamino)-6-(3-fluoro-azetidin-1-yl)-pyridin-4-yl]-tetrahydro-pyran-4-carbonitrile |
| 56 | 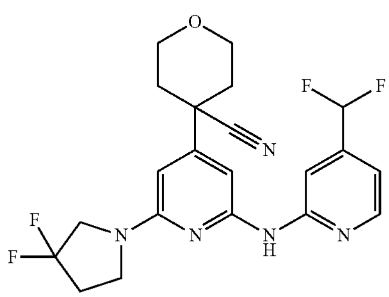 [SMILES: N#CC1(c2cc(Nc3cc(C(F)F)ccn3)nc(N3CCC(F)(F)C3)c2)CCOCC1] | 4-[2-(4-Difluoromethyl-pyridin-2-ylamino)-6-(3,3-difluoro-pyrrolidin-1-yl)-pyridin-4-yl]-tetrahydro-pyran-4-carbonitrile |
| 57 | 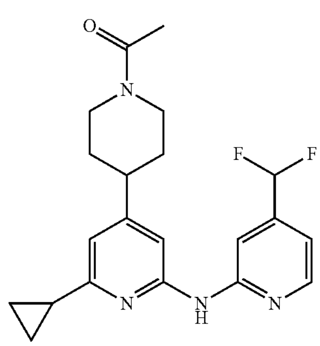 [SMILES: CC(=O)N1CCC(c2cc(Nc3cc(C(F)F)ccn3)nc(C3CC3)c2)CC1] | 1-[6'-Cyclopropyl-2'-(4-difluoromethyl-pyridin-2-ylamino)-3,4,5,6-tetrahydro-2H-[4,4']bipyridinyl-1-yl]-ethanone |

TABLE 1-continued

| No. | Structure | Name |
|---|---|---|
| 58 | 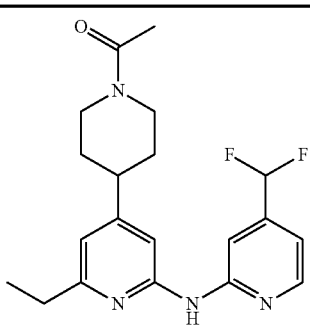 | 1-[2'-(4-Difluoromethyl-pyridin-2-ylamino)-6'-ethyl-3,4,5,6-tetrahydro-2H-[4,4']bipyridinyl-1-yl]-ethanone |
| 59 | 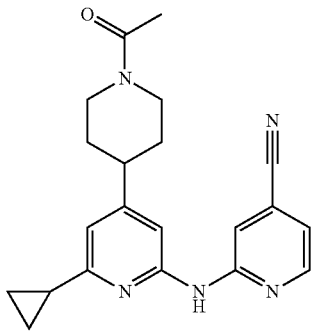 | 2-(1'-Acetyl-6-cyclopropyl-1',2',3',4',5',6'-hexahydro-[4,4']bipyridinyl-2-ylamino)-isonicotinonitrile |
| 60 | 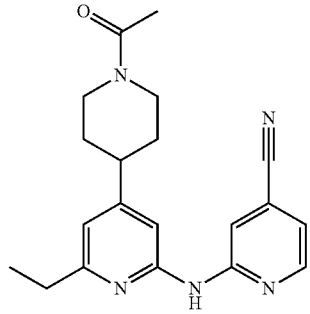 | 2-(1'-Acetyl-6-ethyl-1',2',3',4',5',6'-hexahydro-[4,4']bipyridinyl-2-ylamino)-isonicotinonitrile |
| 61 | 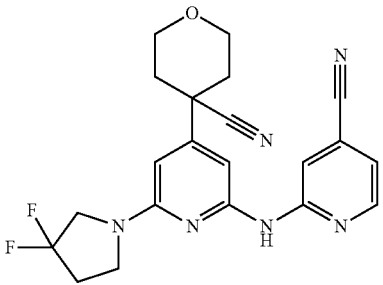 [SMILES: N#Cc1ccnc(Nc2cc(C3(C#N)CCOCC3)cc(N3CCC(F)(F)C3)n2)c1] | 2-[4-(4-Cyano-tetrahydro-pyran-4-yl)-6-(3,3-difluoro-pyrrolidin-1-yl)-pyridin-2-ylamino]-isonicotinonitrile |
| 62 | 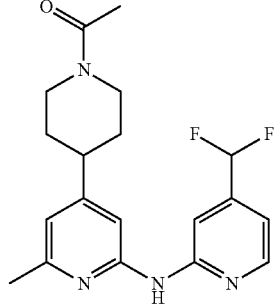 [SMILES: CC(=O)N1CCC(c2cc(C)nc(Nc3cc(C(F)F)ccn3)c2)CC1] | 1-[2'-(4-Difluoromethyl-pyridin-2-ylamino)-6'-methyl-3,4,5,6-tetrahydro-2H-[4,4']bipyridinyl-1-yl]-ethanone |

TABLE 1-continued

| No. | Structure | Name |
|---|---|---|
| 63 | 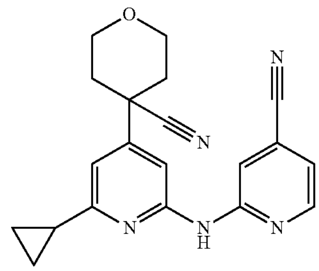 [SMILES: N#Cc1ccnc(Nc2cc(C3(C#N)CCOCC3)cc(C3CC3)n2)c1] | 2-[4-(4-Cyano-tetrahydro-pyran-4-yl)-6-cyclopropyl-pyridin-2-ylamino]-isonicotinonitrile |
| 64 | 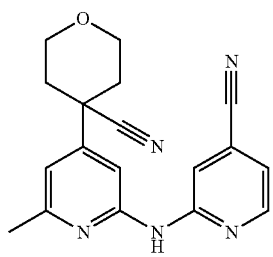 [SMILES: Cc1cc(C2(C#N)CCOCC2)cc(Nc2cc(C#N)ccn2)n1] | 2-[4-(4-Cyano-tetrahydro-pyran-4-yl)-6-methyl-pyridin-2-ylamino]-isonicotinonitrile |
| 67 | 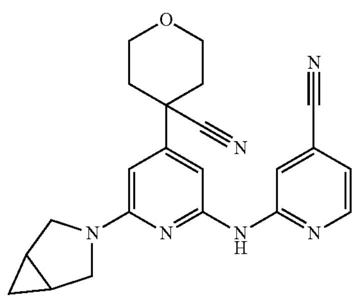 [SMILES: N#Cc1ccnc(Nc2cc(C3(C#N)CCOCC3)cc(N3CC4CC4C3)n2)c1] | 2-[6-(3-Aza-bicyclo[3.1.0]hex-3-yl)-4-(4-cyano-tetrahydro-pyran-4-yl)-pyridin-2-ylamino]-isonicotinonitrile |
| 68 | 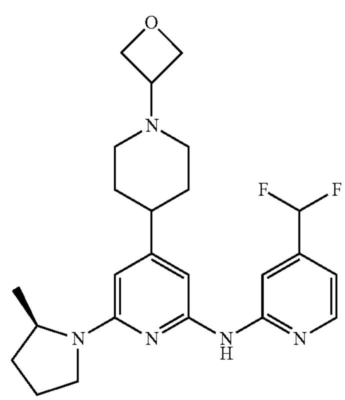 [SMILES: C[C@@H]1CCCN1c1cc(C2CCN(C3COC3)CC2)cc(Nc2cc(C(F)F)ccn2)n1] | (4-Difluoromethyl-pyridin-2-yl)-[6-((R)-2-methyl-pyrrolidin-1-yl)-1'-oxetan-3-yl-1',2',3',4',5',6'-hexahydro-[4,4']bipyridinyl-2-yl]-amine |
| 69 | 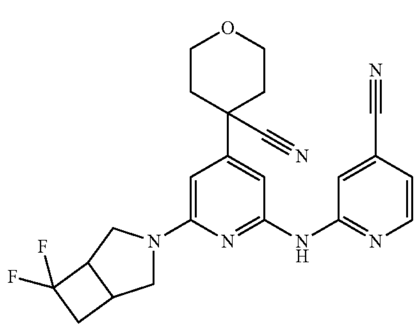 [SMILES: N#Cc1ccnc(Nc2cc(C3(C#N)CCOCC3)cc(N3CC4CC(F)(F)C4C3)n2)c1] | 2-[4-(4-Cyano-tetrahydro-pyran-4-yl)-6-(6,6-difluoro-3-aza-bicyclo[3.2.0]hept-3-yl)-pyridin-2-ylamino]-isonicotinonitrile |

TABLE 1-continued

| No. | Structure | Name |
|---|---|---|
| 70 | [Abs] | 2-[1'-Oxetan-3-yl-6-((R)-2-trifluoromethyl-pyrrolidin-1-yl)-1',2',3',4',5',6'-hexahydro-[4,4']bipyridinyl-2-ylamino]-isonicotinonitrile |
| 71 | 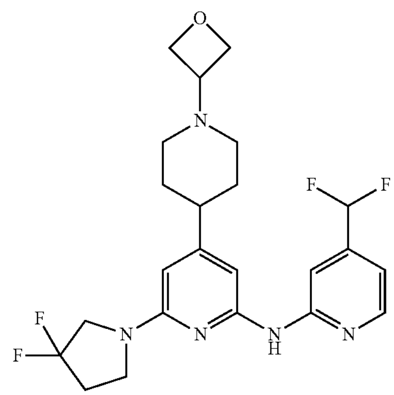 [SMILES: FC(F)c1ccnc(Nc2cc(C3CCN(C4COC4)CC3)cc(N3CCC(F)(F)C3)n2)c1] | (4-Difluoromethyl-pyridin-2-yl)-[6-(3,3-difluoro-pyrrolidin-1-yl)-1'-oxetan-3-yl-1',2',3',4',5',6'-hexahydro-[4,4']bipyridinyl-2-yl]-amine |
| 72 | 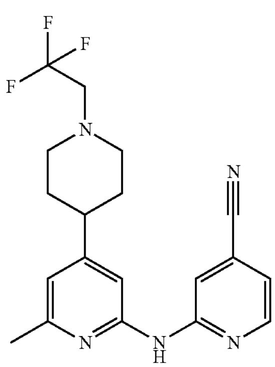 [SMILES: Cc1cc(C2CCN(CC(F)(F)F)CC2)cc(Nc2cc(C#N)ccn2)n1] | 2-[6-Methyl-1'-(2,2,2-trifluoro-ethyl)-1',2',3',4',5',6'-hexahydro-[4,4']bipyridinyl-2-ylamino]-isonicotinonitrile |
| 74 | [Abs] | 2-[4-(4-Cyano-tetrahydro-pyran-4-yl)-6-((R)-2-methyl-pyrrolidin-1-yl)-pyridin-2-ylamino]-isonicotinonitrile |

TABLE 1-continued

| No. | Structure | Name |
|---|---|---|
| 75 | 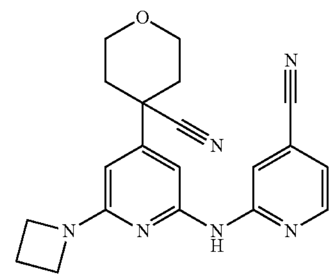 [SMILES: N#Cc1ccnc(Nc2cc(C3(C#N)CCOCC3)cc(N3CCC3)n2)c1] | 2-[6-Azetidin-1-yl-4-(4-cyano-tetrahydro-pyran-4-yl)-pyridin-2-ylamino]-isonicotinonitrile |
| 79 | 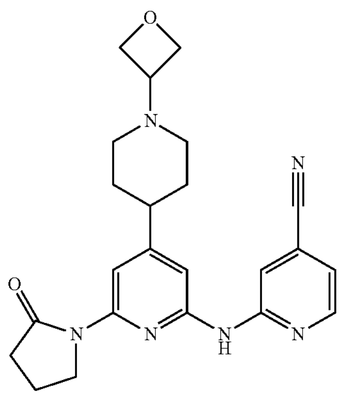 [SMILES: N#Cc1ccnc(Nc2cc(C3CCN(C4COC4)CC3)cc(N3CCCC3=O)n2)c1] | 2-[1'-Oxetan-3-yl-6-(2-oxo-pyrrolidin-1-yl)-1',2',3',4',5',6'-hexahydro-[4,4']bipyridin-yl-2-ylamino]-isonicotinonitrile |
| 80 | 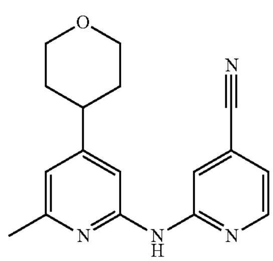 [SMILES: Cc1cc(C2CCOCC2)cc(Nc2cc(C#N)ccn2)n1] | 2-[6-Methyl-4-(tetrahydro-pyran-4-yl)-pyridin-2-ylamino]-isonicotinonitrile |
| 81 | 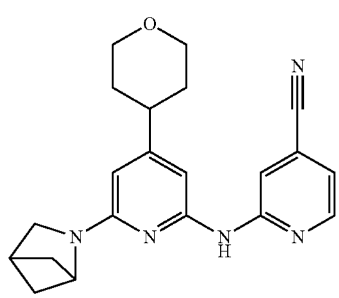 [SMILES: N#Cc1ccnc(Nc2cc(C3CCOCC3)cc(N3CC4CC3C4)n2)c1] | 2-[6-(2-Aza-bicyclo[2.1.1]hex-2-yl)-4-(tetrahydro-pyran-4-yl)-pyridin-2-ylamino]-isonicotinonitrile |
| 82 | 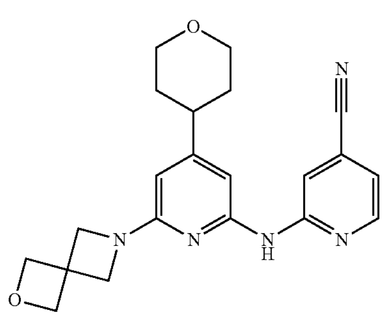 [SMILES: N#Cc1ccnc(Nc2cc(C3CCOCC3)cc(N3CC4(COC4)C3)n2)c1] | 2-[6-(2-Oxa-6-aza-spiro[3.3]hept-6-yl)-4-(tetrahydro-pyran-4-yl)-pyridin-2-ylamino]-isonicotinonitrile |

TABLE 1-continued

| No. | Structure | Name |
|---|---|---|
| 83 | 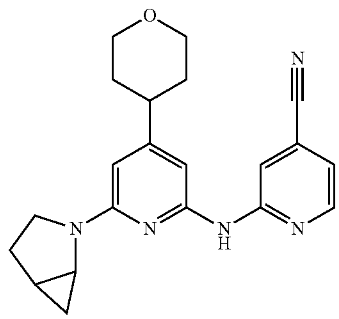 [SMILES: N#Cc1ccnc(Nc2cc(C3CCOCC3)cc(N3CCC4CC43)n2)c1] | 2-[6-(2-Aza-bicyclo[3.1.0]hex-2-yl)-4-(tetrahydro-pyran-4-yl)-pyridin-2-ylamino]-isonicotinonitrile |
| 84 | 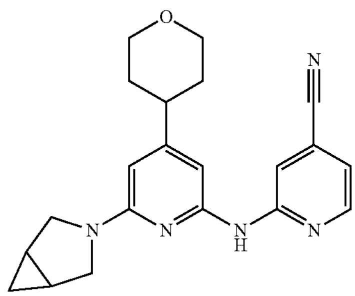 [SMILES: N#Cc1ccnc(Nc2cc(C3CCOCC3)cc(N3CC4CC4C3)n2)c1] | 2-[6-(3-Aza-bicyclo[3.1.0]hex-3-yl)-4-(tetrahydro-pyran-4-yl)-pyridin-2-ylamino]-isonicotinonitrile |
| 85 | 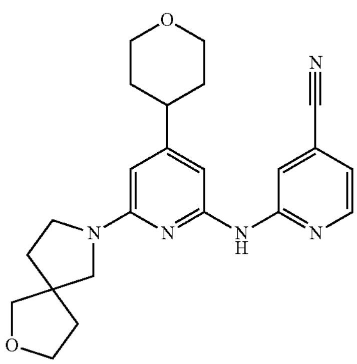 [SMILES: N#Cc1ccnc(Nc2cc(C3CCOCC3)cc(N3CCC4(CCOC4)C3)n2)c1] | 2-[6-(2-Oxa-7-aza-spiro[4.4]non-7-yl)-4-(tetrahydro-pyran-4-yl)-pyridin-2-ylamino]-isonicotinonitrile |
| 86 | 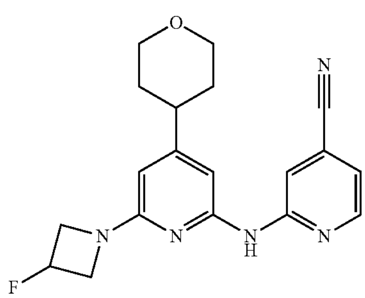 [SMILES: N#Cc1ccnc(Nc2cc(C3CCOCC3)cc(N3CC(F)C3)n2)c1] | 2-[6-(3-Fluoro-azetidin-1-yl)-4-(tetrahydro-pyran-4-yl)-pyridin-2-ylamino]-isonicotinonitrile |
| 87 | 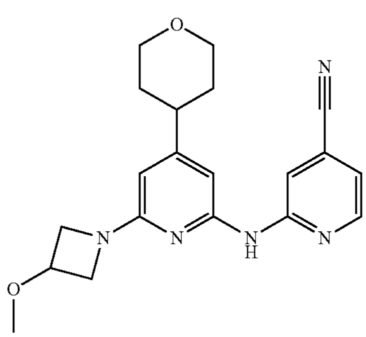 [SMILES: COC1CN(c2cc(C3CCOCC3)cc(Nc3cc(C#N)ccn3)n2)C1] | 2-[6-(3-Methoxy-azetidin-1-yl)-4-(tetrahydro-pyran-4-yl)-pyridin-2-ylamino]-isonicotinonitrile |

TABLE 1-continued

| No. | Structure | Name |
|---|---|---|
| 88 | 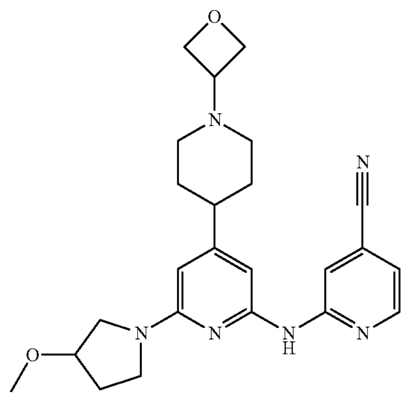 [SMILES: COC1CCN(c2cc(C3CCN(C4COC4)CC3)cc(Nc3cc(C#N)ccn3)n2)C1] | 2-[6-(3-Methoxy-pyrrolidin-1-yl)-1'-oxetan-3-yl-1',2',3',4',5',6'-hexahydro-[4,4']bipyridinyl-2-ylamino]-isonicotinonitrile |
| 89 | 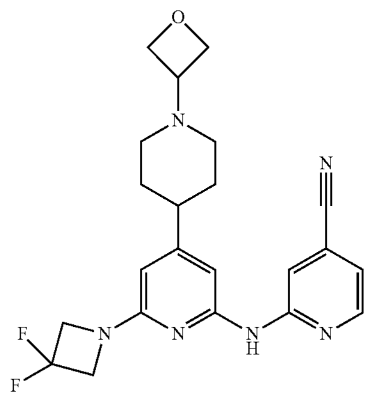 [SMILES: N#Cc1ccnc(Nc2cc(C3CCN(C4COC4)CC3)cc(N3CC(F)(F)C3)n2)c1] | 2-[6-(3,3-Difluoro-azetidin-1-yl)-1'-oxetan-3-yl-1',2',3',4',5',6'-hexahydro-[4,4']bipyridinyl-2-ylamino]-isonicotinonitrile |
| 90 | 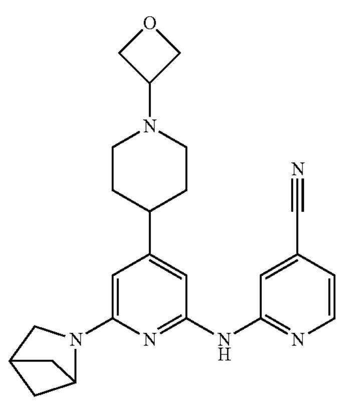 [SMILES: N#Cc1ccnc(Nc2cc(C3CCN(C4COC4)CC3)cc(N3CC4CC3C4)n2)c1] | 2-[6-(2-Aza-bicyclo[2.1.1]hex-2-yl)-1'-oxetan-3-yl-1',2',3',4',5',6'-hexahydro-[4,4']bipyridinyl-2-ylamino]-isonicotinonitrile |
| 91 | 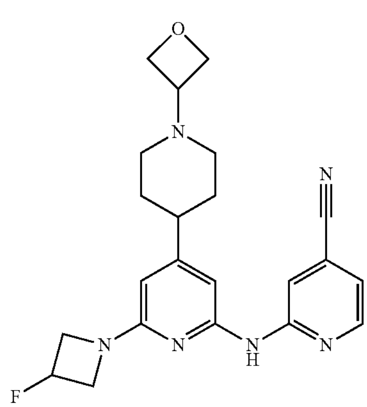 [SMILES: N#Cc1ccnc(Nc2cc(C3CCN(C4COC4)CC3)cc(N3CC(F)C3)n2)c1] | 2-[6-(3-Fluoro-azetidin-1-yl)-1'-oxetan-3-yl-1',2',3',4',5',6'-hexahydro-[4,4']bipyridinyl-2-ylamino]-isonicotinonitrile |

TABLE 1-continued
| No. | Structure | Name |
|---|---|---|
| 92 | 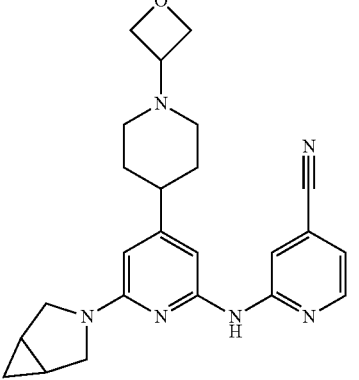 | 2-[6-(3-Aza-bicyclo[3.1.0]hex-3-yl)-1'-oxetan-3-yl-1',2',3',4',5',6'-hexahydro-[4,4']bipyridinyl-2-ylamino]-isonicotinonitrile |
| 93 | 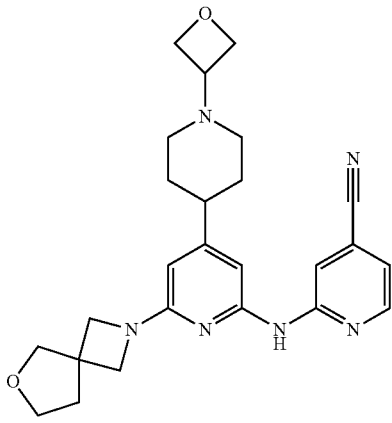 [SMILES: N#Cc1ccnc(Nc2cc(C3CCN(C4COC4)CC3)cc(N3CC4(CCOC4)C3)n2)c1] | 2-[6-(6-Oxa-2-aza-spiro[3.4]oct-2-yl)-1'-oxetan-3-yl-1',2',3',4',5',6'-hexahydro-[4,4']bipyridinyl-2-ylamino]-isonicotinonitrile |
| 94 | 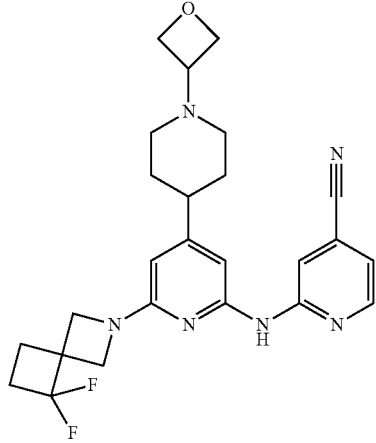 [SMILES: N#Cc1ccnc(Nc2cc(C3CCN(C4COC4)CC3)cc(N3CC4(CCC4(F)F)C3)n2)c1] | 2-[6-(5,5-Difluoro-2-aza-spiro[3.3]hept-2-yl)-1'-oxetan-3-yl-1',2',3',4',5',6'-hexahydro-[4,4']bipyridinyl-2-ylamino]-isonicotinonitrile |

TABLE 1-continued

| No. | Structure | Name |
|---|---|---|
| 95 | 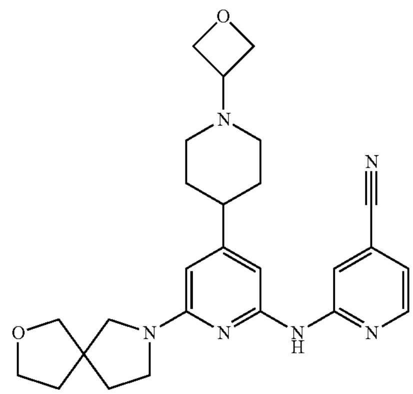 [SMILES: N#Cc1ccnc(Nc2cc(C3CCN(C4COC4)CC3)cc(N3CCC4(CCOC4)C3)n2)c1] | 2-[6-(2-Oxa-7-aza-spiro[4.4]non-7-yl)-1'-oxetan-3-yl-1',2',3',4',5',6'-hexahydro-[4,4']bipyridinyl-2-ylamino]-isonicotinonitrile |
| 96 | 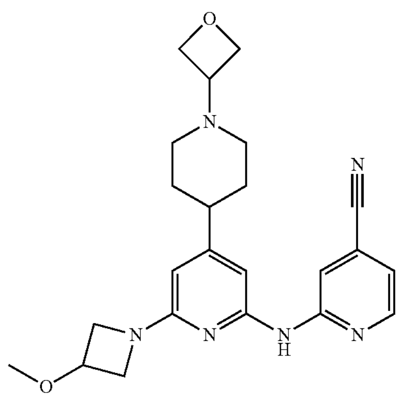 [SMILES: COC1CN(c2cc(C3CCN(C4COC4)CC3)cc(Nc3cc(C#N)ccn3)n2)C1] | 2-[6-(3-Methoxy-azetidin-1-yl)-1'-oxetan-3-yl-1',2',3',4',5',6'-hexahydro-[4,4']bipyridinyl-2-ylamino]-isonicotinonitrile |
| 97 | 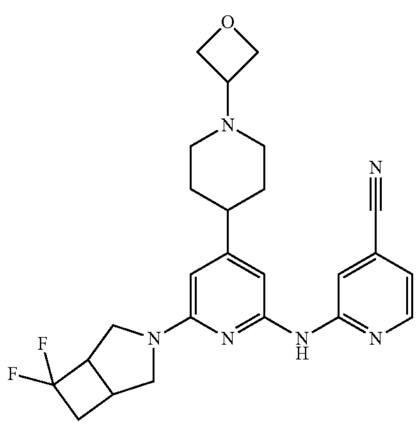 [SMILES: N#Cc1ccnc(Nc2cc(C3CCN(C4COC4)CC3)cc(N3CC4CC(F)(F)C4C3)n2)c1] | 2-[6-(6,6-Difluoro-3-aza-bicyclo[3.2.0]hept-3-yl)-1'-oxetan-3-yl-1',2',3',4',5',6'-hexahydro-[4,4']bipyridinyl-2-ylamino]-isonicotinonitrile |
| 98 | 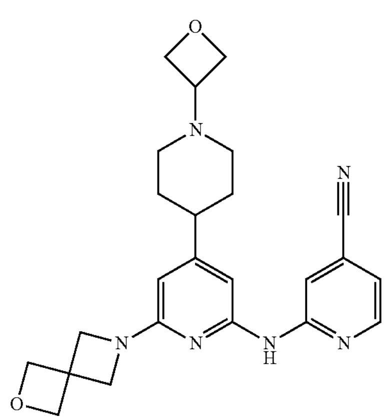 [SMILES: N#Cc1ccnc(Nc2cc(C3CCN(C4COC4)CC3)cc(N3CC4(COC4)C3)n2)c1] | 2-[6-(2-Oxa-6-aza-spiro[3.3]hept-6-yl)-1'-oxetan-3-yl-1',2',3',4',5',6'-hexahydro-[4,4']bipyridinyl-2-ylamino]-isonicotinonitrile |

TABLE 1-continued

| No. | Structure | Name |
|---|---|---|
| 99 | 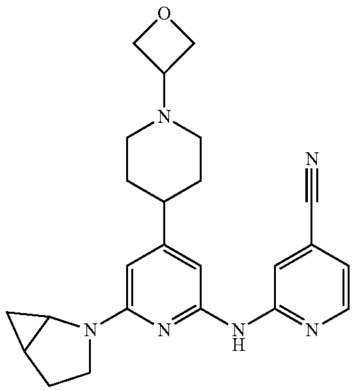 [SMILES: N#Cc1ccnc(Nc2cc(C3CCN(C4COC4)CC3)cc(N3CCC4CC43)n2)c1] | 2-[6-(2-Aza-bicyclo[3.1.0]hex-2-yl)-1'-oxetan-3-yl-1',2',3',4',5',6'-hexahydro-[4,4']bipyridinyl-2-ylamino]-isonicotinonitrile |
| 100 | 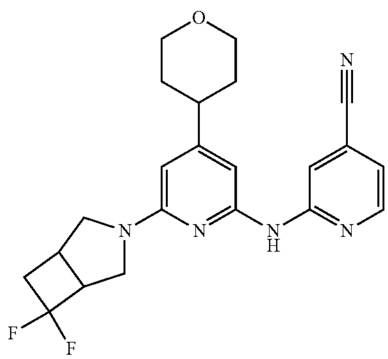 [SMILES: N#Cc1ccnc(Nc2cc(C3CCOCC3)cc(N3CC4CC(F)(F)C4C3)n2)c1] | 2-[6-(6,6-Difluoro-3-aza-bicyclo[3.2.0]hept-3-yl)-4-(tetrahydro-pyran-4-yl)-pyridin-2-ylamino]-isonicotinonitrile |
| 101 | 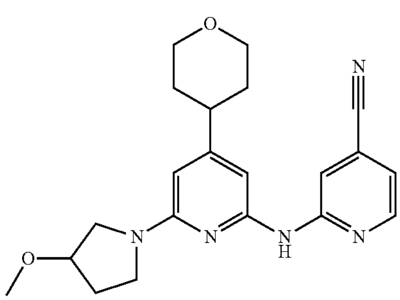 [SMILES: COC1CCN(c2cc(C3CCOCC3)cc(Nc3cc(C#N)ccn3)n2)C1] | 2-[6-(3-Methoxy-pyrrolidin-1-yl)-4-(tetrahydro-pyran-4-yl)-pyridin-2-ylamino]-isonicotinonitrile |
| 102 | 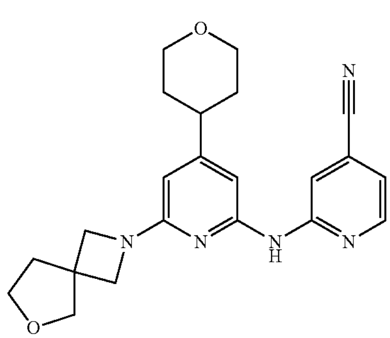 [SMILES: N#Cc1ccnc(Nc2cc(C3CCOCC3)cc(N3CC4(CCOC4)C3)n2)c1] | 2-[6-(6-Oxa-2-aza-spiro[3.4]oct-2-yl)-4-(tetrahydro-pyran-4-yl)-pyridin-2-ylamino]-isonicotinonitrile |

TABLE 1-continued

| No. | Structure | Name |
|---|---|---|
| 103 | 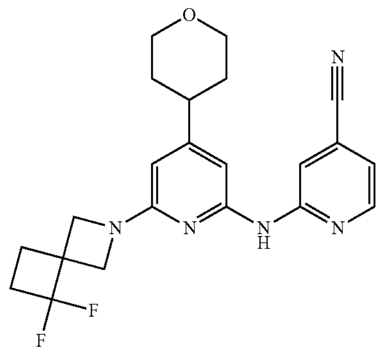 [SMILES: N#Cc1ccnc(Nc2cc(C3CCOCC3)cc(N3CC4(CCC4(F)F)C3)n2)c1] | 2-[6-(5,5-Difluoro-2-aza-spiro[3.3]hept-2-yl)-4-(tetrahydro-pyran-4-yl)-pyridin-2-yl-amino]-isonicotinonitrile |
| 104 | 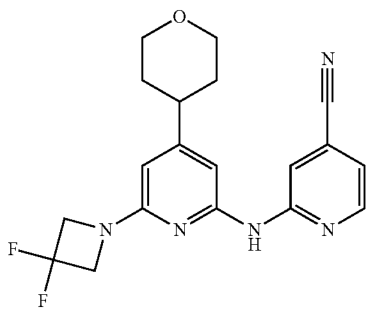 [SMILES: N#Cc1ccnc(Nc2cc(C3CCOCC3)cc(N3CC(F)(F)C3)n2)c1] | 2-[6-(3,3-Difluoro-azetidin-1-yl)-4-(tetrahydro-pyran-4-yl)-pyridin-2-ylamino]-isonicotinonitrile |
| 105 | 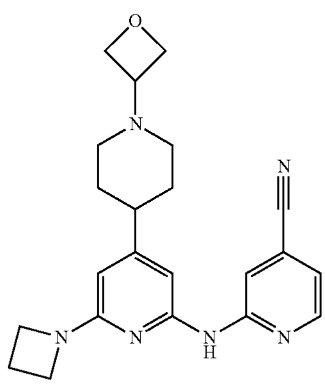 [SMILES: N#Cc1ccnc(Nc2cc(C3CCN(C4COC4)CC3)cc(N3CCC3)n2)c1] | 2-(6-Azetidin-1-yl-1'-oxetan-3-yl-1',2',3',4',5',6'-hexahydro-[4,4']bipyridinyl-2-ylamino)-isonicotinonitrile |
| 107 | 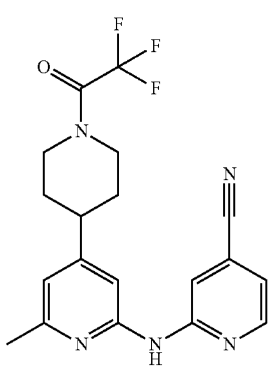 [SMILES: Cc1cc(C2CCN(C(=O)C(F)(F)F)CC2)cc(Nc2cc(C#N)ccn2)n1] | 2-[6-Methyl-1'-(2,2,2-trifluoro-acetyl)-1',2',3',4',5',6'-hexahydro-[4,4']bipyridinyl-2-yl-amino]-isonicotinonitrile |

TABLE 1-continued

| No. | Structure | Name |
|---|---|---|
| 108 | 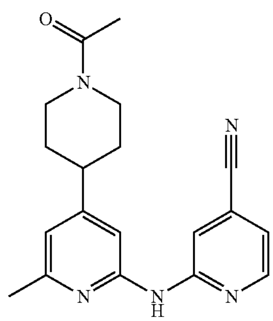 [SMILES: CC(=O)N1CCC(c2cc(C)nc(Nc3cc(C#N)ccn3)c2)CC1] | 2-(1'-Acetyl-6-methyl-1',2',3',4',5',6'-hexahydro-[4,4']bipyridinyl-2-ylamino)-isonicotinonitrile |
| 109 | 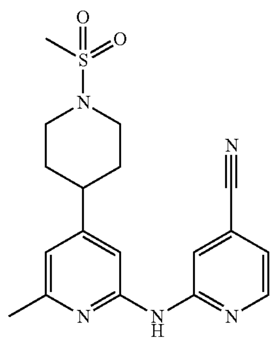 [SMILES: Cc1cc(C2CCN(S(C)(=O)=O)CC2)cc(Nc2cc(C#N)ccn2)n1] | 2-(1'-Methanesulfonyl-6-methyl-1',2',3',4',5',6'-hexahydro-[4,4']bipyridinyl-2-ylamino)-isonicotinonitrile |
| 110 | 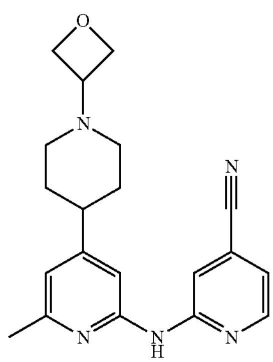 [SMILES: Cc1cc(C2CCN(C3COC3)CC2)cc(Nc2cc(C#N)ccn2)n1] | 2-(6-Methyl-1'-oxetan-3-yl-1',2',3',4',5',6'-hexahydro-[4,4']bipyridinyl-2-ylamino)-isonicotinonitrile |
| 111 | 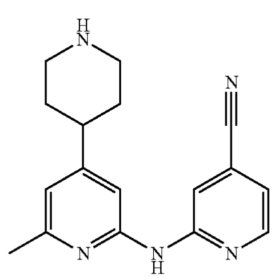 [SMILES: Cc1cc(C2CCNCC2)cc(Nc2cc(C#N)ccn2)n1] | 2-(6-Methyl-1',2',3',4',5',6'-hexahydro-[4,4']bipyridinyl-2-ylamino)-isonicotinonitrile |
| 113 | 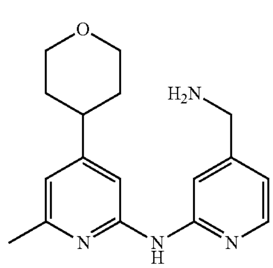 [SMILES: Cc1cc(C2CCOCC2)cc(Nc2cc(CN)ccn2)n1] | (4-Aminomethyl-pyridin-2-yl)-[6-methyl-4-(tetrahydro-pyran-4-yl)-pyridin-2-yl]-amine |

TABLE 1-continued

| No. | Structure | Name |
|---|---|---|
| 114 | 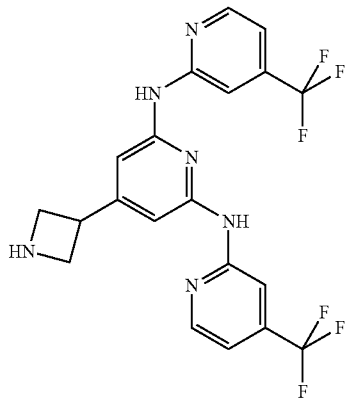 [SMILES: FC(F)(F)c1ccnc(Nc2cc(C3CNC3)cc(Nc3cc(C(F)(F)F)ccn3)n2)c1] | 4-Azetidin-3-yl-N,N'-bis-(4-trifluoromethyl-pyridin-2-yl)-pyridine-2,6-diamine |
| 115 | 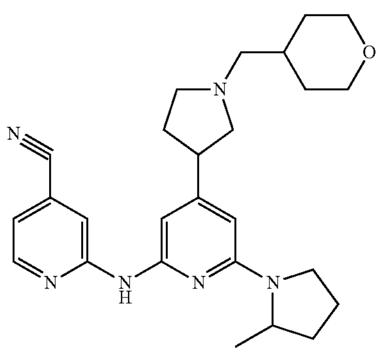 [SMILES: CC1CCCN1c1cc(C2CCN(CC3CCOCC3)C2)cc(Nc2cc(C#N)ccn2)n1] | 2-{6-(2-Methyl-pyrrolidin-1-yl)-4-[1-(tetrahydro-pyran-4-ylmethyl)-pyrrolidin-3-yl]-pyridin-2-ylamino}-isonicotinonitrile |
| 116 | 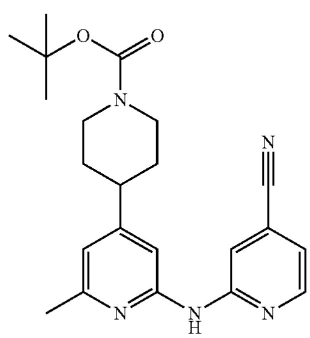 [SMILES: Cc1cc(C2CCN(C(=O)OC(C)(C)C)CC2)cc(Nc2cc(C#N)ccn2)n1] | 2'-(4-Cyano-pyridin-2-ylamino)-6'-methyl-3,4,5,6-tetrahydro-2H-[4,4']bipyridinyl-1-carboxylic acid tert-butyl ester |
| 117 | 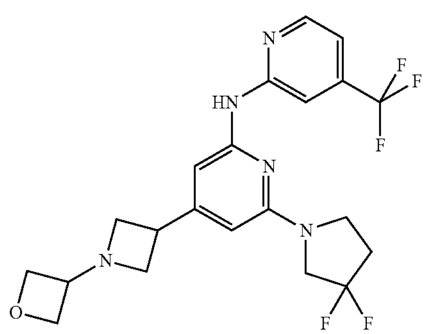 [SMILES: FC1(F)CCN(c2cc(C3CN(C4COC4)C3)cc(Nc3cc(C(F)(F)F)ccn3)n2)C1] | [6-(3,3-Difluoro-pyrrolidin-1-yl)-4-(1-oxetan-3-yl-azetidin-3-yl)-pyridin-2-yl]-(4-trifluoromethyl-pyridin-2-yl)-amine |

TABLE 1-continued

| No. | Structure | Name |
|---|---|---|
| 118 | 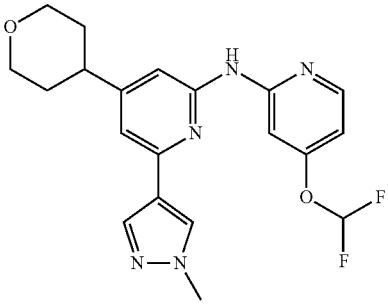 [SMILES: Cn1cc(-c2cc(C3CCOCC3)cc(Nc3cc(OC(F)F)ccn3)n2)cn1] | (4-Difluoromethoxy-pyridin-2-yl)-[6-(1-methyl-1H-pyrazol-4-yl)-4-(tetrahydro-pyran-4-yl)-pyridin-2-yl]-amine |
| 119 | 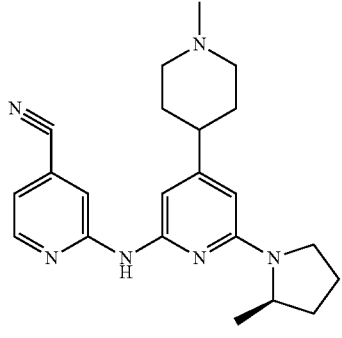 [SMILES: C[C@@H]1CCCN1c1cc(C2CCN(C)CC2)cc(Nc2cc(C#N)ccn2)n1] | 2-[1'-Acetyl-6-((R)-2-methyl-pyrrolidin-1-yl)-1',2',3',4',5',6'-hexahydro-[4,4']bipyridin-yl-2-ylamino]-isonicotinonitrile |
| 121 | 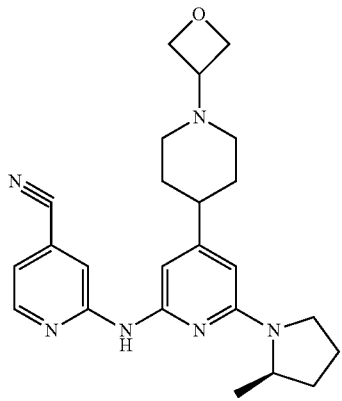 | 2-[6-((R)-2-Methyl-pyrrolidin-1-yl)-1'-oxetan-3-yl-1',2',3',4',5',6'-hexahydro-[4,4']bipyridinyl-2-ylamino]-isonicotinonitrile |
| 122 | 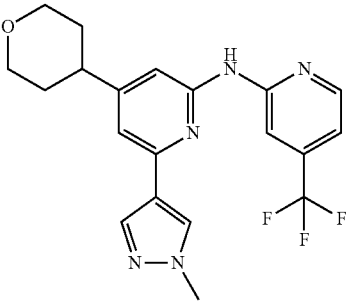 [SMILES: Cn1cc(-c2cc(C3CCOCC3)cc(Nc3cc(C(F)(F)F)ccn3)n2)cn1] | [6-(1-Methyl-1H-pyrazol-4-yl)-4-(tetrahydro-pyran-4-yl)-pyridin-2-yl]-(4-trifluoromethyl-pyridin-2-yl)-amine |

TABLE 1-continued

| No. | Structure | Name |
|---|---|---|
| 123 | 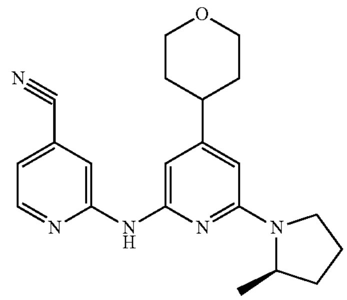 [SMILES: C[C@@H]1CCCN1c1cc(C2CCOCC2)cc(Nc2cc(C#N)ccn2)n1] | 2-[6-((R)-2-Methyl-pyrrolidin-1-yl)-4-(tetrahydro-pyran-4-yl)-pyridin-2-ylamino]-iso-nicotinonitrile |
| 125 | 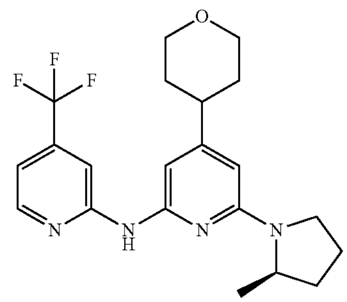 [SMILES: C[C@@H]1CCCN1c1cc(C2CCOCC2)cc(Nc2cc(C(F)(F)F)ccn2)n1] | [6-((R)-2-Methyl-pyrrolidin-1-yl)-4-(tetrahydro-pyran-4-yl)-pyridin-2-yl]-(4-trifluoro-methyl-pyridin-2-yl)-amine |
| 126 | 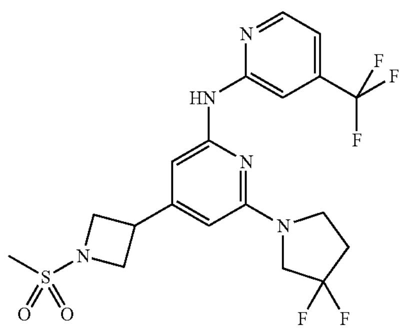 [SMILES: CS(=O)(=O)N1CC(c2cc(Nc3cc(C(F)(F)F)ccn3)nc(N3CCC(F)(F)C3)c2)C1] | [6-(3,3-Difluoro-pyrrolidin-1-yl)-4-(1-methanesulfonyl-azetidin-3-yl)-pyridin-2-yl]-(4-trifluoromethyl-pyridin-2-yl)-amine |
| 127 | 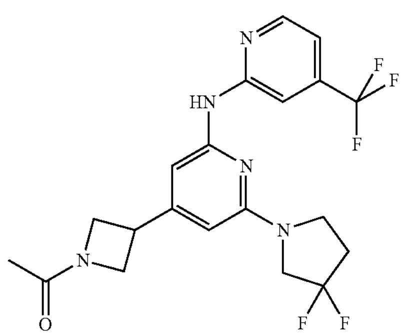 [SMILES: CC(=O)N1CC(c2cc(Nc3cc(C(F)(F)F)ccn3)nc(N3CCC(F)(F)C3)c2)C1] | 1-{3-[243,3-Difluoro-pyrrolidin-1-yl)-6-(4-trifluoromethyl-pyridin-2-ylamino)-pyridin-4-yl]-azetidin-1-yl}-ethanone |
| 130 | 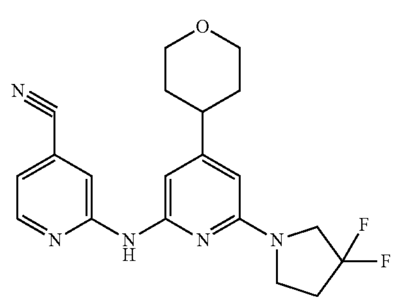 [SMILES: N#Cc1ccnc(Nc2cc(C3CCOCC3)cc(N3CCC(F)(F)C3)n2)c1] | 2-[6-(3,3-Difluoro-pyrrolidin-1-yl)-4-(tetrahydro-pyran-4-yl)-pyridin-2-ylamino]-iso-nicotinonitrile |

TABLE 1-continued

| No. | Structure | Name |
|-----|-----------|------|
| 131 | 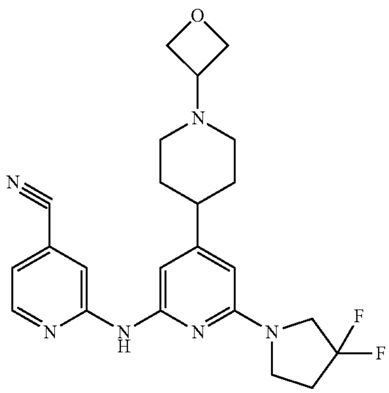 [SMILES: N#Cc1ccnc(Nc2cc(C3CCN(C4COC4)CC3)cc(N3CCC(F)(F)C3)n2)c1] | 2-[6-(3,3-Difluoro-pyrrolidin-1-yl)-1'-oxetan-3-yl-1',2',3',4',5',6'-hexahydro-[4,4']bipyridinyl-2-ylamino]-isonicotinonitrile |
| 132 | 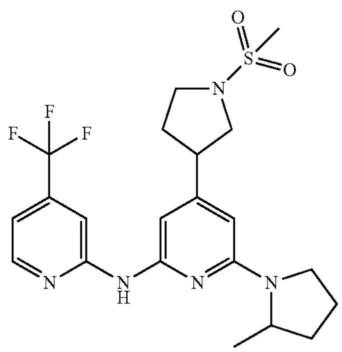 [SMILES: CC1CCCN1c1cc(C2CCN(S(C)(=O)=O)C2)cc(Nc2cc(C(F)(F)F)ccn2)n1] | [4-(1-Methanesulfonyl-pyrrolidin-3-yl)-6-(2-methyl-pyrrolidin-1-yl)-pyridin-2-yl]-(4-trifluoromethyl-pyridin-2-yl)-amine |
| 133 | 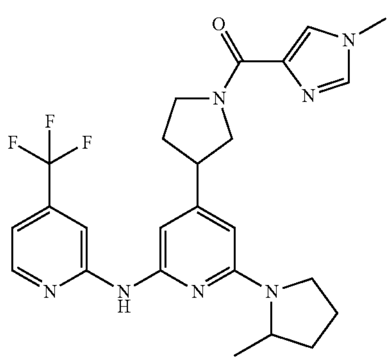 [SMILES: CC1CCCN1c1cc(C2CCN(C(=O)c3cn(C)cn3)C2)cc(Nc2cc(C(F)(F)F)ccn2)n1] | (1-Methyl-1H-imidazol-4-yl)-{3-[2-(2-methyl-pyrrolidin-1-yl)-6-(4-trifluoromethyl-pyridin-2-ylamino)-pyridin-4-yl]-pyrrolidin-1-yl}-methanone |
| 134 | 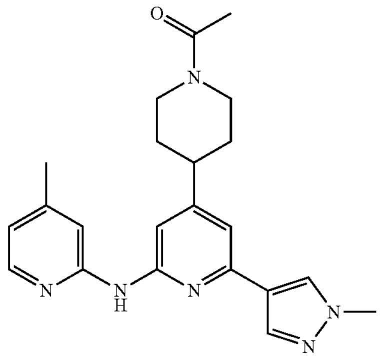 [SMILES: CC(=O)N1CCC(c2cc(Nc3cc(C)ccn3)nc(-c3cnn(C)c3)c2)CC1] | 1-[2'-(1-Methyl-1H-pyrazol-4-yl)-6'-(4-methyl-pyridin-2-ylamino)-3,4,5,6-tetrahydro-2H-[4,4']bipyridinyl-1-yl]-ethanone |

TABLE 1-continued

| No. | Structure | Name |
|---|---|---|
| 135 | 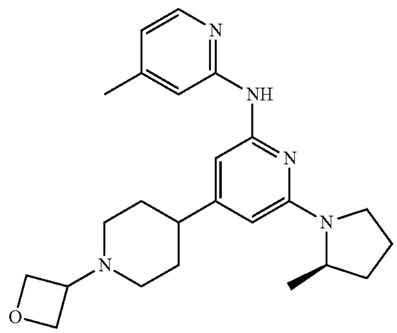 [SMILES: Cc1ccnc(Nc2cc(C3CCN(C4COC4)CC3)cc(N3CCC[C@H]3C)n2)c1] | (4-Methyl-pyridin-2-yl)-[6-((R)-2-methyl-pyrrolidin-1-yl)-1'-oxetan-3-yl-1',2',3',4',5',6'-hexahydro-[4,4']bipyridinyl-2-yl]-amine |
| 136 | 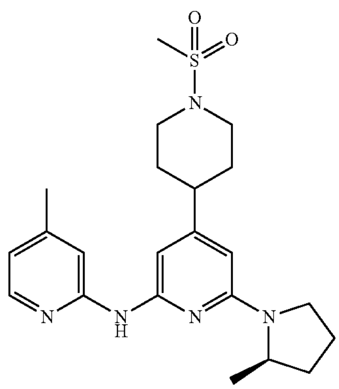 [SMILES: Cc1ccnc(Nc2cc(C3CCN(S(C)(=O)=O)CC3)cc(N3CCC[C@H]3C)n2)c1] | [1'-Methanesulfonyl-6-((R)-2-methyl-pyrrolidin-1-yl)-1',2',3',4',5',6'-hexahydro-[4,4']bipyridinyl-2-yl]-(4-methyl-pyridin-2-yl)-amine |
| 137 | 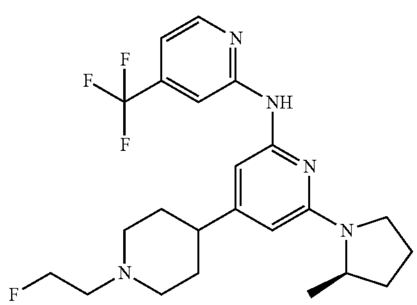 [SMILES: C[C@@H]1CCCN1c1cc(C2CCN(CCF)CC2)cc(Nc2cc(C(F)(F)F)ccn2)n1] | [1'-(2-Fluoro-ethyl)-6-((R)-2-methyl-pyrrolidin-1-yl)-1',2',3',4',5',6'-hexahydro-[4,4']bipyridinyl-2-yl]-(4-trifluoro-methyl-pyridin-2-yl)-amine |
| 138 | 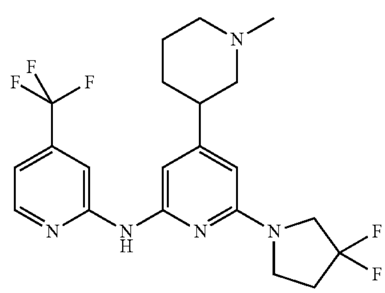 [SMILES: CN1CCCC(c2cc(Nc3cc(C(F)(F)F)ccn3)nc(N3CCC(F)(F)C3)c2)C1] | [6'-(3,3-Difluoro-pyrrolidin-1-yl)-1-methyl-1,2,3,4,5,6-hexahydro-[3,4']bipyridinyl-2'-yl]-(4-trifluoromethyl-pyridin-2-yl)-amine |

TABLE 1-continued

| No. | Structure | Name |
|---|---|---|
| 139 | 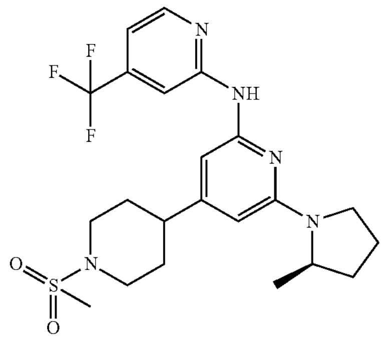 [SMILES: C[C@@H]1CCCN1c1cc(C2CCN(S(C)(=O)=O)CC2)cc(Nc2cc(C(F)(F)F)ccn2)n1] | [1'-Methanesulfonyl-6-((R)-2-methyl-pyrrolidin-1-yl)-1',2',3',4',5',6'-hexahydro-[4,4']bipyridinyl-2-yl]-(4-trifluoromethyl-pyridin-2-yl)-amine |
| 140 | 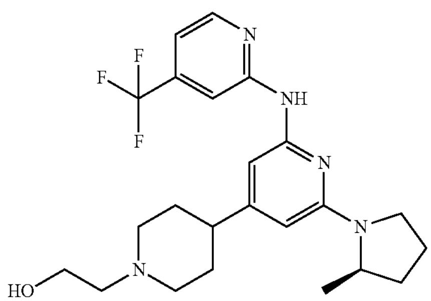 [SMILES: C[C@@H]1CCCN1c1cc(C2CCN(CCO)CC2)cc(Nc2cc(C(F)(F)F)ccn2)n1] | 2-[6'-((R)-2-Methyl-pyrrolidin-1-yl)-2'-(4-trifluoromethyl-pyridin-2-ylamino)-3,4,5,6-tetrahydro-2H-[4,4']bipyridinyl-1-yl]-ethanol |
| 141 | 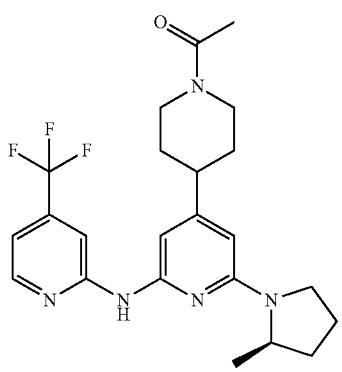 | 1-[2'-((R)-2-Methyl-pyrrolidin-1-yl)-6'-(4-trifluoromethyl-pyridin-2-ylamino)-3,4,5,6-tetrahydro-2H-[4,4']bipyridinyl-1-yl]-ethanone |
| 142 | 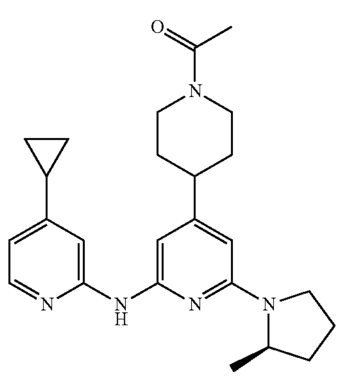 [SMILES: CC(=O)N1CCC(c2cc(Nc3cc(C4CC4)ccn3)nc(N3CCC[C@H]3C)c2)CC1] | 1-[6'-(4-Cyclopropyl-pyridin-2-ylamino)-2'-((R)-2-methyl-pyrrolidin-1-yl)-3,4,5,6-tetrahydro-2H-[4,4']bipyridinyl-1-yl]-ethanone |

TABLE 1-continued
| No. | Structure | Name |
|---|---|---|
| 143 | 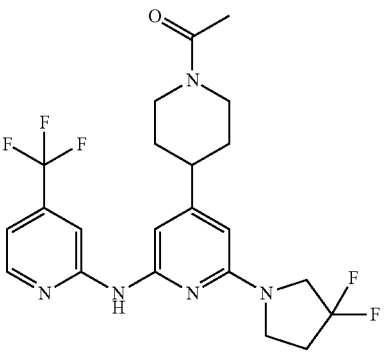 [SMILES: CC(=O)N1CCC(c2cc(Nc3cc(C(F)(F)F)ccn3)nc(N3CCC(F)(F)C3)c2)CC1] | 1-[2'-(3,3-Difluoro-pyrrolidin-1-yl)-6'-(4-trifluoromethyl-pyridin-2-ylamino)-3,4,5,6-tetrahydro-2H-[4,4']bipyridinyl-1-yl]-ethanone |
| 144 | 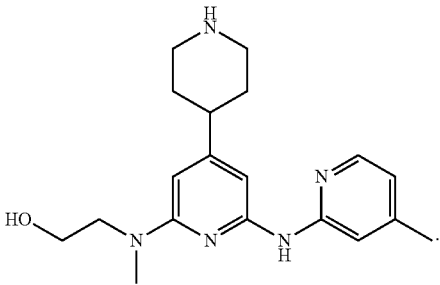 [SMILES: Cc1ccnc(Nc2cc(C3CCNCC3)cc(N(C)CCO)n2)c1] | 2-{Methyl-[6-(4-methyl-pyridin-2-ylamino)-1',2',3',4',5',6'-hexahydro-[4,4']bipyridinyl-2-yl]-amino}-ethanol. |
17. A pharmaceutical composition comprising a compound formula I of claim 1 and a pharmaceutically acceptable carrier, diluent or excipient.
* * * * *